US012473587B2

(12) United States Patent
Wang

(10) Patent No.: US 12,473,587 B2
(45) Date of Patent: Nov. 18, 2025

(54) NUCLEIC ACID CAPTURE METHOD

(71) Applicant: Qing Wang, Owings Mills, MD (US)

(72) Inventor: Qing Wang, Owings Mills, MD (US)

(73) Assignee: Complete Omics Inc., Baltimore, MD (US)

( * ) Notice: Subject to any disclaimer, the term of this patent is extended or adjusted under 35 U.S.C. 154(b) by 1118 days.

(21) Appl. No.: 17/132,099

(22) Filed: Dec. 23, 2020

(65) Prior Publication Data

US 2021/0115503 A1 Apr. 22, 2021

Related U.S. Application Data

(63) Continuation-in-part of application No. 15/911,161, filed on Mar. 4, 2018, now abandoned, which is a continuation-in-part of application No. 15/908,190, filed on Feb. 28, 2018, now abandoned, and a continuation of application No. PCT/US2018/019788, filed on Feb. 26, 2018, said application No. 15/908,190 is a continuation of application No. PCT/US2018/016778, filed on Feb. 4, 2018.

(60) Provisional application No. 62/482,189, filed on Apr. 6, 2017.

(51) Int. Cl.

*C12Q 1/6837* (2018.01)
*C12Q 1/6818* (2018.01)
*C12Q 1/6876* (2018.01)

(52) U.S. Cl.

CPC ......... *C12Q 1/6837* (2013.01); *C12Q 1/6818* (2013.01); *C12Q 1/6876* (2013.01)

(58) Field of Classification Search

CPC ................................ C12Q 1/68; C12Q 1/6876

See application file for complete search history.

(56) References Cited

U.S. PATENT DOCUMENTS

| | | | | |
|---|---|---|---|---|
| 10,844,426 | B2 * | 11/2020 | Daugharthy | C12Q 1/6816 |
| 2006/0255258 | A1 | 11/2006 | Wang et al. | |
| 2014/0031240 | A1 * | 1/2014 | Behlke | C12N 15/1006 536/24.3 |
| 2014/0287410 | A1 * | 9/2014 | Shafer | C12Q 1/6876 435/6.11 |
| 2014/0287468 | A1 * | 9/2014 | Richard | C12Q 1/6888 435/91.53 |
| 2016/0010152 | A1 * | 1/2016 | Shafer | C12Q 1/6876 506/9 |
| 2016/0040218 | A1 * | 2/2016 | Guttman | C12Q 1/6809 506/9 |
| 2018/0136220 | A1 | 5/2018 | Grote et al. | |

FOREIGN PATENT DOCUMENTS

| | | | |
|---|---|---|---|
| EP | 3514545 | B1 | 7/2020 |
| WO | WO2007144606 | A2 | 12/2007 |
| WO | WO 2010/117817 | A2 | 10/2010 |

OTHER PUBLICATIONS

Wang et al., Targeted Sequencing of Both DNA Strands Barcoded and Captured Individually by RNA Probes to Identify Genome-Wide Ultra-Rare Mutations, Scientific Reports, 2017, 7(3356), 1-14. (Year: 2017).*

Lamb, et al., “A practical approach” Gene Probes, Apr. 4, 1995, abstract 1 page.

Office Action for EP18781045.2, Oct. 17, 2023m 5 pages.

Supplementary European Search Report from EP22772303, dated Nov. 19, 2024, 2 pages.

* cited by examiner

*Primary Examiner* — Amy M Bunker

(74) *Attorney, Agent, or Firm* — Ming Zhang

(57) ABSTRACT

A method and a kit for enriching target nucleic acid sequences from a biological sample are disclosed. The method includes preparing, and contacting with the biological sample, a first RNA probe set and a second RNA probe set respectively and concurrently targeting both of the two antiparallel strands of a duplex segment in each target nucleic acid sequence. Each RNA probe in the first and second RNA probe set can be generated by chemical synthesis or by in vitro or in vivo transcription, and can be biotin-labelled to thereby allow capturing of the target nucleic acid sequences by magnetic beads labelled with streptavidin, or can be engineered to a microfluidic channel to facilitate the capturing. The method can be applied to capture double-stranded nucleic acid sequences or single-stranded nucleic acid sequences having duplex segments, and the nucleic acid sequences can include DNAs, RNAs, or DNA-RNA hybrid molecules.

14 Claims, 42 Drawing Sheets

Specification includes a Sequence Listing.

| Gene Symbol | EXON ID | Forward Primer (SEQ ID NO.) | Reverse Primer (SEQ ID NO.) | Amplicon Seq (SEQ ID NO.) | Amplif Eff Constant | GC% of Amplicon |
|---|---|---|---|---|---|---|
| PTEN | 3 | 1 | 305 | 609 | 1.85 | 27.3% |
| FANCL | 3 | 2 | 306 | 610 | 1.99 | 30.1% |
| FANCL | 13 | 3 | 307 | 611 | 1.95 | 35.0% |
| FANCM | 12 | 4 | 308 | 612 | 1.78 | 30.3% |
| NRAS | 6 | 5 | 309 | 613 | 1.90 | 31.7% |
| XPA | 3 | 6 | 310 | 614 | 1.94 | 32.4% |
| XPA | 5 | 7 | 311 | 615 | 1.79 | 34.9% |
| BRCA2 | 9 | 8 | 312 | 616 | 1.85 | 32.8% |
| FANCF | 1 | 9 | 313 | 617 | 1.92 | 32.8% |
| FIP1L1 | 6 | 10 | 314 | 618 | 1.97 | 32.9% |
| BRIP1 | 10 | 11 | 315 | 619 | 1.76 | 33.0% |
| MLH1 | 17 | 12 | 316 | 620 | 1.92 | 33.1% |
| STAG2 | 9 | 13 | 317 | 621 | 1.77 | 33.3% |
| XPO1 | 5 | 14 | 318 | 622 | 1.83 | 33.3% |
| RB1 | 14 | 15 | 319 | 623 | 1.78 | 33.6% |
| NBN | 16 | 16 | 320 | 624 | 1.78 | 33.6% |
| NBN | 10 | 17 | 321 | 625 | 1.94 | 41.7% |
| MDM2 | 4 | 18 | 322 | 626 | 1.78 | 33.8% |
| ATR | 37 | 19 | 323 | 627 | 1.80 | 33.9% |
| FBXO11 | 2 | 20 | 324 | 628 | 1.91 | 34.0% |
| AKAP9 | 20 | 21 | 325 | 629 | 1.80 | 34.1% |
| SDHD | 4 | 22 | 326 | 630 | 1.96 | 34.7% |

FIG. 13A

| Gene Symbol | Exon ID | Forward Primer (SEQ ID NO.) | Reverse Primer (SEQ ID NO.) | Amplicon Seq (SEQ ID NO.) | Amplif Eff Constant | GC% of Amplicon |
|---|---|---|---|---|---|---|
| PIK3CA | 17 | 23 | 327 | 631 | 1.89 | 34.9% |
| CDC73 | 12 | 24 | 328 | 632 | 1.92 | 35.2% |
| ACSL3 | 10 | 25 | 329 | 633 | 1.96 | 35.4% |
| WRN | 16 | 26 | 330 | 634 | 1.94 | 35.4% |
| HSP90AA1 | 6 | 27 | 331 | 635 | 1.77 | 36.0% |
| CDK12 | 7 | 28 | 332 | 636 | 1.76 | 36.0% |
| POT1 | 6 | 29 | 333 | 637 | 1.84 | 36.1% |
| KDM6A | 7 | 30 | 334 | 638 | 1.98 | 36.4% |
| KRAS | 2 | 31 | 335 | 639 | 1.90 | 36.5% |
| BLM | 3 | 32 | 336 | 640 | 1.87 | 36.6% |
| GOLGA5 | 9 | 33 | 337 | 641 | 1.91 | 36.6% |
| PRKAR1A | 11 | 34 | 338 | 642 | 1.91 | 36.7% |
| TMPRSS2 | 3 | 35 | 339 | 643 | 1.89 | 36.8% |
| CLTC | 24 | 36 | 340 | 644 | 1.95 | 36.9% |
| FAS | 8 | 37 | 341 | 645 | 1.99 | 36.9% |
| MSH2 | 9 | 38 | 342 | 646 | 1.91 | 37.0% |
| BUB1B | 3 | 39 | 343 | 647 | 1.75 | 37.0% |
| NF1 | 24 | 40 | 344 | 648 | 1.79 | 37.3% |
| TOP1 | 7 | 41 | 345 | 649 | 1.96 | 37.3% |
| NCOR1 | 17 | 42 | 346 | 650 | 1.87 | 37.3% |
| POLH | 8 | 43 | 347 | 651 | 1.75 | 37.3% |
| SMAD2 | 8 | 44 | 348 | 652 | 1.87 | 37.5% |

FIG. 13B

| Gene Symbol | Exon ID | Forward Primer (SEQ ID NO.) | Reverse Primer (SEQ ID NO.) | Amplicon Seq (SEQ ID NO.) | Amplif Eff Constant | GC% of Amplicon |
|---|---|---|---|---|---|---|
| FUBP1 | 3 | 45 | 349 | 653 | 1.83 | 37.5% |
| RAF1 | 13 | 46 | 350 | 654 | 1.80 | 37.6% |
| SETD2 | 7 | 47 | 351 | 655 | 1.98 | 37.7% |
| DICER1 | 17 | 48 | 352 | 656 | 1.77 | 37.7% |
| FANCC | 7 | 49 | 353 | 657 | 1.89 | 37.7% |
| GPC3 | 4 | 50 | 354 | 658 | 1.98 | 37.7% |
| DDX5 | 11 | 51 | 355 | 659 | 1.79 | 38.0% |
| FAM46C | 2 | 52 | 356 | 660 | 1.96 | 38.1% |
| KAT6B | 9 | 53 | 357 | 661 | 2.00 | 38.1% |
| RAD51C | 7 | 54 | 358 | 662 | 1.91 | 38.4% |
| PPP6C | 6 | 55 | 359 | 663 | 1.91 | 38.4% |
| IDH1 | 4 | 56 | 360 | 664 | 1.82 | 38.4% |
| PMS2 | 9 | 57 | 361 | 665 | 1.96 | 38.5% |
| ATRX | 4 | 58 | 362 | 666 | 1.86 | 38.7% |
| ASXL1 | 2 | 59 | 363 | 667 | 1.85 | 38.7% |
| ASXL1 | 10 | 60 | 364 | 668 | 1.84 | 54.7% |
| PBRM1 | 8 | 61 | 365 | 669 | 2.00 | 38.8% |
| MET | 16 | 62 | 366 | 670 | 1.96 | 38.9% |
| EWSR1 | 12 | 63 | 367 | 671 | 1.89 | 39.0% |
| ATM | 38 | 64 | 368 | 672 | 1.84 | 39.3% |
| PALB2 | 6 | 65 | 369 | 673 | 1.79 | 39.3% |
| SF3B1 | 5 | 66 | 370 | 674 | 1.93 | 39.3% |

FIG. 13C

| Gene Symbol | Exon ID | Forward Primer (SEQ ID NO.) | Reverse Primer (SEQ ID NO.) | Amplicon Seq (SEQ ID NO.) | Amplif Eff Constant | GC% of Amplicon |
|---|---|---|---|---|---|---|
| FANCI | 16 | 67 | 371 | 675 | 1.98 | 39.7% |
| TET2 | 5 | 68 | 372 | 676 | 1.92 | 39.8% |
| TSHR | 6 | 69 | 373 | 677 | 1.97 | 40.0% |
| WHSC1L1 | 19 | 70 | 374 | 678 | 1.76 | 40.2% |
| NFE2L2 | 4 | 71 | 375 | 679 | 2.00 | 40.3% |
| BCOR | 4 | 72 | 376 | 680 | 1.91 | 40.4% |
| ETV5 | 10 | 73 | 377 | 681 | 1.77 | 40.5% |
| CREBBP | 23 | 74 | 378 | 682 | 1.82 | 40.6% |
| SDHAF2 | 3 | 75 | 379 | 683 | 1.82 | 40.7% |
| NPM1 | 11 | 76 | 380 | 684 | 1.86 | 40.7% |
| SPOP | 10 | 77 | 381 | 685 | 1.93 | 40.7% |
| TCF12 | 20 | 78 | 382 | 686 | 1.97 | 40.7% |
| ARID1B | 3 | 79 | 383 | 687 | 1.96 | 40.8% |
| BRAF | 14 | 80 | 384 | 688 | 1.89 | 41.0% |
| FH | 2 | 81 | 385 | 689 | 1.85 | 41.0% |
| ERCC5 | 3 | 82 | 386 | 690 | 1.78 | 41.2% |
| FANCD2 | 8 | 83 | 387 | 691 | 1.78 | 41.3% |
| MTOR | 52 | 84 | 388 | 692 | 1.81 | 41.3% |
| CASP8 | 7 | 85 | 389 | 693 | 1.76 | 41.5% |
| NUP98 | 3 | 86 | 390 | 694 | 1.90 | 41.7% |
| MDM4 | 10 | 87 | 391 | 695 | 1.99 | 41.7% |
| ACVR1 | 7 | 88 | 392 | 696 | 1.83 | 41.8% |

FIG. 13D

| Gene Symbol | Exon ID | Forward Primer (SEQ ID NO.) | Reverse Primer (SEQ ID NO.) | Amplicon Seq (SEQ ID NO.) | Amplif Eff Constant | GC% of Amplicon |
|---|---|---|---|---|---|---|
| ARID2 | 18 | 89 | 393 | 697 | 1.95 | 41.8% |
| MECOM | 6 | 90 | 394 | 698 | 1.76 | 42.0% |
| RET | 16 | 91 | 395 | 699 | 2.00 | 42.0% |
| BCL2 | 1 | 92 | 396 | 700 | 1.99 | 42.0% |
| FUS | 9 | 93 | 397 | 701 | 1.94 | 42.1% |
| TCF7L2 | 4 | 94 | 398 | 702 | 1.94 | 42.4% |
| ATIC | 5 | 95 | 399 | 703 | 1.80 | 42.6% |
| PMS1 | 2 | 96 | 400 | 704 | 1.79 | 42.6% |
| CHD4 | 34 | 97 | 401 | 705 | 1.77 | 42.7% |
| PTPN11 | 8 | 98 | 402 | 706 | 1.88 | 42.8% |
| ABL2 | 3 | 99 | 403 | 707 | 1.78 | 42.9% |
| MAP2K4 | 9 | 100 | 404 | 708 | 1.91 | 42.9% |
| CRTC3 | 5 | 101 | 405 | 709 | 1.96 | 43.0% |
| BRCA1 | 3 | 102 | 406 | 710 | 1.82 | 43.2% |
| LCP1 | 2 | 103 | 407 | 711 | 1.87 | 43.3% |
| FCRL4 | 10 | 104 | 408 | 712 | 1.83 | 43.3% |
| RAC1 | 4 | 105 | 409 | 713 | 1.77 | 43.5% |
| SMARCA4 | 14 | 106 | 410 | 714 | 1.76 | 43.5% |
| HSP90AB1 | 6 | 107 | 411 | 715 | 2.00 | 43.5% |
| TBL1XR1 | 3 | 108 | 412 | 716 | 1.88 | 43.6% |
| VHL | 2 | 109 | 413 | 717 | 1.93 | 43.7% |
| NOTCH2 | 12 | 110 | 414 | 718 | 1.94 | 43.7% |

FIG. 13E

| Gene Symbol | Exon ID | Forward Primer (SEQ ID NO.) | Reverse Primer (SEQ ID NO.) | Amplicon Seq (SEQ ID NO.) | Amplif Eff Constant | GC% of Amplicon |
|---|---|---|---|---|---|---|
| CTNNB1 | 15 | 111 | 415 | 719 | 1.86 | 43.7% |
| POLE | 3 | 112 | 416 | 720 | 1.95 | 43.8% |
| SDHC | 3 | 113 | 417 | 721 | 1.97 | 43.9% |
| KIT | 20 | 114 | 418 | 722 | 1.76 | 44.1% |
| ETV6 | 7 | 115 | 419 | 723 | 1.85 | 44.1% |
| CTCF | 6 | 116 | 420 | 724 | 1.98 | 44.1% |
| MAP2K1 | 9 | 117 | 421 | 725 | 1.97 | 44.2% |
| PSIP1 | 16 | 118 | 422 | 726 | 1.80 | 44.3% |
| RAD21 | 13 | 119 | 423 | 727 | 1.85 | 44.6% |
| KMT2A | 31 | 120 | 424 | 728 | 1.88 | 44.7% |
| CBL | 14 | 121 | 425 | 729 | 1.90 | 44.7% |
| MYB | 4 | 122 | 426 | 730 | 1.87 | 44.7% |
| SYK | 8 | 123 | 427 | 731 | 1.91 | 44.7% |
| ETV1 | 14 | 124 | 428 | 732 | 1.92 | 44.7% |
| BMPR1A | 12 | 125 | 429 | 733 | 1.96 | 44.7% |
| TBX3 | 4 | 126 | 430 | 734 | 1.96 | 44.9% |
| CBFB | 3 | 127 | 431 | 735 | 1.90 | 44.9% |
| DDR2 | 11 | 128 | 432 | 736 | 1.79 | 45.0% |
| NF2 | 5 | 129 | 433 | 737 | 2.00 | 45.0% |
| MSH6 | 7 | 130 | 434 | 738 | 1.88 | 45.1% |
| TSC1 | 2 | 131 | 435 | 739 | 1.86 | 45.3% |
| AFF4 | 12 | 132 | 436 | 740 | 1.91 | 45.3% |

FIG. 13F

| Gene Symbol | Exon ID | Forward Primer (SEQ ID NO.) | Reverse Primer (SEQ ID NO.) | Amplicon Seq (SEQ ID NO.) | Amplif Eff Constant | GC% of Amplicon |
|---|---|---|---|---|---|---|
| FOXP1 | 24 | 133 | 437 | 741 | 1.75 | 45.3% |
| TNFAIP3 | 4 | 134 | 438 | 742 | 1.96 | 45.6% |
| EP300 | 19 | 135 | 439 | 743 | 1.96 | 45.8% |
| MAP3K1 | 18 | 136 | 440 | 744 | 1.80 | 46.0% |
| U2AF1 | 4 | 137 | 441 | 745 | 1.98 | 46.0% |
| ERCC3 | 4 | 138 | 442 | 746 | 1.82 | 46.0% |
| CYLD | 2 | 139 | 443 | 747 | 1.87 | 46.1% |
| IKZF1 | 4 | 140 | 444 | 748 | 1.96 | 46.1% |
| STK11 | 2 | 141 | 445 | 749 | 1.83 | 46.2% |
| PHOX2B | 1 | 142 | 446 | 750 | 1.97 | 46.3% |
| SBDS | 2 | 143 | 447 | 751 | 1.88 | 46.3% |
| SFPQ | 7 | 144 | 448 | 752 | 1.86 | 46.6% |
| WHSC1 | 10 | 145 | 449 | 753 | 1.85 | 46.6% |
| PRRX1 | 4 | 146 | 450 | 754 | 1.80 | 46.7% |
| GNAQ | 4 | 147 | 451 | 755 | 1.76 | 46.8% |
| ERCC4 | 10 | 148 | 452 | 756 | 1.91 | 47.2% |
| FLT3 | 16 | 149 | 453 | 757 | 1.75 | 47.2% |
| MAX | 3 | 150 | 454 | 758 | 1.92 | 47.5% |
| EGFR | 5 | 151 | 455 | 759 | 1.80 | 47.7% |
| RPL22 | 3 | 152 | 456 | 760 | 1.80 | 47.7% |
| SMAD4 | 7 | 153 | 457 | 761 | 1.94 | 48.0% |
| KDR | 20 | 154 | 458 | 762 | 1.82 | 48.0% |

FIG. 13G

| Gene Symbol | Exon ID | Forward Primer (SEQ ID NO.) | Reverse Primer (SEQ ID NO.) | Amplicon Seq (SEQ ID NO.) | Amplif Eff Constant | GC% of Amplicon |
|---|---|---|---|---|---|---|
| CDKN1B | 2 | 155 | 459 | 763 | 1.76 | 48.1% |
| MKL1 | 6 | 156 | 460 | 764 | 1.99 | 48.1% |
| BCL11A | 3 | 157 | 461 | 765 | 1.77 | 48.4% |
| JAK2 | 2 | 158 | 462 | 766 | 1.86 | 48.6% |
| ERBB4 | 5 | 159 | 463 | 767 | 1.87 | 48.7% |
| ERBB3 | 24 | 160 | 464 | 768 | 1.85 | 48.7% |
| PDGFRA | 2 | 161 | 465 | 769 | 1.77 | 48.7% |
| ABL1 | 6 | 162 | 466 | 770 | 1.96 | 48.8% |
| TGFBR2 | 6 | 163 | 467 | 771 | 1.92 | 49.0% |
| EZH2 | 13 | 164 | 468 | 772 | 1.88 | 49.0% |
| ATF1 | 3 | 165 | 469 | 773 | 1.99 | 49.1% |
| XPC | 8 | 166 | 470 | 774 | 1.96 | 49.3% |
| DNAJB1 | 2 | 167 | 471 | 775 | 1.80 | 49.4% |
| USP6 | 2 | 168 | 472 | 776 | 1.79 | 49.4% |
| FGFR2 | 5 | 169 | 473 | 777 | 1.98 | 49.4% |
| RHOA | 4 | 170 | 474 | 778 | 1.96 | 49.5% |
| EXT2 | 9 | 171 | 475 | 779 | 1.89 | 49.7% |
| CDK4 | 5 | 172 | 476 | 780 | 1.92 | 49.7% |
| BTK | 12 | 173 | 477 | 781 | 1.77 | 50.0% |
| PIK3R1 | 3 | 174 | 478 | 782 | 1.83 | 50.0% |
| CUX1 | 8 | 175 | 479 | 783 | 1.77 | 50.0% |
| BCR | 6 | 176 | 480 | 784 | 1.89 | 50.0% |

FIG. 13H

| Gene Symbol | Exon ID | Forward Primer (SEQ ID NO.) | Reverse Primer (SEQ ID NO.) | Amplicon Seq (SEQ ID NO.) | Amplif Eff Constant | GC% of Amplicon |
|---|---|---|---|---|---|---|
| DNMT3A | 10 | 177 | 481 | 785 | 1.94 | 50.0% |
| COL1A1 | 6 | 178 | 482 | 786 | 1.94 | 50.3% |
| ESR1 | 10 | 179 | 483 | 787 | 1.80 | 50.5% |
| ALK | 26 | 180 | 484 | 788 | 1.76 | 51.0% |
| ARHGAP26 | 3 | 181 | 485 | 789 | 1.95 | 51.4% |
| ERCC1 | 6 | 182 | 486 | 790 | 1.94 | 51.6% |
| PTCH1 | 25 | 183 | 487 | 791 | 1.80 | 51.7% |
| AR | 7 | 184 | 488 | 792 | 1.90 | 51.7% |
| NCOA3 | 16 | 185 | 489 | 793 | 1.84 | 51.7% |
| IGF2R | 20 | 186 | 490 | 794 | 1.87 | 52.0% |
| IGF1R | 15 | 187 | 491 | 795 | 1.92 | 52.2% |
| TERT | 10 | 188 | 492 | 796 | 1.76 | 52.2% |
| ROS1 | 4 | 189 | 493 | 797 | 1.95 | 52.3% |
| RUNX1 | 6 | 190 | 494 | 798 | 1.87 | 52.5% |
| XRCC1 | 16 | 191 | 495 | 799 | 1.79 | 52.6% |
| MLLT4 | 11 | 192 | 496 | 800 | 1.85 | 53.2% |
| ARID1A | 17 | 193 | 497 | 801 | 1.96 | 53.2% |
| SDHB | 6 | 194 | 498 | 802 | 1.87 | 53.2% |
| KLF6 | 3 | 195 | 499 | 803 | 1.82 | 53.3% |
| SMAD3 | 7 | 196 | 500 | 804 | 1.96 | 53.3% |
| PAX5 | 7 | 197 | 501 | 805 | 1.85 | 53.3% |
| SMARCB1 | 3 | 198 | 502 | 806 | 1.99 | 53.4% |

FIG. 13I

| Gene Symbol | Exon ID | Forward Primer (SEQ ID NO.) | Reverse Primer (SEQ ID NO.) | Amplicon Seq (SEQ ID NO.) | Amplif Eff Constant | GC% of Amplicon |
|---|---|---|---|---|---|---|
| PRSS1 | 1 | 199 | 503 | 807 | 1.80 | 53.8% |
| ELF4 | 7 | 200 | 504 | 808 | 1.86 | 54.0% |
| FANCA | 13 | 201 | 505 | 809 | 1.90 | 54.0% |
| CALR | 4 | 202 | 506 | 810 | 1.94 | 54.1% |
| EXT1 | 8 | 203 | 507 | 811 | 1.98 | 54.1% |
| TP53 | 6 | 204 | 508 | 812 | 1.93 | 54.3% |
| PDGFRB | 21 | 205 | 509 | 813 | 1.83 | 54.3% |
| FAT1 | 20 | 206 | 510 | 814 | 1.79 | 54.6% |
| KDM5C | 2 | 207 | 511 | 815 | 1.83 | 54.6% |
| KDM5C | 24 | 208 | 512 | 816 | 1.80 | 55.6% |
| WT1 | 7 | 209 | 513 | 817 | 1.76 | 54.6% |
| IDH2 | 3 | 210 | 514 | 818 | 1.88 | 54.7% |
| WAS | 8 | 211 | 515 | 819 | 1.95 | 54.7% |
| MUTYH | 18 | 212 | 516 | 820 | 1.79 | 54.8% |
| MYD88 | 4 | 213 | 517 | 821 | 1.80 | 54.9% |
| PLCG1 | 20 | 214 | 518 | 822 | 1.87 | 54.9% |
| AURKA | 3 | 215 | 519 | 823 | 1.79 | 54.9% |
| MAML1 | 4 | 216 | 520 | 824 | 1.86 | 55.1% |
| SH2B3 | 6 | 217 | 521 | 825 | 1.91 | 55.2% |
| FGFR1 | 5 | 218 | 522 | 826 | 1.92 | 55.5% |
| PPP2R1A | 2 | 219 | 523 | 827 | 1.93 | 55.6% |
| MED12 | 44 | 220 | 524 | 828 | 1.84 | 56.0% |

FIG. 13J

| Gene Symbol | Exon ID | Forward Primer (SEQ ID NO.) | Reverse Primer (SEQ ID NO.) | Amplicon Seq (SEQ ID NO.) | Amplif Eff Constant | GC% of Amplicon |
|---|---|---|---|---|---|---|
| NDRG1 | 2 | 221 | 525 | 829 | 1.84 | 56.0% |
| FANCE | 8 | 222 | 526 | 830 | 1.91 | 56.0% |
| DDB2 | 5 | 223 | 527 | 831 | 1.75 | 56.1% |
| ERCC2 | 16 | 224 | 528 | 832 | 1.98 | 56.1% |
| SRC | 6 | 225 | 529 | 833 | 1.81 | 56.2% |
| AXIN2 | 9 | 226 | 530 | 834 | 1.80 | 56.2% |
| NOTCH4 | 26 | 227 | 531 | 835 | 1.93 | 56.4% |
| GATA3 | 5 | 228 | 532 | 836 | 1.98 | 56.4% |
| EIF4A2 | 1 | 229 | 533 | 837 | 1.97 | 56.5% |
| PRKACA | 2 | 230 | 534 | 838 | 1.83 | 56.7% |
| JAK1 | 3 | 231 | 535 | 839 | 1.89 | 57.1% |
| MYH9 | 5 | 232 | 536 | 840 | 1.85 | 57.1% |
| CHEK2 | 1 | 233 | 537 | 841 | 2.00 | 57.3% |
| FANCG | 9 | 234 | 538 | 842 | 2.00 | 57.3% |
| SUFU | 5 | 235 | 539 | 843 | 1.89 | 57.6% |
| CEBPA | 1 | 236 | 540 | 844 | 1.97 | 57.8% |
| SRGAP3 | 19 | 237 | 541 | 845 | 1.81 | 58.0% |
| NCOR2 | 9 | 238 | 542 | 846 | 1.99 | 58.1% |
| FLCN | 3 | 239 | 543 | 847 | 1.98 | 58.2% |
| CIITA | 10 | 240 | 544 | 848 | 1.85 | 58.7% |
| RBM10 | 5 | 241 | 545 | 849 | 1.99 | 58.7% |
| ETV4 | 2 | 242 | 546 | 850 | 1.98 | 58.7% |

FIG. 13K

| Gene Symbol | Exon ID | Forward Primer (SEQ ID NO.) | Reverse Primer (SEQ ID NO.) | Amplicon Seq (SEQ ID NO.) | Amplif Eff Constant | GC% of Amplicon |
|---|---|---|---|---|---|---|
| CCND1 | 4 | 243 | 547 | 851 | 1.87 | 58.8% |
| ERBB2 | 10 | 244 | 548 | 852 | 1.82 | 58.8% |
| MEN1 | 9 | 245 | 549 | 853 | 1.98 | 58.9% |
| CCNE1 | 4 | 246 | 550 | 854 | 1.84 | 59.1% |
| CDK6 | 2 | 247 | 551 | 855 | 1.77 | 59.3% |
| MYH11 | 1 | 248 | 552 | 856 | 1.97 | 59.4% |
| HLA-A | 5 | 249 | 553 | 857 | 1.99 | 59.4% |
| RNF43 | 5 | 250 | 554 | 858 | 1.87 | 59.7% |
| HLF | 2 | 251 | 555 | 859 | 1.76 | 60.0% |
| AXIN1 | 4 | 252 | 556 | 860 | 1.92 | 60.0% |
| FLT4 | 22 | 253 | 557 | 861 | 1.79 | 60.0% |
| SMO | 7 | 254 | 558 | 862 | 1.98 | 60.2% |
| ACSL6 | 10 | 255 | 559 | 863 | 1.99 | 60.7% |
| AKT1 | 13 | 256 | 560 | 864 | 1.94 | 60.7% |
| H3F3B | 3 | 257 | 561 | 865 | 1.80 | 60.8% |
| RARA | 1 | 258 | 562 | 866 | 1.83 | 60.9% |
| FBXW7 | 2 | 259 | 563 | 867 | 1.79 | 61.2% |
| TACC3 | 5 | 260 | 564 | 868 | 1.87 | 61.3% |
| FGFR3 | 4 | 261 | 565 | 869 | 1.98 | 61.7% |
| TSC2 | 2 | 262 | 566 | 870 | 1.96 | 62.0% |
| MYCN | 1 | 263 | 567 | 871 | 1.84 | 62.0% |
| CSF1R | 17 | 264 | 568 | 872 | 1.92 | 62.0% |

FIG. 13L

| Gene Symbol | Exon ID | Forward Primer (SEQ ID NO.) | Reverse Primer (SEQ ID NO.) | Amplicon Seq (SEQ ID NO.) | Amplif Eff Constant | GC% of Amplicon |
|---|---|---|---|---|---|---|
| APC | 2 | 265 | 569 | 873 | 1.88 | 62.2% |
| NTRK1 | 5 | 266 | 570 | 874 | 1.91 | 62.3% |
| BAP1 | 8 | 267 | 571 | 875 | 1.94 | 62.4% |
| AKT2 | 7 | 268 | 572 | 876 | 1.78 | 62.7% |
| POLD1 | 14 | 269 | 573 | 877 | 1.84 | 62.7% |
| RECQL4 | 10 | 270 | 574 | 878 | 1.86 | 62.9% |
| GNAS | 9 | 271 | 575 | 879 | 1.85 | 62.9% |
| DAXX | 1 | 272 | 576 | 880 | 1.79 | 62.9% |
| GATA2 | 6 | 273 | 577 | 881 | 1.77 | 63.1% |
| PHF6 | 1 | 274 | 578 | 882 | 1.82 | 63.2% |
| MPL | 11 | 275 | 579 | 883 | 1.96 | 63.3% |
| MYC | 2 | 276 | 580 | 884 | 1.93 | 63.3% |
| CNOT3 | 14 | 277 | 581 | 885 | 1.81 | 63.6% |
| CIC | 14 | 278 | 582 | 886 | 1.93 | 63.9% |
| FGFR4 | 14 | 279 | 583 | 887 | 1.90 | 64.2% |
| NOTCH1 | 2 | 280 | 584 | 888 | 1.86 | 64.9% |
| FOXL2 | 1 | 281 | 585 | 889 | 1.78 | 65.3% |
| GNA11 | 4 | 282 | 586 | 890 | 1.98 | 65.3% |
| GATA1 | 1 | 283 | 587 | 891 | 1.95 | 65.4% |
| KLF4 | 2 | 284 | 588 | 892 | 1.95 | 65.5% |
| FANCB | 1 | 285 | 589 | 893 | 1.86 | 65.7% |
| THRAP3 | 1 | 286 | 590 | 894 | 1.80 | 65.7% |

FIG. 13M

| Gene Symbol | Exon ID | Forward Primer (SEQ ID NO.) | Reverse Primer (SEQ ID NO.) | Amplicon Seq (SEQ ID NO.) | Amplif Eff Constant | GC% of Amplicon |
|---|---|---|---|---|---|---|
| RPL5 | 1 | 287 | 591 | 895 | 1.90 | 65.8% |
| JAK3 | 1 | 288 | 592 | 896 | 1.87 | 66.7% |
| NOTCH3 | 2 | 289 | 593 | 897 | 1.91 | 66.7% |
| CDKN2A | 1 | 290 | 594 | 898 | 1.90 | 66.8% |
| H3F3A | 1 | 291 | 595 | 899 | 1.84 | 66.9% |
| HNF1A | 8 | 292 | 596 | 900 | 1.96 | 67.4% |
| NKX2-1 | 1 | 293 | 597 | 901 | 1.88 | 67.5% |
| FOXA1 | 2 | 294 | 598 | 902 | 1.82 | 68.4% |
| CDH1 | 2 | 295 | 599 | 903 | 1.93 | 68.7% |
| CDKN2B | 1 | 296 | 600 | 904 | 1.77 | 68.7% |
| ZFHX3 | 1 | 297 | 601 | 905 | 1.79 | 70.0% |
| HRAS | 5 | 298 | 602 | 906 | 1.79 | 70.0% |
| MYCL1 | 2 | 299 | 603 | 907 | 1.91 | 70.2% |
| PER1 | 1 | 300 | 604 | 908 | 1.80 | 71.1% |
| PER1 | 3 | 301 | 605 | 909 | 1.83 | 60.1% |
| SUZ12 | 1 | 302 | 606 | 910 | 1.79 | 71.6% |
| CDKN2C | 1 | 303 | 607 | 911 | 1.77 | 72.8% |
| NSD1 | 2 | 304 | 608 | 912 | 1.93 | 74.1% |

FIG. 13N

| | Normal Tissue | Tumor Tissue |
|---|---|---|
| Initial mapped reads | 30.7 billion | 25.7 billion |
| Average raw coverage | 240.5 X | 173.9 X |
| Unique read family (URF) | 625 million | 577 million |
| Super read duplexes | 272 million | 231 million |
| Initial mapped reads per super read family | 49.1 | 44.5 |
| Initial mapped reads per super read duplex | 112.9 | 111.3 |
| Super reads per super read duplex | 2.3 | 2.5 |

FIG. 14

| Gene Symbol | Transcript Accession | Nucleotide (genomic) | Amino Acid (protein) | Mutant Allele Fraction | Mutant Allele Fraction in 1 to 1000 spiked normal sample | Mutation Type | Consequence | Confirmed | Detected again in 1:1,000 dilution |
|---|---|---|---|---|---|---|---|---|---|
| FOCAD | CCDS34993 | chr9:20865973 A->G | p.K2104E | 29.41% | 0.029% | Substitution | Non-synonymous | YES | YES |
| KRAS | CCDS8703.1 | chr12:25289551C->A | p.G12V | 27.69% | 0.028% | Substitution | Non-synonymous | YES | YES |
| TRIM59 | CCDS3190 | chr3:160156368 ->T | NA | 23.08% | 0.023% | Insertion | Frameshift | YES | NO |
| GOLGA6L2 | ENST00000312015 | chr15:23685010 C->T | p.E1633K | 23.08% | 0.023% | Substitution | Non-synonymous | YES | YES |
| CAMKK2 | CCDS53837 | chr12:121678328 ->T | NA | 22.58% | 0.023% | Insertion | Frameshift | YES | NO |
| TTC39A | ENST00000262676 | chr1:51767913 C-> | NA | 21.74% | 0.022% | Deletion | Frameshift | YES | NO |
| VEGFC | CCDS43285 | chr4:177605084 A->C | p.M1256R | 21.43% | 0.021% | Substitution | Non-synonymous | YES | NO |
| NBPF15 | CCDS932 | chr1:148594474 C->T | p.S1847L | 19.54% | 0.020% | Substitution | Non-synonymous | YES | YES |
| ALG9 | ENST00000428306 | chr11:111742145 C->G | NA | 16.96% | 0.017% | NA | Splicesite donor | YES | YES |
| OAS1 | ENST00000377508 | chr12:113369718 C->A | NA | 16.95% | 0.017% | NA | Splicesite acceptor | YES | NO |
| NFE2L2 | CCDS42782 | chr2:178097188 C->T | p.D526N | 16.46% | 0.016% | Substitution | Non-synonymous | YES | YES |
| OAS1 | ENST00000377508 | chr12:113369716 A->C | NA | 15.87% | 0.016% | NA | Splicesite acceptor | YES | NO |
| E2F8 | ENST00000396159 | chr11:19263371 T-> | NA | 15.63% | 0.016% | NA | Splicesite donor | YES | NO |
| FUZ | ENST00000421740 | chr19:50314458 G->A | p.S650F | 15.15% | 0.015% | Substitution | Non-synonymous | YES | NO |
| FUZ | ENST00000421740 | chr19:50314459 A->G | p.S649P | 15.07% | 0.015% | Substitution | Non-synonymous | YES | NO |
| ADAM21 | CCDS9804 | chr14:70924632 G->A | p.S416N | 14.67% | 0.015% | Substitution | Non-synonymous | YES | YES |
| COL27A1 | CCDS6802 | chr9:116918267 GCG-> | NA | 14.04% | 0.014% | Deletion | Frameshift | YES | NO |

FIG. 15A

| | | | | | | | | | |
|---|---|---|---|---|---|---|---|---|---|
| USP19 | CCDS43090 | chr3:49155556 A-> | NA | 14.04% | 0.014% | NA | Splicesite acceptor | YES | NO |
| FAM182A | ENST00000246000 | chr20:26061967 G->T | p.A319S | 13.72% | 0.014% | Substitution | Non-synonymous | YES | YES |
| VLDLR | ENST00000397921 | chr9:2622173 C->G | p.T155S | 12.28% | 0.012% | Substitution | Non-synonymous | YES | NO |
| MMEL1 | CCDS30569 | chr1:2560819 CAG-> | NA | 11.94% | 0.012% | Deletion | Frameshift | YES | NO |
| LSM12 | ENST00000411445 | chr17:42141311 ->A | NA | 11.32% | 0.011% | Insertion | Frameshift | YES | YES |
| MFSD4B | CCDS5090 | chr6:111587361 T-> | NA | 10.94% | 0.011% | Deletion | Frameshift | YES | YES |
| NADK | CCDS30565 | chr1:1684348 ->CCT | NA | 10.85% | 0.011% | Insertion | Frameshift | YES | YES |
| PTPRG | CCDS2895 | chr3:62267290 A->G | p.E3818G | 10.71% | 0.011% | Substitution | Non-synonymous | YES | NO |
| CTNNB1 | CCDS2694.1 | chr3:41241445C->A | NA | 10.53% | 0.011% | NA | Splicesite acceptor | YES | YES |
| ZMYND8 | ENST00000372023 | chr20:45867410 A-> | NA | 10.09% | 0.010% | Deletion | Frameshift | YES | NO |
| TP53 | CCDS11118.1 | chr17:7520075A->C | p.F113V | 9.39% | 0.009% | Substitution | Non-synonymous | YES | YES |
| DCD | ENST00000419084 | chr12:55039821 G->A | p.P211S | 8.46% | 0.008% | Substitution | Non-synonymous | YES | NO |
| KCNB2 | CCDS6209 | chr8:73480397 ->A | NA | 8.34% | 0.008% | Insertion | Frameshift | YES | YES |
| ALG9 | ENST00000428306 | chr11:111742141 G->C | p.P761R | 7.98% | 0.008% | Substitution | Non-synonymous | YES | NO |
| PRRT2 | CCDS10654 | chr16:29825016 C-> | NA | 7.80% | 0.008% | Deletion | Frameshift | NO | YES |
| PYGM | CCDS8079 | chr11:64526120 C->A | p.M300I | 7.55% | 0.008% | Substitution | Non-synonymous | YES | YES |
| TP53 | CCDS11118.1 | chr17:7518898A->G | NA | 6.97% | 0.007% | NA | Splice site donor | YES | YES |
| MYO9B | CCDS46010 | chr19:17294680 ->A | NA | 6.56% | 0.007% | Substitution | Splice site donor | YES | YES |
| TUBBP5 | ENST00000290377 | chr9:141070139 C->T | p.L37F | 6.49% | 0.006% | Substitution | Non-synonymous | YES | NO |
| FOXC1 | CCDS4473 | chr6:1612018 CGG-> | NA | 5.96% | 0.006% | Deletion | Frameshift | NO | NO |

FIG. 15B

| | | | | | | | | | |
|---|---|---|---|---|---|---|---|---|---|
| GALNT9 | ENST00000424720 | chr12:132824394 C->A | p.M1146I | 5.44% | 0.005% | Substitution | Non-synonymous | YES | YES |
| RP11-830F9.6 | ENST00000378347 | chr16:89017605 A->G | p.D1079G | 5.29% | 0.005% | Substitution | Non-synonymous | YES | YES |
| SRD5A2 | ENST00000233139 | chr2:31805883 C->G | p.K87N | 5.06% | 0.005% | Substitution | Non-synonymous | YES | YES |
| SMG7 | CCDS1355 | chr1:183515267 ->A | NA | 4.98% | 0.005% | Insertion | Frameshift | N/A | N/A |
| LZTS3 | CCDS13049 | chr20:3146451 G->A | p.R1015W | 4.86% | 0.005% | Substitution | Non-synonymous | N/A | N/A |
| TNFSF9 | CCDS12169 | chr19:6531149 GCT-> | NA | 4.74% | 0.005% | Deletion | Frameshift | N/A | N/A |
| NOP9 | CCDS9624 | chr14:24769850 ->GAG | NA | 4.63% | 0.005% | Insertion | Frameshift | N/A | N/A |
| ABCA2 | CCDS43909 | chr9:139917492 G->A | p.A176V | 4.28% | 0.004% | Substitution | Non-synonymous | N/A | N/A |
| SHC1 | CCDS44233 | chr1:154938890 ->C | NA | 4.14% | 0.004% | Insertion | Frameshift | N/A | N/A |
| RNF43 | CCDS11607.1 | chr17:53792509C->A | p.E318X | 3.99% | 0.004% | Substitution | Nonsense | N/A | N/A |
| RNF43 | CCDS11607.1 | chr17:53790631C->A | p.S502I | 3.66% | 0.004% | Substitution | Non-synonymous | N/A | N/A |
| SMAD4 | CCDS11950.1 | chr18:46835279C->A | p.Y195X | 3.45% | 0.003% | Substitution | Nonsense | N/A | N/A |
| IGSF3 | CCDS30814 | chr1:117158745 A->C | p.D378E | 3.42% | 0.003% | Substitution | Non-synonymous | N/A | N/A |
| FOLR3 | ENST00000456237 | chr11:71850159 A->T | p.E449V | 3.27% | 0.003% | Substitution | Non-synonymous | N/A | N/A |
| CTRC | CCDS156 | chr1:15771154 C->T | p.H547Y | 3.20% | 0.003% | Substitution | Non-synonymous | N/A | N/A |
| NRAP | CCDS7579 | chr10:115348730 T->G | NA | 3.08% | 0.003% | Substitution | Non-synonymous | N/A | N/A |
| RNF43 | CCDS11607.1 | chr17:53790810G->T | p.D442E | 3.07% | 0.003% | Substitution | Non-synonymous | N/A | N/A |
| SH3BP5 | CCDS2625.2 | chr3:15373833 TCC-> | NA | 3.04% | 0.003% | Deletion | Frameshift | N/A | N/A |
| WIZ | ENST00000389282 | chr19:15549933 C->A | p.E1728D | 2.96% | 0.003% | Substitution | Non-synonymous | N/A | N/A |
| HDC | CCDS10134 | chr15:50557790 C->A | p.G31W | 2.85% | 0.003% | Substitution | Non-synonymous | N/A | N/A |

FIG. 15C

| | | | | | | | | | |
|---|---|---|---|---|---|---|---|---|---|
| UBQLNL | CCDS31385 | chr11:5536683 C->T | p.R989Q | 2.82% | 0.003% | Substitution | Non-synonymous | N/A | N/A |
| CDKN2A | CCDS6511.1 | chr9:21961019C->T | p.A169T | 2.69% | 0.003% | Substitution | Non-synonymous | N/A | N/A |
| AHDC1 | CCDS30652 | chr1:27877505 G-> | NA | 2.40% | 0.002% | Deletion | Frameshift | N/A | N/A |
| PTPRS | CCDS45930 | chr19:5208036 G->A | p.T5675M | 2.34% | 0.002% | Substitution | Non-synonymous | N/A | N/A |
| TMEM63A | CCDS31042.1 | chr1:226034840 CTG-> | NA | 2.13% | 0.002% | Deletion | Frameshift | N/A | N/A |
| NOTCH4 | CCDS34420.1 | chr6:32163554 ->C | NA | 2.02% | 0.002% | Insertion | Frameshift | N/A | N/A |
| AZGP1 | CCDS5680.1 | chr7:99573573 T->C | p.Q71R | 1.94% | 0.002% | Substitution | Non-synonymous | N/A | N/A |
| TBC1D29 | CCDS32606.1 | chr17:28890361 G->A | p.R371Q | 1.88% | 0.002% | Substitution | Non-synonymous | N/A | N/A |
| GIGYF2 | CCDS46542.1 | chr2:233697764 GCA-> | NA | 1.84% | 0.002% | Deletion | Frameshift | N/A | N/A |
| KIF7 | CCDS32325.2 | chr15:90171904 G-> | NA | 1.81% | 0.002% | Deletion | Frameshift | N/A | N/A |
| TP53I13 | CCDS42289.1 | chr17:27899242 C->T | p.S596F | 1.79% | 0.002% | Substitution | Non-synonymous | N/A | N/A |
| PCNX3 | CCDS44650.1 | chr11:65385491 C->A | p.L658M | 1.72% | 0.002% | Substitution | Non-synonymous | N/A | N/A |
| EIF3J | CCDS10111.1 | chr15:44829395 GGC-> | NA | 1.71% | 0.002% | Deletion | Frameshift | N/A | N/A |
| SFSWAP | CCDS9273.1 | chr12:132281734 AGA-> | NA | 1.60% | 0.002% | Deletion | Frameshift | N/A | N/A |
| TMC4 | CCDS12882.1 | chr19:54675747 TCC-> | NA | 1.55% | 0.002% | Deletion | Frameshift | N/A | N/A |
| IQSEC2 | CCDS48130.1 | chrX:53264131 TGG-> | NA | 1.43% | 0.001% | Deletion | Frameshift | N/A | N/A |
| C6orf132 | CCDS47428.1 | chr6:42072710 CTC-> | NA | 1.36% | 0.001% | Deletion | Frameshift | N/A | N/A |
| ARX | CCDS14215.1 | chrX:25025356 GGC-> | NA | 1.34% | 0.001% | Deletion | Frameshift | N/A | N/A |
| NHS | ENST00000380057 | chrX:17705855 C->T | p.L22F | 1.24% | 0.001% | Substitution | Non-synonymous | N/A | N/A |
| RAB40C | CCDS10413.1 | chr16:677580 ->C | NA | 1.22% | 0.001% | Insertion | Frameshift | N/A | N/A |

FIG. 15D

| | | | | | | | | | |
|---|---|---|---|---|---|---|---|---|---|
| C16orf91 | CCDS32360.1 | chr16:1476278 C->A | p.Q345H | 1.06% | 0.001% | Substitution | Non-synonymous | N/A | N/A |
| EME2 | CCDS32364.1 | chr16:1824298 TGC-> | NA | 1.04% | 0.001% | Deletion | Frameshift | N/A | N/A |
| ATP13A2 | CCDS175.1 | chr1:17318887 G-> | NA | 0.94% | 0.001% | Deletion | Frameshift | N/A | N/A |
| ZIC3 | CCDS14663.1 | chrX:136648985 CGC-> | NA | 0.74% | 0.001% | Deletion | Frameshift | N/A | N/A |
| NAA30 | CCDS32088.1 | chr14:57858199 AGG-> | NA | 0.61% | 0.001% | Deletion | Frameshift | N/A | N/A |
| NDUFS3 | CCDS7941.1 | chr11:47600646 GGC-> | NA | 0.58% | 0.001% | Deletion | Frameshift | N/A | N/A |
| CCKBR | CCDS7761.1 | chr11:6292451 ->T | NA | 0.49% | 0.000% | Insertion | Frameshift | N/A | N/A |
| RUSC2 | CCDS35008.1 | chr9:35560102 GCT-> | NA | 0.46% | 0.000% | Deletion | Frameshift | N/A | N/A |
| NOS2 | CCDS11223.1 | chr17:26099407 G->A | p.A1631V | 0.42% | 0.000% | Substitution | Non-synonymous | N/A | N/A |
| WASL | CCDS34743.1 | chr7:123388755 GCG-> | NA | 0.38% | 0.000% | Deletion | Frameshift | N/A | N/A |
| SNRNP35 | CCDS45005.1 | chr12:123950763 GA-> | NA | 0.31% | 0.000% | Deletion | Frameshift | N/A | N/A |
| NBPF14 | CCDS30836.1 | chr1:148009468 C->G | p.E1839D | 0.29% | 0.000% | Substitution | Non-synonymous | N/A | N/A |
| FAM104B | CCDS35305.1 | chrX:55172647 G->A | p.P221L | 0.27% | 0.000% | Substitution | Non-synonymous | N/A | N/A |
| TFEB | CCDS4858.1 | chr6:41658830 TGC-> | NA | 0.25% | 0.000% | Deletion | Frameshift | N/A | N/A |
| SEPT9 | CCDS45790.1 | chr17:75478417 G->A | p.G913R | 0.22% | 0.000% | Substitution | Non-synonymous | N/A | N/A |
| ROR2 | CCDS6691.1 | chr9:94486026 TCC-> | NA | 0.15% | 0.000% | Deletion | Frameshift | N/A | N/A |
| PKD2 | CCDS3627.1 | chr4:88929174 GAG-> | NA | 0.12% | 0.000% | Deletion | Frameshift | N/A | N/A |
| GLIS2 | CCDS10511.1 | chr16:4384871 G-> | NA | 0.08% | 0.000% | Deletion | Frameshift | N/A | N/A |
| HECTD4 | CCDS44978.1 | chr12:112622808 T-> | NA | 0.02% | 0.000% | Deletion | Frameshift | N/A | N/A |
| MUC4 | NM_018406 | chr3:195508284 C->A | p.Q10167H | 0.01% | 0.000% | Substitution | Non-synonymous | N/A | N/A |

FIG. 15E

SEQUENCE LISTING

```
<160> NUMBER OF SEQ ID NOS: 914

<210> SEQ ID NO 1
<211> LENGTH: 23
<212> TYPE: DNA
<213> ORGANISM: Homo Sapiens

<400> SEQUENCE: 1

gctcattttt gttaatggtg gct                                               23


<210> SEQ ID NO 2
<211> LENGTH: 27
<212> TYPE: DNA
<213> ORGANISM: Homo Sapiens

<400> SEQUENCE: 2

gaacaatgaa taaaccattt tgtctca                                           27


<210> SEQ ID NO 3
<211> LENGTH: 20
<212> TYPE: DNA
<213> ORGANISM: Homo Sapiens

<400> SEQUENCE: 3

atcatgctga cgcttctcct                                                   20


<210> SEQ ID NO 4
<211> LENGTH: 27
<212> TYPE: DNA
<213> ORGANISM: Homo Sapiens

<400> SEQUENCE: 4

tgcagatttt taaaaagtct cttttcc                                           27


<210> SEQ ID NO 5
<211> LENGTH: 27
<212> TYPE: DNA
<213> ORGANISM: Homo Sapiens

<400> SEQUENCE: 5

agttaataag gacatggttt ctgttct                                           27


<210> SEQ ID NO 6
<211> LENGTH: 26
<212> TYPE: DNA
<213> ORGANISM: Homo Sapiens

<400> SEQUENCE: 6
```

aggaaactag agttcatttt cctttt 26

<210> SEQ ID NO 7
<211> LENGTH: 21
<212> TYPE: DNA
<213> ORGANISM: Homo Sapiens

<400> SEQUENCE: 7
tcgcaagtct gaatcacaac t 21

<210> SEQ ID NO 8
<211> LENGTH: 27
<212> TYPE: DNA
<213> ORGANISM: Homo Sapiens

<400> SEQUENCE: 8
tgtgcattga gagtttttat actagtg 27

<210> SEQ ID NO 9
<211> LENGTH: 21
<212> TYPE: DNA
<213> ORGANISM: Homo Sapiens

<400> SEQUENCE: 9
ccaggttagc tggtaagagg a 21

<210> SEQ ID NO 10
<211> LENGTH: 27
<212> TYPE: DNA
<213> ORGANISM: Homo Sapiens

<400> SEQUENCE: 10
aagcttttca ggataatttc tgttttt 27

<210> SEQ ID NO 11
<211> LENGTH: 22
<212> TYPE: DNA
<213> ORGANISM: Homo Sapiens

<400> SEQUENCE: 11
aggatgatac tggttgacac aa 22

<210> SEQ ID NO 12
<211> LENGTH: 25
<212> TYPE: DNA
<213> ORGANISM: Homo Sapiens

<400> SEQUENCE: 12
tcagcttttc cttaaagtca cttca 25

<210> SEQ ID NO 13
<211> LENGTH: 27
<212> TYPE: DNA
<213> ORGANISM: Homo Sapiens

<400> SEQUENCE: 13
caccatatat taacttctga catttgc 27

<210> SEQ ID NO 14
<211> LENGTH: 25
<212> TYPE: DNA
<213> ORGANISM: Homo Sapiens

<400> SEQUENCE: 14
gctacaaaag agctcaacaa ttttt 25

<210> SEQ ID NO 15
<211> LENGTH: 25
<212> TYPE: DNA
<213> ORGANISM: Homo Sapiens

<400> SEQUENCE: 15
gtgattttct aaaatagcag gctct 25

<210> SEQ ID NO 16
<211> LENGTH: 22
<212> TYPE: DNA
<213> ORGANISM: Homo Sapiens

<400> SEQUENCE: 16
tcaccactga gcaaatgttt ga 22

<210> SEQ ID NO 17
<211> LENGTH: 25
<212> TYPE: DNA
<213> ORGANISM: Homo Sapiens

<400> SEQUENCE: 17
agcagttgtg attctttctt tctac 25

<210> SEQ ID NO 18
<211> LENGTH: 27
<212> TYPE: DNA
<213> ORGANISM: Homo Sapiens

<400> SEQUENCE: 18
ttggaagtat aatagcagtt cttttct 27

<210> SEQ ID NO 19
<211> LENGTH: 25
<212> TYPE: DNA
<213> ORGANISM: Homo Sapiens

<400> SEQUENCE: 19
tgacagctat gctaatagtg tttct 25

<210> SEQ ID NO 20
<211> LENGTH: 20
<212> TYPE: DNA
<213> ORGANISM: Homo Sapiens

<400> SEQUENCE: 20
tgggtgcttg ggtgtgtata 20

<210> SEQ ID NO 21
<211> LENGTH: 22
<212> TYPE: DNA
<213> ORGANISM: Homo Sapiens

<400> SEQUENCE: 21
tctgtcttct cctctcttcc tt 22

<210> SEQ ID NO 22
<211> LENGTH: 23
<212> TYPE: DNA
<213> ORGANISM: Homo Sapiens

<400> SEQUENCE: 22
tggttaggag aatgagttgt tgt 23

<210> SEQ ID NO 23
<211> LENGTH: 22
<212> TYPE: DNA
<213> ORGANISM: Homo Sapiens

<400> SEQUENCE: 23
tgcatctgtg gcattaaatg gt 22

<210> SEQ ID NO 24
<211> LENGTH: 24
<212> TYPE: DNA
<213> ORGANISM: Homo Sapiens

<400> SEQUENCE: 24
atggttttta tgacacagag ttgt 24

<210> SEQ ID NO 25
<211> LENGTH: 27
<212> TYPE: DNA
<213> ORGANISM: Homo Sapiens

<400> SEQUENCE: 25
aggatcactt tatatggatc acttttt 27

<210> SEQ ID NO 26
<211> LENGTH: 20
<212> TYPE: DNA
<213> ORGANISM: Homo Sapiens

<400> SEQUENCE: 26
tgtgtacatg gtgccagaat 20

<210> SEQ ID NO 27
<211> LENGTH: 26
<212> TYPE: DNA
<213> ORGANISM: Homo Sapiens

<400> SEQUENCE: 27
agtcaatttt tctttcttct cttgca 26

<210> SEQ ID NO 28
<211> LENGTH: 19
<212> TYPE: DNA
<213> ORGANISM: Homo Sapiens

<400> SEQUENCE: 28
ttggaggcca ctgctatgg 19

<210> SEQ ID NO 29
<211> LENGTH: 27
<212> TYPE: DNA
<213> ORGANISM: Homo Sapiens

<400> SEQUENCE: 29
aaatgtattc actgtcttct ctttctt 27

<210> SEQ ID NO 30
<211> LENGTH: 23
<212> TYPE: DNA

<213> ORGANISM: Homo Sapiens

<400> SEQUENCE: 30
tgtgtgactc taaattgact gca 23

<210> SEQ ID NO 31
<211> LENGTH: 27
<212> TYPE: DNA
<213> ORGANISM: Homo Sapiens

<400> SEQUENCE: 31
tgtgtgacat gttctaatat agtcaca 27

<210> SEQ ID NO 32
<211> LENGTH: 22
<212> TYPE: DNA
<213> ORGANISM: Homo Sapiens

<400> SEQUENCE: 32
atgcaaagta cctaactcca ct 22

<210> SEQ ID NO 33
<211> LENGTH: 20
<212> TYPE: DNA
<213> ORGANISM: Homo Sapiens

<400> SEQUENCE: 33
tgtttgtgcc tcactttgca 20

<210> SEQ ID NO 34
<211> LENGTH: 21
<212> TYPE: DNA
<213> ORGANISM: Homo Sapiens

<400> SEQUENCE: 34
acacgtcttg gggatatcac t 21

<210> SEQ ID NO 35
<211> LENGTH: 26
<212> TYPE: DNA
<213> ORGANISM: Homo Sapiens

<400> SEQUENCE: 35
actggtatgg aaatattaca gtcctg 26

<210> SEQ ID NO 36
<211> LENGTH: 25
<212> TYPE: DNA
<213> ORGANISM: Homo Sapiens

<400> SEQUENCE: 36
gccatgtttt acatttgagt tcaca 25

<210> SEQ ID NO 37
<211> LENGTH: 20
<212> TYPE: DNA
<213> ORGANISM: Homo Sapiens

<400> SEQUENCE: 37
acaaggctga gacctgagtt 20

<210> SEQ ID NO 38
<211> LENGTH: 22

<212> TYPE: DNA
<213> ORGANISM: Homo Sapiens

<400> SEQUENCE: 38
tgtcactttg ttctgtttgc ag 22

<210> SEQ ID NO 39
<211> LENGTH: 20
<212> TYPE: DNA
<213> ORGANISM: Homo Sapiens

<400> SEQUENCE: 39
tggctgttgt cactattgca 20

<210> SEQ ID NO 40
<211> LENGTH: 22
<212> TYPE: DNA
<213> ORGANISM: Homo Sapiens

<400> SEQUENCE: 40
gctgtttctc ttttctccac ca 22

<210> SEQ ID NO 41
<211> LENGTH: 22
<212> TYPE: DNA
<213> ORGANISM: Homo Sapiens

<400> SEQUENCE: 41
actgtgtatt catgttcccc tt 22

<210> SEQ ID NO 42
<211> LENGTH: 25
<212> TYPE: DNA
<213> ORGANISM: Homo Sapiens

<400> SEQUENCE: 42
ggatttaact ttgtttttct ctgcc 25

<210> SEQ ID NO 43
<211> LENGTH: 25
<212> TYPE: DNA
<213> ORGANISM: Homo Sapiens

<400> SEQUENCE: 43
agacttcgag tgtttaaatg aaaga 25

<210> SEQ ID NO 44
<211> LENGTH: 26
<212> TYPE: DNA
<213> ORGANISM: Homo Sapiens

<400> SEQUENCE: 44
tcagaagttc tggaaatact tcattt 26

<210> SEQ ID NO 45
<211> LENGTH: 25
<212> TYPE: DNA
<213> ORGANISM: Homo Sapiens

<400> SEQUENCE: 45
atgcttcaga tgttgtatgt aatgt 25

<210> SEQ ID NO 46

<211> LENGTH: 21
<212> TYPE: DNA
<213> ORGANISM: Homo Sapiens

<400> SEQUENCE: 46
ctactcatgc ccctcaaact t 21

<210> SEQ ID NO 47
<211> LENGTH: 24
<212> TYPE: DNA
<213> ORGANISM: Homo Sapiens

<400> SEQUENCE: 47
tcttaaatga tcctcttctc ccag 24

<210> SEQ ID NO 48
<211> LENGTH: 25
<212> TYPE: DNA
<213> ORGANISM: Homo Sapiens

<400> SEQUENCE: 48
gcgatgtgca tatataatgg aaagg 25

<210> SEQ ID NO 49
<211> LENGTH: 20
<212> TYPE: DNA
<213> ORGANISM: Homo Sapiens

<400> SEQUENCE: 49
aatcctgttt gcagcgtgag 20

<210> SEQ ID NO 50
<211> LENGTH: 26
<212> TYPE: DNA
<213> ORGANISM: Homo Sapiens

<400> SEQUENCE: 50
actccattca gaaagtaatt ttcacc 26

<210> SEQ ID NO 51
<211> LENGTH: 24
<212> TYPE: DNA
<213> ORGANISM: Homo Sapiens

<400> SEQUENCE: 51
tcaggatttt tcctttctct ctcc 24

<210> SEQ ID NO 52
<211> LENGTH: 21
<212> TYPE: DNA
<213> ORGANISM: Homo Sapiens

<400> SEQUENCE: 52
gagttctagg ctactgtggc t 21

<210> SEQ ID NO 53
<211> LENGTH: 23
<212> TYPE: DNA
<213> ORGANISM: Homo Sapiens

<400> SEQUENCE: 53
gtgaatacac tttctgctgg ttt 23

<210> SEQ ID NO 54
<211> LENGTH: 22
<212> TYPE: DNA
<213> ORGANISM: Homo Sapiens

<400> SEQUENCE: 54
aaccaagtca gtaaggccat at 22

<210> SEQ ID NO 55
<211> LENGTH: 23
<212> TYPE: DNA
<213> ORGANISM: Homo Sapiens

<400> SEQUENCE: 55
aaacccttct gtttctttca cag 23

<210> SEQ ID NO 56
<211> LENGTH: 22
<212> TYPE: DNA
<213> ORGANISM: Homo Sapiens

<400> SEQUENCE: 56
tcctgtgagt gttctgtatg tt 22

<210> SEQ ID NO 57
<211> LENGTH: 20
<212> TYPE: DNA
<213> ORGANISM: Homo Sapiens

<400> SEQUENCE: 57
gctgggaaca tttgtcattt 20

<210> SEQ ID NO 58
<211> LENGTH: 24
<212> TYPE: DNA
<213> ORGANISM: Homo Sapiens

<400> SEQUENCE: 58
tgccgtttcg agaattttat tcac 24

<210> SEQ ID NO 59
<211> LENGTH: 21
<212> TYPE: DNA
<213> ORGANISM: Homo Sapiens

<400> SEQUENCE: 59
tgcacactga aattaggacg t 21

<210> SEQ ID NO 60
<211> LENGTH: 23
<212> TYPE: DNA
<213> ORGANISM: Homo Sapiens

<400> SEQUENCE: 60
tttttccccc ttgatccttc tag 23

<210> SEQ ID NO 61
<211> LENGTH: 20
<212> TYPE: DNA
<213> ORGANISM: Homo Sapiens

<400> SEQUENCE: 61
acttattgag catgcctggt 20

<210> SEQ ID NO 62
<211> LENGTH: 20
<212> TYPE: DNA
<213> ORGANISM: Homo Sapiens

<400> SEQUENCE: 62
acgcagtgct aaccaagttc 20

<210> SEQ ID NO 63
<211> LENGTH: 25
<212> TYPE: DNA
<213> ORGANISM: Homo Sapiens

<400> SEQUENCE: 63
ttttatatga tctttcctgg ttggc 25

<210> SEQ ID NO 64
<211> LENGTH: 20
<212> TYPE: DNA
<213> ORGANISM: Homo Sapiens

<400> SEQUENCE: 64
aagaatgcct gggactgagg 20

<210> SEQ ID NO 65
<211> LENGTH: 27
<212> TYPE: DNA
<213> ORGANISM: Homo Sapiens

<400> SEQUENCE: 65
aaagtgtaga ctaatgatgt gactttt 27

<210> SEQ ID NO 66
<211> LENGTH: 24
<212> TYPE: DNA
<213> ORGANISM: Homo Sapiens

<400> SEQUENCE: 66
tgtactcttt ttcctgttgc tgtt 24

<210> SEQ ID NO 67
<211> LENGTH: 24
<212> TYPE: DNA
<213> ORGANISM: Homo Sapiens

<400> SEQUENCE: 67
aagcaaactt gttctgtttt tacc 24

<210> SEQ ID NO 68
<211> LENGTH: 21
<212> TYPE: DNA
<213> ORGANISM: Homo Sapiens

<400> SEQUENCE: 68
tgtgtgtttc tgtgggtttc t 21

<210> SEQ ID NO 69
<211> LENGTH: 22
<212> TYPE: DNA
<213> ORGANISM: Homo Sapiens

<400> SEQUENCE: 69
tgtttttgtc cctctctctt gc 22

<210> SEQ ID NO 70
<211> LENGTH: 26
<212> TYPE: DNA
<213> ORGANISM: Homo Sapiens

<400> SEQUENCE: 70
acatactttg tatcatctta ttggca 26

<210> SEQ ID NO 71
<211> LENGTH: 23
<212> TYPE: DNA
<213> ORGANISM: Homo Sapiens

<400> SEQUENCE: 71
tgttttcctt tgtgtcattc cct 23

<210> SEQ ID NO 72
<211> LENGTH: 23
<212> TYPE: DNA
<213> ORGANISM: Homo Sapiens

<400> SEQUENCE: 72
ggattcagtg aggaatgctt tca 23

<210> SEQ ID NO 73
<211> LENGTH: 23
<212> TYPE: DNA
<213> ORGANISM: Homo Sapiens

<400> SEQUENCE: 73
acacagaatt tgttaagcaa cgt 23

<210> SEQ ID NO 74
<211> LENGTH: 27
<212> TYPE: DNA
<213> ORGANISM: Homo Sapiens

<400> SEQUENCE: 74
tctcatcata ccactattat tttgcag 27

<210> SEQ ID NO 75
<211> LENGTH: 20
<212> TYPE: DNA
<213> ORGANISM: Homo Sapiens

<400> SEQUENCE: 75
acacagcctt ctcaacctct 20

<210> SEQ ID NO 76
<211> LENGTH: 25
<212> TYPE: DNA
<213> ORGANISM: Homo Sapiens

<400> SEQUENCE: 76
ctctcggtgt atttctctac ttacc 25

<210> SEQ ID NO 77
<211> LENGTH: 23
<212> TYPE: DNA
<213> ORGANISM: Homo Sapiens

<400> SEQUENCE: 77
tcactgtgat agccttatct gct 23

<210> SEQ ID NO 78
<211> LENGTH: 24
<212> TYPE: DNA
<213> ORGANISM: Homo Sapiens

<400> SEQUENCE: 78
gttaatctta acctgtgctt tgcc 24

<210> SEQ ID NO 79
<211> LENGTH: 20
<212> TYPE: DNA
<213> ORGANISM: Homo Sapiens

<400> SEQUENCE: 79
actccaacac tgttgctcct 20

<210> SEQ ID NO 80
<211> LENGTH: 20
<212> TYPE: DNA
<213> ORGANISM: Homo Sapiens

<400> SEQUENCE: 80
gccagagtcc tttagcccta 20

<210> SEQ ID NO 81
<211> LENGTH: 23
<212> TYPE: DNA
<213> ORGANISM: Homo Sapiens

<400> SEQUENCE: 81
tcctgggttt cttttcaact tgt 23

<210> SEQ ID NO 82
<211> LENGTH: 24
<212> TYPE: DNA
<213> ORGANISM: Homo Sapiens

<400> SEQUENCE: 82
tcctgaagtg agatcttaca tcct 24

<210> SEQ ID NO 83
<211> LENGTH: 20
<212> TYPE: DNA
<213> ORGANISM: Homo Sapiens

<400> SEQUENCE: 83
gaccagaaag gctcagttcc 20

<210> SEQ ID NO 84
<211> LENGTH: 23
<212> TYPE: DNA
<213> ORGANISM: Homo Sapiens

<400> SEQUENCE: 84
aaacattgat ttggcttttc cca 23

<210> SEQ ID NO 85
<211> LENGTH: 20
<212> TYPE: DNA
<213> ORGANISM: Homo Sapiens

<400> SEQUENCE: 85
tgtctccatt tcccaccaca 20

<210> SEQ ID NO 86
<211> LENGTH: 26
<212> TYPE: DNA
<213> ORGANISM: Homo Sapiens

<400> SEQUENCE: 86
atttactctg gattttgctt tttcag 26

<210> SEQ ID NO 87
<211> LENGTH: 22
<212> TYPE: DNA
<213> ORGANISM: Homo Sapiens

<400> SEQUENCE: 87
tgagatgttt ttgccttcac ag 22

<210> SEQ ID NO 88
<211> LENGTH: 21
<212> TYPE: DNA
<213> ORGANISM: Homo Sapiens

<400> SEQUENCE: 88 tccccttgt cttaaaccac a 21

<210> SEQ ID NO 89
<211> LENGTH: 20
<212> TYPE: DNA
<213> ORGANISM: Homo Sapiens

<400> SEQUENCE: 89
ttgacgtgcc attctcttgc 20

<210> SEQ ID NO 90
<211> LENGTH: 20
<212> TYPE: DNA
<213> ORGANISM: Homo Sapiens

<400> SEQUENCE: 90
tttgggacga cttattgccc 20

<210> SEQ ID NO 91
<211> LENGTH: 27
<212> TYPE: DNA
<213> ORGANISM: Homo Sapiens

<400> SEQUENCE: 91
agagtaactt caatgtcttt attccat 27

<210> SEQ ID NO 92
<211> LENGTH: 20
<212> TYPE: DNA
<213> ORGANISM: Homo Sapiens

<400> SEQUENCE: 92
gatctccggt tgggattcct 20

<210> SEQ ID NO 93
<211> LENGTH: 23
<212> TYPE: DNA
<213> ORGANISM: Homo Sapiens

<400> SEQUENCE: 93
gcattttctc tgttcaacaa gca 23

<210> SEQ ID NO 94
<211> LENGTH: 22
<212> TYPE: DNA
<213> ORGANISM: Homo Sapiens

<400> SEQUENCE: 94
gtttgtgaca taagcagaac gc 22

<210> SEQ ID NO 95
<211> LENGTH: 21
<212> TYPE: DNA
<213> ORGANISM: Homo Sapiens

<400> SEQUENCE: 95
tgacagccag attcgtcttt g 21

<210> SEQ ID NO 96
<211> LENGTH: 22
<212> TYPE: DNA
<213> ORGANISM: Homo Sapiens

<400> SEQUENCE: 96
tggaagtctg tgagttctct ga 22

<210> SEQ ID NO 97
<211> LENGTH: 26
<212> TYPE: DNA
<213> ORGANISM: Homo Sapiens

<400> SEQUENCE: 97
atgttcttcc tttaggtata gtctca 26

<210> SEQ ID NO 98
<211> LENGTH: 20
<212> TYPE: DNA
<213> ORGANISM: Homo Sapiens

<400> SEQUENCE: 98
cctgaagcag tccaggactt 20

<210> SEQ ID NO 99
<211> LENGTH: 22
<212> TYPE: DNA
<213> ORGANISM: Homo Sapiens

<400> SEQUENCE: 99
agcttaagaa aagtgacgtg gt 22

<210> SEQ ID NO 100
<211> LENGTH: 27
<212> TYPE: DNA
<213> ORGANISM: Homo Sapiens

<400> SEQUENCE: 100
tccttgagtg taaggcaatt aataact 27

<210> SEQ ID NO 101
<211> LENGTH: 24
<212> TYPE: DNA
<213> ORGANISM: Homo Sapiens

<400> SEQUENCE: 101
gtctgtggat tgacttcttt tcct 24

<210> SEQ ID NO 102
<211> LENGTH: 27
<212> TYPE: DNA
<213> ORGANISM: Homo Sapiens

<400> SEQUENCE: 102
tgagcctcat ttattttctt tttctcc 27

<210> SEQ ID NO 103
<211> LENGTH: 24
<212> TYPE: DNA
<213> ORGANISM: Homo Sapiens

<400> SEQUENCE: 103
tcccttatgt tcttcttctc tcca 24

<210> SEQ ID NO 104
<211> LENGTH: 25
<212> TYPE: DNA
<213> ORGANISM: Homo Sapiens

<400> SEQUENCE: 104
gcactttaat actaacagga acagc 25

<210> SEQ ID NO 105
<211> LENGTH: 24
<212> TYPE: DNA
<213> ORGANISM: Homo Sapiens

<400> SEQUENCE: 105
tgtcctcagt ctgtactaaa ctca 24

<210> SEQ ID NO 106
<211> LENGTH: 22
<212> TYPE: DNA
<213> ORGANISM: Homo Sapiens

<400> SEQUENCE: 106
agcagatttg tatgaaagcc ct 22

<210> SEQ ID NO 107
<211> LENGTH: 20
<212> TYPE: DNA
<213> ORGANISM: Homo Sapiens

<400> SEQUENCE: 107
accctgttac acgcttgtaa 20

<210> SEQ ID NO 108
<211> LENGTH: 23
<212> TYPE: DNA
<213> ORGANISM: Homo Sapiens

<400> SEQUENCE: 108
actgaatttg ttttagggca cat 23

<210> SEQ ID NO 109
<211> LENGTH: 20
<212> TYPE: DNA

<213> ORGANISM: Homo Sapiens

<400> SEQUENCE: 109
caccggtgtg gctctttaac 20

<210> SEQ ID NO 110
<211> LENGTH: 20
<212> TYPE: DNA
<213> ORGANISM: Homo Sapiens

<400> SEQUENCE: 110
ccgttgggtt ttctcttcca 20

<210> SEQ ID NO 111
<211> LENGTH: 23
<212> TYPE: DNA
<213> ORGANISM: Homo Sapiens

<400> SEQUENCE: 111
ttctattctt ccttgctttg tgc 23

<210> SEQ ID NO 112
<211> LENGTH: 21
<212> TYPE: DNA
<213> ORGANISM: Homo Sapiens

<400> SEQUENCE: 112
aggatggtct tgtgtctgtg t 21

<210> SEQ ID NO 113
<211> LENGTH: 24
<212> TYPE: DNA
<213> ORGANISM: Homo Sapiens

<400> SEQUENCE: 113
agttattttc aaacggtctg gttt 24

<210> SEQ ID NO 114
<211> LENGTH: 20
<212> TYPE: DNA
<213> ORGANISM: Homo Sapiens

<400> SEQUENCE: 114
aaatggccct tgtcttgcag 20

<210> SEQ ID NO 115
<211> LENGTH: 21
<212> TYPE: DNA
<213> ORGANISM: Homo Sapiens

<400> SEQUENCE: 115
tctcccttcc tcctttgaac a 21

<210> SEQ ID NO 116
<211> LENGTH: 23
<212> TYPE: DNA
<213> ORGANISM: Homo Sapiens

<400> SEQUENCE: 116
agttaaagtt cggttgtttt cgt 23

<210> SEQ ID NO 117
<211> LENGTH: 20

<212> TYPE: DNA
<213> ORGANISM: Homo Sapiens

<400> SEQUENCE: 117
gcaaggagcc aggcattttt 20

<210> SEQ ID NO 118
<211> LENGTH: 21
<212> TYPE: DNA
<213> ORGANISM: Homo Sapiens

<400> SEQUENCE: 118
tccattggat tccttcgcaa g 21

<210> SEQ ID NO 119
<211> LENGTH: 20
<212> TYPE: DNA
<213> ORGANISM: Homo Sapiens

<400> SEQUENCE: 119
ttgtcagctt tttgggggtc 20

<210> SEQ ID NO 120
<211> LENGTH: 23
<212> TYPE: DNA
<213> ORGANISM: Homo Sapiens

<400> SEQUENCE: 120
ggtttacgtg catattttct ggc 23

<210> SEQ ID NO 121
<211> LENGTH: 20
<212> TYPE: DNA
<213> ORGANISM: Homo Sapiens

<400> SEQUENCE: 121
ggcactttcc ttctggttca 20

<210> SEQ ID NO 122
<211> LENGTH: 24
<212> TYPE: DNA
<213> ORGANISM: Homo Sapiens

<400> SEQUENCE: 122
tggtggtgca tactttattt gtct 24

<210> SEQ ID NO 123
<211> LENGTH: 23
<212> TYPE: DNA
<213> ORGANISM: Homo Sapiens

<400> SEQUENCE: 123
aagtggtttc ctcagataga gca 23

<210> SEQ ID NO 124
<211> LENGTH: 20
<212> TYPE: DNA
<213> ORGANISM: Homo Sapiens

<400> SEQUENCE: 124
agcgtttcag ctccagactc 20

<210> SEQ ID NO 125

<211> LENGTH: 20
<212> TYPE: DNA
<213> ORGANISM: Homo Sapiens

<400> SEQUENCE: 125
agcaaccatt tttgtgccca 20

<210> SEQ ID NO 126
<211> LENGTH: 20
<212> TYPE: DNA
<213> ORGANISM: Homo Sapiens

<400> SEQUENCE: 126
tatgtctcct cttccctgcc 20

<210> SEQ ID NO 127
<211> LENGTH: 20
<212> TYPE: DNA
<213> ORGANISM: Homo Sapiens

<400> SEQUENCE: 127
gtcctgctcc tgatcctgtt 20

<210> SEQ ID NO 128
<211> LENGTH: 20
<212> TYPE: DNA
<213> ORGANISM: Homo Sapiens

<400> SEQUENCE: 128
cttctccctg gctctgactc 20

<210> SEQ ID NO 129
<211> LENGTH: 20
<212> TYPE: DNA
<213> ORGANISM: Homo Sapiens

<400> SEQUENCE: 129
atctcaatcg cctgctctcc 20

<210> SEQ ID NO 130
<211> LENGTH: 22
<212> TYPE: DNA
<213> ORGANISM: Homo Sapiens

<400> SEQUENCE: 130
agaccttttc ctccctcatt ca 22

<210> SEQ ID NO 131
<211> LENGTH: 23
<212> TYPE: DNA
<213> ORGANISM: Homo Sapiens

<400> SEQUENCE: 131
acatctggga ttttgcttca ttg 23

<210> SEQ ID NO 132
<211> LENGTH: 24
<212> TYPE: DNA
<213> ORGANISM: Homo Sapiens

<400> SEQUENCE: 132
tcagaccacg gtttctattt ttca 24

<210> SEQ ID NO 133
<211> LENGTH: 25
<212> TYPE: DNA
<213> ORGANISM: Homo Sapiens

<400> SEQUENCE: 133
atcttctgtt acattctgct tcaca 25

<210> SEQ ID NO 134
<211> LENGTH: 20
<212> TYPE: DNA
<213> ORGANISM: Homo Sapiens

<400> SEQUENCE: 134
ttttcacccc gctcccctta 20

<210> SEQ ID NO 135
<211> LENGTH: 20
<212> TYPE: DNA
<213> ORGANISM: Homo Sapiens

<400> SEQUENCE: 135
tccttaaggc ctctgtgctt 20

<210> SEQ ID NO 136
<211> LENGTH: 22
<212> TYPE: DNA
<213> ORGANISM: Homo Sapiens

<400> SEQUENCE: 136
ggtcatttgc tgtgtttgtt ga 22

<210> SEQ ID NO 137
<211> LENGTH: 27
<212> TYPE: DNA
<213> ORGANISM: Homo Sapiens

<400> SEQUENCE: 137
ccataatata aagttgttgc gttttgt 27

<210> SEQ ID NO 138
<211> LENGTH: 22
<212> TYPE: DNA
<213> ORGANISM: Homo Sapiens

<400> SEQUENCE: 138
gttctgagtt agctgcacat tt 22

<210> SEQ ID NO 139
<211> LENGTH: 20
<212> TYPE: DNA
<213> ORGANISM: Homo Sapiens

<400> SEQUENCE: 139
ttctggcctt gttaatggcg 20

<210> SEQ ID NO 140
<211> LENGTH: 23
<212> TYPE: DNA
<213> ORGANISM: Homo Sapiens

<400> SEQUENCE: 140
aaatcccttc ctctctttct cag 23

<210> SEQ ID NO 141
<211> LENGTH: 20
<212> TYPE: DNA
<213> ORGANISM: Homo Sapiens

<400> SEQUENCE: 141 tacaccoctg tcctctctgt 20

<210> SEQ ID NO 142
<211> LENGTH: 20
<212> TYPE: DNA
<213> ORGANISM: Homo Sapiens

<400> SEQUENCE: 142
agacctcaga caaggcatct 20

<210> SEQ ID NO 143
<211> LENGTH: 20
<212> TYPE: DNA
<213> ORGANISM: Homo Sapiens

<400> SEQUENCE: 143
actttctctc ctgccctcac 20

<210> SEQ ID NO 144
<211> LENGTH: 24
<212> TYPE: DNA
<213> ORGANISM: Homo Sapiens

<400> SEQUENCE: 144
cacttcagtt atgtacctga tggg 24

<210> SEQ ID NO 145
<211> LENGTH: 20
<212> TYPE: DNA
<213> ORGANISM: Homo Sapiens

<400> SEQUENCE: 145
ttccccattc cccattccaa 20

<210> SEQ ID NO 146
<211> LENGTH: 20
<212> TYPE: DNA
<213> ORGANISM: Homo Sapiens

<400> SEQUENCE: 146
tgctgaacgc atttggctta 20

<210> SEQ ID NO 147
<211> LENGTH: 21
<212> TYPE: DNA
<213> ORGANISM: Homo Sapiens

<400> SEQUENCE: 147
tcattgtgtc ttccctcctc t 21

<210> SEQ ID NO 148
<211> LENGTH: 23
<212> TYPE: DNA
<213> ORGANISM: Homo Sapiens

<400> SEQUENCE: 148
tgttgacaat gttttctccc aca 23

<210> SEQ ID NO 149
<211> LENGTH: 27
<212> TYPE: DNA
<213> ORGANISM: Homo Sapiens

<400> SEQUENCE: 149
acatttttaa tgctcctttc tttgaca 27

<210> SEQ ID NO 150
<211> LENGTH: 21
<212> TYPE: DNA
<213> ORGANISM: Homo Sapiens

<400> SEQUENCE: 150
agcaaaagga gtgacattcc t 21

<210> SEQ ID NO 151
<211> LENGTH: 25
<212> TYPE: DNA
<213> ORGANISM: Homo Sapiens

<400> SEQUENCE: 151
tctcatcatt tcactgagat atgca 25

<210> SEQ ID NO 152
<211> LENGTH: 23
<212> TYPE: DNA
<213> ORGANISM: Homo Sapiens

<400> SEQUENCE: 152
tgaacttgtc acttcattgg tca 23

<210> SEQ ID NO 153
<211> LENGTH: 23
<212> TYPE: DNA
<213> ORGANISM: Homo Sapiens

<400> SEQUENCE: 153
aggcagcctt tataaaagca aat 23

<210> SEQ ID NO 154
<211> LENGTH: 21
<212> TYPE: DNA
<213> ORGANISM: Homo Sapiens

<400> SEQUENCE: 154
acccattttc cttcctggac a 21

<210> SEQ ID NO 155
<211> LENGTH: 21
<212> TYPE: DNA
<213> ORGANISM: Homo Sapiens

<400> SEQUENCE: 155
aaaaatttcc cctgcgctta g 21

<210> SEQ ID NO 156
<211> LENGTH: 20
<212> TYPE: DNA
<213> ORGANISM: Homo Sapiens

<400> SEQUENCE: 156
agacatgatg cttcgcttga 20

<210> SEQ ID NO 157
<211> LENGTH: 20
<212> TYPE: DNA
<213> ORGANISM: Homo Sapiens

<400> SEQUENCE: 157
tgcacgttgt ttgtagctgt 20

<210> SEQ ID NO 158
<211> LENGTH: 22
<212> TYPE: DNA
<213> ORGANISM: Homo Sapiens

<400> SEQUENCE: 158
gtttcccctg gatttatgtg gt 22

<210> SEQ ID NO 159
<211> LENGTH: 20
<212> TYPE: DNA
<213> ORGANISM: Homo Sapiens

<400> SEQUENCE: 159
acgtgcatgt cctttttccc 20

<210> SEQ ID NO 160
<211> LENGTH: 25
<212> TYPE: DNA
<213> ORGANISM: Homo Sapiens

<400> SEQUENCE: 160
tgtctctacc tcctacatct tatct 25

<210> SEQ ID NO 161
<211> LENGTH: 25
<212> TYPE: DNA
<213> ORGANISM: Homo Sapiens

<400> SEQUENCE: 161
ggttgtttct atttgctaat gctgt 25

<210> SEQ ID NO 162
<211> LENGTH: 25
<212> TYPE: DNA
<213> ORGANISM: Homo Sapiens

<400> SEQUENCE: 162
agcacttcct gaaataattt cacct 25

<210> SEQ ID NO 163
<211> LENGTH: 20
<212> TYPE: DNA
<213> ORGANISM: Homo Sapiens

<400> SEQUENCE: 163
atgggcctca ctgtctgttt 20

<210> SEQ ID NO 164
<211> LENGTH: 20
<212> TYPE: DNA
<213> ORGANISM: Homo Sapiens

<400> SEQUENCE: 164
gtcctcatgg ctctgtgact 20

<210> SEQ ID NO 165
<211> LENGTH: 20
<212> TYPE: DNA
<213> ORGANISM: Homo Sapiens

<400> SEQUENCE: 165
cccacctgca ttgttcatca 20

<210> SEQ ID NO 166
<211> LENGTH: 27
<212> TYPE: DNA
<213> ORGANISM: Homo Sapiens

<400> SEQUENCE: 166
ggataactat gttcttcctt ttcatca 27

<210> SEQ ID NO 167
<211> LENGTH: 20
<212> TYPE: DNA
<213> ORGANISM: Homo Sapiens

<400> SEQUENCE: 167
ctggcacact tcttcacctc 20

<210> SEQ ID NO 168
<211> LENGTH: 20
<212> TYPE: DNA
<213> ORGANISM: Homo Sapiens

<400> SEQUENCE: 168
cctcagggat ggtagtgaca 20

<210> SEQ ID NO 169
<211> LENGTH: 25
<212> TYPE: DNA
<213> ORGANISM: Homo Sapiens

<400> SEQUENCE: 169
catccatgga atatgttctt ttgca 25

<210> SEQ ID NO 170
<211> LENGTH: 20
<212> TYPE: DNA
<213> ORGANISM: Homo Sapiens

<400> SEQUENCE: 170
ccttgcactc ttgtggttgt 20

<210> SEQ ID NO 171
<211> LENGTH: 23
<212> TYPE: DNA
<213> ORGANISM: Homo Sapiens

<400> SEQUENCE: 171
aaggtttcca attcaccttt cag 23

<210> SEQ ID NO 172
<211> LENGTH: 20
<212> TYPE: DNA
<213> ORGANISM: Homo Sapiens

<400> SEQUENCE: 172
ggtccccatc cattcttcct 20

<210> SEQ ID NO 173
<211> LENGTH: 22
<212> TYPE: DNA
<213> ORGANISM: Homo Sapiens

<400> SEQUENCE: 173
ccaatctgct tatgaccagg ag 22

<210> SEQ ID NO 174
<211> LENGTH: 21
<212> TYPE: DNA
<213> ORGANISM: Homo Sapiens

<400> SEQUENCE: 174
ggtgggattt tgttgtttgc a 21

<210> SEQ ID NO 175
<211> LENGTH: 20
<212> TYPE: DNA
<213> ORGANISM: Homo Sapiens

<400> SEQUENCE: 175
tgaccaattt ggcttcgtcc 20

<210> SEQ ID NO 176
<211> LENGTH: 21
<212> TYPE: DNA
<213> ORGANISM: Homo Sapiens

<400> SEQUENCE: 176
tcaaagctgc ttctgtcatc t 21

<210> SEQ ID NO 177
<211> LENGTH: 20
<212> TYPE: DNA
<213> ORGANISM: Homo Sapiens

<400> SEQUENCE: 177
ggctaatggt tctcagagct 20

<210> SEQ ID NO 178
<211> LENGTH: 22
<212> TYPE: DNA
<213> ORGANISM: Homo Sapiens

<400> SEQUENCE: 178
gcctttcaat tcactgtcct ca 22

<210> SEQ ID NO 179
<211> LENGTH: 20
<212> TYPE: DNA
<213> ORGANISM: Homo Sapiens

<400> SEQUENCE: 179
tcagcagggt ttttcttgct 20

<210> SEQ ID NO 180
<211> LENGTH: 20
<212> TYPE: DNA
<213> ORGANISM: Homo Sapiens

<400> SEQUENCE: 180
ggttttcctc tccttcccca 20

<210> SEQ ID NO 181
<211> LENGTH: 20
<212> TYPE: DNA
<213> ORGANISM: Homo Sapiens

<400> SEQUENCE: 181
ccatgacact ccttccacct 20

<210> SEQ ID NO 182
<211> LENGTH: 23
<212> TYPE: DNA
<213> ORGANISM: Homo Sapiens

<400> SEQUENCE: 182
tgtaattcct ggcttctagg ttt 23

<210> SEQ ID NO 183
<211> LENGTH: 20
<212> TYPE: DNA
<213> ORGANISM: Homo Sapiens

<400> SEQUENCE: 183
cgtgttcccg tttcctcttg 20

<210> SEQ ID NO 184
<211> LENGTH: 21
<212> TYPE: DNA
<213> ORGANISM: Homo Sapiens

<400> SEQUENCE: 184
cctctgtgta tctccttccc a 21

<210> SEQ ID NO 185
<211> LENGTH: 20
<212> TYPE: DNA
<213> ORGANISM: Homo Sapiens

<400> SEQUENCE: 185
gctttctttt tgctccccca 20

<210> SEQ ID NO 186
<211> LENGTH: 21
<212> TYPE: DNA
<213> ORGANISM: Homo Sapiens

<400> SEQUENCE: 186
acttttaccc tggatttgcc c 21

<210> SEQ ID NO 187
<211> LENGTH: 21
<212> TYPE: DNA
<213> ORGANISM: Homo Sapiens

<400> SEQUENCE: 187
ggtggggttt tgttaacgtg a 21

<210> SEQ ID NO 188
<211> LENGTH: 24
<212> TYPE: DNA

<213> ORGANISM: Homo Sapiens

<400> SEQUENCE: 188
agtgtaaagt taaccttgct gtgt 24

<210> SEQ ID NO 189
<211> LENGTH: 20
<212> TYPE: DNA
<213> ORGANISM: Homo Sapiens

<400> SEQUENCE: 189
gtatcaaggc tgccctgact 20

<210> SEQ ID NO 190
<211> LENGTH: 20
<212> TYPE: DNA
<213> ORGANISM: Homo Sapiens

<400> SEQUENCE: 190
ttcaggccac caacctcatt 20

<210> SEQ ID NO 191
<211> LENGTH: 20
<212> TYPE: DNA
<213> ORGANISM: Homo Sapiens

<400> SEQUENCE: 191
gtgctgattc cctgatgtgc 20

<210> SEQ ID NO 192
<211> LENGTH: 20
<212> TYPE: DNA
<213> ORGANISM: Homo Sapiens

<400> SEQUENCE: 192
accaacatgg atggagtggt 20

<210> SEQ ID NO 193
<211> LENGTH: 19
<212> TYPE: DNA
<213> ORGANISM: Homo Sapiens

<400> SEQUENCE: 193
tgcccaccct aatcctgtg 19

<210> SEQ ID NO 194
<211> LENGTH: 20
<212> TYPE: DNA
<213> ORGANISM: Homo Sapiens

<400> SEQUENCE: 194
ctgcctctct tttctcccca 20

<210> SEQ ID NO 195
<211> LENGTH: 20
<212> TYPE: DNA
<213> ORGANISM: Homo Sapiens

<400> SEQUENCE: 195
gaagtcatgg gctgcttgtc 20

<210> SEQ ID NO 196
<211> LENGTH: 20

<212> TYPE: DNA
<213> ORGANISM: Homo Sapiens

<400> SEQUENCE: 196
ccaagctgtg aaggcctttt 20

<210> SEQ ID NO 197
<211> LENGTH: 20
<212> TYPE: DNA
<213> ORGANISM: Homo Sapiens

<400> SEQUENCE: 197
cctccttctc acgtgtctgt 20

<210> SEQ ID NO 198
<211> LENGTH: 20
<212> TYPE: DNA
<213> ORGANISM: Homo Sapiens

<400> SEQUENCE: 198
agcagagtga cccagtgatg 20

<210> SEQ ID NO 199
<211> LENGTH: 20
<212> TYPE: DNA
<213> ORGANISM: Homo Sapiens

<400> SEQUENCE: 199
tcctctctgg atcctcgtga 20

<210> SEQ ID NO 200
<211> LENGTH: 20
<212> TYPE: DNA
<213> ORGANISM: Homo Sapiens

<400> SEQUENCE: 200
ggagctgctc ctcatcctac 20

<210> SEQ ID NO 201
<211> LENGTH: 23
<212> TYPE: DNA
<213> ORGANISM: Homo Sapiens

<400> SEQUENCE: 201
tgaagttttt gtctgtttct ccc 23

<210> SEQ ID NO 202
<211> LENGTH: 20
<212> TYPE: DNA
<213> ORGANISM: Homo Sapiens

<400> SEQUENCE: 202
actggatctg cttcacacct 20

<210> SEQ ID NO 203
<211> LENGTH: 20
<212> TYPE: DNA
<213> ORGANISM: Homo Sapiens

<400> SEQUENCE: 203
ctttccctca ttccctcccc 20

<210> SEQ ID NO 204

<211> LENGTH: 20
<212> TYPE: DNA
<213> ORGANISM: Homo Sapiens

<400> SEQUENCE: 204
ttgggcctgt gttatctcct 20

<210> SEQ ID NO 205
<211> LENGTH: 20
<212> TYPE: DNA
<213> ORGANISM: Homo Sapiens

<400> SEQUENCE: 205
cctgaccctt ctccctatcc 20

<210> SEQ ID NO 206
<211> LENGTH: 20
<212> TYPE: DNA
<213> ORGANISM: Homo Sapiens

<400> SEQUENCE: 206
tccctttctc ccctctttga 20

<210> SEQ ID NO 207
<211> LENGTH: 20
<212> TYPE: DNA
<213> ORGANISM: Homo Sapiens

<400> SEQUENCE: 207
actcaagtcc ctttcccctc 20

<210> SEQ ID NO 208
<211> LENGTH: 20
<212> TYPE: DNA
<213> ORGANISM: Homo Sapiens

<400> SEQUENCE: 208
tcttcacttc agttgcccct 20

<210> SEQ ID NO 209
<211> LENGTH: 20
<212> TYPE: DNA
<213> ORGANISM: Homo Sapiens

<400> SEQUENCE: 209
ccacactgag cctttttccc 20

<210> SEQ ID NO 210
<211> LENGTH: 19
<212> TYPE: DNA
<213> ORGANISM: Homo Sapiens

<400> SEQUENCE: 210
catgatgcgc tgtgtgtcc 19

<210> SEQ ID NO 211
<211> LENGTH: 20
<212> TYPE: DNA
<213> ORGANISM: Homo Sapiens

<400> SEQUENCE: 211
aggaagggca gtgaggattc 20

<210> SEQ ID NO 212
<211> LENGTH: 20
<212> TYPE: DNA
<213> ORGANISM: Homo Sapiens

<400> SEQUENCE: 212
caaaaagtgc cagccctcac 20

<210> SEQ ID NO 213
<211> LENGTH: 20
<212> TYPE: DNA
<213> ORGANISM: Homo Sapiens

<400> SEQUENCE: 213
actaagttgc cacaggacct 20

<210> SEQ ID NO 214
<211> LENGTH: 20
<212> TYPE: DNA
<213> ORGANISM: Homo Sapiens

<400> SEQUENCE: 214
gggctctggg gcattaacat 20

<210> SEQ ID NO 215
<211> LENGTH: 20
<212> TYPE: DNA
<213> ORGANISM: Homo Sapiens

<400> SEQUENCE: 215
cgaagtctcg ctcttttccc 20

<210> SEQ ID NO 216
<211> LENGTH: 25
<212> TYPE: DNA
<213> ORGANISM: Homo Sapiens

<400> SEQUENCE: 216
tgttttgttg ttcttggcat tttct 25

<210> SEQ ID NO 217
<211> LENGTH: 20
<212> TYPE: DNA
<213> ORGANISM: Homo Sapiens

<400> SEQUENCE: 217
acctgcccag atccttaacc 20

<210> SEQ ID NO 218
<211> LENGTH: 20
<212> TYPE: DNA
<213> ORGANISM: Homo Sapiens

<400> SEQUENCE: 218
ctctctccac ccaaaccctt 20

<210> SEQ ID NO 219
<211> LENGTH: 21
<212> TYPE: DNA
<213> ORGANISM: Homo Sapiens

<400> SEQUENCE: 219
tcccctcctc ttcttgttct c 21

<210> SEQ ID NO 220
<211> LENGTH: 21
<212> TYPE: DNA
<213> ORGANISM: Homo Sapiens

<400> SEQUENCE: 220
cgacttcagt cttccacttc c 21

<210> SEQ ID NO 221
<211> LENGTH: 20
<212> TYPE: DNA
<213> ORGANISM: Homo Sapiens

<400> SEQUENCE: 221
tcagcaggaa gtgttgacct 20

<210> SEQ ID NO 222
<211> LENGTH: 20
<212> TYPE: DNA
<213> ORGANISM: Homo Sapiens

<400> SEQUENCE: 222
gaggccaggc atttttcact 20

<210> SEQ ID NO 223
<211> LENGTH: 20
<212> TYPE: DNA
<213> ORGANISM: Homo Sapiens

<400> SEQUENCE: 223
caacacagtc tctccctcca 20

<210> SEQ ID NO 224
<211> LENGTH: 19
<212> TYPE: DNA
<213> ORGANISM: Homo Sapiens

<400> SEQUENCE: 224
ttgctgctgc ctcgcttat 19

<210> SEQ ID NO 225
<211> LENGTH: 20
<212> TYPE: DNA
<213> ORGANISM: Homo Sapiens

<400> SEQUENCE: 225
actgttctga cacaccccac 20

<210> SEQ ID NO 226
<211> LENGTH: 20
<212> TYPE: DNA
<213> ORGANISM: Homo Sapiens

<400> SEQUENCE: 226
ctctaaatcc ctcgccctgg 20

<210> SEQ ID NO 227
<211> LENGTH: 20
<212> TYPE: DNA
<213> ORGANISM: Homo Sapiens

<400> SEQUENCE: 227
aacctctacc cacccattcc 20

<210> SEQ ID NO 228
<211> LENGTH: 20
<212> TYPE: DNA
<213> ORGANISM: Homo Sapiens

<400> SEQUENCE: 228
tcctctctcc ccactctcag 20

<210> SEQ ID NO 229
<211> LENGTH: 18
<212> TYPE: DNA
<213> ORGANISM: Homo Sapiens

<400> SEQUENCE: 229
aaaaacgggt ggttgggc 18

<210> SEQ ID NO 230
<211> LENGTH: 20
<212> TYPE: DNA
<213> ORGANISM: Homo Sapiens

<400> SEQUENCE: 230
acagacagcc gaacagacac 20

<210> SEQ ID NO 231
<211> LENGTH: 25
<212> TYPE: DNA
<213> ORGANISM: Homo Sapiens

<400> SEQUENCE: 231
ttctttttag tctagtgctc cacta 25

<210> SEQ ID NO 232
<211> LENGTH: 19
<212> TYPE: DNA
<213> ORGANISM: Homo Sapiens

<400> SEQUENCE: 232
taagcccggg acttccttg 19

<210> SEQ ID NO 233
<211> LENGTH: 20
<212> TYPE: DNA
<213> ORGANISM: Homo Sapiens

<400> SEQUENCE: 233
ggggttttga ttggctgagg 20

<210> SEQ ID NO 234
<211> LENGTH: 20
<212> TYPE: DNA
<213> ORGANISM: Homo Sapiens

<400> SEQUENCE: 234
cctagggtga ggcttatggg 20

<210> SEQ ID NO 235
<211> LENGTH: 20
<212> TYPE: DNA
<213> ORGANISM: Homo Sapiens

<400> SEQUENCE: 235
gggtggccat taacacacaa 20

<210> SEQ ID NO 236
<211> LENGTH: 20
<212> TYPE: DNA
<213> ORGANISM: Homo Sapiens

<400> SEQUENCE: 236
ctgcgaggag gggagaattc 20

<210> SEQ ID NO 237
<211> LENGTH: 20
<212> TYPE: DNA
<213> ORGANISM: Homo Sapiens

<400> SEQUENCE: 237
tcccattccc gtgtttcctt 20

<210> SEQ ID NO 238
<211> LENGTH: 20
<212> TYPE: DNA
<213> ORGANISM: Homo Sapiens

<400> SEQUENCE: 238
aggctctgat gtgcttctct 20

<210> SEQ ID NO 239
<211> LENGTH: 20
<212> TYPE: DNA
<213> ORGANISM: Homo Sapiens

<400> SEQUENCE: 239
gttttctgtc tgcctctgcc 20

<210> SEQ ID NO 240
<211> LENGTH: 20
<212> TYPE: DNA
<213> ORGANISM: Homo Sapiens

<400> SEQUENCE: 240
accctcaccc taaatctggc 20

<210> SEQ ID NO 241
<211> LENGTH: 19
<212> TYPE: DNA
<213> ORGANISM: Homo Sapiens

<400> SEQUENCE: 241
ctgagcctgc cctactctg 19

<210> SEQ ID NO 242
<211> LENGTH: 18
<212> TYPE: DNA
<213> ORGANISM: Homo Sapiens

<400> SEQUENCE: 242
cgcgcgtaca cacacaca 18

<210> SEQ ID NO 243
<211> LENGTH: 20
<212> TYPE: DNA
<213> ORGANISM: Homo Sapiens

<400> SEQUENCE: 243
cctctctcct tctgcctcag 20

<210> SEQ ID NO 244
<211> LENGTH: 22
<212> TYPE: DNA
<213> ORGANISM: Homo Sapiens

<400> SEQUENCE: 244
tcgctgttag acatctctct ca 22

<210> SEQ ID NO 245
<211> LENGTH: 20
<212> TYPE: DNA
<213> ORGANISM: Homo Sapiens

<400> SEQUENCE: 245
tgagacccct tcagacccta 20

<210> SEQ ID NO 246
<211> LENGTH: 20
<212> TYPE: DNA
<213> ORGANISM: Homo Sapiens

<400> SEQUENCE: 246
gtgtttcctt ggggtcatgg 20

<210> SEQ ID NO 247
<211> LENGTH: 18
<212> TYPE: DNA
<213> ORGANISM: Homo Sapiens

<400> SEQUENCE: 247
ctcgctcatc cccgaggg 18

<210> SEQ ID NO 248
<211> LENGTH: 20
<212> TYPE: DNA
<213> ORGANISM: Homo Sapiens

<400> SEQUENCE: 248
ggcagctccg ggtctataaa 20

<210> SEQ ID NO 249
<211> LENGTH: 20
<212> TYPE: DNA
<213> ORGANISM: Homo Sapiens

<400> SEQUENCE: 249
ccctcacctt cccctctttt 20

<210> SEQ ID NO 250
<211> LENGTH: 20
<212> TYPE: DNA
<213> ORGANISM: Homo Sapiens

<400> SEQUENCE: 250
ctgtccttcc ctgacctcag 20

<210> SEQ ID NO 251
<211> LENGTH: 18
<212> TYPE: DNA
<213> ORGANISM: Homo Sapiens

<400> SEQUENCE: 251
tggtctctcg gcgggaag 18

<210> SEQ ID NO 252
<211> LENGTH: 20
<212> TYPE: DNA
<213> ORGANISM: Homo Sapiens

<400> SEQUENCE: 252
tgagttaacg gctgcctctt 20

<210> SEQ ID NO 253
<211> LENGTH: 20
<212> TYPE: DNA
<213> ORGANISM: Homo Sapiens

<400> SEQUENCE: 253
cacctggctc cactgtgtag 20

<210> SEQ ID NO 254
<211> LENGTH: 20
<212> TYPE: DNA
<213> ORGANISM: Homo Sapiens

<400> SEQUENCE: 254
cccctgctaa tgtctgaggt 20

<210> SEQ ID NO 255
<211> LENGTH: 18
<212> TYPE: DNA
<213> ORGANISM: Homo Sapiens

<400> SEQUENCE: 255
ctggccacac tgggtctc 18

<210> SEQ ID NO 256
<211> LENGTH: 20
<212> TYPE: DNA
<213> ORGANISM: Homo Sapiens

<400> SEQUENCE: 256
cactgtggcc ttgtttcctg 20

<210> SEQ ID NO 257
<211> LENGTH: 18
<212> TYPE: DNA
<213> ORGANISM: Homo Sapiens

<400> SEQUENCE: 257
ctcactcctc ccctgctc 18

<210> SEQ ID NO 258
<211> LENGTH: 20
<212> TYPE: DNA
<213> ORGANISM: Homo Sapiens

<400> SEQUENCE: 258
tagttggcga gtgggcttta 20

<210> SEQ ID NO 259
<211> LENGTH: 19
<212> TYPE: DNA
<213> ORGANISM: Homo Sapiens

<400> SEQUENCE: 259
ctggtttagc gacacgagc 19

<210> SEQ ID NO 260
<211> LENGTH: 20
<212> TYPE: DNA
<213> ORGANISM: Homo Sapiens

<400> SEQUENCE: 260
cctctgctga ctctgtctcc 20

<210> SEQ ID NO 261
<211> LENGTH: 19
<212> TYPE: DNA
<213> ORGANISM: Homo Sapiens

<400> SEQUENCE: 261
cattggttgc ggccatctc 19

<210> SEQ ID NO 262
<211> LENGTH: 18
<212> TYPE: DNA
<213> ORGANISM: Homo Sapiens

<400> SEQUENCE: 262
ccactgcaac ccgactcc 18

<210> SEQ ID NO 263
<211> LENGTH: 18
<212> TYPE: DNA
<213> ORGANISM: Homo Sapiens

<400> SEQUENCE: 263
caggagggcg gggtaaag 18

<210> SEQ ID NO 264
<211> LENGTH: 18
<212> TYPE: DNA
<213> ORGANISM: Homo Sapiens

<400> SEQUENCE: 264
cgcctcttcc caccctag 18

<210> SEQ ID NO 265
<211> LENGTH: 18
<212> TYPE: DNA
<213> ORGANISM: Homo Sapiens

<400> SEQUENCE: 265
cgtgaccgac atgtggct 18

<210> SEQ ID NO 266
<211> LENGTH: 20
<212> TYPE: DNA
<213> ORGANISM: Homo Sapiens

<400> SEQUENCE: 266
ctgagacctg gggactgatc 20

<210> SEQ ID NO 267
<211> LENGTH: 20
<212> TYPE: DNA

<213> ORGANISM: Homo Sapiens

<400> SEQUENCE: 267
agggtttcct tctcgctgat 20

<210> SEQ ID NO 268
<211> LENGTH: 18
<212> TYPE: DNA
<213> ORGANISM: Homo Sapiens

<400> SEQUENCE: 268
aggtgtggtg ttgcccac 18

<210> SEQ ID NO 269
<211> LENGTH: 20
<212> TYPE: DNA
<213> ORGANISM: Homo Sapiens

<400> SEQUENCE: 269
tacccactcc atttcccacc 20

<210> SEQ ID NO 270
<211> LENGTH: 18
<212> TYPE: DNA
<213> ORGANISM: Homo Sapiens

<400> SEQUENCE: 270
ctgggctggc gtatgacg 18

<210> SEQ ID NO 271
<211> LENGTH: 20
<212> TYPE: DNA
<213> ORGANISM: Homo Sapiens

<400> SEQUENCE: 271
ccgctcagtg tctctctctt 20

<210> SEQ ID NO 272
<211> LENGTH: 19
<212> TYPE: DNA
<213> ORGANISM: Homo Sapiens

<400> SEQUENCE: 272
caggaagcct gtgttccgt 19

<210> SEQ ID NO 273
<211> LENGTH: 20
<212> TYPE: DNA
<213> ORGANISM: Homo Sapiens

<400> SEQUENCE: 273
gaacttgccg gttaagcagg 20

<210> SEQ ID NO 274
<211> LENGTH: 20
<212> TYPE: DNA
<213> ORGANISM: Homo Sapiens

<400> SEQUENCE: 274
gtatcaacgc tctgtgggtc 20

<210> SEQ ID NO 275
<211> LENGTH: 20

<212> TYPE: DNA
<213> ORGANISM: Homo Sapiens

<400> SEQUENCE: 275
tgcttctctt ccttctcccc 20

<210> SEQ ID NO 276
<211> LENGTH: 18
<212> TYPE: DNA
<213> ORGANISM: Homo Sapiens

<400> SEQUENCE: 276
ctttgtgtgc cccgctcc 18

<210> SEQ ID NO 277
<211> LENGTH: 19
<212> TYPE: DNA
<213> ORGANISM: Homo Sapiens

<400> SEQUENCE: 277
aggcctcttg tttcctccc 19

<210> SEQ ID NO 278
<211> LENGTH: 20
<212> TYPE: DNA
<213> ORGANISM: Homo Sapiens

<400> SEQUENCE: 278
ctatgggtgc ccttctccac 20

<210> SEQ ID NO 279
<211> LENGTH: 19
<212> TYPE: DNA
<213> ORGANISM: Homo Sapiens

<400> SEQUENCE: 279
gaggacctgt gggactctg 19

<210> SEQ ID NO 280
<211> LENGTH: 20
<212> TYPE: DNA
<213> ORGANISM: Homo Sapiens

<400> SEQUENCE: 280
gggtgagact gacctctctt 20

<210> SEQ ID NO 281
<211> LENGTH: 18
<212> TYPE: DNA
<213> ORGANISM: Homo Sapiens

<400> SEQUENCE: 281
ctgcagttcg cttgtgcc 18

<210> SEQ ID NO 282
<211> LENGTH: 18
<212> TYPE: DNA
<213> ORGANISM: Homo Sapiens

<400> SEQUENCE: 282
cacccaccgc tgtgttgc 18

<210> SEQ ID NO 283

<211> LENGTH: 19
<212> TYPE: DNA
<213> ORGANISM: Homo Sapiens

<400> SEQUENCE: 283
aggaagggag cctcaaagg 19

<210> SEQ ID NO 284
<211> LENGTH: 19
<212> TYPE: DNA
<213> ORGANISM: Homo Sapiens

<400> SEQUENCE: 284
gactctcctg tctccgctc 19

<210> SEQ ID NO 285
<211> LENGTH: 18
<212> TYPE: DNA
<213> ORGANISM: Homo Sapiens

<400> SEQUENCE: 285
cctcctctgc gttcgacg 18

<210> SEQ ID NO 286
<211> LENGTH: 20
<212> TYPE: DNA
<213> ORGANISM: Homo Sapiens

<400> SEQUENCE: 286
actacatttc ccaggaggca 20

<210> SEQ ID NO 287
<211> LENGTH: 18
<212> TYPE: DNA
<213> ORGANISM: Homo Sapiens

<400> SEQUENCE: 287
ccgtccgcgc tacatact 18

<210> SEQ ID NO 288
<211> LENGTH: 20
<212> TYPE: DNA
<213> ORGANISM: Homo Sapiens

<400> SEQUENCE: 288
cagtggctca ggaaaccaag 20

<210> SEQ ID NO 289
<211> LENGTH: 20
<212> TYPE: DNA
<213> ORGANISM: Homo Sapiens

<400> SEQUENCE: 289
gctgatcctc caccttcctt 20

<210> SEQ ID NO 290
<211> LENGTH: 19
<212> TYPE: DNA
<213> ORGANISM: Homo Sapiens

<400> SEQUENCE: 290
gaacatggtg cgcaggttc 19

<210> SEQ ID NO 291
<211> LENGTH: 20
<212> TYPE: DNA
<213> ORGANISM: Homo Sapiens

<400> SEQUENCE: 291
gtgtgttggg ggatagcctc 20

<210> SEQ ID NO 292
<211> LENGTH: 18
<212> TYPE: DNA
<213> ORGANISM: Homo Sapiens

<400> SEQUENCE: 292
cacgtctgcc cctctctc 18

<210> SEQ ID NO 293
<211> LENGTH: 19
<212> TYPE: DNA
<213> ORGANISM: Homo Sapiens

<400> SEQUENCE: 293
ggcagaagag aggcagaca 19

<210> SEQ ID NO 294
<211> LENGTH: 20
<212> TYPE: DNA
<213> ORGANISM: Homo Sapiens

<400> SEQUENCE: 294
tattaccggc agaaccagca 20

<210> SEQ ID NO 295
<211> LENGTH: 20
<212> TYPE: DNA
<213> ORGANISM: Homo Sapiens

<400> SEQUENCE: 295
cacccggttc catctacctt 20

<210> SEQ ID NO 296
<211> LENGTH: 18
<212> TYPE: DNA
<213> ORGANISM: Homo Sapiens

<400> SEQUENCE: 296
cgatgagggt ctggccag 18

<210> SEQ ID NO 297
<211> LENGTH: 18
<212> TYPE: DNA
<213> ORGANISM: Homo Sapiens

<400> SEQUENCE: 297
cgctgctgcc ttgatggg 18

<210> SEQ ID NO 298
<211> LENGTH: 20
<212> TYPE: DNA
<213> ORGANISM: Homo Sapiens

<400> SEQUENCE: 298
actcactgac cctctccctt 20

<210> SEQ ID NO 299
<211> LENGTH: 20
<212> TYPE: DNA
<213> ORGANISM: Homo Sapiens

<400> SEQUENCE: 299
agcgaggaca tctggaagaa 20

<210> SEQ ID NO 300
<211> LENGTH: 19
<212> TYPE: DNA
<213> ORGANISM: Homo Sapiens

<400> SEQUENCE: 300
caagaggcca atgaggggg 19

<210> SEQ ID NO 301
<211> LENGTH: 20
<212> TYPE: DNA
<213> ORGANISM: Homo Sapiens

<400> SEQUENCE: 301
ctacctgtaa ctgggcctgt 20

<210> SEQ ID NO 302
<211> LENGTH: 18
<212> TYPE: DNA
<213> ORGANISM: Homo Sapiens

<400> SEQUENCE: 302
gatggcgcct cagaagca 18

<210> SEQ ID NO 303
<211> LENGTH: 18
<212> TYPE: DNA
<213> ORGANISM: Homo Sapiens

<400> SEQUENCE: 303
gggctccgta gacgcttt 18

<210> SEQ ID NO 304
<211> LENGTH: 20
<212> TYPE: DNA
<213> ORGANISM: Homo Sapiens

<400> SEQUENCE: 304
ctgccttctc ccctgaagag 20

<210> SEQ ID NO 305
<211> LENGTH: 27
<212> TYPE: DNA
<213> ORGANISM: Homo Sapiens

<400> SEQUENCE: 305
agttgtttta gaagatattt gcaagca 27

<210> SEQ ID NO 306
<211> LENGTH: 27
<212> TYPE: DNA
<213> ORGANISM: Homo Sapiens

<400> SEQUENCE: 306
tcttatcttc actgaaaaca taaacct 27

<210> SEQ ID NO 307
<211> LENGTH: 25
<212> TYPE: DNA
<213> ORGANISM: Homo Sapiens

<400> SEQUENCE: 307
actgaaagct aggcacattt tatga 25

<210> SEQ ID NO 308
<211> LENGTH: 23
<212> TYPE: DNA
<213> ORGANISM: Homo Sapiens

<400> SEQUENCE: 308
gggggaaaag aacatctgaa aat 23

<210> SEQ ID NO 309
<211> LENGTH: 26
<212> TYPE: DNA
<213> ORGANISM: Homo Sapiens

<400> SEQUENCE: 309
tgagaataca tttccaaact tgtcct 26

<210> SEQ ID NO 310
<211> LENGTH: 25
<212> TYPE: DNA
<213> ORGANISM: Homo Sapiens

<400> SEQUENCE: 310
acattagcaa ttaagaacac catct 25

<210> SEQ ID NO 311
<211> LENGTH: 23
<212> TYPE: DNA
<213> ORGANISM: Homo Sapiens

<400> SEQUENCE: 311
tggtaaaaca caatccttca cga 23

<210> SEQ ID NO 312
<211> LENGTH: 24
<212> TYPE: DNA
<213> ORGANISM: Homo Sapiens

<400> SEQUENCE: 312
acctgtagtt caactaaaca gagg 24

<210> SEQ ID NO 313
<211> LENGTH: 20
<212> TYPE: DNA
<213> ORGANISM: Homo Sapiens

<400> SEQUENCE: 313
acgcaactga caggaggaat 20

<210> SEQ ID NO 314
<211> LENGTH: 23
<212> TYPE: DNA
<213> ORGANISM: Homo Sapiens

<400> SEQUENCE: 314
tgccttattt ccctattgat gca 23

<210> SEQ ID NO 315
<211> LENGTH: 25
<212> TYPE: DNA
<213> ORGANISM: Homo Sapiens

<400> SEQUENCE: 315
tcactaaata cgtttcacag gtaga 25

<210> SEQ ID NO 316
<211> LENGTH: 25
<212> TYPE: DNA
<213> ORGANISM: Homo Sapiens

<400> SEQUENCE: 316
tcagaaacga tcagttgaaa tttca 25

<210> SEQ ID NO 317
<211> LENGTH: 27
<212> TYPE: DNA
<213> ORGANISM: Homo Sapiens

<400> SEQUENCE: 317
tgcataagtt atcaaaacac ttaaggt 27

<210> SEQ ID NO 318
<211> LENGTH: 23
<212> TYPE: DNA
<213> ORGANISM: Homo Sapiens

<400> SEQUENCE: 318
tttatgctct cccaataagc tcc 23

<210> SEQ ID NO 319
<211> LENGTH: 19
<212> TYPE: DNA
<213> ORGANISM: Homo Sapiens

<400> SEQUENCE: 319
gcgcccggct gaaattttt 19

<210> SEQ ID NO 320
<211> LENGTH: 24
<212> TYPE: DNA
<213> ORGANISM: Homo Sapiens

<400> SEQUENCE: 320
ctcaaaggta catgagaaag gtga 24

<210> SEQ ID NO 321
<211> LENGTH: 25
<212> TYPE: DNA
<213> ORGANISM: Homo Sapiens

<400> SEQUENCE: 321
acaatagtac ggtaatgaag aagct 25

<210> SEQ ID NO 322
<211> LENGTH: 24
<212> TYPE: DNA
<213> ORGANISM: Homo Sapiens

<400> SEQUENCE: 322
atggctacat gtaactagtg agat 24

<210> SEQ ID NO 323
<211> LENGTH: 27
<212> TYPE: DNA
<213> ORGANISM: Homo Sapiens

<400> SEQUENCE: 323
tcctagtcct ttaaaacttt tacgtga 27

<210> SEQ ID NO 324
<211> LENGTH: 22
<212> TYPE: DNA
<213> ORGANISM: Homo Sapiens

<400> SEQUENCE: 324
actttcaacc actctgaaag gt 22

<210> SEQ ID NO 325
<211> LENGTH: 23
<212> TYPE: DNA
<213> ORGANISM: Homo Sapiens

<400> SEQUENCE: 325
actttgcact gaaaaagtac aca 23

<210> SEQ ID NO 326
<211> LENGTH: 20
<212> TYPE: DNA
<213> ORGANISM: Homo Sapiens

<400> SEQUENCE: 326
gacagctcct tcaagaggga 20

<210> SEQ ID NO 327
<211> LENGTH: 21
<212> TYPE: DNA
<213> ORGANISM: Homo Sapiens

<400> SEQUENCE: 327
catacaggtt gccttactgg t 21

<210> SEQ ID NO 328
<211> LENGTH: 26
<212> TYPE: DNA
<213> ORGANISM: Homo Sapiens

<400> SEQUENCE: 328
agtttaaaat catatgcaca acctca 26

<210> SEQ ID NO 329
<211> LENGTH: 25
<212> TYPE: DNA
<213> ORGANISM: Homo Sapiens

<400> SEQUENCE: 329
gcgggtgata cttctttaat actca 25

<210> SEQ ID NO 330
<211> LENGTH: 20
<212> TYPE: DNA
<213> ORGANISM: Homo Sapiens

<400> SEQUENCE: 330 tgcacccccca taaatccaaa 20

<210> SEQ ID NO 331
<211> LENGTH: 22
<212> TYPE: DNA
<213> ORGANISM: Homo Sapiens

<400> SEQUENCE: 331
acagacagaa attcactctg ca 22

<210> SEQ ID NO 332
<211> LENGTH: 25
<212> TYPE: DNA
<213> ORGANISM: Homo Sapiens

<400> SEQUENCE: 332
aacaaacctt atttcccaca tgtaa 25

<210> SEQ ID NO 333
<211> LENGTH: 24
<212> TYPE: DNA
<213> ORGANISM: Homo Sapiens

<400> SEQUENCE: 333
tcaataatgc atttccactc caaa 24

<210> SEQ ID NO 334
<211> LENGTH: 24
<212> TYPE: DNA
<213> ORGANISM: Homo Sapiens

<400> SEQUENCE: 334
tgaagtgatc ggaatacatg taga 24

<210> SEQ ID NO 335
<211> LENGTH: 21
<212> TYPE: DNA
<213> ORGANISM: Homo Sapiens

<400> SEQUENCE: 335
ggtcctgcac cagtaatatg c 21

<210> SEQ ID NO 336
<211> LENGTH: 20
<212> TYPE: DNA
<213> ORGANISM: Homo Sapiens

<400> SEQUENCE: 336
gcctatgtga cagcaaacca 20

<210> SEQ ID NO 337
<211> LENGTH: 22
<212> TYPE: DNA
<213> ORGANISM: Homo Sapiens

<400> SEQUENCE: 337
tcagtggcat cttttcacaa gt 22

<210> SEQ ID NO 338
<211> LENGTH: 23
<212> TYPE: DNA
<213> ORGANISM: Homo Sapiens

<400> SEQUENCE: 338
tcaggggtat ctcacatact agc 23

<210> SEQ ID NO 339
<211> LENGTH: 21
<212> TYPE: DNA
<213> ORGANISM: Homo Sapiens

<400> SEQUENCE: 339
ggaacaaaga aaaggccagg a 21

<210> SEQ ID NO 340
<211> LENGTH: 25
<212> TYPE: DNA
<213> ORGANISM: Homo Sapiens

<400> SEQUENCE: 340
tctatggtaa aagatctcag gtcat 25

<210> SEQ ID NO 341
<211> LENGTH: 25
<212> TYPE: DNA
<213> ORGANISM: Homo Sapiens

<400> SEQUENCE: 341
tcaaggaaag ctgataccta tttca 25

<210> SEQ ID NO 342
<211> LENGTH: 20
<212> TYPE: DNA
<213> ORGANISM: Homo Sapiens

<400> SEQUENCE: 342
ttccaacctc caatgaccca 20

<210> SEQ ID NO 343
<211> LENGTH: 24
<212> TYPE: DNA
<213> ORGANISM: Homo Sapiens

<400> SEQUENCE: 343
tgtccttgtg aaataaaaag accc 24

<210> SEQ ID NO 344
<211> LENGTH: 24
<212> TYPE: DNA
<213> ORGANISM: Homo Sapiens

<400> SEQUENCE: 344
aaacccacta atacttgaag gtca 24

<210> SEQ ID NO 345
<211> LENGTH: 20
<212> TYPE: DNA
<213> ORGANISM: Homo Sapiens

<400> SEQUENCE: 345
cccacttcca aactcaagcc 20

<210> SEQ ID NO 346
<211> LENGTH: 24
<212> TYPE: DNA

<213> ORGANISM: Homo Sapiens

<400> SEQUENCE: 346
aacaaaaacc tgagaaacca gaac 24

<210> SEQ ID NO 347
<211> LENGTH: 20
<212> TYPE: DNA
<213> ORGANISM: Homo Sapiens

<400> SEQUENCE: 347
taaattgcaa agcccacccc 20

<210> SEQ ID NO 348
<211> LENGTH: 21
<212> TYPE: DNA
<213> ORGANISM: Homo Sapiens

<400> SEQUENCE: 348
tgaggggaac atatgtgcaa c 21

<210> SEQ ID NO 349
<211> LENGTH: 23
<212> TYPE: DNA
<213> ORGANISM: Homo Sapiens

<400> SEQUENCE: 349
acgtttacat actgaacaca ggt 23

<210> SEQ ID NO 350
<211> LENGTH: 21
<212> TYPE: DNA
<213> ORGANISM: Homo Sapiens

<400> SEQUENCE: 350
ccgagcagtc aaatgaactc a 21

<210> SEQ ID NO 351
<211> LENGTH: 23
<212> TYPE: DNA
<213> ORGANISM: Homo Sapiens

<400> SEQUENCE: 351
acagcaatcg tgaacaaata cct 23

<210> SEQ ID NO 352
<211> LENGTH: 27
<212> TYPE: DNA
<213> ORGANISM: Homo Sapiens

<400> SEQUENCE: 352
ttttcattcg tatatgcttt tcaaaca 27

<210> SEQ ID NO 353
<211> LENGTH: 22
<212> TYPE: DNA
<213> ORGANISM: Homo Sapiens

<400> SEQUENCE: 353
tgaaacctga gaagaaggat gt 22

<210> SEQ ID NO 354
<211> LENGTH: 20

<212> TYPE: DNA
<213> ORGANISM: Homo Sapiens

<400> SEQUENCE: 354
aggacttcac tgtgacctgg 20

<210> SEQ ID NO 355
<211> LENGTH: 20
<212> TYPE: DNA
<213> ORGANISM: Homo Sapiens

<400> SEQUENCE: 355
tgcttcaatg gaggagctca 20

<210> SEQ ID NO 356
<211> LENGTH: 22
<212> TYPE: DNA
<213> ORGANISM: Homo Sapiens

<400> SEQUENCE: 356
ggaccaagac atcacattcc ag 22

<210> SEQ ID NO 357
<211> LENGTH: 20
<212> TYPE: DNA
<213> ORGANISM: Homo Sapiens

<400> SEQUENCE: 357
aatgtgggat cctcgcctta 20

<210> SEQ ID NO 358
<211> LENGTH: 27
<212> TYPE: DNA
<213> ORGANISM: Homo Sapiens

<400> SEQUENCE: 358
cagtataatt aacccaatat tcggagt 27

<210> SEQ ID NO 359
<211> LENGTH: 20
<212> TYPE: DNA
<213> ORGANISM: Homo Sapiens

<400> SEQUENCE: 359
tgtgttattg gcaggaacgt 20

<210> SEQ ID NO 360
<211> LENGTH: 22
<212> TYPE: DNA
<213> ORGANISM: Homo Sapiens

<400> SEQUENCE: 360
agaaagtaca gaagaagggg ga 22

<210> SEQ ID NO 361
<211> LENGTH: 23
<212> TYPE: DNA
<213> ORGANISM: Homo Sapiens

<400> SEQUENCE: 361
tgtactgaaa tgccaatgga act 23

<210> SEQ ID NO 362

<211> LENGTH: 21
<212> TYPE: DNA
<213> ORGANISM: Homo Sapiens

<400> SEQUENCE: 362
tgtcccttca acatcaacca a 21

<210> SEQ ID NO 363
<211> LENGTH: 22
<212> TYPE: DNA
<213> ORGANISM: Homo Sapiens

<400> SEQUENCE: 363
tgaaaccctc atgttaagca ac 22

<210> SEQ ID NO 364
<211> LENGTH: 18
<212> TYPE: DNA
<213> ORGANISM: Homo Sapiens

<400> SEQUENCE: 364
aagccgtccg agatgacc 18

<210> SEQ ID NO 365
<211> LENGTH: 20
<212> TYPE: DNA
<213> ORGANISM: Homo Sapiens

<400> SEQUENCE: 365
ggccaatctg ctctaaacca 20

<210> SEQ ID NO 366
<211> LENGTH: 24
<212> TYPE: DNA
<213> ORGANISM: Homo Sapiens

<400> SEQUENCE: 366
tgcaaaccac aaaagtatac tcca 24

<210> SEQ ID NO 367
<211> LENGTH: 22
<212> TYPE: DNA
<213> ORGANISM: Homo Sapiens

<400> SEQUENCE: 367
acaaagcacg atatgaagca ca 22

<210> SEQ ID NO 368
<211> LENGTH: 23
<212> TYPE: DNA
<213> ORGANISM: Homo Sapiens

<400> SEQUENCE: 368
tcctaaacgt aagaagcaac act 23

<210> SEQ ID NO 369
<211> LENGTH: 23
<212> TYPE: DNA
<213> ORGANISM: Homo Sapiens

<400> SEQUENCE: 369
tatgtaagac acgagacact gga 23

<210> SEQ ID NO 370
<211> LENGTH: 24
<212> TYPE: DNA
<213> ORGANISM: Homo Sapiens

<400> SEQUENCE: 370
tcacaaccat taaaacagga gaca 24

<210> SEQ ID NO 371
<211> LENGTH: 25
<212> TYPE: DNA
<213> ORGANISM: Homo Sapiens

<400> SEQUENCE: 371
agacaacgtc ttcctatgat agaaa 25

<210> SEQ ID NO 372
<211> LENGTH: 23
<212> TYPE: DNA
<213> ORGANISM: Homo Sapiens

<400> SEQUENCE: 372
cccaagattt aagaccaaag gct 23

<210> SEQ ID NO 373
<211> LENGTH: 27
<212> TYPE: DNA
<213> ORGANISM: Homo Sapiens

<400> SEQUENCE: 373
tcaaaataga atttagttga tggaggg 27

<210> SEQ ID NO 374
<211> LENGTH: 20
<212> TYPE: DNA
<213> ORGANISM: Homo Sapiens

<400> SEQUENCE: 374
gcaatcccag gccagagata 20

<210> SEQ ID NO 375
<211> LENGTH: 27
<212> TYPE: DNA
<213> ORGANISM: Homo Sapiens

<400> SEQUENCE: 375
tggagttttt ctattaacca ggttatt 27

<210> SEQ ID NO 376
<211> LENGTH: 21
<212> TYPE: DNA
<213> ORGANISM: Homo Sapiens

<400> SEQUENCE: 376
tgcagatatg gcatcaacag a 21

<210> SEQ ID NO 377
<211> LENGTH: 20
<212> TYPE: DNA
<213> ORGANISM: Homo Sapiens

<400> SEQUENCE: 377
ctccaaacct ctacctggca 20

<210> SEQ ID NO 378
<211> LENGTH: 20
<212> TYPE: DNA
<213> ORGANISM: Homo Sapiens

<400> SEQUENCE: 378
tgtgcagtcc aggaaacaga 20

<210> SEQ ID NO 379
<211> LENGTH: 23
<212> TYPE: DNA
<213> ORGANISM: Homo Sapiens

<400> SEQUENCE: 379
ttatgctgct tatcataccc agt 23

<210> SEQ ID NO 380
<211> LENGTH: 22
<212> TYPE: DNA
<213> ORGANISM: Homo Sapiens

<400> SEQUENCE: 380
tcatgtcccc agaaaatcca gt 22

<210> SEQ ID NO 381
<211> LENGTH: 24
<212> TYPE: DNA
<213> ORGANISM: Homo Sapiens

<400> SEQUENCE: 381
ctgactctag atacctggct aaac 24

<210> SEQ ID NO 382
<211> LENGTH: 27
<212> TYPE: DNA
<213> ORGANISM: Homo Sapiens

<400> SEQUENCE: 382
aaaaaggcac catctaaaag aaatagt 27

<210> SEQ ID NO 383
<211> LENGTH: 22
<212> TYPE: DNA
<213> ORGANISM: Homo Sapiens

<400> SEQUENCE: 383
cttggagcaa gtaagagcat gt 22

<210> SEQ ID NO 384
<211> LENGTH: 22
<212> TYPE: DNA
<213> ORGANISM: Homo Sapiens

<400> SEQUENCE: 384
cgcagacaaa tttcaggaag ga 22

<210> SEQ ID NO 385
<211> LENGTH: 23
<212> TYPE: DNA
<213> ORGANISM: Homo Sapiens

<400> SEQUENCE: 385
gcctacttca tccaaaatag cca 23

<210> SEQ ID NO 386
<211> LENGTH: 27
<212> TYPE: DNA
<213> ORGANISM: Homo Sapiens

<400> SEQUENCE: 386
tctctaacac gactataatt ttcctct 27

<210> SEQ ID NO 387
<211> LENGTH: 24
<212> TYPE: DNA
<213> ORGANISM: Homo Sapiens

<400> SEQUENCE: 387
tcaagagata aagtccataa gcct 24

<210> SEQ ID NO 388
<211> LENGTH: 19
<212> TYPE: DNA
<213> ORGANISM: Homo Sapiens

<400> SEQUENCE: 388
cccatttgga agcagctcg 19

<210> SEQ ID NO 389
<211> LENGTH: 20
<212> TYPE: DNA
<213> ORGANISM: Homo Sapiens

<400> SEQUENCE: 389
tggctaacca agtctcagga 20

<210> SEQ ID NO 390
<211> LENGTH: 25
<212> TYPE: DNA
<213> ORGANISM: Homo Sapiens

<400> SEQUENCE: 390
ccagttatat cacaaataaa gcccc 25

<210> SEQ ID NO 391
<211> LENGTH: 20
<212> TYPE: DNA
<213> ORGANISM: Homo Sapiens

<400> SEQUENCE: 391
atctgaagat ggggctggtg 20

<210> SEQ ID NO 392
<211> LENGTH: 24
<212> TYPE: DNA
<213> ORGANISM: Homo Sapiens

<400> SEQUENCE: 392
aacattgcat attacccaca aaga 24

<210> SEQ ID NO 393
<211> LENGTH: 25
<212> TYPE: DNA
<213> ORGANISM: Homo Sapiens

<400> SEQUENCE: 393
acaacaggaa gtaaactcat tttcc 25

<210> SEQ ID NO 394
<211> LENGTH: 20
<212> TYPE: DNA
<213> ORGANISM: Homo Sapiens

<400> SEQUENCE: 394
agaattcagg caatcaccca 20

<210> SEQ ID NO 395
<211> LENGTH: 21
<212> TYPE: DNA
<213> ORGANISM: Homo Sapiens

<400> SEQUENCE: 395
agggtgtttc tgtaacctcc a 21

<210> SEQ ID NO 396
<211> LENGTH: 20
<212> TYPE: DNA
<213> ORGANISM: Homo Sapiens

<400> SEQUENCE: 396
accaatttcc tgtgcagaga 20

<210> SEQ ID NO 397
<211> LENGTH: 20
<212> TYPE: DNA
<213> ORGANISM: Homo Sapiens

<400> SEQUENCE: 397
acagaaagct cccactcctc 20

<210> SEQ ID NO 398
<211> LENGTH: 25
<212> TYPE: DNA
<213> ORGANISM: Homo Sapiens

<400> SEQUENCE: 398
agacaattca agcttcagaa tctct 25

<210> SEQ ID NO 399
<211> LENGTH: 24
<212> TYPE: DNA
<213> ORGANISM: Homo Sapiens

<400> SEQUENCE: 399
ctcctctcag tcttctaaaa tggt 24

<210> SEQ ID NO 400
<211> LENGTH: 21
<212> TYPE: DNA
<213> ORGANISM: Homo Sapiens

<400> SEQUENCE: 400
tggaagggtt tatatcgggc t 21

<210> SEQ ID NO 401
<211> LENGTH: 23
<212> TYPE: DNA
<213> ORGANISM: Homo Sapiens

<400> SEQUENCE: 401
tctgaaccac aatcaacttc tcc 23

<210> SEQ ID NO 402
<211> LENGTH: 21
<212> TYPE: DNA
<213> ORGANISM: Homo Sapiens

<400> SEQUENCE: 402
aacactgtga aaagcaaagc t 21

<210> SEQ ID NO 403
<211> LENGTH: 22
<212> TYPE: DNA
<213> ORGANISM: Homo Sapiens

<400> SEQUENCE: 403
tctactgcca atgccttagt tc 22

<210> SEQ ID NO 404
<211> LENGTH: 20
<212> TYPE: DNA
<213> ORGANISM: Homo Sapiens

<400> SEQUENCE: 404
gtggcaaggt tgaatcagca 20

<210> SEQ ID NO 405
<211> LENGTH: 25
<212> TYPE: DNA
<213> ORGANISM: Homo Sapiens

<400> SEQUENCE: 405
tgctttaaaa tctactccta ccagg 25

<210> SEQ ID NO 406
<211> LENGTH: 21
<212> TYPE: DNA
<213> ORGANISM: Homo Sapiens

<400> SEQUENCE: 406
tggagccaca taacacattc a 21

<210> SEQ ID NO 407
<211> LENGTH: 22
<212> TYPE: DNA
<213> ORGANISM: Homo Sapiens

<400> SEQUENCE: 407
agagaatgat gcaatttggg gt 22

<210> SEQ ID NO 408
<211> LENGTH: 21
<212> TYPE: DNA
<213> ORGANISM: Homo Sapiens

<400> SEQUENCE: 408
tttgcagcca gaatctcttc c 21

<210> SEQ ID NO 409
<211> LENGTH: 24
<212> TYPE: DNA
<213> ORGANISM: Homo Sapiens

<400> SEQUENCE: 409
agagaacaga gaaagcttga aact 24

<210> SEQ ID NO 410
<211> LENGTH: 20
<212> TYPE: DNA
<213> ORGANISM: Homo Sapiens

<400> SEQUENCE: 410
cactgagagc cttgaaagcc 20

<210> SEQ ID NO 411
<211> LENGTH: 22
<212> TYPE: DNA
<213> ORGANISM: Homo Sapiens

<400> SEQUENCE: 411
ggaaacatcc tgcacgttaa gt 22

<210> SEQ ID NO 412
<211> LENGTH: 20
<212> TYPE: DNA
<213> ORGANISM: Homo Sapiens

<400> SEQUENCE: 412
acactgacat tgggagttgg 20

<210> SEQ ID NO 413
<211> LENGTH: 25
<212> TYPE: DNA
<213> ORGANISM: Homo Sapiens

<400> SEQUENCE: 413
tgtacttacc acaacaacct tatct 25

<210> SEQ ID NO 414
<211> LENGTH: 20
<212> TYPE: DNA
<213> ORGANISM: Homo Sapiens

<400> SEQUENCE: 414
gggccttgca gtaaaaggag 20

<210> SEQ ID NO 415
<211> LENGTH: 23
<212> TYPE: DNA
<213> ORGANISM: Homo Sapiens

<400> SEQUENCE: 415
gcttgatctg gagttaatcg aga 23

<210> SEQ ID NO 416
<211> LENGTH: 20
<212> TYPE: DNA
<213> ORGANISM: Homo Sapiens

<400> SEQUENCE: 416
gtgggtttta gcttgtcgca 20

<210> SEQ ID NO 417
<211> LENGTH: 20
<212> TYPE: DNA
<213> ORGANISM: Homo Sapiens

<400> SEQUENCE: 417
ctggctccag aatccttcct 20

<210> SEQ ID NO 418
<211> LENGTH: 20
<212> TYPE: DNA
<213> ORGANISM: Homo Sapiens

<400> SEQUENCE: 418
aagggggatt ctatgcctgg 20

<210> SEQ ID NO 419
<211> LENGTH: 21
<212> TYPE: DNA
<213> ORGANISM: Homo Sapiens

<400> SEQUENCE: 419
agcatcctcc caaaagaagg a 21

<210> SEQ ID NO 420
<211> LENGTH: 24
<212> TYPE: DNA
<213> ORGANISM: Homo Sapiens

<400> SEQUENCE: 420
aatacagtaa ggagtggaga agtc 24

<210> SEQ ID NO 421
<211> LENGTH: 23
<212> TYPE: DNA
<213> ORGANISM: Homo Sapiens

<400> SEQUENCE: 421
cctgacaaat ccagagtata cgc 23

<210> SEQ ID NO 422
<211> LENGTH: 24
<212> TYPE: DNA
<213> ORGANISM: Homo Sapiens

<400> SEQUENCE: 422
agacccatta aaacctattc ctca 24

<210> SEQ ID NO 423
<211> LENGTH: 21
<212> TYPE: DNA
<213> ORGANISM: Homo Sapiens

<400> SEQUENCE: 423
ggcaaaagcc tttgatgaag c 21

<210> SEQ ID NO 424
<211> LENGTH: 20
<212> TYPE: DNA
<213> ORGANISM: Homo Sapiens

<400> SEQUENCE: 424
gtggaataac acctccagcc 20

<210> SEQ ID NO 425
<211> LENGTH: 25
<212> TYPE: DNA

<213> ORGANISM: Homo Sapiens

<400> SEQUENCE: 425
tgatttttaa agtagcagaa tggca 25

<210> SEQ ID NO 426
<211> LENGTH: 21
<212> TYPE: DNA
<213> ORGANISM: Homo Sapiens

<400> SEQUENCE: 426
tgagtcacac accaatgaag a 21

<210> SEQ ID NO 427
<211> LENGTH: 23
<212> TYPE: DNA
<213> ORGANISM: Homo Sapiens

<400> SEQUENCE: 427
gtgaaatatg caacagcttc tca 23

<210> SEQ ID NO 428
<211> LENGTH: 23
<212> TYPE: DNA
<213> ORGANISM: Homo Sapiens

<400> SEQUENCE: 428
tttacacgga atttcagtgg tgg 23

<210> SEQ ID NO 429
<211> LENGTH: 21
<212> TYPE: DNA
<213> ORGANISM: Homo Sapiens

<400> SEQUENCE: 429
acgaatcact tcttcagggg a 21

<210> SEQ ID NO 430
<211> LENGTH: 20
<212> TYPE: DNA
<213> ORGANISM: Homo Sapiens

<400> SEQUENCE: 430
aaggaaagcc ccttgagttt 20

<210> SEQ ID NO 431
<211> LENGTH: 25
<212> TYPE: DNA
<213> ORGANISM: Homo Sapiens

<400> SEQUENCE: 431
acaacccaca gtattttaaa ttgca 25

<210> SEQ ID NO 432
<211> LENGTH: 21
<212> TYPE: DNA
<213> ORGANISM: Homo Sapiens

<400> SEQUENCE: 432
ccccagtaag tcccttcaaa t 21

<210> SEQ ID NO 433
<211> LENGTH: 24

<212> TYPE: DNA
<213> ORGANISM: Homo Sapiens

<400> SEQUENCE: 433
accacatatc tgctatgtct tcct 24

<210> SEQ ID NO 434
<211> LENGTH: 24
<212> TYPE: DNA
<213> ORGANISM: Homo Sapiens

<400> SEQUENCE: 434
tgactgaatg agaacttaag tggg 24

<210> SEQ ID NO 435
<211> LENGTH: 21
<212> TYPE: DNA
<213> ORGANISM: Homo Sapiens

<400> SEQUENCE: 435
ccctcccatc ttcctctaac c 21

<210> SEQ ID NO 436
<211> LENGTH: 20
<212> TYPE: DNA
<213> ORGANISM: Homo Sapiens

<400> SEQUENCE: 436
acactggcat gcaacatgtt 20

<210> SEQ ID NO 437
<211> LENGTH: 20
<212> TYPE: DNA
<213> ORGANISM: Homo Sapiens

<400> SEQUENCE: 437
aaacaggcct gagaaagctt 20

<210> SEQ ID NO 438
<211> LENGTH: 19
<212> TYPE: DNA
<213> ORGANISM: Homo Sapiens

<400> SEQUENCE: 438
atccgtgatc tgcaggcat 19

<210> SEQ ID NO 439
<211> LENGTH: 19
<212> TYPE: DNA
<213> ORGANISM: Homo Sapiens

<400> SEQUENCE: 439
ccacacctgg ccaagctta 19

<210> SEQ ID NO 440
<211> LENGTH: 23
<212> TYPE: DNA
<213> ORGANISM: Homo Sapiens

<400> SEQUENCE: 440
tctgtcatca cactcaaaga tgc 23

<210> SEQ ID NO 441

<211> LENGTH: 18
<212> TYPE: DNA
<213> ORGANISM: Homo Sapiens

<400> SEQUENCE: 441
tctgacacgc aagcccag 18

<210> SEQ ID NO 442
<211> LENGTH: 19
<212> TYPE: DNA
<213> ORGANISM: Homo Sapiens

<400> SEQUENCE: 442
gcgcagaaag tgacagtgc 19

<210> SEQ ID NO 443
<211> LENGTH: 21
<212> TYPE: DNA
<213> ORGANISM: Homo Sapiens

<400> SEQUENCE: 443
ccccctcgat tgttaacatg a 21

<210> SEQ ID NO 444
<211> LENGTH: 20
<212> TYPE: DNA
<213> ORGANISM: Homo Sapiens

<400> SEQUENCE: 444
tcatgaactt cccacacagc 20

<210> SEQ ID NO 445
<211> LENGTH: 20
<212> TYPE: DNA
<213> ORGANISM: Homo Sapiens

<400> SEQUENCE: 445
tcccaacacc ggaaaggata 20

<210> SEQ ID NO 446
<211> LENGTH: 20
<212> TYPE: DNA
<213> ORGANISM: Homo Sapiens

<400> SEQUENCE: 446
catcccagcc atacaggact 20

<210> SEQ ID NO 447
<211> LENGTH: 20
<212> TYPE: DNA
<213> ORGANISM: Homo Sapiens

<400> SEQUENCE: 447
ctatgctgca gctgttaccc 20

<210> SEQ ID NO 448
<211> LENGTH: 20
<212> TYPE: DNA
<213> ORGANISM: Homo Sapiens

<400> SEQUENCE: 448
tggaaggcag taaaggctga 20

<210> SEQ ID NO 449
<211> LENGTH: 20
<212> TYPE: DNA
<213> ORGANISM: Homo Sapiens

<400> SEQUENCE: 449
acactctgac aggtcaagca 20

<210> SEQ ID NO 450
<211> LENGTH: 20
<212> TYPE: DNA
<213> ORGANISM: Homo Sapiens

<400> SEQUENCE: 450
taaaccctac cccaagcagc 20

<210> SEQ ID NO 451
<211> LENGTH: 21
<212> TYPE: DNA
<213> ORGANISM: Homo Sapiens

<400> SEQUENCE: 451
actcaaggca taaaagctgg g 21

<210> SEQ ID NO 452
<211> LENGTH: 20
<212> TYPE: DNA
<213> ORGANISM: Homo Sapiens

<400> SEQUENCE: 452
cctgacaaag tgcaggactc 20

<210> SEQ ID NO 453
<211> LENGTH: 21
<212> TYPE: DNA
<213> ORGANISM: Homo Sapiens

<400> SEQUENCE: 453
gtgattttcg tggaagtggg t 21

<210> SEQ ID NO 454
<211> LENGTH: 20
<212> TYPE: DNA
<213> ORGANISM: Homo Sapiens

<400> SEQUENCE: 454
tccaagctag tagtggccag 20

<210> SEQ ID NO 455
<211> LENGTH: 20
<212> TYPE: DNA
<213> ORGANISM: Homo Sapiens

<400> SEQUENCE: 455
ggtcacacat gggtctgagg 20

<210> SEQ ID NO 456
<211> LENGTH: 19
<212> TYPE: DNA
<213> ORGANISM: Homo Sapiens

<400> SEQUENCE: 456
caggccacac acacacttc 19

<210> SEQ ID NO 457
<211> LENGTH: 24
<212> TYPE: DNA
<213> ORGANISM: Homo Sapiens

<400> SEQUENCE: 457
atagccctta caacaaaaac aaga 24

<210> SEQ ID NO 458
<211> LENGTH: 20
<212> TYPE: DNA
<213> ORGANISM: Homo Sapiens

<400> SEQUENCE: 458
gccagagcag gattaggaga 20

<210> SEQ ID NO 459
<211> LENGTH: 20
<212> TYPE: DNA
<213> ORGANISM: Homo Sapiens

<400> SEQUENCE: 459
cagtgcgtgc tcctttagtg 20

<210> SEQ ID NO 460
<211> LENGTH: 22
<212> TYPE: DNA
<213> ORGANISM: Homo Sapiens

<400> SEQUENCE: 460
gctctgaaaa tgctctttgg ga 22

<210> SEQ ID NO 461
<211> LENGTH: 26
<212> TYPE: DNA
<213> ORGANISM: Homo Sapiens

<400> SEQUENCE: 461
tggacatttg tagaagaaat aaggct 26

<210> SEQ ID NO 462
<211> LENGTH: 20
<212> TYPE: DNA
<213> ORGANISM: Homo Sapiens

<400> SEQUENCE: 462
caccttcgcc tttactgcag 20

<210> SEQ ID NO 463
<211> LENGTH: 22
<212> TYPE: DNA
<213> ORGANISM: Homo Sapiens

<400> SEQUENCE: 463
attccttgac cacatcaaac ct 22

<210> SEQ ID NO 464
<211> LENGTH: 20
<212> TYPE: DNA
<213> ORGANISM: Homo Sapiens

<400> SEQUENCE: 464
agcacctcct actccctact 20

<210> SEQ ID NO 465
<211> LENGTH: 21
<212> TYPE: DNA
<213> ORGANISM: Homo Sapiens

<400> SEQUENCE: 465
gacacccaaa caaggaactc a 21

<210> SEQ ID NO 466
<211> LENGTH: 20
<212> TYPE: DNA
<213> ORGANISM: Homo Sapiens

<400> SEQUENCE: 466
gagaccctct cttcagagcc 20

<210> SEQ ID NO 467
<211> LENGTH: 20
<212> TYPE: DNA
<213> ORGANISM: Homo Sapiens

<400> SEQUENCE: 467
caatgatgct ggtccacacc 20

<210> SEQ ID NO 468
<211> LENGTH: 21
<212> TYPE: DNA
<213> ORGANISM: Homo Sapiens

<400> SEQUENCE: 468
aggagcttca tgacagactc a 21

<210> SEQ ID NO 469
<211> LENGTH: 21
<212> TYPE: DNA
<213> ORGANISM: Homo Sapiens

<400> SEQUENCE: 469
tgcagggctt catacaagag a 21

<210> SEQ ID NO 470
<211> LENGTH: 19
<212> TYPE: DNA
<213> ORGANISM: Homo Sapiens

<400> SEQUENCE: 470
ctcctcttct ctggcagcc 19

<210> SEQ ID NO 471
<211> LENGTH: 20
<212> TYPE: DNA
<213> ORGANISM: Homo Sapiens

<400> SEQUENCE: 471
ctgctcccct gtgaatcagt 20

<210> SEQ ID NO 472
<211> LENGTH: 20
<212> TYPE: DNA
<213> ORGANISM: Homo Sapiens

<400> SEQUENCE: 472
agatcctgca cttgctcact 20

<210> SEQ ID NO 473
<211> LENGTH: 19
<212> TYPE: DNA
<213> ORGANISM: Homo Sapiens

<400> SEQUENCE: 473
tccctccatg ctcctctct 19

<210> SEQ ID NO 474
<211> LENGTH: 20
<212> TYPE: DNA
<213> ORGANISM: Homo Sapiens

<400> SEQUENCE: 474
caaatatcag ggtgcagggc 20

<210> SEQ ID NO 475
<211> LENGTH: 20
<212> TYPE: DNA
<213> ORGANISM: Homo Sapiens

<400> SEQUENCE: 475
gattcatttc tgctgggccc 20

<210> SEQ ID NO 476
<211> LENGTH: 20
<212> TYPE: DNA
<213> ORGANISM: Homo Sapiens

<400> SEQUENCE: 476
ggtagtccag ggtatgtggg 20

<210> SEQ ID NO 477
<211> LENGTH: 22
<212> TYPE: DNA
<213> ORGANISM: Homo Sapiens

<400> SEQUENCE: 477
cacttatgca aggagaatgc tg 22

<210> SEQ ID NO 478
<211> LENGTH: 20
<212> TYPE: DNA
<213> ORGANISM: Homo Sapiens

<400> SEQUENCE: 478
acaaaggaac tgatgccctc 20

<210> SEQ ID NO 479
<211> LENGTH: 20
<212> TYPE: DNA
<213> ORGANISM: Homo Sapiens

<400> SEQUENCE: 479
cctccccaca tccatggtac 20

<210> SEQ ID NO 480
<211> LENGTH: 18
<212> TYPE: DNA
<213> ORGANISM: Homo Sapiens

<400> SEQUENCE: 480
ctgacgaggg cacacaga 18

<210> SEQ ID NO 481
<211> LENGTH: 20
<212> TYPE: DNA
<213> ORGANISM: Homo Sapiens

<400> SEQUENCE: 481
attctcccat tgcacagcct 20

<210> SEQ ID NO 482
<211> LENGTH: 20
<212> TYPE: DNA
<213> ORGANISM: Homo Sapiens

<400> SEQUENCE: 482
ttctgtcatc catgctcccc 20

<210> SEQ ID NO 483
<211> LENGTH: 20
<212> TYPE: DNA
<213> ORGANISM: Homo Sapiens

<400> SEQUENCE: 483
aagctacagc caggtcactt 20

<210> SEQ ID NO 484
<211> LENGTH: 20
<212> TYPE: DNA
<213> ORGANISM: Homo Sapiens

<400> SEQUENCE: 484
tacctggagg atgatggctg 20

<210> SEQ ID NO 485
<211> LENGTH: 20
<212> TYPE: DNA
<213> ORGANISM: Homo Sapiens

<400> SEQUENCE: 485
atctgggacc aagagtagcc 20

<210> SEQ ID NO 486
<211> LENGTH: 19
<212> TYPE: DNA
<213> ORGANISM: Homo Sapiens

<400> SEQUENCE: 486
ctgaatgagg cagggaagc 19

<210> SEQ ID NO 487
<211> LENGTH: 20
<212> TYPE: DNA
<213> ORGANISM: Homo Sapiens

<400> SEQUENCE: 487
acatccccgt gtcactactg 20

<210> SEQ ID NO 488
<211> LENGTH: 20
<212> TYPE: DNA
<213> ORGANISM: Homo Sapiens

<400> SEQUENCE: 488
attccctgca cttctaggca 20

<210> SEQ ID NO 489
<211> LENGTH: 23
<212> TYPE: DNA
<213> ORGANISM: Homo Sapiens

<400> SEQUENCE: 489
cagagtcaca aaataacacc cca 23

<210> SEQ ID NO 490
<211> LENGTH: 20
<212> TYPE: DNA
<213> ORGANISM: Homo Sapiens

<400> SEQUENCE: 490
gccaggtgaa agcacacgta 20

<210> SEQ ID NO 491
<211> LENGTH: 18
<212> TYPE: DNA
<213> ORGANISM: Homo Sapiens

<400> SEQUENCE: 491
atctacctgc cctgcacg 18

<210> SEQ ID NO 492
<211> LENGTH: 18
<212> TYPE: DNA
<213> ORGANISM: Homo Sapiens

<400> SEQUENCE: 492
cacaggctgt ggaggtcc 18

<210> SEQ ID NO 493
<211> LENGTH: 20
<212> TYPE: DNA
<213> ORGANISM: Homo Sapiens

<400> SEQUENCE: 493
cactagagtg gtgcagccta 20

<210> SEQ ID NO 494
<211> LENGTH: 19
<212> TYPE: DNA
<213> ORGANISM: Homo Sapiens

<400> SEQUENCE: 494
gtaccagccc caagtggat 19

<210> SEQ ID NO 495
<211> LENGTH: 20
<212> TYPE: DNA
<213> ORGANISM: Homo Sapiens

<400> SEQUENCE: 495
gtctcccatt ctctgcctct 20

<210> SEQ ID NO 496
<211> LENGTH: 20
<212> TYPE: DNA
<213> ORGANISM: Homo Sapiens

<400> SEQUENCE: 496
ctgactgggg tccacaaact 20

<210> SEQ ID NO 497
<211> LENGTH: 20
<212> TYPE: DNA
<213> ORGANISM: Homo Sapiens

<400> SEQUENCE: 497
cattcccagc taccctcctc 20

<210> SEQ ID NO 498
<211> LENGTH: 24
<212> TYPE: DNA
<213> ORGANISM: Homo Sapiens

<400> SEQUENCE: 498
tcttaaagca attaaggagc acct 24

<210> SEQ ID NO 499
<211> LENGTH: 19
<212> TYPE: DNA
<213> ORGANISM: Homo Sapiens

<400> SEQUENCE: 499
cagcattgtc ctcaggcac 19

<210> SEQ ID NO 500
<211> LENGTH: 21
<212> TYPE: DNA
<213> ORGANISM: Homo Sapiens

<400> SEQUENCE: 500
ataagagcat gaccctgcat g 21

<210> SEQ ID NO 501
<211> LENGTH: 19
<212> TYPE: DNA
<213> ORGANISM: Homo Sapiens

<400> SEQUENCE: 501
caggagagtg tgcactggg 19

<210> SEQ ID NO 502
<211> LENGTH: 19
<212> TYPE: DNA
<213> ORGANISM: Homo Sapiens

<400> SEQUENCE: 502
acaggtgtcc ccagagatg 19

<210> SEQ ID NO 503
<211> LENGTH: 20
<212> TYPE: DNA
<213> ORGANISM: Homo Sapiens

<400> SEQUENCE: 503
ctgaggcagg gcatgatact 20

<210> SEQ ID NO 504
<211> LENGTH: 19
<212> TYPE: DNA

<213> ORGANISM: Homo Sapiens

<400> SEQUENCE: 504
cacctcacct gagtcccag 19

<210> SEQ ID NO 505
<211> LENGTH: 18
<212> TYPE: DNA
<213> ORGANISM: Homo Sapiens

<400> SEQUENCE: 505
ccgccacgag ctcagaag 18

<210> SEQ ID NO 506
<211> LENGTH: 20
<212> TYPE: DNA
<213> ORGANISM: Homo Sapiens

<400> SEQUENCE: 506
tctccccatg acagccattt 20

<210> SEQ ID NO 507
<211> LENGTH: 20
<212> TYPE: DNA
<213> ORGANISM: Homo Sapiens

<400> SEQUENCE: 507
ctcctcaggc atgggttctt 20

<210> SEQ ID NO 508
<211> LENGTH: 18
<212> TYPE: DNA
<213> ORGANISM: Homo Sapiens

<400> SEQUENCE: 508
gtggcaagtg gctcctga 18

<210> SEQ ID NO 509
<211> LENGTH: 20
<212> TYPE: DNA
<213> ORGANISM: Homo Sapiens

<400> SEQUENCE: 509
ccctaccctg cctcaacata 20

<210> SEQ ID NO 510
<211> LENGTH: 24
<212> TYPE: DNA
<213> ORGANISM: Homo Sapiens

<400> SEQUENCE: 510
aagtataccc aaccattcaa ctct 24

<210> SEQ ID NO 511
<211> LENGTH: 20
<212> TYPE: DNA
<213> ORGANISM: Homo Sapiens

<400> SEQUENCE: 511
tacattctcc caaccccacc 20

<210> SEQ ID NO 512
<211> LENGTH: 20

<212> TYPE: DNA
<213> ORGANISM: Homo Sapiens

<400> SEQUENCE: 512
tggtgatgtg cagtcaacag 20

<210> SEQ ID NO 513
<211> LENGTH: 18
<212> TYPE: DNA
<213> ORGANISM: Homo Sapiens

<400> SEQUENCE: 513
ggcctgtctg tgtgctca 18

<210> SEQ ID NO 514
<211> LENGTH: 19
<212> TYPE: DNA
<213> ORGANISM: Homo Sapiens

<400> SEQUENCE: 514
gagccaccca cttcaggag 19

<210> SEQ ID NO 515
<211> LENGTH: 20
<212> TYPE: DNA
<213> ORGANISM: Homo Sapiens

<400> SEQUENCE: 515
agggtgggtg gaagtttagt 20

<210> SEQ ID NO 516
<211> LENGTH: 19
<212> TYPE: DNA
<213> ORGANISM: Homo Sapiens

<400> SEQUENCE: 516
gagacacggt tgggagagg 19

<210> SEQ ID NO 517
<211> LENGTH: 20
<212> TYPE: DNA
<213> ORGANISM: Homo Sapiens

<400> SEQUENCE: 517
cccacctaca cattccctca 20

<210> SEQ ID NO 518
<211> LENGTH: 20
<212> TYPE: DNA
<213> ORGANISM: Homo Sapiens

<400> SEQUENCE: 518
cagcttccta tgcccagagg 20

<210> SEQ ID NO 519
<211> LENGTH: 18
<212> TYPE: DNA
<213> ORGANISM: Homo Sapiens

<400> SEQUENCE: 519
ctgagcgtgg tggcagtc 18

<210> SEQ ID NO 520

<211> LENGTH: 18
<212> TYPE: DNA
<213> ORGANISM: Homo Sapiens

<400> SEQUENCE: 520
ctgtccctgc tcgtcaca 18

<210> SEQ ID NO 521
<211> LENGTH: 20
<212> TYPE: DNA
<213> ORGANISM: Homo Sapiens

<400> SEQUENCE: 521
cgtacccaga agacaatggc 20

<210> SEQ ID NO 522
<211> LENGTH: 24
<212> TYPE: DNA
<213> ORGANISM: Homo Sapiens

<400> SEQUENCE: 522
ggctttgaaa tggaactgaa aact 24

<210> SEQ ID NO 523
<211> LENGTH: 20
<212> TYPE: DNA
<213> ORGANISM: Homo Sapiens

<400> SEQUENCE: 523
ccaagagtcc ccacatctgg 20

<210> SEQ ID NO 524
<211> LENGTH: 20
<212> TYPE: DNA
<213> ORGANISM: Homo Sapiens

<400> SEQUENCE: 524
atggggttct ccttgggaag 20

<210> SEQ ID NO 525
<211> LENGTH: 20
<212> TYPE: DNA
<213> ORGANISM: Homo Sapiens

<400> SEQUENCE: 525
ggggtagcca ggaagatctc 20

<210> SEQ ID NO 526
<211> LENGTH: 20
<212> TYPE: DNA
<213> ORGANISM: Homo Sapiens

<400> SEQUENCE: 526
ctgcagcact tctttgtcca 20

<210> SEQ ID NO 527
<211> LENGTH: 19
<212> TYPE: DNA
<213> ORGANISM: Homo Sapiens

<400> SEQUENCE: 527
gtgagggagg gaaaggcag 19

<210> SEQ ID NO 528
<211> LENGTH: 20
<212> TYPE: DNA
<213> ORGANISM: Homo Sapiens

<400> SEQUENCE: 528
tacacctccc ctcttggaac 20

<210> SEQ ID NO 529
<211> LENGTH: 20
<212> TYPE: DNA
<213> ORGANISM: Homo Sapiens

<400> SEQUENCE: 529
ctgaggggca atagggaagg 20

<210> SEQ ID NO 530
<211> LENGTH: 20
<212> TYPE: DNA
<213> ORGANISM: Homo Sapiens

<400> SEQUENCE: 530
gcactcggca gatctcagta 20

<210> SEQ ID NO 531
<211> LENGTH: 20
<212> TYPE: DNA
<213> ORGANISM: Homo Sapiens

<400> SEQUENCE: 531
tcatcccttc catcacctcc 20

<210> SEQ ID NO 532
<211> LENGTH: 20
<212> TYPE: DNA
<213> ORGANISM: Homo Sapiens

<400> SEQUENCE: 532
gagccctgtt cttgctgatc 20

<210> SEQ ID NO 533
<211> LENGTH: 20
<212> TYPE: DNA
<213> ORGANISM: Homo Sapiens

<400> SEQUENCE: 533
gcgccctatg accttcacta 20

<210> SEQ ID NO 534
<211> LENGTH: 21
<212> TYPE: DNA
<213> ORGANISM: Homo Sapiens

<400> SEQUENCE: 534
cagagtgtgc ctaggaagtt g 21

<210> SEQ ID NO 535
<211> LENGTH: 20
<212> TYPE: DNA
<213> ORGANISM: Homo Sapiens

<400> SEQUENCE: 535
attcgcccgt agattgaccc 20

<210> SEQ ID NO 536
<211> LENGTH: 18
<212> TYPE: DNA
<213> ORGANISM: Homo Sapiens

<400> SEQUENCE: 536
ccacagggac aagggctg 18

<210> SEQ ID NO 537
<211> LENGTH: 20
<212> TYPE: DNA
<213> ORGANISM: Homo Sapiens

<400> SEQUENCE: 537
tgggattcga accaccaaac 20

<210> SEQ ID NO 538
<211> LENGTH: 19
<212> TYPE: DNA
<213> ORGANISM: Homo Sapiens

<400> SEQUENCE: 538
gacaccaacc cgtctaccc 19

<210> SEQ ID NO 539
<211> LENGTH: 20
<212> TYPE: DNA
<213> ORGANISM: Homo Sapiens

<400> SEQUENCE: 539
ccaccttgca tgggtactca 20

<210> SEQ ID NO 540
<211> LENGTH: 20
<212> TYPE: DNA
<213> ORGANISM: Homo Sapiens

<400> SEQUENCE: 540
acaaccttag gttccaagcc 20

<210> SEQ ID NO 541
<211> LENGTH: 19
<212> TYPE: DNA
<213> ORGANISM: Homo Sapiens

<400> SEQUENCE: 541
gaggccccag gaagaatcc 19

<210> SEQ ID NO 542
<211> LENGTH: 19
<212> TYPE: DNA
<213> ORGANISM: Homo Sapiens

<400> SEQUENCE: 542
ccctgcctct gtgtgtctg 19

<210> SEQ ID NO 543
<211> LENGTH: 19
<212> TYPE: DNA
<213> ORGANISM: Homo Sapiens

<400> SEQUENCE: 543
ccatgcctgg aactgcttc 19

<210> SEQ ID NO 544
<211> LENGTH: 18
<212> TYPE: DNA
<213> ORGANISM: Homo Sapiens

<400> SEQUENCE: 544
catctccacc acccaggg 18

<210> SEQ ID NO 545
<211> LENGTH: 19
<212> TYPE: DNA
<213> ORGANISM: Homo Sapiens

<400> SEQUENCE: 545
ctgaggctgg ccacttgaa 19

<210> SEQ ID NO 546
<211> LENGTH: 19
<212> TYPE: DNA
<213> ORGANISM: Homo Sapiens

<400> SEQUENCE: 546
ccaaaggcca aaggaggtc 19

<210> SEQ ID NO 547
<211> LENGTH: 18
<212> TYPE: DNA
<213> ORGANISM: Homo Sapiens

<400> SEQUENCE: 547
aaggctgcct gggacatc 18

<210> SEQ ID NO 548
<211> LENGTH: 19
<212> TYPE: DNA
<213> ORGANISM: Homo Sapiens

<400> SEQUENCE: 548
tccccttccc tgactccag 19

<210> SEQ ID NO 549
<211> LENGTH: 18
<212> TYPE: DNA
<213> ORGANISM: Homo Sapiens

<400> SEQUENCE: 549
gacacaggct ggagctcc 18

<210> SEQ ID NO 550
<211> LENGTH: 18
<212> TYPE: DNA
<213> ORGANISM: Homo Sapiens

<400> SEQUENCE: 550
ccagggggag aaggacct 18

<210> SEQ ID NO 551
<211> LENGTH: 20
<212> TYPE: DNA
<213> ORGANISM: Homo Sapiens

<400> SEQUENCE: 551
ccaagccgct taatccttcc 20

<210> SEQ ID NO 552
<211> LENGTH: 20
<212> TYPE: DNA
<213> ORGANISM: Homo Sapiens

<400> SEQUENCE: 552
tgcccccaga atgacaacta 20

<210> SEQ ID NO 553
<211> LENGTH: 20
<212> TYPE: DNA
<213> ORGANISM: Homo Sapiens

<400> SEQUENCE: 553
aatctcagac cccacccttc 20

<210> SEQ ID NO 554
<211> LENGTH: 20
<212> TYPE: DNA
<213> ORGANISM: Homo Sapiens

<400> SEQUENCE: 554
cccaccttga acacgcaaat 20

<210> SEQ ID NO 555
<211> LENGTH: 20
<212> TYPE: DNA
<213> ORGANISM: Homo Sapiens

<400> SEQUENCE: 555
cctcctctac tgctaaggcc 20

<210> SEQ ID NO 556
<211> LENGTH: 20
<212> TYPE: DNA
<213> ORGANISM: Homo Sapiens

<400> SEQUENCE: 556
gaccgcaaag ccggtactta 20

<210> SEQ ID NO 557
<211> LENGTH: 20
<212> TYPE: DNA
<213> ORGANISM: Homo Sapiens

<400> SEQUENCE: 557 caccctttc ccgtctgaag 20

<210> SEQ ID NO 558
<211> LENGTH: 19
<212> TYPE: DNA
<213> ORGANISM: Homo Sapiens

<400> SEQUENCE: 558
gacctcagac cgaagtccc 19

<210> SEQ ID NO 559
<211> LENGTH: 18
<212> TYPE: DNA
<213> ORGANISM: Homo Sapiens

<400> SEQUENCE: 559
agggaagggt gcaggtag 18

<210> SEQ ID NO 560
<211> LENGTH: 19
<212> TYPE: DNA
<213> ORGANISM: Homo Sapiens

<400> SEQUENCE: 560
atatgtgggg agcatgcgt 19

<210> SEQ ID NO 561
<211> LENGTH: 19
<212> TYPE: DNA
<213> ORGANISM: Homo Sapiens

<400> SEQUENCE: 561
gctccaggcc tttgtctta 19

<210> SEQ ID NO 562
<211> LENGTH: 20
<212> TYPE: DNA
<213> ORGANISM: Homo Sapiens

<400> SEQUENCE: 562
tcaaaggcgg ccaaagaatt 20

<210> SEQ ID NO 563
<211> LENGTH: 20
<212> TYPE: DNA
<213> ORGANISM: Homo Sapiens

<400> SEQUENCE: 563
cccactttct ccccctcaat 20

<210> SEQ ID NO 564
<211> LENGTH: 19
<212> TYPE: DNA
<213> ORGANISM: Homo Sapiens

<400> SEQUENCE: 564
ttctacacga ccaggccag 19

<210> SEQ ID NO 565
<211> LENGTH: 18
<212> TYPE: DNA
<213> ORGANISM: Homo Sapiens

<400> SEQUENCE: 565
cctgaaccct ggaccctg 18

<210> SEQ ID NO 566
<211> LENGTH: 18
<212> TYPE: DNA
<213> ORGANISM: Homo Sapiens

<400> SEQUENCE: 566
cgaagtcctg ggagcccc 18

<210> SEQ ID NO 567
<211> LENGTH: 20
<212> TYPE: DNA
<213> ORGANISM: Homo Sapiens

<400> SEQUENCE: 567
tcggatggct acagtctgtg 20

<210> SEQ ID NO 568
<211> LENGTH: 20
<212> TYPE: DNA
<213> ORGANISM: Homo Sapiens

<400> SEQUENCE: 568
cagacctggg tggctatgag 20

<210> SEQ ID NO 569
<211> LENGTH: 18
<212> TYPE: DNA
<213> ORGANISM: Homo Sapiens

<400> SEQUENCE: 569
cagcaagcct ggccatgg 18

<210> SEQ ID NO 570
<211> LENGTH: 18
<212> TYPE: DNA
<213> ORGANISM: Homo Sapiens

<400> SEQUENCE: 570
tcctccccaa ctcccact 18

<210> SEQ ID NO 571
<211> LENGTH: 20
<212> TYPE: DNA
<213> ORGANISM: Homo Sapiens

<400> SEQUENCE: 571
ccagagagta gaacagggca 20

<210> SEQ ID NO 572
<211> LENGTH: 19
<212> TYPE: DNA
<213> ORGANISM: Homo Sapiens

<400> SEQUENCE: 572
ctggcctcac actgtctgg 19

<210> SEQ ID NO 573
<211> LENGTH: 20
<212> TYPE: DNA
<213> ORGANISM: Homo Sapiens

<400> SEQUENCE: 573
gtaaaaactg cacccagcct 20

<210> SEQ ID NO 574
<211> LENGTH: 18
<212> TYPE: DNA
<213> ORGANISM: Homo Sapiens

<400> SEQUENCE: 574
tcacccctag gcccatga 18

<210> SEQ ID NO 575
<211> LENGTH: 18
<212> TYPE: DNA
<213> ORGANISM: Homo Sapiens

<400> SEQUENCE: 575
agtctccgga gccccatg 18

<210> SEQ ID NO 576
<211> LENGTH: 19
<212> TYPE: DNA
<213> ORGANISM: Homo Sapiens

<400> SEQUENCE: 576
cctctatatc cccgccccc 19

<210> SEQ ID NO 577
<211> LENGTH: 18
<212> TYPE: DNA
<213> ORGANISM: Homo Sapiens

<400> SEQUENCE: 577
cacctgtgcc cgctccta 18

<210> SEQ ID NO 578
<211> LENGTH: 18
<212> TYPE: DNA
<213> ORGANISM: Homo Sapiens

<400> SEQUENCE: 578
agggttccgt ggggactc 18

<210> SEQ ID NO 579
<211> LENGTH: 18
<212> TYPE: DNA
<213> ORGANISM: Homo Sapiens

<400> SEQUENCE: 579
taccaggcag ggttggtg 18

<210> SEQ ID NO 580
<211> LENGTH: 18
<212> TYPE: DNA
<213> ORGANISM: Homo Sapiens

<400> SEQUENCE: 580
cgtcgttgtc tccccgaa 18

<210> SEQ ID NO 581
<211> LENGTH: 19
<212> TYPE: DNA
<213> ORGANISM: Homo Sapiens

<400> SEQUENCE: 581
ctgcttcccc accatcctg 19

<210> SEQ ID NO 582
<211> LENGTH: 20
<212> TYPE: DNA
<213> ORGANISM: Homo Sapiens

<400> SEQUENCE: 582
gtatgggctc agctgcaatt 20

<210> SEQ ID NO 583
<211> LENGTH: 20
<212> TYPE: DNA

<213> ORGANISM: Homo Sapiens

<400> SEQUENCE: 583
ttgtggggta ggacagtgac 20

<210> SEQ ID NO 584
<211> LENGTH: 20
<212> TYPE: DNA
<213> ORGANISM: Homo Sapiens

<400> SEQUENCE: 584
ctcgacaaag caacaggtcc 20

<210> SEQ ID NO 585
<211> LENGTH: 20
<212> TYPE: DNA
<213> ORGANISM: Homo Sapiens

<400> SEQUENCE: 585
agtgcaaggt cacagaggtc 20

<210> SEQ ID NO 586
<211> LENGTH: 20
<212> TYPE: DNA
<213> ORGANISM: Homo Sapiens

<400> SEQUENCE: 586
aaatgagcct ctcagtgccc 20

<210> SEQ ID NO 587
<211> LENGTH: 19
<212> TYPE: DNA
<213> ORGANISM: Homo Sapiens

<400> SEQUENCE: 587
ctctctgggg gctgagact 19

<210> SEQ ID NO 588
<211> LENGTH: 18
<212> TYPE: DNA
<213> ORGANISM: Homo Sapiens

<400> SEQUENCE: 588
cacccacgaa aacccacc 18

<210> SEQ ID NO 589
<211> LENGTH: 19
<212> TYPE: DNA
<213> ORGANISM: Homo Sapiens

<400> SEQUENCE: 589
tctgcgaagt cctgggaag 19

<210> SEQ ID NO 590
<211> LENGTH: 20
<212> TYPE: DNA
<213> ORGANISM: Homo Sapiens

<400> SEQUENCE: 590
taacttccat cagaggcgct 20

<210> SEQ ID NO 591
<211> LENGTH: 20

<212> TYPE: DNA
<213> ORGANISM: Homo Sapiens

<400> SEQUENCE: 591
atgcatctaa agccccgaga 20

<210> SEQ ID NO 592
<211> LENGTH: 19
<212> TYPE: DNA
<213> ORGANISM: Homo Sapiens

<400> SEQUENCE: 592
catcctcccc cagtgtctg 19

<210> SEQ ID NO 593
<211> LENGTH: 18
<212> TYPE: DNA
<213> ORGANISM: Homo Sapiens

<400> SEQUENCE: 593
cacacacagg gcccactg 18

<210> SEQ ID NO 594
<211> LENGTH: 20
<212> TYPE: DNA
<213> ORGANISM: Homo Sapiens

<400> SEQUENCE: 594
gacttttcga gggcctttcc 20

<210> SEQ ID NO 595
<211> LENGTH: 19
<212> TYPE: DNA
<213> ORGANISM: Homo Sapiens

<400> SEQUENCE: 595
gggcagacgg ggaaactta 19

<210> SEQ ID NO 596
<211> LENGTH: 19
<212> TYPE: DNA
<213> ORGANISM: Homo Sapiens

<400> SEQUENCE: 596
ctgtcacagg ccaagggag 19

<210> SEQ ID NO 597
<211> LENGTH: 20
<212> TYPE: DNA
<213> ORGANISM: Homo Sapiens

<400> SEQUENCE: 597
caggtcttta ggaggagggg 20

<210> SEQ ID NO 598
<211> LENGTH: 19
<212> TYPE: DNA
<213> ORGANISM: Homo Sapiens

<400> SEQUENCE: 598
ctctagctgg ccggtcttc 19

<210> SEQ ID NO 599

<211> LENGTH: 20
<212> TYPE: DNA
<213> ORGANISM: Homo Sapiens

<400> SEQUENCE: 599
tttccaaccc ctccctactc 20

<210> SEQ ID NO 600
<211> LENGTH: 20
<212> TYPE: DNA
<213> ORGANISM: Homo Sapiens

<400> SEQUENCE: 600
ttttacgcgt ggaatgcaca 20

<210> SEQ ID NO 601
<211> LENGTH: 20
<212> TYPE: DNA
<213> ORGANISM: Homo Sapiens

<400> SEQUENCE: 601
aagagggaaa agttgccact 20

<210> SEQ ID NO 602
<211> LENGTH: 18
<212> TYPE: DNA
<213> ORGANISM: Homo Sapiens

<400> SEQUENCE: 602
ccctcgcctc cctcactg 18

<210> SEQ ID NO 603
<211> LENGTH: 20
<212> TYPE: DNA
<213> ORGANISM: Homo Sapiens

<400> SEQUENCE: 603
gcgtatgatg gaggcgtagt 20

<210> SEQ ID NO 604
<211> LENGTH: 18
<212> TYPE: DNA
<213> ORGANISM: Homo Sapiens

<400> SEQUENCE: 604
aggatggccg cagagatg 18

<210> SEQ ID NO 605
<211> LENGTH: 19
<212> TYPE: DNA
<213> ORGANISM: Homo Sapiens

<400> SEQUENCE: 605
cagacctctc ctccagcct 19

<210> SEQ ID NO 606
<211> LENGTH: 19
<212> TYPE: DNA
<213> ORGANISM: Homo Sapiens

<400> SEQUENCE: 606
caaagcctcg cacacactc 19

<210> SEQ ID NO 607
<211> LENGTH: 20
<212> TYPE: DNA
<213> ORGANISM: Homo Sapiens

<400> SEQUENCE: 607
gtaacgattg cccagtgctc 20

<210> SEQ ID NO 608
<211> LENGTH: 19
<212> TYPE: DNA
<213> ORGANISM: Homo Sapiens

<400> SEQUENCE: 608
caccccagcg cactagtta 19

<210> SEQ ID NO 609
<211> LENGTH: 143
<212> TYPE: DNA
<213> ORGANISM: Homo Sapiens

<400> SEQUENCE: 609
gctcattttt gttaatggtg gctttttgtt tgtttgtttt gttttaaggt ttttggattc 60
aaagcataaa aaccattaca agatatacaa tctgtaagta tgttttctta tttgtatgct 120
tgcaaatatc ttctaaaaca act 143

<210> SEQ ID NO 610
<211> LENGTH: 143
<212> TYPE: DNA
<213> ORGANISM: Homo Sapiens

<400> SEQUENCE: 610
gaacaatgaa taaaccattt tgtctcatta aaattttaga ttattatgta gttggcagct 60
gagaacaata cttagtggat accatcgaat agtacaacag gtaagtcctt tttaaaaggt 120
ttatgttttc agtgaagata aga 143

<210> SEQ ID NO 611
<211> LENGTH: 160
<212> TYPE: DNA
<213> ORGANISM: Homo Sapiens

<400> SEQUENCE: 611
atcatgctga cgcttctcct ttatctttta aaatttgcag tggctgagag gactactaac 60
tagtagacag agttttaaca tcatatttgg tgaatgtcca tattgtagta aggtaagcaa 120
attgttaatc acatctcata aaatgtgcct agctttcagt 160

<210> SEQ ID NO 612
<211> LENGTH: 241
<212> TYPE: DNA
<213> ORGANISM: Homo Sapiens

<400> SEQUENCE: 612
tgcagatttt taaaaagtct cttttccatt attttttcaa cttataggaa tgaggcaaag 60
tagcctaaag aaagattggt tcttatcaga agaagaattt aaattatgga acagacttta 120
tagattaagg gacagtgatg aaattaaaga gataacattg cctcaagttc agttttcttc 180
tttacaaaat gaggaaaaca aaccagtaag ttgaatatat tttcagatgt tcttttcccc 240
c 241

<210> SEQ ID NO 613
<211> LENGTH: 104
<212> TYPE: DNA
<213> ORGANISM: Homo Sapiens

<400> SEQUENCE: 613
agttaataag gacatggttt ctgttctttt tttacagata cttttaaagt tttgtcagaa 60
aagagccact ttcaaggtag gacaagtttg gaaatgtatt ctca 104

<210> SEQ ID NO 614
<211> LENGTH: 173
<212> TYPE: DNA
<213> ORGANISM: Homo Sapiens

<400> SEQUENCE: 614
aggaaactag agttcatttt ccttttctta ggacctgtta tggaatttga ttatgtaata 60
tgcgaagaat gtgggaaaga atttatggat tcttatctta tgaaccactt tgatttgcca 120
acttgtgata actgcaggta cttattttag atggtgttct taattgctaa tgt 173

<210> SEQ ID NO 615
<211> LENGTH: 209
<212> TYPE: DNA
<213> ORGANISM: Homo Sapiens

<400> SEQUENCE: 615
tcgcaagtct gaatcacaac ttatttaaat atggattttg tgttgtagat tgtgaagagg 60
tctcttgaag tttggggtag tcaagaagca ttagaagaag caaaggaagt ccgacaggaa 120
aaccgagaaa aaatgaaaca gaagaaattt gataaaaaag taaaaggtag atggccacat 180
tttatatcgt gaaggattgt gttttacca 209

<210> SEQ ID NO 616
<211> LENGTH: 192
<212> TYPE: DNA
<213> ORGANISM: Homo Sapiens

<400> SEQUENCE: 616
tgtgcattga gagtttttat actagtgatt ttaaactata atttttgcag aatgtgaaaa 60
gctatttttc caatcatgat gaaagtctga agaaaaatga tagatttatc gcttctgtga 120
cagacagtga aaacacaaat caaagagaag ctgcaagtca tggtaagtcc tctgtttagt 180
tgaactacag gt 192

<210> SEQ ID NO 617
<211> LENGTH: 332
<212> TYPE: DNA
<213> ORGANISM: Homo Sapiens

<400> SEQUENCE: 617
ccaggttagc tggtaagagg atttttttgg agaaaaaaat gatatttaga aagttaattt 60
ctaattccgg aatggaataa aaacaatatg agtagtgtaa tcttgtagaa aaagagttgt 120
ataatcttgt agaatttctc attctgtggt acaacccagg ggtaaactat tattccagta 180
gtcagtacac ttttctagat aaatcttgag tgaaaaccag caatttcttt ttccttgtgg 240
tctgattcct ttttctaatc catgaaggcc atcttgtaga ttacatttat cattaatgca 300
agaataaaga caattcctcc tgtcagttgc gt 332

<210> SEQ ID NO 618
<211> LENGTH: 155
<212> TYPE: DNA
<213> ORGANISM: Homo Sapiens

<400> SEQUENCE: 618
aagcttttca ggataatttc tgtttttttt tgtttgtttg tttttaggag ttatggtaca 60
gcacctgtaa atcttaacat caagacaggg ggaagagttt atggaactac aggtaaaatt 120
tgtattttct gttgcatcaa tagggaaata aggca 155

<210> SEQ ID NO 619
<211> LENGTH: 212
<212> TYPE: DNA
<213> ORGANISM: Homo Sapiens

<400> SEQUENCE: 619
aggatgatac tggttgacac aattgtttta ttttatttca gttggttaga agcaaacgct 60
gaatatcttg tagaaagaga ttatgaatca gcttgtaaaa tatggagtgg aaatgaaatg 120
ctcttaactt tacacaaaat gggtatcacc actgctactt ttcccatttt gcaggtaaga 180 tatttttttct acctgtgaaa cgtatttagt ga 212

<210> SEQ ID NO 620
<211> LENGTH: 151
<212> TYPE: DNA
<213> ORGANISM: Homo Sapiens

<400> SEQUENCE: 620
tcagcttttc cttaaagtca cttcattttt attttcagtg aagaactgtt ctaccagata 60
ctcatttatg attttgccaa ttttggtgtt ctcaggttat cggtaagttt agatcctttt 120
cacttctgaa atttcaactg atcgtttctg a 151

<210> SEQ ID NO 621
<211> LENGTH: 150
<212> TYPE: DNA
<213> ORGANISM: Homo Sapiens

<400> SEQUENCE: 621
caccatatat taacttctga catttgcaaa tttcaggagt tgtcacagca gaaatgttta 60
gacatatgca gaactctgag ataattcgaa aaatgactga agaattcgat gaggtaactt 120
actaccttaa gtgttttgat aacttatgca 150

<210> SEQ ID NO 622
<211> LENGTH: 150
<212> TYPE: DNA
<213> ORGANISM: Homo Sapiens

<400> SEQUENCE: 622
gctacaaaag agctcaacaa ttttttttatt acgtgcaatt tttttaatag gaataaaaaa 60
atacgttgtt ggcctcatta tcaagacgtc atctgaccca acttgtgtag aggtaagagt 120
ttattttgga gcttattggg agagcataaa 150

<210> SEQ ID NO 623
<211> LENGTH: 146
<212> TYPE: DNA
<213> ORGANISM: Homo Sapiens

<400> SEQUENCE: 623
gtgattttct aaaatagcag gctcttattt ttctttttgt ttgtttgtag cgatacaaac 60
ttggagttcg cttgtattac cgagtaatgg aatccatgct taaatcagta agttaaaaac 120
aatataaaaa aatttcagcc gggcgc 146

<210> SEQ ID NO 624
<211> LENGTH: 128
<212> TYPE: DNA
<213> ORGANISM: Homo Sapiens

<400> SEQUENCE: 624
tcaccactga gcaaatgttt gaaattatgt taattttgac aggtacaaaa tcaacatgca 60
aaagaagagt ctcttgctga tgatcttttt aggtaaagtt tgattcacct ttctcatgta 120
cctttgag 128

<210> SEQ ID NO 625
<211> LENGTH: 199
<212> TYPE: DNA
<213> ORGANISM: Homo Sapiens

<400> SEQUENCE: 625
agcagttgtg attctttctt tctacttgtg tgatttacag gattaaagac aacaactcca 60
ggaccaagcc tttcacaagg cgtgtcagtt gatgaaaaac taatgccaag cgccccagtg 120
aacactacaa catacgtagc tgacacagaa tcagagcaag cagatacatg gtaaagcttc 180
ttcattaccg tactattgt 199

<210> SEQ ID NO 626
<211> LENGTH: 160
<212> TYPE: DNA
<213> ORGANISM: Homo Sapiens

<400> SEQUENCE: 626
ttggaagtat aatagcagtt cttttctctt tataggttag accaaagcca ttgcttttga 60
agttattaaa gtctgttggt gcacaaaaag acacttatac tatgaaagag gtaagctgaa 120
tcaagagata agtagtatct cactagttac atgtagccat 160

<210> SEQ ID NO 627
<211> LENGTH: 177
<212> TYPE: DNA
<213> ORGANISM: Homo Sapiens

<400> SEQUENCE: 627
tgacagctat gctaatagtg tttcttgtct atataattgc agatctctac aatatggaaa 60
tcagttcata tatcagtcaa tgccacgaat gttaactcta tggcttgatt atggtacaaa 120
ggcatatgaa tgggaaaaag gtataactct tcacgtaaaa gttttaaagg actagga 177

<210> SEQ ID NO 628
<211> LENGTH: 159
<212> TYPE: DNA
<213> ORGANISM: Homo Sapiens

<400> SEQUENCE: 628
tgggtgcttg ggtgtgtata aacacatgat actgtatcat agcaataaga tttgtaaaac 60
attgcaatgg ctgaaaaact gtctaacagg aaattttaag tgttattcca aagaagaaca 120
agcctaaaag taagttaacc tttcagagtg gttgaaagt 159

<210> SEQ ID NO 629
<211> LENGTH: 176
<212> TYPE: DNA
<213> ORGANISM: Homo Sapiens

<400> SEQUENCE: 629
tctgtcttct cctctcttcc tttacacaaa cttaaacaga atggaaatga aaaccaagga 60
gaagttgaag aacaaacatt taaagaaaag gaattagaca gaaaacctga agatgtgcct 120
cctgagattt tgtctaatga aaggtataca aaatgtgtac tttttcagtg caaagt 176

<210> SEQ ID NO 630
<211> LENGTH: 150
<212> TYPE: DNA
<213> ORGANISM: Homo Sapiens

<400> SEQUENCE: 630
tggttaggag aatgagttgt tgttgttgat gttgtttttt aaccacacag acctttccaa 60
ataaaagatt ccagttgcat atgaaatatt agatcacaag tacagtaagt aatatttctc 120
taacatgtca tccctcttga aggagctgtc 150

<210> SEQ ID NO 631
<211> LENGTH: 152
<212> TYPE: DNA
<213> ORGANISM: Homo Sapiens

<400> SEQUENCE: 631
tgcatctgtg gcattaaatg gtgatacata ttatttgaat ttcagattta cggcaagata 60
tgctaacact tcaaattatt cgtattatgg aaaatatctg gcaaaatcaa ggtcttgatc 120
ttcggtaggt aaccagtaag gcaacctgta tg 152

<210> SEQ ID NO 632
<211> LENGTH: 108
<212> TYPE: DNA
<213> ORGANISM: Homo Sapiens

<400> SEQUENCE: 632
atggttttta tgacacagag ttgtgatttt ttttcttttt cacagtttct caagcaagac 60
ctcccccaaa tcagaagaaa ggtgaggttg tgcatatgat tttaaact 108

<210> SEQ ID NO 633
<211> LENGTH: 161
<212> TYPE: DNA
<213> ORGANISM: Homo Sapiens

<400> SEQUENCE: 633
aggatcactt tatatggatc actttttctt attttgtagt cttcaaaaat taaaaaagga 60
agcaaagggg atacatccat gttgaaacca acactgatgg cagcagttcc ggtaagaagt 120
gacccttatt taatattgag tattaaagaa gtatcacccg c 161

<210> SEQ ID NO 634
<211> LENGTH: 158
<212> TYPE: DNA
<213> ORGANISM: Homo Sapiens

<400> SEQUENCE: 634
tgtgtacatg gtgccagaat atttgttttt cttcttatag aatgtccaac atcccagctt 60
gcttccttgg atcagcacag tcagaaaatg ttctaacaga tattaaattg tgagtaattt 120
ttttccctca acttttattt tggatttatg ggggtgca 158

<210> SEQ ID NO 635
<211> LENGTH: 200
<212> TYPE: DNA
<213> ORGANISM: Homo Sapiens

<400> SEQUENCE: 635
agtcaatttt tctttcttct cttgcaggtg aacctatggg tcgtggaaca aaagttatcc 60
tacacctgaa agaagaccaa actgagtact tggaggaacg aagaataaag gagattgtga 120
agaaacattc tcagtttatt ggatatccca ttactctttt tgtaagtttt tatgtaattg 180
cagagtgaat ttctgtctgt 200

<210> SEQ ID NO 636
<211> LENGTH: 150
<212> TYPE: DNA
<213> ORGANISM: Homo Sapiens

<400> SEQUENCE: 636
ttggaggcca ctgctatggc ttatgaaaat aattgttttt tgttttacag tgggcaaatc 60
aaactagcag attttggact tgctcggctc tataactctg aagagaggta aggcattaat 120
taaaattaca tgtgggaaat aaggtttgtt 150

<210> SEQ ID NO 637
<211> LENGTH: 194
<212> TYPE: DNA
<213> ORGANISM: Homo Sapiens

<400> SEQUENCE: 637
aaatgtattc actgtcttct ctttctttag gttccagcaa caaattatat atatacaccc 60
ctgaatcaac ttaagggtgg tacaattgtc aatgtctatg gtgttgtgaa gttctttaag 120
cccccatatc taagcaaagg aactggtagg tattaaaact ggtggagttt tttggagtgg 180
aaatgcatta ttga 194

<210> SEQ ID NO 638
<211> LENGTH: 154
<212> TYPE: DNA
<213> ORGANISM: Homo Sapiens

<400> SEQUENCE: 638
tgtgtgactc taaattgact gcattaattt tctcactctc gtcttgcagc attttcagtt 60
agctttggtt gactgtaatc cctgcacttt gtccaatgct gaaagtaagt attattaagt 120
actgtagttt tctacatgta ttccgatcac ttca 154

<210> SEQ ID NO 639
<211> LENGTH: 211
<212> TYPE: DNA
<213> ORGANISM: Homo Sapiens

<400> SEQUENCE: 639
tgtgtgacat gttctaatat agtcacattt tcattatttt tattataagg cctgctgaaa 60
atgactgaat ataaacttgt ggtagttgga gctggtggcg taggcaagag tgccttgacg 120
atacagctaa ttcagaatca ttttgtggac gaatatgatc caacaataga ggtaaatctt 180
gttttaatat gcatattact ggtgcaggac c 211

<210> SEQ ID NO 640
<211> LENGTH: 183
<212> TYPE: DNA
<213> ORGANISM: Homo Sapiens

<400> SEQUENCE: 640
atgcaaagta cctaactcca ctgatttctt tttccctcac tttttaggat tatggctgct 60
gttcctcaaa ataatctaca ggagcaacta gaacgtcact cagccagaac acttaataat 120
aaattaagtc tttcaaaacc aaaattttcg taagtgtttt gactggtttg ctgtcacata 180
ggc 183

<210> SEQ ID NO 641
<211> LENGTH: 161
<212> TYPE: DNA
<213> ORGANISM: Homo Sapiens

<400> SEQUENCE: 641
tgtttgtgcc tcactttgca ggagttccac tatatagaag aagatcttta tcgaacaaag 60
aacacattgc aaagcagaat taaagatcga gacgaagaaa ttcaaaaact caggaatcag 120
gtatgaatca ctattcacaa cttgtgaaaa gatgccactg a 161

<210> SEQ ID NO 642
<211> LENGTH: 150
<212> TYPE: DNA
<213> ORGANISM: Homo Sapiens

<400> SEQUENCE: 642
acacgtcttg ggatatcac ttttgttatt tttattttta gggaagcaca ctgagaaagc 60
ggaagatgta tgaggaattc cttagtaaag tctctatttt aggtgagttg taaagtgtgt 120
taactttgct agtatgtgag atacccctga 150

<210> SEQ ID NO 643
<211> LENGTH: 155
<212> TYPE: DNA
<213> ORGANISM: Homo Sapiens

<400> SEQUENCE: 643
actggtatgg aaatattaca gtcctgtaat tctttcttct aggtcatatt gaacattcca 60
gatacctatc attactcgat gctgttgata acagcaagat ggctttgaac tcagtaagtg 120
gttaattatt accttcctgg ccttttcttt gttcc 155

<210> SEQ ID NO 644
<211> LENGTH: 198
<212> TYPE: DNA
<213> ORGANISM: Homo Sapiens

<400> SEQUENCE: 644
gccatgtttt acatttgagt tcacagaaag gaaatgttta ttctaggtct gcttcgcctg 60
tgtagatggg aaagaattcc gtcttgctca gatgtgtgga cttcatattg ttgtacatgc 120
agatgaatta gaagaactta tcaactacta tcaggtatta acgagacttt tatatgacct 180
gagatctttt accataga 198

<210> SEQ ID NO 645
<211> LENGTH: 160
<212> TYPE: DNA
<213> ORGANISM: Homo Sapiens

<400> SEQUENCE: 645
acaaggctga gacctgagtt gataaaattt ctttgttctt tcagtgaaga gaaaggaagt 60
acagaaaaca tgcagaaagc acagaaagga aaaccaaggt tctcatgaat ctccaacttt 120
aaatcctgta ggtattgaaa taggtatcag ctttccttga 160

<210> SEQ ID NO 646
<211> LENGTH: 173
<212> TYPE: DNA
<213> ORGANISM: Homo Sapiens

<400> SEQUENCE: 646
tgtcactttg ttctgtttgc aggtggaaaa ccatgaattc cttgtaaaac cttcatttga 60
tcctaatctc agtgaattaa gagaaataat gaatgacttg gaaaagaaga tgcagtcaac 120
attaataagt gcagccagag atcttggtaa gaatgggtca ttggaggttg gaa 173

<210> SEQ ID NO 647
<211> LENGTH: 135
<212> TYPE: DNA
<213> ORGANISM: Homo Sapiens

<400> SEQUENCE: 647
tggctgttgt cactattgca tatgctaact ttttctgttt acatttcagg gcatttgaat 60
atgaaattcg attttacact ggaaatgacc ctctggatgt ttgggatagg tgggtctttt 120
tatttcacaa ggaca 135

<210> SEQ ID NO 648
<211> LENGTH: 150
<212> TYPE: DNA
<213> ORGANISM: Homo Sapiens

<400> SEQUENCE: 648
gctgtttctc ttttctccac cattctatag gaataagatg gtagaatacc tgacagactg 60
ggttatggga acatcaaacc aagcagcaga tgatgatgta aaatgtctta caaggtaaaa 120
aaagaatgac cttcaagtat tagtgggttt 150

<210> SEQ ID NO 649
<211> LENGTH: 150
<212> TYPE: DNA
<213> ORGANISM: Homo Sapiens

<400> SEQUENCE: 649
actgtgtatt catgttcccc tttctagtgc tgattataaa cctaagaaaa ttaaaacaga 60
agataccaag aaggagaaga aaagaaaact agaagaagaa gaggttagta aagagactta 120
ggtcctttgg ggcttgagtt tggaagtggg 150

<210> SEQ ID NO 650
<211> LENGTH: 150
<212> TYPE: DNA
<213> ORGANISM: Homo Sapiens

<400> SEQUENCE: 650
ggatttaact ttgtttttct ctgcctgatt gggttctctc tttattttag tttctacaga 60
gcctgtggag acctctcgat ggacagaaga agaaatggaa gttgctaaaa aaggtaaatt 120
gtagtagttc tggtttctca ggtttttgtt 150

<210> SEQ ID NO 651
<211> LENGTH: 158
<212> TYPE: DNA
<213> ORGANISM: Homo Sapiens

<400> SEQUENCE: 651
agacttcgag tgtttaaatg aaagattaaa gtctcaatac ttttttaggt acaatggtgg 60
ctgttgcaat tagcccagga actagaggag agactgacta aagaccgaaa tgatgtaaga 120
ttttctttct ttattcctgg ggtgggcttt gcaattta 158

<210> SEQ ID NO 652
<211> LENGTH: 128
<212> TYPE: DNA
<213> ORGANISM: Homo Sapiens

<400> SEQUENCE: 652
tcagaagttc tggaaatact tcatttattt ttaaatcctt ttgttttagg ctctccagca 60
gaactatctc ctactactct ttcccctgtt aatcatagct tgggtaagtt gcacatatgt 120
tcccctca 128

<210> SEQ ID NO 653
<211> LENGTH: 152
<212> TYPE: DNA
<213> ORGANISM: Homo Sapiens

<400> SEQUENCE: 653
atgcttcaga tgttgtatgt aatgtattct ttttatttta tgtgtagatg gctcttggac 60
aagtccgagc agtacaacac actgggaggg aatgccctct ccttttaaag gcaggaattt 120
ttatttatta cctgtgttca gtatgtaaac gt 152

<210> SEQ ID NO 654
<211> LENGTH: 133
<212> TYPE: DNA
<213> ORGANISM: Homo Sapiens

<400> SEQUENCE: 654
ctactcatgc ccctcaaact tatttttaat aatttctttt cccttcacag ctatttgcat 60
gcaaagaaca tcatccatag agacatgaaa tccaacagta tcctttggtt gttgagttca 120
tttgactgct cgg 133

<210> SEQ ID NO 655
<211> LENGTH: 151
<212> TYPE: DNA
<213> ORGANISM: Homo Sapiens

<400> SEQUENCE: 655
tcttaaatga tcctcttctc ccagataata gatgccactc aaaaaggaaa ttgctctcgt 60
ttcatgaatc acagctgtga accaaattgt gaaacccaaa aagtaagttg aggtggattt 120
agagtttgag gtatttgttc acgattgctg t 151

<210> SEQ ID NO 656
<211> LENGTH: 151
<212> TYPE: DNA
<213> ORGANISM: Homo Sapiens

<400> SEQUENCE: 656
gcgatgtgca tatataatgg aaaggttttt gttattttca gggtccacca atgagctgtg 60
tacgattggc tgaaagagtt gtagctctca tttgctgtga gaaactgcac aaaattggta 120
aggatgtttg aaaagcatat acgaatgaaa a 151

<210> SEQ ID NO 657
<211> LENGTH: 151
<212> TYPE: DNA
<213> ORGANISM: Homo Sapiens

<400> SEQUENCE: 657
aatcctgttt gcagcgtgag ttaacctgca actgattttg ttttacagat ggttttatca 60
ttagcgtctg aactcagaga gaatcatctt aatggattta acactcaaag gcggtaggtg 120
ttaaactaaa catccttctt ctcaggtttc a 151

<210> SEQ ID NO 658
<211> LENGTH: 151
<212> TYPE: DNA
<213> ORGANISM: Homo Sapiens

<400> SEQUENCE: 658
actccattca gaaagtaatt ttcacctttt tttttttttc aaggaaactg agaagaaaat 60
atggcacttc aaatatccta tcttcttcct gtgtataggg ctagacttac aggtagagtg 120
aagctatggg accaggtcac agtgaagtcc t 151

<210> SEQ ID NO 659
<211> LENGTH: 171
<212> TYPE: DNA
<213> ORGANISM: Homo Sapiens

<400> SEQUENCE: 659
tcaggatttt tcctttctct ctcctattat tagacttatt cgtctaatgg aagagatcat 60
gagtgagaag gagaataaaa ccattgtttt tgtggaaacc aaaagaagat gtgatgagct 120
taccagaaaa atgaggagag atgggtatgt gtgagctcct ccattgaagc a 171

<210> SEQ ID NO 660
<211> LENGTH: 339
<212> TYPE: DNA
<213> ORGANISM: Homo Sapiens

<400> SEQUENCE: 660
gagttctagg ctactgtggc tttttccagt agatttagat gagattatgt gttttgaaat 60
gttttgtggg atcccttaga aagcatcact tcagggcaga gacactcaat attgccagcc 120
agcttgggtt ctaaagtgat ttaatcaaat tcatgctcct gatctttttt ttcccccttc 180
ctttggctat gaaaacccaa agcccggagt gattgttttc tccttgcttt aagcagtgaa 240
gttatcctaa tgcaaaagag cttagtagaa aatgagtggt ttaccttttt ttctaaaagt 300
atattttcaa gtttattctg gaatgtgatg tcttggtcc 339

<210> SEQ ID NO 661
<211> LENGTH: 176
<212> TYPE: DNA
<213> ORGANISM: Homo Sapiens

<400> SEQUENCE: 661
gtgaatacac tttctgctgg ttttaaatga cagatactga aataaaaata aacatcaaac 60
aagaaagtgc agatgtaaat gtgattggaa acaaggatgt cgttactgaa gaggatttgg 120
atgtttttaa gcaggcccag gaactttctt gggaggtaag gcgaggatcc cacatt 176

<210> SEQ ID NO 662
<211> LENGTH: 159
<212> TYPE: DNA
<213> ORGANISM: Homo Sapiens

<400> SEQUENCE: 662
aaccaagtca gtaaggccat atacagttat tatgtttttt actctcaggg gaaagttggg 60
gacatgctgc tacaatacgg ctaatctttc attgggaccg aaagcaaagg tcagtacaga 120
aacaagttaa taactccgaa tattgggtta attatactg 159

<210> SEQ ID NO 663
<211> LENGTH: 151
<212> TYPE: DNA
<213> ORGANISM: Homo Sapiens

<400> SEQUENCE: 663
aaacccttct gtttctttca cagatgagtg ccaaaccaaa tatggaaatg ctaatgcctg 60
gagatactgt accaaagttt ttgacatgct cacagtagca gctgtaagtt tctattttta 120
aagtctcatg tacgttcctg ccaataacac a 151

<210> SEQ ID NO 664
<211> LENGTH: 164
<212> TYPE: DNA
<213> ORGANISM: Homo Sapiens

<400> SEQUENCE: 664
tcctgtgagt gttctgtatg ttaacacttt tattccttgt tttgttttag gcgataaact 60
acattcagtt gagtctgcaa gactgggagg aactggggtg ataagaaatc tattcactgt 120
caaggtgaga attagcaaat tttccccctt cttctgtact ttct 164

<210> SEQ ID NO 665
<211> LENGTH: 161
<212> TYPE: DNA
<213> ORGANISM: Homo Sapiens

<400> SEQUENCE: 665
gctgggaaca tttgtcattt attcttttct actccttgta ttttgtgcag gtctgcagac 60
tcgtgaatga ggtctaccac atgtataatc gacaccagta tccatttgtt gttcttaaca 120
tttctgttga ttcaggtaag ttccattggc atttcagtac a 161

<210> SEQ ID NO 666
<211> LENGTH: 124
<212> TYPE: DNA
<213> ORGANISM: Homo Sapiens

<400> SEQUENCE: 666
tgccgtttcg agaattttat tcacttttat atttatgtct cacatctagg gaactagctc 60
ttcagaaaaa tccaagtctt caggatcgtc acgatcaaag aggttggttg atgttgaagg 120
gaca 124

<210> SEQ ID NO 667
<211> LENGTH: 155
<212> TYPE: DNA
<213> ORGANISM: Homo Sapiens

<400> SEQUENCE: 667
tgcacactga aattaggacg tttatatttc ttcaggtatt agaaaactac tcggatgctc 60
caatgacacc aaaacagatt ctgcaggtca tagaggcaga aggactaaag gaaatgaggt 120
ttgtattgtt cttgttgctt aacatgaggg tttca 155

<210> SEQ ID NO 668
<211> LENGTH: 150
<212> TYPE: DNA
<213> ORGANISM: Homo Sapiens

<400> SEQUENCE: 668
tttttccccc ttgatccttc taggtgggga cggatggcct gttgcgtctc agcagcagtg 60
cactaaataa cgagtttttt acccatgcgg ctcagagctg gcgggagcgc ctggctgatg 120
gtatgtagac ttggtcatct cggacggctt 150

<210> SEQ ID NO 669
<211> LENGTH: 152
<212> TYPE: DNA
<213> ORGANISM: Homo Sapiens

<400> SEQUENCE: 669
acttattgag catgcctggt tttttgtctt ccagcaatat ccagattatt atgcaataat 60
taaggagcct atagatctca agaccattgc ccagaggata caggtatgaa gatgaccata 120
agtaaatgat tgtggtttag agcagattgg cc 152

<210> SEQ ID NO 670
<211> LENGTH: 162
<212> TYPE: DNA
<213> ORGANISM: Homo Sapiens

<400> SEQUENCE: 670
acgcagtgct aaccaagttc tttcttttgc acagggcatt ttggttgtgt atatcatggg 60
actttgttgg acaatgatgg caagaaaatt cactgtgctg tgaaatcctt gaacagtaag 120
tggcatttta tttaaccatg gagtatactt ttgtggtttg ca 162

<210> SEQ ID NO 671
<211> LENGTH: 100
<212> TYPE: DNA
<213> ORGANISM: Homo Sapiens

<400> SEQUENCE: 671
ttttatatga tctttcctgg ttggcaggac ccatggatga aggaccagat cttgatctag 60
gtaattttga attctagttg tgcttcatat cgtgctttgt 100

<210> SEQ ID NO 672
<211> LENGTH: 163
<212> TYPE: DNA
<213> ORGANISM: Homo Sapiens

<400> SEQUENCE: 672
aagaatgcct gggactgagg ggagatattt ttgtttgtca gagtcagagc actttttccg 60
atgctgtttg gataaaaaat cacaaagaac aatgcttgct gttgtggact acatgagaag 120
acaaaagagg taatgtaatg agtgttgctt cttacgttta gga 163

<210> SEQ ID NO 673
<211> LENGTH: 150
<212> TYPE: DNA
<213> ORGANISM: Homo Sapiens

<400> SEQUENCE: 673
aaagtgtaga ctaatgatgt gacttttgtt ttcacagact gaaacagcag agcttcctgc 60
ttctgatagc ataaacccag gcaacctaca attggtttca gagttaaagg tcagaagaat 120
attctcttcc agtgtctcgt gtcttacata 150

<210> SEQ ID NO 674
<211> LENGTH: 150
<212> TYPE: DNA
<213> ORGANISM: Homo Sapiens

<400> SEQUENCE: 674
tgtactcttt ttcctgttgc tgttcttttc tgcaggaggg aaaacccctg atcctaaaat 60
gaatgctagg acttacatgg atgtaatgcg agaacaacac ttgactaaag aagaagtatg 120
taaacctgtc tcctgtttta atggttgtga 150

<210> SEQ ID NO 675
<211> LENGTH: 151
<212> TYPE: DNA
<213> ORGANISM: Homo Sapiens

<400> SEQUENCE: 675
aagcaaactt gttctgtttt tacccactga ttctttttca gccccttctc aaagtcagca 60
tgtcaatgag agactgcttg atacttgtcc ttcggaaagc tatgtttgcc aagtatgtag 120
catctttttc tatcatagga agacgttgtc t 151

<210> SEQ ID NO 676
<211> LENGTH: 161
<212> TYPE: DNA
<213> ORGANISM: Homo Sapiens

<400> SEQUENCE: 676
tgtgtgtttc tgtgggtttc tttaaggttt ggacagaagg gtaaagctat taggattgaa 60
agagtcatct atactggtaa agaaggcaaa agttctcagg gatgtcctat tgctaagtgg 120
gtaagtgtga cttgataaag cctttggtct taaatcttgg g 161

<210> SEQ ID NO 677
<211> LENGTH: 150
<212> TYPE: DNA
<213> ORGANISM: Homo Sapiens

<400> SEQUENCE: 677
tgtttttgtc cctctctctt gcagtgaaat tacagacaac ccttacatga cgtcaatccc 60
tgtgaatgct tttcagggac tatgcaatga aaccttgaca ctgtgagtat taccagttct 120
actccctcca tcaactaaat tctattttga 150

<210> SEQ ID NO 678
<211> LENGTH: 169
<212> TYPE: DNA
<213> ORGANISM: Homo Sapiens

<400> SEQUENCE: 678
acatactttg tatcatctta ttggcagcac tggaagaagc tgcaaaacgt ttccaggaat 60
tgaaagcaca aagagaaagt aaagaagccc tagagattga aaaaaactca agaaaacccc 120
ctccctacaa acacatcaaa gtaagtcttt atctctggcc tgggattgc 169

<210> SEQ ID NO 679
<211> LENGTH: 159
<212> TYPE: DNA
<213> ORGANISM: Homo Sapiens

<400> SEQUENCE: 679
tgttttcctt tgtgtcattc ccttttatca ggttgcccac attcccaaat cagatgcttt 60
gtactttgat gactgcatgc agcttttggc gcagacattc ccgtttgtag atgacaatga 120
ggtgaggtat aaaataacct ggttaataga aaaactcca 159

<210> SEQ ID NO 680
<211> LENGTH: 166
<212> TYPE: DNA
<213> ORGANISM: Homo Sapiens

<400> SEQUENCE: 680
ggattcagtg aggaatgctt tcatgaagtt ggtgtatctt tttaaatagg aaaatccttg 60
taaatgatgg tgacgcttca aaagccagac tggaactgag ggaagagaat cccttgaacc 120
acaacgtggt aagagattaa tagcttctgt tgatgccata tctgca 166

<210> SEQ ID NO 681
<211> LENGTH: 163
<212> TYPE: DNA
<213> ORGANISM: Homo Sapiens

<400> SEQUENCE: 681
acacagaatt tgttaagcaa cgtagtcttt cttttaaatt ctctttcagg tttttcatat 60
gaaaaagatc cccgattata ctttgacgac acttgtgttg tgcctgagag actggaaggt 120
aagtagcccc atccaaggtt tgttgccagg tagaggtttg gag 163

<210> SEQ ID NO 682
<211> LENGTH: 133
<212> TYPE: DNA
<213> ORGANISM: Homo Sapiens

<400> SEQUENCE: 682
tctcatcata ccactattat tttgcagttt tgtgtgcgac aactgcttga agaaaactgg 60
cagacctcga aaagaaaaca aattcagtgc taagagtaag tttcgggaag ctttctgttt 120
cctggactgc aca 133

<210> SEQ ID NO 683
<211> LENGTH: 182
<212> TYPE: DNA
<213> ORGANISM: Homo Sapiens

<400> SEQUENCE: 683
acacagcctt ctcaacctct ttttcttttt ttctttcttg tttttagtct ttttgctaaa 60
gaacatctgc agcacatgac agaaaagcag ctgaacctct atgaccgcct gattaacgag 120
cctagtaatg actgggatat ttactactgg gccacaggta ctgggtatga taagcagcat 180
aa 182

<210> SEQ ID NO 684
<211> LENGTH: 150
<212> TYPE: DNA
<213> ORGANISM: Homo Sapiens

<400> SEQUENCE: 684
ctctcggtgt atttctctac ttacctgtaa taatgctttt gtcttaatag ggtggttctc 60
ttcccaaagt ggaagccaaa ttcatcaatt atgtgaagaa ttgcttccgg atgactgacc 120
aagaggtaac tggattttct ggggacatga 150

<210> SEQ ID NO 685
<211> LENGTH: 150
<212> TYPE: DNA
<213> ORGANISM: Homo Sapiens

<400> SEQUENCE: 685
tcactgtgat agccttatct gcttgtttct ctttgacttt gtagctcgtt ctccggtttt 60
tagtgccatg tttgaacatg aaatggagga gagcaaaaag gtatgtaaca agatgaagac 120
atgtctgttt agccaggtat ctagagtcag 150

<210> SEQ ID NO 686
<211> LENGTH: 150
<212> TYPE: DNA
<213> ORGANISM: Homo Sapiens

<400> SEQUENCE: 686
gttaatctta acctgtgctt tgcctcctgt tctgtcttga ctttgccaga aaaatcgagt 60
tgagcagcaa cttcacgagc atttgcaaga tgcaatgtcc ttcttaaagg atgtctgtga 120
ggtactattt cttttagatg gtgccttttt 150

<210> SEQ ID NO 687
<211> LENGTH: 120
<212> TYPE: DNA
<213> ORGANISM: Homo Sapiens

<400> SEQUENCE: 687
actccaacac tgttgctcct aattactgtt ttatcctact tttaggactc tggagatgcc 60
acatggaaag aaacattctg gttggcaagt atcttcttac atgctcttac ttgctccaag 120

<210> SEQ ID NO 688
<211> LENGTH: 122
<212> TYPE: DNA
<213> ORGANISM: Homo Sapiens

<400> SEQUENCE: 688
gccagagtcc tttagcccta ctcaggttaa aatgatgttt tgtttttcag ttacttacac 60
gccaagtcaa tcatccacag agacctcaag agtaatagta tccttcctga aatttgtctg 120
cg 122

<210> SEQ ID NO 689
<211> LENGTH: 229
<212> TYPE: DNA
<213> ORGANISM: Homo Sapiens

<400> SEQUENCE: 689
tcctgggttt cttttcaact tgtaatagtg ttgtattctt gtctttaggc aagccaaaat 60
tccttccgga tagaatatga tacctttggt gaactaaagg tgccaaatga taagtattat 120
ggcgcccaga ccgtgagatc tacgatgaac tttaagattg gaggtgtgac agaacgcatg 180
ccagtaagtg gcatttgtgg aaatgttggc tattttggat gaagtaggc 229

<210> SEQ ID NO 690

<211> LENGTH: 182
<212> TYPE: DNA
<213> ORGANISM: Homo Sapiens

<400> SEQUENCE: 690
tcctgaagtg agatcttaca tcctttcttc tcataggtga agagaaggca gagaaaggac 60
ttagcgtcca gtgactccag gaaaacgaca gagaagcttc tgaaaacatt tttgaaaaga 120
caagccatca aaactgcctt cagaagcaaa aggcaagagg aaaattatag tcgtgttaga 180
ga 182

<210> SEQ ID NO 691
<211> LENGTH: 150
<212> TYPE: DNA
<213> ORGANISM: Homo Sapiens

<400> SEQUENCE: 691
gaccagaaag gctcagttcc ctgttttctc ttcctaacat tttagcaaga acagtgatga 60
aatcaacata cctcgactca ttgtcagtca actaaaatgg cttgacagag ttgtggatgg 120
caaggtaggc ttatggactt tatctcttga 150

<210> SEQ ID NO 692
<211> LENGTH: 150
<212> TYPE: DNA
<213> ORGANISM: Homo Sapiens

<400> SEQUENCE: 692
aaacattgat ttggcttttc ccatttatta ttctgtaggt tgctatgacc cgagagaagt 60
ttccagagaa gattccattt agactaacaa gaatgttgac caatgctatg gaggtgagtg 120
gatatcggga acgagctgct tccaaatggg 150

<210> SEQ ID NO 693
<211> LENGTH: 176
<212> TYPE: DNA
<213> ORGANISM: Homo Sapiens

<400> SEQUENCE: 693
tgtctccatt tcccaccaca gggtcatgct ctatcagatt tcagaagaag tgagcagatc 60
agaattgagg tcttttaagt ttcttttgca agaggaaatc tccaaatgca aactggatga 120
tgacatggta agacctggta tcttactgag atttagtcct gagacttggt tagcca 176

<210> SEQ ID NO 694
<211> LENGTH: 156
<212> TYPE: DNA
<213> ORGANISM: Homo Sapiens

<400> SEQUENCE: 694
atttactctg gattttgctt tttcagatac tggctttggc actactagtg gaggggcatt 60
tggaacatct gcatttggtt ctagcaacaa tactggaggc ctctttggaa attcacagac 120
taaaccaggt aggggcttta tttgtgatat aactgg 156

<210> SEQ ID NO 695
<211> LENGTH: 151
<212> TYPE: DNA
<213> ORGANISM: Homo Sapiens

<400> SEQUENCE: 695
tgagatgttt ttgccttcac aggtgattga agtgggaaaa aatgatgacc tggaggactc 60
taagtcctta agtgatgata ccgatgtaga ggttacctct gaggtatgaa tctttagcaa 120
gaactatttt gcaccagccc catcttcaga t 151

<210> SEQ ID NO 696
<211> LENGTH: 165
<212> TYPE: DNA
<213> ORGANISM: Homo Sapiens

<400> SEQUENCE: 696 tccccttgt cttaaaccac aggatttatt ggatcattcg tgtacatcag gaagtggctc 60
tggtcttcct tttctggtac aaagaacagt ggctcgccag attacactgt tggagtgtgt 120
cggtaattct ttttttcct ttctttgtgg gtaatatgca atgtt 165

<210> SEQ ID NO 697
<211> LENGTH: 153
<212> TYPE: DNA
<213> ORGANISM: Homo Sapiens

<400> SEQUENCE: 697
ttgacgtgcc attctcttgc ttcctcttcc tcaaaaagga taagcactgt tcaaaggatg 60
ccctacttgc aggattaaaa caagatgaac caggacaagc aggaagtcag aagtcttcta 120
ccaagtaagg aaaatgagtt tacttcctgt tgt 153

<210> SEQ ID NO 698
<211> LENGTH: 150
<212> TYPE: DNA
<213> ORGANISM: Homo Sapiens

<400> SEQUENCE: 698
tttgggacga cttattgccc ttcaatttcc tcatggccaa aggcttattc atagggcttc 60
ttgactaaag cccttggagc actgggtttt tcttgaagta tatggtgagt taatgacttg 120
aatctgcaat tgggtgattg cctgaattct 150

<210> SEQ ID NO 699
<211> LENGTH: 157
<212> TYPE: DNA
<213> ORGANISM: Homo Sapiens

<400> SEQUENCE: 699
agagtaactt caatgtcttt attccatctt ctctttaggg tcggattcca gttaaatgga 60
tggcaattga atccctttt gatcatatct acaccacgca aagtgatgtg taagtgtggg 120
tgttgctctc ttggggtgga ggttacagaa acaccct 157

<210> SEQ ID NO 700
<211> LENGTH: 264
<212> TYPE: DNA
<213> ORGANISM: Homo Sapiens

<400> SEQUENCE: 700
gatctccggt tgggattcct gcggattgac atttctgtga agcagaagtc tgggaatcga 60
tctggaaatc ctcctaattt ttactccctc tccccgcgac tcctgattca ttgggaagtt 120
tcaaatcagc tataactgga gagtgctgaa gattgatggg atcgttgcct tatgcatttg 180
ttttggtttt acaaaaagga aacttgacag aggatcatgc tgtacttaaa aaatacaagt 240
aagttctctg cacaggaaat tggt 264

<210> SEQ ID NO 701
<211> LENGTH: 159
<212> TYPE: DNA
<213> ORGANISM: Homo Sapiens

<400> SEQUENCE: 701
gcattttctc tgttcaacaa gcagaacagg ataattcaga caacaacacc atctttgtgc 60
aaggcctggg tgagaatgtt acaattgagt ctgtggctga ttacttcaag cagattggta 120
ttattaaggt acttgtggag aggagtggga gctttctgt 159

<210> SEQ ID NO 702
<211> LENGTH: 151
<212> TYPE: DNA
<213> ORGANISM: Homo Sapiens

<400> SEQUENCE: 702
gtttgtgaca taagcagaac gctttgattt ggtttctttc tacagctcca ttttcagtcc 60
ggcagcacac attactctgc gtacaaaacg attgaacacc agattgcagt tcaggtagga 120
aacgcaagag attctgaagc ttgaattgtc t 151

<210> SEQ ID NO 703
<211> LENGTH: 155
<212> TYPE: DNA
<213> ORGANISM: Homo Sapiens

<400> SEQUENCE: 703
tgacagccag attcgtcttt gttttataga gttgttgcct gcaatctcta tccctttgta 60
aagacagtgg cttctccagg tgtaactgtt gaggaggctg tggagcaaat tgacattggt 120
aagtcagaaa aaccatttta gaagactgag aggag 155

<210> SEQ ID NO 704
<211> LENGTH: 190
<212> TYPE: DNA
<213> ORGANISM: Homo Sapiens

<400> SEQUENCE: 704
tggaagtctg tgagttctct gatctttact tctttttttag gcacacctgt tgtccttaac 60
tgactttccg ggtcatcagc acttcttcag aagtgttcct tttccctccc agcaaatatg 120
gaagactgac tatcctgata ttcccagaca ttctttgctg tgatttgtaa gcccgatata 180
aacccttcca 190

<210> SEQ ID NO 705
<211> LENGTH: 150
<212> TYPE: DNA
<213> ORGANISM: Homo Sapiens

<400> SEQUENCE: 705
atgttcttcc tttaggtata gtctcaataa catttcttcc cctaggtgct gctgatgtag 60
agaaggtgga ggaaaagtca gcaatagatc tgacccctat tgtggtagaa gacaaaggtg 120
ggtgtttgga gaagttgatt gtggttcaga 150

<210> SEQ ID NO 706
<211> LENGTH: 152
<212> TYPE: DNA
<213> ORGANISM: Homo Sapiens

<400> SEQUENCE: 706
cctgaagcag tccaggactt atgtgaccgt ggtctctttt tcttctagtt gatcatacca 60
gggttgtcct acacgatggt gatcccaatg agcctgtttc agattacatc aatgcaaata 120
tcatcatggt aagctttgct tttcacagtg tt 152

<210> SEQ ID NO 707
<211> LENGTH: 154
<212> TYPE: DNA
<213> ORGANISM: Homo Sapiens

<400> SEQUENCE: 707
agcttaagaa aagtgacgtg gtcaattttt ttcttaaata gatcactttg ccagctgtgt 60
ggaggatgga tttgagggag acaagactgg aggcagtagt ccaggtgaga gatgttgaga 120
tgttgcagat ttgaactaag gcattggcag taga 154

<210> SEQ ID NO 708
<211> LENGTH: 156
<212> TYPE: DNA
<213> ORGANISM: Homo Sapiens

<400> SEQUENCE: 708
tccttgagtg taaggcaatt aataacttac acttgtcttt atgttccagc ctgaaagaat 60
agacccaagc gcatcacgac aaggatatga tgtccgctct gatgtctgga gtttggggat 120
cacattggta tgtttatgct gattcaacct tgccac 156

<210> SEQ ID NO 709
<211> LENGTH: 151
<212> TYPE: DNA
<213> ORGANISM: Homo Sapiens

<400> SEQUENCE: 709
gtctgtggat tgacttcttt tccttttatg ttgttctggt ttttaaaggc agcagcctcc 60
ttggaaagac gaaaagcatc ctgggttcag gctgacatct gcacttaaca ggtacatggg 120
ttgtttcctg gtaggagtag attttaaagc a 151

<210> SEQ ID NO 710
<211> LENGTH: 125
<212> TYPE: DNA
<213> ORGANISM: Homo Sapiens

<400> SEQUENCE: 710
tgagcctcat ttattttctt tttctccccc cctaccctgc tagtctggag ttgatcaagg 60
aacctgtctc cacaaagtgt gaccacatat tttgcaagta agtttgaatg tgttatgtgg 120
ctcca 125

<210> SEQ ID NO 711
<211> LENGTH: 150
<212> TYPE: DNA
<213> ORGANISM: Homo Sapiens

<400> SEQUENCE: 711
tcccttatgt tcttcttctc tccagatctg ttacctaaag caataaaaaa tggccagagg 60
atcagtgtcc gatgaggaaa tgatggagct cagagaagct tttgccaaag ttggtgagta 120
gacctggtac cccaaattgc atcattctct 150

<210> SEQ ID NO 712

<211> LENGTH: 150
<212> TYPE: DNA
<213> ORGANISM: Homo Sapiens

<400> SEQUENCE: 712
gcactttaat actaacagga acagccttga aaatgtcttt tctttccagt acaccccaaa 60
aagggagatt tggtatactc tgagatccag actactcagc tgggagaaga agaggaaggt 120
acgtctttgg gaagagattc tggctgcaaa 150

<210> SEQ ID NO 713
<211> LENGTH: 154
<212> TYPE: DNA
<213> ORGANISM: Homo Sapiens

<400> SEQUENCE: 713
tgtcctcagt ctgtactaaa ctcaaaccaa gttctcatgc attactaggt tggagaaacg 60
tacggtaagg atataacctc ccggggcaaa gacaagccga ttgccgtatg taaaactttc 120
agtccacttc agtttcaagc tttctctgtt ctct 154

<210> SEQ ID NO 714
<211> LENGTH: 131
<212> TYPE: DNA
<213> ORGANISM: Homo Sapiens

<400> SEQUENCE: 714
agcagatttg tatgaaagcc cttacatttt ttctaggtat gaagtagctc cgaggtctga 60
tagtgaagaa agtggctcag aagaagagga agaggtaaga gtgcatttcc tggctttcaa 120
ggctctcagt g 131

<210> SEQ ID NO 715
<211> LENGTH: 216
<212> TYPE: DNA
<213> ORGANISM: Homo Sapiens

<400> SEQUENCE: 715
accctgttac acgcttgtaa ttgactcttc taggtgagcc cattggcagg ggtaccaaag 60
tgatcctcca tcttaaagaa gatcagacag agtacctaga agagaggcgg gtcaaagaag 120
tagtgaagaa gcattctcag ttcataggct atcccatcac cctttatgtg agtatggact 180
tttaaatctt ttacacttaa cgtgcaggat gtttcc 216

<210> SEQ ID NO 716
<211> LENGTH: 156
<212> TYPE: DNA
<213> ORGANISM: Homo Sapiens

<400> SEQUENCE: 716
actgaatttg ttttagggca cattgaatac tttactttcc ttttcctcag catcaacaac 60
agcaacttgt gattggcggt gaccggatat tcagttgcac atccccacat caatgcactg 120
ccaatggtaa gactctccaa ctcccaatgt cagtgt 156

<210> SEQ ID NO 717
<211> LENGTH: 213
<212> TYPE: DNA
<213> ORGANISM: Homo Sapiens

<400> SEQUENCE: 717
caccggtgtg gctctttaac aacctttgct tgtcccgata ggtcaccttt ggctcttcag 60
agatgcaggg acacacgatg ggcttctggt taaccaaact gaattatttg tgccatctct 120
caatgttgac ggacagccta tttttgccaa tatcacactg ccaggtactg acgttttact 180
ttttaaaaag ataaggttgt tgtggtaagt aca 213

<210> SEQ ID NO 718
<211> LENGTH: 158
<212> TYPE: DNA
<213> ORGANISM: Homo Sapiens

<400> SEQUENCE: 718
ccgttgggtt ttctcttcca ggggttaatt gtgaaattaa ttttgatgac tgtgcaagta 60
acccttgtat ccatggaatc tgtatggatg gcattaatcg ctacagttgt gtctgctcac 120
caggattcac aggtaaagct ccttttactg caaggccc 158

<210> SEQ ID NO 719
<211> LENGTH: 135
<212> TYPE: DNA
<213> ORGANISM: Homo Sapiens

<400> SEQUENCE: 719
ttctattctt ccttgctttg tgcatgttta tctagactgc tgatcttgga cttgatattg 60
gtgcccaggg agaacccctt ggatatcgcc aggatggtat gtgtctcata tttctcgatt 120
aactccagat caagc 135

<210> SEQ ID NO 720
<211> LENGTH: 153
<212> TYPE: DNA
<213> ORGANISM: Homo Sapiens

<400> SEQUENCE: 720
aggatggtct tgtgtctgtg ttgactgatt ctcttgtaga ccgagatttt agatgaagat 60
aagcgcttag gcagtgcagt ggattactac tttattcaag atgacggaag cagatttaag 120
gtaagcccct gactgcgaca agctaaaacc cac 153

<210> SEQ ID NO 721
<211> LENGTH: 157
<212> TYPE: DNA
<213> ORGANISM: Homo Sapiens

<400> SEQUENCE: 721
agttattttc aaacggtctg gttttatttt agtgctgttc ctttgggaac cacggccaaa 60
gaagagatgg agcggttctg gaataagaat ataggttcaa accgtcctct gtctccccac 120
attactatct acaggtaagg aaggattctg gagccag 157

<210> SEQ ID NO 722
<211> LENGTH: 161
<212> TYPE: DNA
<213> ORGANISM: Homo Sapiens

<400> SEQUENCE: 722
aaatggccct tgtcttgcag gtatgacata atgaagactt gctgggatgc agatccccta 60
aaaagaccaa cattcaagca aattgttcag ctaattgaga agcagatttc agagagcacc 120
aatcatgtga gtataccctg gccaggcata gaatccccct t 161

<210> SEQ ID NO 723

<211> LENGTH: 170
<212> TYPE: DNA
<213> ORGANISM: Homo Sapiens

<400> SEQUENCE: 723
tctcccttcc tcctttgaac aaacagaaca gaacaaacat gacctatgag aaaatgtcca 60
gagccctgcg ccactactac aaactaaaca ttatcaggaa ggagccagga caaaggcttt 120
tgttcaggta gcacttcctt tttctccttt ccttcttttg ggaggatgct 170

<210> SEQ ID NO 724
<211> LENGTH: 179
<212> TYPE: DNA
<213> ORGANISM: Homo Sapiens

<400> SEQUENCE: 724
agttaaagtt cggttgtttt cgtatttcag gtcagcaaat taaaacgtca cattcgctct 60
catactggag agcgtccgtt tcagtgcagt ttgtgcagtt atgccagcag ggacacatac 120
aagctgaaaa ggcacatgag aacccattca ggtaggactt ctccactcct tactgtatt 179

<210> SEQ ID NO 725
<211> LENGTH: 154
<212> TYPE: DNA
<213> ORGANISM: Homo Sapiens

<400> SEQUENCE: 725
gcaaggagcc aggcattttt cttatctcaa catgtgtttg cagcctcctc caaaactgcc 60
cagtggagtg ttcagtctgg aatttcaaga ttttgtgaat aaatggtaag ttggctcctt 120
gttctctgga agcgtatact ctggatttgt cagg 154

<210> SEQ ID NO 726
<211> LENGTH: 158
<212> TYPE: DNA
<213> ORGANISM: Homo Sapiens

<400> SEQUENCE: 726
tccattggat tccttcgcaa gggtcaaaga ctctaaatgg aggatctgat gctcaagatg 60
gtaatcagcc acaacataac ggggagagca atgaagacag caaagacaac catgaagcca 120
gcacgaagaa aaagtgagga ataggtttta atgggtct 158

<210> SEQ ID NO 727
<211> LENGTH: 166
<212> TYPE: DNA
<213> ORGANISM: Homo Sapiens

<400> SEQUENCE: 727
ttgtcagctt tttgggggtc atttttattc aggatgaaga tgcatcaggg ggcgatcaag 60
atcaggaaga aagaagatgg aacaaaagga ctcagcagat gcttcatggt cttcaggtat 120
tgccgctgtt gtctcagagg aaaatgcttc atcaaaggct tttgcc 166

<210> SEQ ID NO 728
<211> LENGTH: 150
<212> TYPE: DNA
<213> ORGANISM: Homo Sapiens

<400> SEQUENCE: 728
ggtttacgtg catattttct ggcttacggg ttttctttat ttcctttcag atgcctggaa 60
gtcattgaca gataaagtcc aggaagctcg atcaaatgcc cgcctaaagc agctctcatt 120
tgcaggtaat ggctggaggt gttattccac 150

<210> SEQ ID NO 729
<211> LENGTH: 150
<212> TYPE: DNA
<213> ORGANISM: Homo Sapiens

<400> SEQUENCE: 729
ggcactttcc ttctggttca gagcatgtga ttgcgaccag cagattgata gctgtacgta 60
tgaagcaatg tataatattc agtcccaggc gccatctatc accgagagca gcacctttgg 120
taagttgcca ttctgctact ttaaaaatca 150

<210> SEQ ID NO 730
<211> LENGTH: 150
<212> TYPE: DNA
<213> ORGANISM: Homo Sapiens

<400> SEQUENCE: 730
tggtggtgca tactttattt gtctagaatc gaacagatgt gcagtgccag caccgatggc 60
agaaagtact aaaccctgag ctcatcaagg gtccttggac caaagaagaa gatcagagag 120
taagttcttt cttcattggt gtgtgactca 150

<210> SEQ ID NO 731
<211> LENGTH: 150
<212> TYPE: DNA
<213> ORGANISM: Homo Sapiens

<400> SEQUENCE: 731
aagtggtttc ctcagataga gcagtaattg tccatgctct ctctaaccag gaaatgttaa 60
ttttggaggc cgtccacaac ttccaggttc ccatcctgcg gtaagtgtca ctaggaatac 120
cactgaatga gaagctgttg catatttcac 150

<210> SEQ ID NO 732
<211> LENGTH: 150
<212> TYPE: DNA
<213> ORGANISM: Homo Sapiens

<400> SEQUENCE: 732
agcgtttcag ctccagactc tttttgacca atattgtttc ctctttcaga agtgcctagc 60
tgccactcca tttatatgag gcaagaaggc ttcctggctc atcccagcag aacagaagtt 120
aagttgtcca ccactgaaat tccgtgtaaa 150

<210> SEQ ID NO 733
<211> LENGTH: 208
<212> TYPE: DNA
<213> ORGANISM: Homo Sapiens

<400> SEQUENCE: 733
agcaaccatt tttgtgccca tgttttctca ttcccttata gggatcgtgg aagaatacca 60
attgccatat tacaacatgg taccgagtga tccgtcatac gaagatatgc gtgaggttgt 120
gtgtgtcaaa cgtttgcggc caattgtgtc taatcggtgg aacagtgatg aagtgagtgg 180
aactcagtcc cctgaagaag tgattcgt 208

<210> SEQ ID NO 734
<211> LENGTH: 196
<212> TYPE: DNA

<213> ORGANISM: Homo Sapiens

<400> SEQUENCE: 734
tatgtctcct cttccctgcc cctgcagact atattgaact ccatgcacaa ataccagccc 60
cggttccaca ttgtaagagc caatgacatc ttgaaactcc cttatagtac atttcggaca 120
tacttgttcc ccgaaactga attcatcgct gtgactgcat accagaatga taaggtaaac 180
tcaaggggct ttcctt 196

<210> SEQ ID NO 735
<211> LENGTH: 198
<212> TYPE: DNA
<213> ORGANISM: Homo Sapiens

<400> SEQUENCE: 735
gtcctgctcc tgatcctgtt tgtattgatt tttctaaaag gcttttgtgg ccacaggaac 60
caatctgtct ctccagtttt ttccggccag ctggcaggga gaacagcgac aaacacctag 120
ccgagagtat gtcgacttag aaagagaagc aggcaaggta ggaaacattt ctttgcaatt 180
taaaatactg tgggttgt 198

<210> SEQ ID NO 736
<211> LENGTH: 151
<212> TYPE: DNA
<213> ORGANISM: Homo Sapiens

<400> SEQUENCE: 736
cttctccctg gctctgactc acccttgttt tataacagat gctgcaatgt acaacaactc 60
tgaagccctg cccacctctc ctatggcacc cacaacctat ggtatatgtg attcctaatt 120
acacaaatta atttgaaggg acttactggg g 151

<210> SEQ ID NO 737
<211> LENGTH: 151
<212> TYPE: DNA
<213> ORGANISM: Homo Sapiens

<400> SEQUENCE: 737
atctcaatcg cctgctctcc ctttcttctt tccagtatgg tgactacgac cccagtgttc 60
acaagcgggg atttttggcc caagaggaat tgcttccaaa aagggtaaga gattaaattc 120
ccttttcagg aagacatagc agatatgtgg t 151

<210> SEQ ID NO 738
<211> LENGTH: 182
<212> TYPE: DNA
<213> ORGANISM: Homo Sapiens

<400> SEQUENCE: 738 agacctttc ctccctcatt cacaggctgg cttattagct gtaatggccc agatgggttg 60
ttacgtccct gctgaagtgt gcaggctcac accaattgat agagtgttta ctagacttgg 120
tgcctcagac agaataatgt caggtgagtt ttttgtttcc cacttaagtt ctcattcagt 180
ca 182

<210> SEQ ID NO 739
<211> LENGTH: 150
<212> TYPE: DNA
<213> ORGANISM: Homo Sapiens

<400> SEQUENCE: 739
acatctggga ttttgcttca ttgtacatat gttttcttcc ttcagtgacc atgaaagaca 60
ccaggttgac agcactggaa actgaagtac cagttgtcgc tagaacaggt aagctataac 120
caggccagtg gttagaggaa gatgggaggg 150

<210> SEQ ID NO 740
<211> LENGTH: 150
<212> TYPE: DNA
<213> ORGANISM: Homo Sapiens

<400> SEQUENCE: 740
tcagaccacg gtttctattt ttcatctaga atgaagatga taaccgagcc agtgagagca 60
agaaacccaa aacggaggac aagaattcag caggccataa gccatccagc aacagagagt 120
acgttcccaa aacatgttgc atgccagtgt 150

<210> SEQ ID NO 741
<211> LENGTH: 150
<212> TYPE: DNA
<213> ORGANISM: Homo Sapiens

<400> SEQUENCE: 741
atcttctgtt acattctgct tcacaggcca ttctcgaatc tccagaaaag cagctaacac 60
taaatgagat ctataactgg ttcacacgaa tgtttgctta cttccgacgc aacgcggcca 120
cgtggaaggt aagctttctc aggcctgttt 150

<210> SEQ ID NO 742
<211> LENGTH: 193
<212> TYPE: DNA
<213> ORGANISM: Homo Sapiens

<400> SEQUENCE: 742
ttttcacccc gctcccctta gaactggaat gatgaatggg acaatcttat caaaatggct 60
tccacagaca cacccatggc ccgaagtgga cttcagtaca actcactgga agaaatacac 120
atatttgtcc tttgcaacat cctcagaagg ccaatcattg tcatttcagg tgagatgcct 180
gcagatcacg gat 193

<210> SEQ ID NO 743
<211> LENGTH: 153
<212> TYPE: DNA
<213> ORGANISM: Homo Sapiens

<400> SEQUENCE: 743
tccttaaggc ctctgtgctt tttaacaaat ggtttctttt gcagttggag ttctctccac 60
agacactgtg ttgctacggc aaacagttgt gcacaatacc tcgtgatgcc acttattaca 120
gttaccagaa caggtaagct tggccaggtg tgg 153

<210> SEQ ID NO 744
<211> LENGTH: 198
<212> TYPE: DNA
<213> ORGANISM: Homo Sapiens

<400> SEQUENCE: 744
ggtcatttgc tgtgtttgtt gacaggtgcc aatttgctaa ttgacagcac tggtcagaga 60
ctaagaattg cagattttgg agctgcagcc aggttggcat caaaaggaac tggtgcagga 120
gagtttcagg gacaattact ggggacaatt gcatttatgg cacctgaggt gagaagcatc 180
tttgagtgtg atgacaga 198

<210> SEQ ID NO 745
<211> LENGTH: 150
<212> TYPE: DNA
<213> ORGANISM: Homo Sapiens

<400> SEQUENCE: 745
ccataatata aagttgttgc gttttgtatt tcagaccatt gccctcttga acatttaccg 60
taaccctcaa aactcttccc agtctgctga cggtttgcgc tgtaagttca tacaagttcc 120
ttccccggtt ccctgggctt gcgtgtcaga 150

<210> SEQ ID NO 746
<211> LENGTH: 150
<212> TYPE: DNA
<213> ORGANISM: Homo Sapiens

<400> SEQUENCE: 746
gttctgagtt agctgcacat ttacctgttg gatgttatct gtatttgcag ttgtgtactg 60
tcagctatgg aaaagtcaag ctggtcttga agcacaacag gtaagagatt ccatgacagg 120
cctgtcccaa ggcactgtca ctttctgcgc 150

<210> SEQ ID NO 747
<211> LENGTH: 165
<212> TYPE: DNA
<213> ORGANISM: Homo Sapiens

<400> SEQUENCE: 747
ttctggcctt gttaatggcg tgttctgctt tttctttcag tttcccccttt tctagggtga 60 ggatggttct acacagccac ccggagttcc ttagttgaaa ggtgcgccct gctgtgacag 120
gtattctttc tttatgtttt tctttcatgt taacaatcga ggggg 165

<210> SEQ ID NO 748
<211> LENGTH: 115
<212> TYPE: DNA
<213> ORGANISM: Homo Sapiens

<400> SEQUENCE: 748
aaatcccttc ctctctttct cagataacct gaggaccatg gatgctgatg agggtcaaga 60
catgtcccaa gtttcaggtg agaccttatg agatagctgt gtgggaagtt catga 115

<210> SEQ ID NO 749
<211> LENGTH: 130
<212> TYPE: DNA
<213> ORGANISM: Homo Sapiens

<400> SEQUENCE: 749
tacacccctg tcctctctgt cccagggaaa ttcaactact gaggaggtta cggcacaaaa 60
atgtcatcca gctggtggat gtgttataca acgaagagaa gcagaaaata tatcctttcc 120
ggtgttggga 130

<210> SEQ ID NO 750
<211> LENGTH: 242
<212> TYPE: DNA
<213> ORGANISM: Homo Sapiens

<400> SEQUENCE: 750
agacctcaga caaggcatct cataggaggc tttttcataa aactaggctc tgctggtagt 60
aaggaggcca gtttggaggc aggcgttgag ctgtgcacat ctccccactc cagccacctt 120
ctccatatcc atcttttatt tcatttttcc acttggctga gccatccaga accttttcaa 180
tgtataaaat ggaatattct tacctcaatt cctctgccta cgagtcctgt atggctggga 240
tg 242

<210> SEQ ID NO 751
<211> LENGTH: 175
<212> TYPE: DNA
<213> ORGANISM: Homo Sapiens

<400> SEQUENCE: 751
actttctctc ctgccctcac aagggaaaaa gaccttgatg aagttctgca gacccactca 60
gtgtttgtaa atgtttccta aggtcaggtt gccaagaagg aagatctcat cagtgcgttt 120
ggaacagatg accaaactga aatctgtaag caggcgggta acagctgcag catag 175

<210> SEQ ID NO 752
<211> LENGTH: 176
<212> TYPE: DNA
<213> ORGANISM: Homo Sapiens

<400> SEQUENCE: 752
cacttcagtt atgtacctga tgggtatttc taggcaagag gaggaacgac gtagaagaga 60
ggaagagatg atgattcgtc aacgtgagat ggaagaacaa atgaggcgcc aaagagagga 120
aagttacagc cgaatgggct acatggatcc agtaagtcag cctttactgc cttcca 176

<210> SEQ ID NO 753
<211> LENGTH: 178
<212> TYPE: DNA
<213> ORGANISM: Homo Sapiens

<400> SEQUENCE: 753
ttccccattc cccattccaa ggtaatgtaa atgggaaaaa aagaaaccac acaaagagga 60
tacaggaccc tacagaagat gctgaagctg aggacacacc caggaaaaga ctcaggacgg 120
acaagcacag tcttcggaag gtaattgtgt tccaggtttg cttgacctgt cagagtgt 178

<210> SEQ ID NO 754
<211> LENGTH: 167
<212> TYPE: DNA
<213> ORGANISM: Homo Sapiens

<400> SEQUENCE: 754
tgctgaacgc atttggctta tttctccctt tcacactttc aaaaatagat cctcgtccct 60
cccaagatgt tgtttacacg aggggcttca taacggattc taacggaaga cactgaaaag 120
gtaacttgtc agagggggaa gagggtggct gcttggggta gggttta 167

<210> SEQ ID NO 755
<211> LENGTH: 201
<212> TYPE: DNA
<213> ORGANISM: Homo Sapiens

<400> SEQUENCE: 755
tcattgtgtc ttccctcctc tagctatctt aatgacttgg accgcgtagc tgaccctgcc 60
tacctgccta cgcaacaaga tgtgcttaga gttcgagtcc ccaccacagg gatcatcgaa 120
tacccctttg acttacaaag tgtcattttc aggtagtaac tgagtccatg aaacctattt 180
cccagctttt atgccttgag t 201

<210> SEQ ID NO 756
<211> LENGTH: 159
<212> TYPE: DNA
<213> ORGANISM: Homo Sapiens

<400> SEQUENCE: 756
tgttgacaat gttttctccc acagggaaaa agcaagcatg gttgtccctg aagaaagaga 60
aggcagagat gaaacaaact tagacctagt aagaggcaca gcatctgcag atgtttccac 120
tgacactcgg aaagccggtg agtcctgcac tttgtcagg 159

<210> SEQ ID NO 757
<211> LENGTH: 163
<212> TYPE: DNA
<213> ORGANISM: Homo Sapiens

<400> SEQUENCE: 757
acatttttaa tgctcctttc tttgacagaa aaagcagaca gctctgaaag agaggcactc 60
atgtcagaac tcaagatgat gacccagctg ggaagccacg agaatattgt gaacctgctg 120
ggggcgtgca cactgtcagg taacccactt ccacgaaaat cac 163

<210> SEQ ID NO 758
<211> LENGTH: 202
<212> TYPE: DNA
<213> ORGANISM: Homo Sapiens

<400> SEQUENCE: 758
agcaaaagga gtgacattcc taatgtgttc tttctcccat tcttctaggc tgacaaacgg 60
gctcatcata atgcactgga acgaaaacgt agggaccaca tcaaagacag ctttcacagt 120
ttgcgggact cagtcccatc actccaagga gagaaggtga gtttcctgag aaagctgagt 180
agctggccac tactagcttg ga 202

<210> SEQ ID NO 759
<211> LENGTH: 151
<212> TYPE: DNA
<213> ORGANISM: Homo Sapiens

<400> SEQUENCE: 759
tctcatcatt tcactgagat atgcatctat tacttttaca tttcaggcca aaagtgtgat 60
ccaagctgtc ccaatgggag ctgctggggt gcaggagagg agaactgcca gaaacgtaag 120
tcagtgaaca gcctcagacc catgtgtgac c 151

<210> SEQ ID NO 760
<211> LENGTH: 195
<212> TYPE: DNA
<213> ORGANISM: Homo Sapiens

<400> SEQUENCE: 760
tgaacttgtc acttcattgg tcaatttaat gatttctaca ggagcagttt ttgcaagaaa 60
ggatcaaagt gaacggaaaa gctgggaacc ttggtggagg ggtggtgacc atcgaaagga 120
gcaagagcaa gatcaccgtg acatccgagg tgcctttctc caaaaggtac aggagggaag 180
tgtgtgtgtg gcctg 195

<210> SEQ ID NO 761
<211> LENGTH: 196

<212> TYPE: DNA
<213> ORGANISM: Homo Sapiens

<400> SEQUENCE: 761
aggcagcctt tataaaagca aattaaccca tgtgggcctt aatttttaga cagcactacc 60
acctggactg gaagtaggac tgcaccatac acacctaatt tgcctcacca ccaaaacggc 120
catcttcagc accacccgcc tatgccgccc catcccggac attactgtaa gctcttgttt 180
ttgttgtaag ggctat 196

<210> SEQ ID NO 762
<211> LENGTH: 150
<212> TYPE: DNA
<213> ORGANISM: Homo Sapiens

<400> SEQUENCE: 762
acccattttc cttcctggac atgctgcctg cagggccact catggtgatt gtggaattct 60
gcaaatttgg aaacctgtcc acttacctga ggagcaagag aaatgaattt gtcccctaca 120
aggtatgtca tctcctaatc ctgctctggc 150

<210> SEQ ID NO 763
<211> LENGTH: 181
<212> TYPE: DNA
<213> ORGANISM: Homo Sapiens

<400> SEQUENCE: 763
aaaaatttcc cctgcgctta gattcttcta ctcaaaacaa aagagccaac agaacagaag 60
aaaatgtttc agacggttcc ccaaatgccg gttctgtgga gcagacgccc aagaagcctg 120
gcctcagaag acgtcaaacg taaacagctc ggtgggttga tcactaaagg agcacgcact 180
g 181

<210> SEQ ID NO 764
<211> LENGTH: 156
<212> TYPE: DNA
<213> ORGANISM: Homo Sapiens

<400> SEQUENCE: 764
agacatgatg cttcgcttga aggtaatctt tacggttctt ctctcaacag ctttgaaaag 60
tccagccgca tttcatgagc agagaaggag cttggagcgg gccagggtaa ggtacctttt 120
ttccccctca gaactcccaa agagcatttt cagagc 156

<210> SEQ ID NO 765
<211> LENGTH: 184
<212> TYPE: DNA
<213> ORGANISM: Homo Sapiens

<400> SEQUENCE: 765
tgcacgttgt ttgtagctgt agtgcttgat tttgggtttc tttcacagat aaacttctgc 60
actggagggg cctctcctcc cctcgttctg cacatggagc tctaatcccc acgcctggga 120
tgagtgcaga atatgccccg cagggtattt gtaagttgag ccttatttct tctacaaatg 180
tcca 184

<210> SEQ ID NO 766
<211> LENGTH: 175
<212> TYPE: DNA
<213> ORGANISM: Homo Sapiens

<400> SEQUENCE: 766
gtttcccctg gatttatgtg gtagtagtta actgctgctt ctgtttttag gtttcagaag 60
caggcaacag gaacaagatg tgaactgttt ctcttctgca gaaaaagagg ctcttcctcc 120
tcctcccgcg acggtgggtg tgctgtcctt tatcgctgca gtaaaggcga aggtg 175

<210> SEQ ID NO 767
<211> LENGTH: 150
<212> TYPE: DNA
<213> ORGANISM: Homo Sapiens

<400> SEQUENCE: 767
acgtgcatgt cctttttccc ttttcgtgtt ctgcaggtgg acgttgccat aagtcctgta 60
ctggccgttg ctggggaccc acagaaaatc attgccagac ttgtaagtgt tcatcagtga 120
gagcacacag gtttgatgtg gtcaaggaat 150

<210> SEQ ID NO 768
<211> LENGTH: 150
<212> TYPE: DNA
<213> ORGANISM: Homo Sapiens

<400> SEQUENCE: 768
tgtctctacc tcctacatct tatctccagg ttggatgatt gatgagaaca ttcgcccaac 60
ctttaaagaa ctagccaatg agttcaccag gatggcccga gacccaccac ggtatctggt 120
cataaaggtg agtagggagt aggaggtgct 150

<210> SEQ ID NO 769
<211> LENGTH: 152
<212> TYPE: DNA
<213> ORGANISM: Homo Sapiens

<400> SEQUENCE: 769
ggttgtttct atttgctaat gctgtttctg ttgacttttg acttttctag tttcccagag 60
ctatggggac ttcccatccg gcgttcctgg tcttaggctg tcttctcaca ggtacggagc 120
ccagtcctct ctgagttcct tgtttgggtg tc 152

<210> SEQ ID NO 770
<211> LENGTH: 164
<212> TYPE: DNA
<213> ORGANISM: Homo Sapiens

<400> SEQUENCE: 770
agcacttcct gaaataattt caccttcgtt tttttccttc tgcaggagga caccatggag 60
gtggaagagt tcttgaaaga agctgcagtc atgaaagaga tcaaacaccc taacctggtg 120
cagctccttg gtgagtaagc ccggggctct gaagagaggg tctc 164

<210> SEQ ID NO 771
<211> LENGTH: 194
<212> TYPE: DNA
<213> ORGANISM: Homo Sapiens

<400> SEQUENCE: 771
atgggcctca ctgtctgttt ttgctatagg tgggaactgc aagatacatg gctccagaag 60
tcctagaatc caggatgaat ttggagaatg ttgagtcctt caagcagacc gatgtctact 120
ccatggctct ggtgctctgg gaaatgacat ctcgctgtaa tgcagtggga ggtaggtgtg 180
gaccagcatc attg 194

<210> SEQ ID NO 772
<211> LENGTH: 151
<212> TYPE: DNA
<213> ORGANISM: Homo Sapiens

<400> SEQUENCE: 772
gtcctcatgg ctctgtgact gtgcctcttg tcaggtgtat gagtttagag tcaaagaatc 60
tagcatcata gctccagctc ccgctgagga tgtggatact cctccaagga aaaagaagag 120
gaaacaccgg tgagtctgtc atgaagctcc t 151

<210> SEQ ID NO 773
<211> LENGTH: 173
<212> TYPE: DNA
<213> ORGANISM: Homo Sapiens

<400> SEQUENCE: 773
cccacctgca ttgttcatca tgttaatgcc agttcttttt taggtatcat ctttatcaga 60
aagtgaggag tcccaggact catccgacag cataggctcc tcacagaaag cccacgggat 120
cctagcacgg cgcccatctt acaggtgagt actctcttgt atgaagccct gca 173

<210> SEQ ID NO 774
<211> LENGTH: 152
<212> TYPE: DNA
<213> ORGANISM: Homo Sapiens

<400> SEQUENCE: 774
ggataactat gttcttcctt ttcatcatag atattcttac tgattctccg ggctctgcag 60
ctcttgaccc ggctggtatt gtctctacag ccaattcctc tgaagtcagc aacagcaaag 120
gtgaggtgcg cagggctgcc agagaagagg ag 152

<210> SEQ ID NO 775
<211> LENGTH: 154
<212> TYPE: DNA
<213> ORGANISM: Homo Sapiens

<400> SEQUENCE: 775
ctggcacact tcttcacctc ctctccttac tcttgtttcc agatcctgcc cctgagcttt 60
catgagctgt tgaaccatct ggaattcaca ggcctgtcat gagagacacg atgagaagtc 120
cttaaaggta gatcactgat tcacagggga gcag 154

<210> SEQ ID NO 776
<211> LENGTH: 156
<212> TYPE: DNA
<213> ORGANISM: Homo Sapiens

<400> SEQUENCE: 776
cctcagggat ggtagtgaca gtcttatttc ctattgatac aggatttttt tccttgattc 60
cttcgtggga ctcaagacag gggtgccctg tttactcagc ccactgtgct caacctcttg 120
caggagtgtg caggtgagtg agcaagtgca ggatct 156

<210> SEQ ID NO 777
<211> LENGTH: 158
<212> TYPE: DNA
<213> ORGANISM: Homo Sapiens

<400> SEQUENCE: 777

```
catccatgga atatgttctt ttgcatacag atgccatctc atccggagat gatgaggatg     60

acaccgatgg tgcggaagat tttgtcagtg agaacagtaa caacaagagt aagtaactgc    120

ccggctccga tggtccccga gagaggagca tggaggga                            158


<210> SEQ ID NO 778
<211> LENGTH: 182
<212> TYPE: DNA
<213> ORGANISM: Homo Sapiens

<400> SEQUENCE: 778

ccttgcactc ttgtggttgt ttttcccatt acaggtagag ttggctttgt gggacacagc     60

tgggcaggaa gattatgatc gcctgaggcc cctctcctac ccagataccg atgttatact    120

gatgtgtttt tccatcgaca gccctgatag tttaggtgag tggccctgca ccctgatatt    180

tg                                                                   182


<210> SEQ ID NO 779
<211> LENGTH: 157
<212> TYPE: DNA
<213> ORGANISM: Homo Sapiens

<400> SEQUENCE: 779

aaggtttcca attcaccttt cagctcttca tggaaccagc caggagagag aactggtcag     60

ctgctaatca ccaaatgaac tccctgatct ggcctaggga acagtgggat tcacaggcat    120

gggtgactta gaaaaccggg cccagcagaa atgaatc                             157


<210> SEQ ID NO 780
<211> LENGTH: 169
<212> TYPE: DNA
<213> ORGANISM: Homo Sapiens

<400> SEQUENCE: 780

ggtccccatc cattcttcct attcccttta ggttgttaca ctctggtacc gagctcccga     60

agttcttctg cagtccacat atgcaacacc tgtggacatg tggagtgttg gctgtatctt    120

tgcagagatg tttcgtcgaa agtatgggac ccacataccc tggactacc                169


<210> SEQ ID NO 781
<211> LENGTH: 150
<212> TYPE: DNA
<213> ORGANISM: Homo Sapiens

<400> SEQUENCE: 781

ccaatctgct tatgaccagg agccactcaa gcagcactct cccttcacag gtggtattcc     60

aaacacatga ctcggagtca ggctgagcaa ctgctaaagc aagaggtaag tgtggaacca    120

ctagcacaca gcattctcct tgcataagtg                                     150


<210> SEQ ID NO 782
<211> LENGTH: 150
<212> TYPE: DNA
<213> ORGANISM: Homo Sapiens

<400> SEQUENCE: 782

ggtgggattt tgttgtttgc agctttgact ctcccggatc ttgcagagca gtttgcccct     60

cctgacattg ccccgcctct tcttatcaag ctcgtggaag ccattgaaaa gaaaggtaac    120

cagactgcta gagggcatca gttcctttgt                                     150
```

<210> SEQ ID NO 783
<211> LENGTH: 150
<212> TYPE: DNA
<213> ORGANISM: Homo Sapiens

<400> SEQUENCE: 783
tgaccaattt ggcttcgtcc tcttcctttg cagaaagctg caggagacac agatgtccac 60
cacctcaaag ctggaggaag ctgagcataa ggttcagagc ctacaaacag gtttgatact 120
ctccttccta gtaccatgga tgtggggagg 150

<210> SEQ ID NO 784
<211> LENGTH: 150
<212> TYPE: DNA
<213> ORGANISM: Homo Sapiens

<400> SEQUENCE: 784
tcaaagctgc ttctgtcatc tgtgtgaaca tgcgcttttc tctctgcaga acctgagagc 60
cagaagcaac aaagatgcca aggatccaac gaccaagaac tctctggaaa gtgagttctg 120
catgctgagg tctctgtgtg ccctcgtcag 150

<210> SEQ ID NO 785
<211> LENGTH: 150
<212> TYPE: DNA
<213> ORGANISM: Homo Sapiens

<400> SEQUENCE: 785
ggctaatggt tctcagagct aagtatcaag gatttcattc tcctttgtag ggatcctgga 60
gcgggttgtg agaaggaatg ggcgcgtgga tcgtagcctg aaagacgagt gtgatacggt 120
gaaaggatgg aggctgtgca atgggagaat 150

<210> SEQ ID NO 786
<211> LENGTH: 151
<212> TYPE: DNA
<213> ORGANISM: Homo Sapiens

<400> SEQUENCE: 786
gcctttcaat tcactgtcct cactctgact tctcttgttt gttctagaac tttgctcccc 60
agctgtctta tggctatgat gagaaatcaa ccggaggaat ttccgtgcct ggccccatgg 120
tgagccagca gggggagcat ggatgacaga a 151

<210> SEQ ID NO 787
<211> LENGTH: 190
<212> TYPE: DNA
<213> ORGANISM: Homo Sapiens

<400> SEQUENCE: 787
tcagcagggt ttttcttgct tgttttcagg ctttgtggat ttgaccctcc atgatcaggt 60
ccaccttcta gaatgtgcct ggctagagat cctgatgatt ggtctcgtct ggcgctccat 120
ggagcaccca gggaagctac tgtttgctcc taacttgctc ttggacaggt aagtgacctg 180
gctgtagctt 190

<210> SEQ ID NO 788
<211> LENGTH: 151
<212> TYPE: DNA
<213> ORGANISM: Homo Sapiens

<400> SEQUENCE: 788
ggttttcctc tccttcccca cagggcgagc tactatagaa agggaggctg tgccatgctg 60
ccagttaagt ggatgccccc agaggccttc atggaaggaa tattcacttc taaaacagac 120
acatggtaag tcagccatca tcctccaggt a 151

<210> SEQ ID NO 789
<211> LENGTH: 138
<212> TYPE: DNA
<213> ORGANISM: Homo Sapiens

<400> SEQUENCE: 789
ccatgacact ccttccacct catggcccct ttctgttttc cagcaagatc tttgcaggag 60
tttgccactg tcctcaggaa tcttgaagat gaacggatac ggatggtgag tagggctggg 120
ctactcttgg tcccagat 138

<210> SEQ ID NO 790
<211> LENGTH: 153
<212> TYPE: DNA
<213> ORGANISM: Homo Sapiens

<400> SEQUENCE: 790
tgtaattcct ggcttctagg tttctaattc tgattttctc ctccagaaag atccccagca 60
ggccctcaag gagctggcta agatgtgtat cctggccgac tgcacattga tcctcgcctg 120
gaggtgagat gagggcttcc ctgcctcatt cag 153

<210> SEQ ID NO 791
<211> LENGTH: 151
<212> TYPE: DNA
<213> ORGANISM: Homo Sapiens

<400> SEQUENCE: 791
cgtgttcccg tttcctcttg atctcccagg tatttctttg ctgtgctggc gatcctcacc 60
atcctcggcg ttctcaatgg gctggttttg cttcccgtgc ttttgtcttt ctttggacca 120
tatcctgagg tcagtagtga cacggggatg t 151

<210> SEQ ID NO 792
<211> LENGTH: 178
<212> TYPE: DNA
<213> ORGANISM: Homo Sapiens

<400> SEQUENCE: 792
cctctgtgta tctccttccc aggtaccgca tgcacaagtc ccggatgtac agccagtgtg 60
tccgaatgag gcacctctct caagagtttg gatggctcca aatcaccccc caggaattcc 120
tgtgcatgaa agcactgcta ctcttcagca ttagtaagtg cctagaagtg cagggaat 178

<210> SEQ ID NO 793
<211> LENGTH: 172
<212> TYPE: DNA
<213> ORGANISM: Homo Sapiens

<400> SEQUENCE: 793
gctttctttt tgctccccca gggcctggtg aaatccccat gggaatgggg gctaatccct 60
atggccaagc agcagcatct aaccaactgg gttcctggcc cgatggcatg ttgtccatgg 120
aacaagtttc tcatggcact caaaataggt ggggtgttat tttgtgactc tg 172

<210> SEQ ID NO 794
<211> LENGTH: 150

<212> TYPE: DNA
<213> ORGANISM: Homo Sapiens

<400> SEQUENCE: 794
acttttaccc tggatttgcc cattcagaac agccacccca tcttttctct caactgggag 60
tgtgtggtca gtttcctgtg gaacacagag gctgcctgtc ccattcagac aacgacggat 120
acagaccagg tacgtgtgct ttcacctggc 150

<210> SEQ ID NO 795
<211> LENGTH: 157
<212> TYPE: DNA
<213> ORGANISM: Homo Sapiens

<400> SEQUENCE: 795
ggtggggttt tgttaacgtg aatttaatct ttttgacaga aataacagca ggctggggaa 60
tggagtgctg tatgcctctg tgaacccgga gtacttcagc gctgctgatg gtaagagtcc 120
gggccaccag cactgccagc gtgcagggca ggtagat 157

<210> SEQ ID NO 796
<211> LENGTH: 157
<212> TYPE: DNA
<213> ORGANISM: Homo Sapiens

<400> SEQUENCE: 796
agtgtaaagt taaccttgct gtgtattttc ccttatttta ggctgctcct gcgtttggtg 60
gatgatttct tgttggtgac acctcacctc acccacgcga aaaccttcct caggtgaggc 120
ccgtgccgtg tgtctgtggg gacctccaca gcctgtg 157

<210> SEQ ID NO 797
<211> LENGTH: 153
<212> TYPE: DNA
<213> ORGANISM: Homo Sapiens

<400> SEQUENCE: 797
gtatcaaggc tgccctgact gtcatgctcc ctgtcttcca cagcgggagt cgtgtgaggt 60
tggctgtagc agcgcggaag gtgcatatga agaggaagta ctgggtaaga ggacacacac 120
gacttttaaa aaataggctg caccactcta gtg 153

<210> SEQ ID NO 798
<211> LENGTH: 181
<212> TYPE: DNA
<213> ORGANISM: Homo Sapiens

<400> SEQUENCE: 798
ttcaggccac caacctcatt ctgttttgtt ctctatcgtg tccccacagg gaaaagcttc 60
actctgacca tcactgtctt cacaaaccca ccgcaagtcg ccacctacca cagagccatc 120
aaaatcacag tggatgggcc ccgagaacct cgaagtaagt gcatccactt ggggctggta 180
c 181

<210> SEQ ID NO 799
<211> LENGTH: 156
<212> TYPE: DNA
<213> ORGANISM: Homo Sapiens

<400> SEQUENCE: 799
gtgctgattc cctgatgtgc cttctacctc ttttcttctc tcccgccagg gagctcgagg 60
acaatatgag tgaccgggtt cagtttgtga tcacagcaca ggaatgggat cccagctttg 120
aggaggtgag taccaaagag gcagagaatg ggagac 156

<210> SEQ ID NO 800
<211> LENGTH: 156
<212> TYPE: DNA
<213> ORGANISM: Homo Sapiens

<400> SEQUENCE: 800
accaacatgg atggagtggt cactgtgacg cccagaagta tggacgcaga aacctacgtg 60
gaaggccagc gcatctcaga aaccaccatg ctgcagagtg gcatgaaagt gcagtttggg 120
gcgtcccatg tatttaagtt tgtggacccc agtcag 156

<210> SEQ ID NO 801
<211> LENGTH: 156
<212> TYPE: DNA
<213> ORGANISM: Homo Sapiens

<400> SEQUENCE: 801
tgcccaccct aatcctgtgt ttctttgcct cctatagaca tgattcctat ggcaatcagt 60
tctccaccca aggcacccct tctggcagcc ccttccccag ccagcagact acaatgtatc 120
aacagcaaca gcaggtgagg agggtagctg ggaatg 156

<210> SEQ ID NO 802
<211> LENGTH: 154
<212> TYPE: DNA
<213> ORGANISM: Homo Sapiens

<400> SEQUENCE: 802
ctgcctctct tttctcccca tacaggacgg gctctacgag tgcattctct gtgcctgctg 60
tagcaccagc tgccccagct actggtggaa cggagacaaa tatctggggc ctgcagttct 120
tatgcaggtg aggtgctcct taattgcttt aaga 154

<210> SEQ ID NO 803
<211> LENGTH: 184
<212> TYPE: DNA
<213> ORGANISM: Homo Sapiens

<400> SEQUENCE: 803
gaagtcatgg gctgcttgtc ctgtgctctc tccccaggag aaaagcctta cagatgctca 60
tgggaagggt gtgagtggcg ttttgcaaga agtgatgagt taaccaggca cttccgaaag 120
cacaccgggg ccaagccttt taaatgctcc cactgtgaca ggtacgtgcc tgaggacaat 180
gctg 184

<210> SEQ ID NO 804
<211> LENGTH: 150
<212> TYPE: DNA
<213> ORGANISM: Homo Sapiens

<400> SEQUENCE: 804
ccaagctgtg aaggcctttt aacagaccac cttccttctg attcccagag accccacccc 60
ctggctacct gagtgaagat ggagaaacca gtgaccacca gatgaaccac agcatggacg 120
caggtcagtc atgcagggtc atgctcttat 150

<210> SEQ ID NO 805
<211> LENGTH: 150

<212> TYPE: DNA
<213> ORGANISM: Homo Sapiens

<400> SEQUENCE: 805
cctccttctc acgtgtctgt gtttcttttc tcctccatgc tatggcagtg gtgccccgtg 60
ctgatgagac aatacttggt gcagccccag gcagtccttt tccaggtaat ttcctaggga 120
cccaaatgat gcccagtgca cactctcctg 150

<210> SEQ ID NO 806
<211> LENGTH: 204
<212> TYPE: DNA
<213> ORGANISM: Homo Sapiens

<400> SEQUENCE: 806
agcagagtga cccagtgatg tttgtctgtt acagatcacg gatacacgac tctagccacc 60
agtgtgaccc tgttaaaagc ctcggaagtg gaagagattc tggatggcaa cgatgagaag 120
tacaaggctg tgtccatcag cacagagccc cccacctacc tcaggtaatg cgttcctggc 180
cagggcatct ctggggacac ctgt 204

<210> SEQ ID NO 807
<211> LENGTH: 130
<212> TYPE: DNA
<213> ORGANISM: Homo Sapiens

<400> SEQUENCE: 807
tcctctctgg atcctcgtga ggtataaaga cgagtcctcc accaccagtc aggcacactc 60
taccaccatg aatccactcc tgatccttac ctttgtggca gctgctcgtg agtatcatgc 120
cctgcctcag 130

<210> SEQ ID NO 808
<211> LENGTH: 150
<212> TYPE: DNA
<213> ORGANISM: Homo Sapiens

<400> SEQUENCE: 808
ggagctgctc ctcatcctac tcacctttcc ctcatagtcc ggaagaccaa gggcaaccga 60
agtacctcac ctgtcactga ccccagcatc cccattagga agaaatcaaa ggatggcaaa 120
ggtatggaca gctgggactc aggtgaggtg 150

<210> SEQ ID NO 809
<211> LENGTH: 150
<212> TYPE: DNA
<213> ORGANISM: Homo Sapiens

<400> SEQUENCE: 809
tgaagttttt gtctgtttct ccccctgcag catctgatgc tgttcagatg cagagagagt 60
ggagctttgc gcggacacac cctctgctca cctcactgta ccgcagggtg agtggatgtg 120
gtattatacc tgcttctgag ctcgtggcgg 150

<210> SEQ ID NO 810
<211> LENGTH: 157
<212> TYPE: DNA
<213> ORGANISM: Homo Sapiens

<400> SEQUENCE: 810
actggatctg cttcacacct aggtcccgac atctgtggcc ctggcaccaa gaaggttcat 60
gtcatcttca actacaaggg caagaacgtg ctgatcaaca aggacatccg ttgcaaggtg 120
tgcctggggg tggtggcaaa tggctgtcat ggggaga 157

<210> SEQ ID NO 811
<211> LENGTH: 157
<212> TYPE: DNA
<213> ORGANISM: Homo Sapiens

<400> SEQUENCE: 811
ctttccctca ttccctcccc actgcctact tctacttcct cccaggttat gagcagccgt 60
tttctgccct acgacaacat catcacagac gccgtgctca gccttgacga ggacacggtg 120
ctttcaacaa cagaggtaag aacccatgcc tgaggag 157

<210> SEQ ID NO 812
<211> LENGTH: 151
<212> TYPE: DNA
<213> ORGANISM: Homo Sapiens

<400> SEQUENCE: 812
ttgggcctgt gttatctcct aggttggctc tgactgtacc accatccact acaactacat 60
gtgtaacagt tcctgcatgg gcggcatgaa ccggaggccc atcctcacca tcatcacact 120
ggaagactcc aggtcaggag ccacttgcca c 151

<210> SEQ ID NO 813
<211> LENGTH: 151
<212> TYPE: DNA
<213> ORGANISM: Homo Sapiens

<400> SEQUENCE: 813
cctgaccctt ctccctatcc ccagctatga gatcatgcag aagtgctggg aagagaagtt 60
tgagattcgg cccccccttct cccagctggt gctgcttctc gagagactgt tgggcgaagg 120
ttacaaaaag gtatgttgag gcagggtagg g 151

<210> SEQ ID NO 814
<211> LENGTH: 185
<212> TYPE: DNA
<213> ORGANISM: Homo Sapiens

<400> SEQUENCE: 814
tccctttctc ccctctttga atgaagaggg aaggtgccca cctgtccacc atggctgtga 60
agatgatccg tgccctgagg gatccgaatg tgtgtctgat ccctgggagg agaaacacac 120
ctgtgtctgt cccagcggca ggtttggtca gtgcccaggt gagagttgaa tggttgggta 180
tactt 185

<210> SEQ ID NO 815
<211> LENGTH: 152
<212> TYPE: DNA
<213> ORGANISM: Homo Sapiens

<400> SEQUENCE: 815
actcaagtcc ctttcccctc tctaccctct caggactggc agccaccctt tgctgtggaa 60
gtggacaact tcaggtttac cccccgaatc cagaggctga atgagctaga ggtgagaaga 120
ctaggagctg gtggtggggt tgggagaatg ta 152

<210> SEQ ID NO 816
<211> LENGTH: 169

<212> TYPE: DNA
<213> ORGANISM: Homo Sapiens

<400> SEQUENCE: 816
tcttcacttc agttgcccct acctattctt gctctcctcc gcaggtccag ggcttactgg 60
agaatggaga cagtgtgacc agtcctgaga aggtagcccc ggaggagggc tcaggtaaga 120
gaggtaggtc taggtgtggt gtgggtaggc tgttgactgc acatcacca 169

<210> SEQ ID NO 817
<211> LENGTH: 152
<212> TYPE: DNA
<213> ORGANISM: Homo Sapiens

<400> SEQUENCE: 817
ccacactgag cctttttccc ttctttgtgt ttgcagccac agcacagggt acgagagcga 60
taaccacaca acgcccatcc tctgcggagc ccaatacaga atacacacgc acggtgtctt 120
cagaggcatt caggtgagca cacagacagg cc 152

<210> SEQ ID NO 818
<211> LENGTH: 150
<212> TYPE: DNA
<213> ORGANISM: Homo Sapiens

<400> SEQUENCE: 818
catgatgcgc tgtgtgtccc tgcttctaga tgccgacaaa aggatcaagg tggcgaagcc 60
cgtggtggag atggatggtg atgagatgac ccgtattatc tggcagttca tcaaggagaa 120
ggtagtgccc cctcctgaag tgggtggctc 150

<210> SEQ ID NO 819
<211> LENGTH: 137
<212> TYPE: DNA
<213> ORGANISM: Homo Sapiens

<400> SEQUENCE: 819
aggaagggca gtgaggattc actggagtct cttcacctct cccaggcatg tcagccacgt 60
ggggtgggac ccccagaatg gatttgacgt gagtaacttc agagtctctt ggactccact 120
aaacttccac ccaccct 137

<210> SEQ ID NO 820
<211> LENGTH: 115
<212> TYPE: DNA
<213> ORGANISM: Homo Sapiens

<400> SEQUENCE: 820
caaaaagtgc cagccctcac ctccctgtct tcttgtctag gttttccgtg tgtatcaggg 60
ccaacagcca gggacctgta tggtaagtct cctaggcctc tcccaaccgt gtctc 115

<210> SEQ ID NO 821
<211> LENGTH: 184
<212> TYPE: DNA
<213> ORGANISM: Homo Sapiens

<400> SEQUENCE: 821
actaagttgc cacaggacct gcagcctgcc cactctcccc taggtgccgc cggatggtgg 60
tggttgtctc tgatgattac ctgcagagca aggaatgtga cttccagacc aaatttgcac 120
tcagcctctc tccaggtaag ctcaaccctg ctctggcaag agaatgaggg aatgtgtagg 180
tggg 184

<210> SEQ ID NO 822
<211> LENGTH: 153
<212> TYPE: DNA
<213> ORGANISM: Homo Sapiens

<400> SEQUENCE: 822
gggctctggg gcattaacat atcccattgt gtcctgtttc caggagcctg actacggggc 60
cctgtatgag ggacgcaacc ctggcttcta tgtagaggca aaccctatgc caactttcaa 120
ggtacagctc aggcctctgg gcataggaag ctg 153

<210> SEQ ID NO 823
<211> LENGTH: 142
<212> TYPE: DNA
<213> ORGANISM: Homo Sapiens

<400> SEQUENCE: 823
cgaagtctcg ctcttttccc ataggctgga gtgcaatggt gtgatctcag ctcactgcaa 60
cctctgcttc ctgggtttaa gtgattctcc tgcctcagcc tcccgagtag ctgggattac 120
aggtgactgc caccacgctc ag 142

<210> SEQ ID NO 824
<211> LENGTH: 156
<212> TYPE: DNA
<213> ORGANISM: Homo Sapiens

<400> SEQUENCE: 824
tgttttgttg ttcttggcat tttctaggag aagcaacagt ttcagcgcca tctgacccgc 60
ccaccacccc agtaccaaga cccgacacaa ggcagcttcc cacagcaggt tggacagttc 120
acaggtaggg ggtgtctgtg tgacgagcag ggacag 156

<210> SEQ ID NO 825
<211> LENGTH: 174
<212> TYPE: DNA
<213> ORGANISM: Homo Sapiens

<400> SEQUENCE: 825
acctgcccag atccttaacc tcagcctctt ctccagcagg ctggagagca cagaagcaga 60
gatgcatatt ccctcagccc tagagcctag cacgtccagc tccccaaggg gcagcacaga 120
ttcccttaac caaggtgggt aaaccaatag ctaggccatt gtcttctggg tacg 174

<210> SEQ ID NO 826
<211> LENGTH: 119
<212> TYPE: DNA
<213> ORGANISM: Homo Sapiens

<400> SEQUENCE: 826
ctctctccac ccaaaccctt gtaggatggc agctgtgacc cgggatttcg gtgagatgct 60
tctgcactct ggccgggtcc tgccagccga aggtaagttt tcagttccat ttcaaagcc 119

<210> SEQ ID NO 827
<211> LENGTH: 162
<212> TYPE: DNA
<213> ORGANISM: Homo Sapiens

<400> SEQUENCE: 827
tcccctcctc ttcttgttct ctcattagct tcgcctcaac agcatcaaga agctgtccac 60
catcgccttg gcccttgggg ttgaaaggac ccgaagtgag cttctgcctt tccttacagg 120
taacaaaggg gacccctggg gcccagatgt ggggactctt gg 162

<210> SEQ ID NO 828
<211> LENGTH: 150
<212> TYPE: DNA
<213> ORGANISM: Homo Sapiens

<400> SEQUENCE: 828
cgacttcagt cttccacttc ctatttccac ccagttccag cgccaggggc ttcagcagac 60
ccagcagcag caacagacag cagctttggt ccggcaactt caacaacagc tctctagtaa 120
gcctgcctgc cttcccaagg agaaccccat 150

<210> SEQ ID NO 829
<211> LENGTH: 150
<212> TYPE: DNA
<213> ORGANISM: Homo Sapiens

<400> SEQUENCE: 829
tcagcaggaa gtgttgacct tttggccttt gtctccttgc aggcaggtga cagcagggac 60
atgtctcggg agatgcagga tgtagacctc gctgaggtga agcctttggt ggagaaaggg 120
gaggtgagtg gagatcttcc tggctacccc 150

<210> SEQ ID NO 830
<211> LENGTH: 150
<212> TYPE: DNA
<213> ORGANISM: Homo Sapiens

<400> SEQUENCE: 830
gaggccaggc atttttcact agggcctctg ctttgcagac agatcttgga gctgccctgg 60
aaggaggaaa ctttcttggt gttgcagtca ctcctagagc ggcaggtgag caggctgccc 120
tggggaagag tggacaaaga agtgctgcag 150

<210> SEQ ID NO 831
<211> LENGTH: 157
<212> TYPE: DNA
<213> ORGANISM: Homo Sapiens

<400> SEQUENCE: 831
caacacagtc tctccctcca gcatctggtt ttgtagcctg gatgtgtctg ctagtagccg 60
aatggtggtc acaggagaca acgtggggaa cgtgatcctg ctgaacatgg acggcaaaga 120
ggtgcgttct ccgaggtcct gcctttccct ccctcac 157

<210> SEQ ID NO 832
<211> LENGTH: 155
<212> TYPE: DNA
<213> ORGANISM: Homo Sapiens

<400> SEQUENCE: 832
ttgctgctgc ctcgcttatc gtgacctctg ttgctctcca gatcatcggc cgtggcaatg 60
accaggtggc catcagctcc aaatttgaga cccgggagga tattggtatg ctgccagtgg 120
ggctggtttc tgtgggttcc aagaggggag gtgta 155

<210> SEQ ID NO 833
<211> LENGTH: 162
<212> TYPE: DNA

<213> ORGANISM: Homo Sapiens

<400> SEQUENCE: 833
actgttctga cacaccccac ccctctctgc aggtggagtg accacctttg tggccctcta 60
tgactatgag tctaggacgg agacagacct gtccttcaag aaaggcgagc ggctccagat 120
tgtcaacaac acgtgagtgc ccccttccct attgcccctc ag 162

<210> SEQ ID NO 834
<211> LENGTH: 169
<212> TYPE: DNA
<213> ORGANISM: Homo Sapiens

<400> SEQUENCE: 834
ctctaaatcc ctcgccctgg ctgtgtcctc aggtgctgtg tggccagtca gcagagggac 60
aggaatcatt cggccactgt tcagacggga gccacaccct tctccaatcc aagcctggct 120
ccagaagagt gagtgtcttt acctgacatt actgagatct gccgagtgc 169

<210> SEQ ID NO 835
<211> LENGTH: 156
<212> TYPE: DNA
<213> ORGANISM: Homo Sapiens

<400> SEQUENCE: 835
aacctctacc cacccattcc tttccagggc actgaagcca aaggcagaag ttgatgagga 60
tggagttgtg atgtgctcag gccctgagga gggagaggag gtgggccagg tgaaagggct 120
ggggcaagaa tggtctggag gtgatggaag ggatga 156

<210> SEQ ID NO 836
<211> LENGTH: 179
<212> TYPE: DNA
<213> ORGANISM: Homo Sapiens

<400> SEQUENCE: 836
tcctctctcc ccactctcag tctgcagcca ggagagcagg gacgtcctgt gcgaactgtc 60
agaccaccac aaccacactc tggaggagga atgccaatgg ggaccctgtc tgcaatgcct 120
gtgggctcta ctacaagctt cacaatgtaa gtggactggg atcagcaaga acagggctc 179

<210> SEQ ID NO 837
<211> LENGTH: 138
<212> TYPE: DNA
<213> ORGANISM: Homo Sapiens

<400> SEQUENCE: 837
aaaaacgggt ggttgggcgc cgctgtcttt tcagtcgggc gctgagtggt ttttcggatc 60
atgtctggtg gctccgcgga ttataacagg tatgcagtct gttggcggtc gcggtctgta 120
gtgaaggtca tagggcgc 138

<210> SEQ ID NO 838
<211> LENGTH: 150
<212> TYPE: DNA
<213> ORGANISM: Homo Sapiens

<400> SEQUENCE: 838
acagacagcc gaacagacac ggcaggtctc atgagccttc ccagccaccg tagtgccggt 60
gccctgagaa caggactgag tgatggcttc caactccagc gatggtgagg ctgagtcctg 120
ttactatagc aacttcctag gcacactctg 150

<210> SEQ ID NO 839
<211> LENGTH: 156
<212> TYPE: DNA
<213> ORGANISM: Homo Sapiens

<400> SEQUENCE: 839
ttctttttag tctagtgctc cactagctcc tctcctactg agctggggta agaagcggag 60
cgtatacgga ggaggcggga tgcatttctg catcgagcgc acaaaggtgt ggcggagggg 120
gctccagagc tgggaggggt caatctacgg gcgaat 156

<210> SEQ ID NO 840
<211> LENGTH: 154
<212> TYPE: DNA
<213> ORGANISM: Homo Sapiens

<400> SEQUENCE: 840
taagcccggg acttccttgc ctctcttggt agtggtgaat ctggagctgg caagacggag 60
aacaccaaga aggtcatcca gtatctggcg tacgtggcgt cctcgcacaa gagcaagaag 120
gaccaggtga gtgctgcagc ccttgtccct gtgg 154

<210> SEQ ID NO 841
<211> LENGTH: 150
<212> TYPE: DNA
<213> ORGANISM: Homo Sapiens

<400> SEQUENCE: 841
ggggttttga ttggctgagg gtggagtttg tatctgcagg tttagcgcca ctctgctggc 60
tgaggctgcg gagagtgtgc ggctccaggt gggctcacgc ggtgagtcat atggggaact 120
tctgttgggt gtttggtggt tcgaatccca 150

<210> SEQ ID NO 842
<211> LENGTH: 150
<212> TYPE: DNA
<213> ORGANISM: Homo Sapiens

<400> SEQUENCE: 842
cctagggtga ggcttatggg cttttactcc tcagggcagg agacgctgca gagcattact 60
tggacctgct ggccctgttg ctggatagct cggagccaag ggtgggtgtg tcttcaagct 120
tctctgcaat ggggtagacg ggttggtgtc 150

<210> SEQ ID NO 843
<211> LENGTH: 151
<212> TYPE: DNA
<213> ORGANISM: Homo Sapiens

<400> SEQUENCE: 843
gggtggccat taacacacaa tgggctttct atcctgggcc tcagatcgtt ggtgtctgca 60
ctgaagagct acactcagcc cagcagtgga acgggcaggg catcctggag ctgctgcgga 120
cagtgcctat gtgagtaccc atgcaaggtg g 151

<210> SEQ ID NO 844
<211> LENGTH: 334
<212> TYPE: DNA
<213> ORGANISM: Homo Sapiens

<400> SEQUENCE: 844
ctgcgaggag gggagaattc ttggggctga gctgggagcc cggcaactct agtatttagg 60
ataaccttgt gccttggaaa tgcaaactca ccgctccaat gcctactgag tagggggagc 120
aaatcgtgcc ttgtcatttt atttggaggt ttcctgcctc cttcccgagg ctacagcaga 180
cccccatgag agaaggaggg gagcaggccc gtggcaggag gagggctcag ggagctgaga 240
tcccgacaag cccgccagcc ccagccgctc ctccacgcct gtccttagaa aggggtggaa 300
acatagggac ttggggcttg gaacctaagg ttgt 334

<210> SEQ ID NO 845
<211> LENGTH: 150
<212> TYPE: DNA
<213> ORGANISM: Homo Sapiens

<400> SEQUENCE: 845
tcccattccc gtgtttcctt gcagtgacag cccacacagc gagccagggg ccatcgatga 60
agttgaccat gacaatggca ctgagcctca taccagcgat gaaggtgagt gagggggatc 120
ctggggacaa gggattcttc ctggggcctc 150

<210> SEQ ID NO 846
<211> LENGTH: 129
<212> TYPE: DNA
<213> ORGANISM: Homo Sapiens

<400> SEQUENCE: 846
aggctctgat gtgcttctct ctctcccttt gcagccgctg tacaaccagc cctccgacac 60
ccggcagtat catgagaaca tcaaaatgtg agtgctcgcg ggcagccgtg cagacacaca 120
gaggcaggg 129

<210> SEQ ID NO 847
<211> LENGTH: 165
<212> TYPE: DNA
<213> ORGANISM: Homo Sapiens

<400> SEQUENCE: 847
gttttctgtc tgcctctgcc attcccagtg tgaccactcg tgctcagccg tatctcagca 60
ggaggacagg tgccggagca gctcgtgcag ctaagcagcc aactgcagaa acgtcaggtg 120
ggtggtgcat tcgcaggcat gctgaagaag cagttccagg catgg 165

<210> SEQ ID NO 848
<211> LENGTH: 150
<212> TYPE: DNA
<213> ORGANISM: Homo Sapiens

<400> SEQUENCE: 848
accctcaccc taaatctggc acctgcttct ccatctccag agcacaagac gtcccccacc 60
caatgcccgg cagctggaga ggtctccaac aagcttccaa aatggcctgg tgagtgatgc 120
gggatctctc tgccctgggt ggtggagatg 150

<210> SEQ ID NO 849
<211> LENGTH: 150
<212> TYPE: DNA
<213> ORGANISM: Homo Sapiens

<400> SEQUENCE: 849
ctgagcctgc cctactctgt atctccccgt atagatccgt ggccagctgc agtcgcacgg 60
cgtgcaagca cgggaggttc ggctgatgcg gaacaaatct tcaggtgagc ttttgttcta 120
gtgccctccc cttcaagtgg ccagcctcag 150

<210> SEQ ID NO 850
<211> LENGTH: 150
<212> TYPE: DNA
<213> ORGANISM: Homo Sapiens

<400> SEQUENCE: 850
cgcgcgtaca cacacacaca cacacacaca cacacacaca cacacacaca cacgttctta 60
tgtaaccgag cccgggtaaa gcagggctgc agaaagcaga aacggcgagc ccggctcctg 120
ggagcaggtg ggacctcctt tggcctttgg 150

<210> SEQ ID NO 851
<211> LENGTH: 199
<212> TYPE: DNA
<213> ORGANISM: Homo Sapiens

<400> SEQUENCE: 851
cctctctcct tctgcctcag atgtgaagtt catttccaat ccgccctcca tggtggcagc 60
ggggagcgtg gtggccgcag tgcaaggcct gaacctgagg agccccaaca acttcctgtc 120
ctactaccgc ctcacacgct tcctctccag agtgatcaag tgtgacccgg taagtgaggg 180
tgatgtccca ggcagcctt 199

<210> SEQ ID NO 852
<211> LENGTH: 153
<212> TYPE: DNA
<213> ORGANISM: Homo Sapiens

<400> SEQUENCE: 852
tcgctgttag acatctctct cactgcctgt ctctggttct gtcctcaggc cacccctgtt 60
ctccgatgtg taagggctcc cgctgctggg gagagagttc tgaggattgt cagagccgtg 120
agtctcaggg aggcctggag tcagggaagg gga 153

<210> SEQ ID NO 853
<211> LENGTH: 207
<212> TYPE: DNA
<213> ORGANISM: Homo Sapiens

<400> SEQUENCE: 853
tgagacccct tcagacccta cagagacccc actgctctca cagctacaac tactgccggg 60
aagacgagga gatctacaag gagttctttg aagtagccaa tgatgtcatc cccaacctgc 120
tgaaggaggc agccagcttg ctggaggcgg gcgaggagcg gccgggggag caaagccagg 180
tgaaaggctg gagctccagc ctgtgtc 207

<210> SEQ ID NO 854
<211> LENGTH: 154
<212> TYPE: DNA
<213> ORGANISM: Homo Sapiens

<400> SEQUENCE: 854
gtgtttcctt ggggtcatgg gggtggcttc atgttagttt ttgcaggatc cagatgaaga 60
aatggccaaa atcgacagga cggcgaggga ccagtgtggg agccaggtag gtccgcccgg 120
ggttgggcct ctgtggaggt ccttctcccc ctgg 154

<210> SEQ ID NO 855

<211> LENGTH: 118
<212> TYPE: DNA
<213> ORGANISM: Homo Sapiens

<400> SEQUENCE: 855
ctcgctcatc cccgaggggc ccctgcaacc tctccgcgcg aagacggctt cagccctgca 60
gggaaagaaa agtaacttcg cttttctcgg aggaaccagg aaggattaag cggcttgg 118

<210> SEQ ID NO 856
<211> LENGTH: 160
<212> TYPE: DNA
<213> ORGANISM: Homo Sapiens

<400> SEQUENCE: 856
ggcagctccg ggtctataaa gagaggcgtc cgaggacgcg cagggagatt tggacgctcc 60
ggcctgggag gtgcgtcaga tccgagctcg ccatccagtt tcctctccac tagtcccccc 120
agttggagat ctgtaagtag tagttgtcat tctgggggca 160

<210> SEQ ID NO 857
<211> LENGTH: 175
<212> TYPE: DNA
<213> ORGANISM: Homo Sapiens

<400> SEQUENCE: 857
ccctcacctt cccctctttt cccagagctg tcttcccagc ccaccatccc catcgtgggc 60
atcattgctg gcctggttct ccttggagct gtgatcactg gagctgtggt cgctgccgtg 120
atgtggagga ggaagagctc aggtggagaa ggggtgaagg gtggggtctg agatt 175

<210> SEQ ID NO 858
<211> LENGTH: 154
<212> TYPE: DNA
<213> ORGANISM: Homo Sapiens

<400> SEQUENCE: 858
ctgtccttcc ctgacctcag cccaacctct actgtgtgcc tctgcaggct cggatggcgg 60
gtgagcgagg agccagtgct gtcctctttg acatcactga ggatcgagct gctgctgagc 120
aggtacccag ggacatttgc gtgttcaagg tggg 154

<210> SEQ ID NO 859
<211> LENGTH: 185
<212> TYPE: DNA
<213> ORGANISM: Homo Sapiens

<400> SEQUENCE: 859
tggtctctcg gcgggaagcc gtgcacgcct ccagcgttga cactttcccg gtgcactttt 60
tctggtggga ggggagagcg gagcaggctc acgtgtaacc gcgcaggagc ctcctctggc 120
ttgagccctt tcttggtaag tcccaaacct tcccaagaca accttggcct tagcagtaga 180
ggagg 185

<210> SEQ ID NO 860
<211> LENGTH: 150
<212> TYPE: DNA
<213> ORGANISM: Homo Sapiens

<400> SEQUENCE: 860
tgagttaacg gctgcctctt tctcctggac agggatggga tccccccata caggatccgt 60
aagcagcacc gcagggagat gcaggagagc gtgcaggtca atgggcgggt gcccctacct 120
cacattcccg taagtaccgg ctttgcggtc 150

<210> SEQ ID NO 861
<211> LENGTH: 155
<212> TYPE: DNA
<213> ORGANISM: Homo Sapiens

<400> SEQUENCE: 861
cacctggctc cactgtgtag ctgaggacct gtggctgagc ccgctgacca tggaagatct 60
tgtctgctac agcttccagg tggccagagg gatggagttc ctggcttccc gaaaggtgag 120
cttcccccga aggcccttca gacgggaaaa gggtg 155

<210> SEQ ID NO 862
<211> LENGTH: 161
<212> TYPE: DNA
<213> ORGANISM: Homo Sapiens

<400> SEQUENCE: 862
cccctgctaa tgtctgaggt ccccccttctg ttcaggagtc atgactctgt tctccatcaa 60
gagcaaccac cccgggctgc tgagtgagaa ggctgccagc aagatcaacg agaccatgct 120
gcgcctgggt gagtggcccc gggggacttc ggtctgaggt c 161

<210> SEQ ID NO 863
<211> LENGTH: 150
<212> TYPE: DNA
<213> ORGANISM: Homo Sapiens

<400> SEQUENCE: 863
ctggccacac tgggtctccc taacacactc ctcttctcac ccctgcagcc cccgcagcct 60
gatgacctct ccattgtgtg tttcacaagc ggcacgacag gtaagcagag gcacgcagat 120
ccccagccat ggctacctgc acccttccct 150

<210> SEQ ID NO 864
<211> LENGTH: 163
<212> TYPE: DNA
<213> ORGANISM: Homo Sapiens

<400> SEQUENCE: 864
cactgtggcc ttgtttcctg cctgcaggct tggcgggggc tccgaggacg ccaaggagat 60
catgcagcat cgcttctttg ccggtatcgt gtggcagcac gtgtacgaga agaaggtgcg 120
gctgctcccc gcatattcac gcgcacgcat gctccccaca tat 163

<210> SEQ ID NO 865
<211> LENGTH: 199
<212> TYPE: DNA
<213> ORGANISM: Homo Sapiens

<400> SEQUENCE: 865
ctcactcctc ccctgctcgc tgcaggcccg ggaccgtggc gcttcgagag attcgtcgtt 60
atcagaagtc gaccgagctg ctcatccgga agctgccctt ccagaggttg gtgagggaga 120
tcgcgcagga tttcaaaacc gacctgaggt ttcagagcgc agccatcggt gcgctgcagg 180
taagacaaag gcctggagc 199

<210> SEQ ID NO 866
<211> LENGTH: 197
<212> TYPE: DNA

<213> ORGANISM: Homo Sapiens

<400> SEQUENCE: 866
tagttggcga gtgggcttta ggacccaacg ggaacccgtg cctcttgcag cagcctaacc 60
cagaagcagg ggggaatcct gaatcgagct gagagggctt ccccggttct cctgggaacc 120
ccatcggccc cctgccagca cacacctgag caggtaggac catgcacacc ccttcccaat 180
tctttggccg cctttga 197

<210> SEQ ID NO 867
<211> LENGTH: 170
<212> TYPE: DNA
<213> ORGANISM: Homo Sapiens

<400> SEQUENCE: 867
ctggtttagc gacacgagca ccgcttcttc ctcagtaccg cgccggagcc ttccgcagct 60
gccgcttcag tccgaaggag gaagggaacc aacccacttt ctcggcgccg cggctctttt 120
ctaaaagtgt gagtggcccc gggagaggga attgaggggg agaaagtggg 170

<210> SEQ ID NO 868
<211> LENGTH: 150
<212> TYPE: DNA
<213> ORGANISM: Homo Sapiens

<400> SEQUENCE: 868
cctctgctga ctctgtctcc ccaggcagct gcattcagcc tcagcggagg acacgcctgt 60
ggtgcagttg gcagccgaga ccccaacagc agagagcaag gtaaggggtg cttgtgtggg 120
tacctgtgct cctggcctgg tcgtgtagaa 150

<210> SEQ ID NO 869
<211> LENGTH: 120
<212> TYPE: DNA
<213> ORGANISM: Homo Sapiens

<400> SEQUENCE: 869
cattggttgc ggccatctct gccttgcaga cgctccatcc tcgggagatg acgaagacgg 60
ggaggacgag gctgaggaca caggtgtgga cacaggtagg agcagggtcc agggttcagg 120

<210> SEQ ID NO 870
<211> LENGTH: 150
<212> TYPE: DNA
<213> ORGANISM: Homo Sapiens

<400> SEQUENCE: 870
ccactgcaac ccgactccgg agctccgagc atcccttagt tttaagtcat ggcgggtgcg 60
aacgggtctc tgctgcaggc ggctccgtga cagctcctgc ttcacatggg tagaggagag 120
acggcaaacg tcggggctcc caggacttcg 150

<210> SEQ ID NO 871
<211> LENGTH: 250
<212> TYPE: DNA
<213> ORGANISM: Homo Sapiens

<400> SEQUENCE: 871
caggagggcg gggtaaagcc gctttcctct cctttctccc tccccccttgt ctgcgccaca 60 gccccccttct ctccccgccc cccgggtgtg tcagattttt cagttaataa tatccccccga 120 gcttcaaagc gcaggctgtg acagtcatct gtctggacgc gctgggtgga tgcgggggggc 180 tcctgggaac tgtgttggag ccgagcaagc gctagccagg cgcaagcgcg cacagactgt 240
agccatccga 250

<210> SEQ ID NO 872
<211> LENGTH: 158
<212> TYPE: DNA
<213> ORGANISM: Homo Sapiens

<400> SEQUENCE: 872
cgcctcttcc caccctagac ctggacaagg aggatggacg gcccctggag ctccgggacc 60
tgcttcactt ctccagccaa gtagcccagg gcatggcctt cctcgcttcc aagaatgtga 120
gtaggaacct ggccctggct catagccacc caggtctg 158

<210> SEQ ID NO 873
<211> LENGTH: 119
<212> TYPE: DNA
<213> ORGANISM: Homo Sapiens

<400> SEQUENCE: 873
cgtgaccgac atgtggctgt attggtgcag cccgccaggg tgtcactgga gacagaatgg 60
aggtgctgcc ggactcggaa atggggtagg tgctggagcc accatggcca ggcttgctg 119

<210> SEQ ID NO 874
<211> LENGTH: 151
<212> TYPE: DNA
<213> ORGANISM: Homo Sapiens

<400> SEQUENCE: 874
ctgagacctg ggactgatc ctcctgcacc cctccccagc accatcgtga agagtggtct 60
ccgtttcgtg gcgccagatg ccttccattt cactcctcgg ctcagtcgcc tgtgagtgtg 120
gccagtgctg ggcagtggga gttggggagg a 151

<210> SEQ ID NO 875
<211> LENGTH: 157
<212> TYPE: DNA
<213> ORGANISM: Homo Sapiens

<400> SEQUENCE: 875
agggtttcct tctcgctgat tccttgtctt ggtctccact agggccctgg ggggaggacg 60
aggagtggac agacaaggcc cggcgggtca tcatggagcg tatcggcctc gccactgcag 120
ggtaagggcc ctgtgcctgc cctgttctac tctctgg 157

<210> SEQ ID NO 876
<211> LENGTH: 150
<212> TYPE: DNA
<213> ORGANISM: Homo Sapiens

<400> SEQUENCE: 876
aggtgtggtg ttgcccacca gcccctcacc cgcagtctgt ctgcaggatg aagtcgctca 60
cacagtcacc gagagccggg tcctccagaa caccaggcac ccgttcctca ctgtgagttg 120
ccctcccctt cccagacagt gtgaggccag 150

<210> SEQ ID NO 877
<211> LENGTH: 153
<212> TYPE: DNA
<213> ORGANISM: Homo Sapiens

<400> SEQUENCE: 877
tacccactcc atttcccacc ttctcccctc ccaggccatg cacgaggggc tgctgatgcc 60
cgtggtgaag tcagagggcg gcgaggacta cacgggagcc actgtcatcg agcccctcaa 120
agggtgaggc cccaggctgg gtgcagtttt tac 153

<210> SEQ ID NO 878
<211> LENGTH: 151
<212> TYPE: DNA
<213> ORGANISM: Homo Sapiens

<400> SEQUENCE: 878
ctgggctggc gtatgacggc tgtcgctcct gcatttgcag gtgtctggcc tgccaccgtg 60
tctcaaggcg gcctgcatac actcgggcat gaccaggaag caacgggaat ctgtcctgca 120
gaaggtgggg gcctcatggg cctaggggtg a 151

<210> SEQ ID NO 879
<211> LENGTH: 143
<212> TYPE: DNA
<213> ORGANISM: Homo Sapiens

<400> SEQUENCE: 879
ccgctcagtg tctctctctt gctctcgctc tcgctctccc cctctttctc tctttctctc 60
tttttccgcg aggcctacac gacgccaggg gtttgggtgc gtgttgggga gggggagggg 120
gagcccatgg ggctccggag act 143

<210> SEQ ID NO 880
<211> LENGTH: 224
<212> TYPE: DNA
<213> ORGANISM: Homo Sapiens

<400> SEQUENCE: 880
caggaagcct gtgttccgta cgacaatatg gcggcgctta gttgcatgaa ggcggaaact 60
ctgtgacttc cggtccgtag tggggcctgc ggtgggagtg ggaaggaagg cggagggaac 120
catgcgaggt tctgagaatt gcggcgaggg tcgcctcgag agacggtttc tgaggtgggg 180
gccggacggt gcggggatca gaggcggggg cggggatata gagg 224

<210> SEQ ID NO 881
<211> LENGTH: 214
<212> TYPE: DNA
<213> ORGANISM: Homo Sapiens

<400> SEQUENCE: 881
gaacttgccg gttaagcagg cccccgtgtc tctccctgtt cccctgcaga aggccgggag 60
tgtgtcaact gtggggccac agccacccct ctctggcggc gggacggcac cggccactac 120
ctgtgcaatg cctgtggcct ctaccacaag atgaatgggc agaaccgacc actcatcaag 180
cccaagcgaa gactggtagg agcgggcaca ggtg 214

<210> SEQ ID NO 882
<211> LENGTH: 220
<212> TYPE: DNA
<213> ORGANISM: Homo Sapiens

<400> SEQUENCE: 882
gtatcaacgc tctgtgggtc gtgtgcgtgc gaggggggcg acgtaagggc gctccgcgag 60
cccgtctctc ctcgaatgaa aggaaacaac ctccggcgac agagccccgc tctcaggcac 120
tgctggagaa ccgagaccga cttctttctc tttaccctca ttggcgcttc tctcctgcag 180
tccgcctctg ggccctgccg gtgagtcccc acggaaccct 220

<210> SEQ ID NO 883
<211> LENGTH: 158
<212> TYPE: DNA
<213> ORGANISM: Homo Sapiens

<400> SEQUENCE: 883
tgcttctctt ccttctcccc caggagactg aggcatgccc tgtggccctc acttccagac 60
ctgcaccggg tcctaggcca gtaccttagg gacactgcag ccctgagccc ggtgagtgtg 120
cttccctccc ctgtgcccac caccaaccct gcctggta 158

<210> SEQ ID NO 884
<211> LENGTH: 297
<212> TYPE: DNA
<213> ORGANISM: Homo Sapiens

<400> SEQUENCE: 884
ctttgtgtgc cccgctccag cagcctcccg cgacgatgcc cctcaacgtt agcttcacca 60
acaggaacta tgacctcgac tacgactcgg tgcagccgta tttctactgc gacgaggagg 120
agaacttcta ccagcagcag cagcagagcg agctgcagcc cccggcgccc agcgaggata 180
tctggaagaa attcgagctg ctgcccaccc cgcccctgtc ccctagccgc cgctccgggc 240
tctgctcgcc ctcctacgtt gcggtcacac ccttctccct tcggggagac aacgacg 297

<210> SEQ ID NO 885
<211> LENGTH: 151
<212> TYPE: DNA
<213> ORGANISM: Homo Sapiens

<400> SEQUENCE: 885
aggcctcttg tttcctcccc aggcccctga gcctctgagc tccttgaagt ccatggcgga 60
acgggcagcc atcagctctg gcattgagga ccctgtgcca acgctgcacc tgaccgagcg 120
aggtgaggga cccaggatgg tggggaagca g 151

<210> SEQ ID NO 886
<211> LENGTH: 166
<212> TYPE: DNA
<213> ORGANISM: Homo Sapiens

<400> SEQUENCE: 886
ctatgggtgc ccttctccac agatcatcca gctgaccccg gtgcctgtga gcacacccag 60
cggcctggtg ccgcccctga gcccagccac actccctgga cccacctctc agcctcagaa 120
ggtcctgttg ccctcctcca ccaggtaatt gcagctgagc ccatac 166

<210> SEQ ID NO 887
<211> LENGTH: 151
<212> TYPE: DNA
<213> ORGANISM: Homo Sapiens

<400> SEQUENCE: 887
gaggacctgt gggactctgc actgaggccc tctctcccct ccagggccgc ctgcctgtga 60
agtggatggc gcccgaggcc ttgtttgacc gggtgtacac acaccagagt gacgtgtgag 120
tcctgccggc ggtcactgtc ctaccccaca a 151

<210> SEQ ID NO 888
<211> LENGTH: 154
<212> TYPE: DNA
<213> ORGANISM: Homo Sapiens

<400> SEQUENCE: 888
gggtgagact gacctctctt ctcctgcccc tgcctaggcc cgcgatgctc ccagcccggt 60
gagacctgcc tgaatggcgg gaagtgtgaa gcggccaatg gcacggaggc ctgcgtgtga 120
gtaccacccc tgcgggacct gttgctttgt cgag 154

<210> SEQ ID NO 889
<211> LENGTH: 343
<212> TYPE: DNA
<213> ORGANISM: Homo Sapiens

<400> SEQUENCE: 889
ctgcagttcg cttgtgcccg gcagcccgag ctcgccatga tgcattgctc ttactgggac 60
cacgacagca agaccggcgc gctgcattcg cgcctcgatc tctgagagcc caccgcatgc 120
cggtgcagac ggatgcgagg atgcagggac gcgcgacgcc ggccccggtc gcagccgacg 180
acgccgccgc cagcctgacc tcacaccctc tgggcccgcc tctggagcca gcgcccaggg 240
tccctctgtg ctttttcgct ttcctaagct cctgtcgctc ctctttgtcc cctcagttta 300
tgtcctcctg tgctcacctc cctgacctct gtgaccttgc act 343

<210> SEQ ID NO 890
<211> LENGTH: 199
<212> TYPE: DNA
<213> ORGANISM: Homo Sapiens

<400> SEQUENCE: 890
cacccaccgc tgtgttgcag ctacctgacc gacgttgacc gcatcgccac cttgggctac 60
ctgcccaccc agcaggacgt gctgcgggtc cgcgtgccca ccaccggcat catcgagtac 120
cctttcgacc tggagaacat catcttccgg taccgcccgg gccacagcag gcggggaggg 180
ggcactgaga ggctcattt 199

<210> SEQ ID NO 891
<211> LENGTH: 127
<212> TYPE: DNA
<213> ORGANISM: Homo Sapiens

<400> SEQUENCE: 891
aggaagggag cctcaaaggc caaggccagc caggacaccc cctgggatca cactgagctt 60
gccacatccc caaggcggcc gaaccctccg caaccaccag cccaggtcag tctcagcccc 120
cagagag 127

<210> SEQ ID NO 892
<211> LENGTH: 206
<212> TYPE: DNA
<213> ORGANISM: Homo Sapiens

<400> SEQUENCE: 892
gactctcctg tctccgctcc ctgccttgct cgcaggcagc cacctggcga gtctgacatg 60
gctgtcagcg acgcgctgct cccatctttc tccacgttcg cgtctggccc ggcgggaagg 120
gagaagacac tgcgtcaagc aggtgccccg aataacgtga gtatcgctcc gggccgccgg 180
gaacgcccgg tgggttttcg tgggtg 206

<210> SEQ ID NO 893
<211> LENGTH: 166
<212> TYPE: DNA
<213> ORGANISM: Homo Sapiens

<400> SEQUENCE: 893
cctcctctgc gttcgacgca gcctccgccc ggcctcccag gatgcagcgc gctggcggga 60
ggtttggagc agatggatac cgtatcgacg tggggcctcc ggtatgttgc cgctgcgttg 120
aggtaggatg gggctggcga gtcttccctt cccaggactt cgcaga 166

<210> SEQ ID NO 894
<211> LENGTH: 169
<212> TYPE: DNA
<213> ORGANISM: Homo Sapiens

<400> SEQUENCE: 894
actacatttc ccaggaggca gcgggtctac gccgtcgccg tcgtcggaga gcggagacgc 60
tgggcgcgct gtggggcggg ggcgaggttc gggctggttg ttccgttgcg agctgcagct 120
gcgatctctg tggtaggccc aggtgagtga gcgcctctga tggaagtta 169

<210> SEQ ID NO 895
<211> LENGTH: 155
<212> TYPE: DNA
<213> ORGANISM: Homo Sapiens

<400> SEQUENCE: 895
ccgtccgcgc tacatactgc gcctgcgcaa gggctgtggc ccttttccca ccccctagcg 60
ccgctgggcc tgcaggtctc tgtcgagcag cggacgccgg tctctgttcc gcaggatggt 120
gagtggatgc ctcggtctcg gggctttaga tgcat 155

<210> SEQ ID NO 896
<211> LENGTH: 162
<212> TYPE: DNA
<213> ORGANISM: Homo Sapiens

<400> SEQUENCE: 896
cagtggctca ggaaaccaag gggcccacac aggaaggagc cgagtgggac tttcctctcg 60
ctgcctcccg gctctgcccg cccttcgaaa gtccagggtc cctgcccgct aggtaagagc 120
tggcgatgcc gcagggctcg gcccagacac tgggggagga tg 162

<210> SEQ ID NO 897
<211> LENGTH: 153
<212> TYPE: DNA
<213> ORGANISM: Homo Sapiens

<400> SEQUENCE: 897
gctgatcctc caccttcctt cacccccaca cagccccccc ttgcctggac ggaagcccgt 60
gtgcaaatgg aggtcgttgc acccagctgc cctcccggga ggctgcctgc ctgtgagtgc 120
ctggctcaga gccaccagtg ggccctgtgt gtg 153

<210> SEQ ID NO 898
<211> LENGTH: 220
<212> TYPE: DNA
<213> ORGANISM: Homo Sapiens

<400> SEQUENCE: 898
gaacatggtg cgcaggttct tggtgaccct ccggattcgg cgcgcgtgcg gcccgccgcg 60
agtgagggtt ttcgtggttc acatcccgcg gctcacgggg gagtgggcag cgccaggggc 120
gcccgccgct gtggccctcg tgctgatgct actgaggagc cagcgtctag ggcagcagcc 180
gcttcctaga agaccaggta ggaaaggccc tcgaaaagtc 220

<210> SEQ ID NO 899
<211> LENGTH: 148
<212> TYPE: DNA
<213> ORGANISM: Homo Sapiens

<400> SEQUENCE: 899
gtgtgttggg ggatagcctc ggtgtcagcc atctttcaat tgtgttcgca gccgccgccg 60
cgccgccgtc gctctccaac gccagcgccg cctctcgctc gccgagctcc agccgaagga 120 gaagggggt aagtttcccc gtctgccc 148

<210> SEQ ID NO 900
<211> LENGTH: 193
<212> TYPE: DNA
<213> ORGANISM: Homo Sapiens

<400> SEQUENCE: 900
cacgtctgcc cctctctccc ctgcggccag ccctctacag ccacaagccc gaggtggccc 60
agtacaccca cacgggcctg ctcccgcaga ctatgctcat caccgacacc accaacctga 120
gcgccctggc cagcctcacg cccaccaagc aggtaaggtc caggcctgct ggccctccct 180
tggcctgtga cag 193

<210> SEQ ID NO 901
<211> LENGTH: 240
<212> TYPE: DNA
<213> ORGANISM: Homo Sapiens

<400> SEQUENCE: 901
ggcagaagag aggcagacag actgacagac acgtagacca acagtgcggc cccagggttc 60
gtccccagac tcgctcgctc atttgttggc gactggggct cagcgcagcg aagcccgatg 120
tggtccggag gcagtgggaa ggcgcggggc tgggaggccg cggcgggagg gaggagcagc 180
cccggcaggc tcaggtgaaa cccccaccct gtccctcagc cccctcctcc taaagacctg 240

<210> SEQ ID NO 902
<211> LENGTH: 348
<212> TYPE: DNA
<213> ORGANISM: Homo Sapiens

<400> SEQUENCE: 902
tattaccggc agaaccagca gcgctggcag aactccatcc gccactcgct gtccttcaat 60
gactgcttcg tcaaggtggc acgctccccg gacaagccgg gcaagggctc ctactggacg 120
ctgcacccgg actccggcaa catgttcgag aacggctgct acttgcgccg ccagaagcgc 180
ttcaagtgcg agaagcagcc gggggccggc ggcgggggcg ggagcggaag cgggggcagc 240
ggcgccaagg gcggccctga gagccgcaag gacccctctg gcgcctctaa ccccagcgcc 300
gactcgcccc tccatcgggg tgtgcacggg aagaccggcc agctagag 348

<210> SEQ ID NO 903
<211> LENGTH: 198
<212> TYPE: DNA
<213> ORGANISM: Homo Sapiens

<400> SEQUENCE: 903
cacccggttc catctacctt tcccccaccc caggtctcct cttggctctg ccaggagccg 60
gagccctgcc accctggctt tgacgccgag agctacacgt tcacggtgcc ccggcgccac 120
ctggagagag gccgcgtcct gggcagaggt gagggcgcgc tgccggtgtc cctgggcgga 180
gtagggaggg gttggaaa 198

<210> SEQ ID NO 904
<211> LENGTH: 259
<212> TYPE: DNA
<213> ORGANISM: Homo Sapiens

<400> SEQUENCE: 904
cgatgagggt ctggccagcg ccgcggcgcg gggactagtg gagaaggtgc gacagctcct 60
ggaagccggc gcggatccca acggagtcaa ccgtttcggg aggcgcgcga tccaggtagc 120
tggggcccca gggcctcgcc ggcagggggc gcgcgaacgc ggggcgcggc ctcggcggat 180
cggggctgga acctagatcg ccgatgtaga tttgtacagg agtctccgtt ggccggaggt 240
gtgcattcca cgcgtaaaa 259

<210> SEQ ID NO 905
<211> LENGTH: 150
<212> TYPE: DNA
<213> ORGANISM: Homo Sapiens

<400> SEQUENCE: 905
cgctgctgcc ttgatgggct ccgcggcccg agcgcctctt ttcgggatta aaagcgccgc 60
cagctcccgc cgccgccgcc gtcgccagca gcgccgctgc agccgccgcc gccggagaag 120
caaccgcgta agtggcaact tttccctctt 150

<210> SEQ ID NO 906
<211> LENGTH: 150
<212> TYPE: DNA
<213> ORGANISM: Homo Sapiens

<400> SEQUENCE: 906
actcactgac cctctccctt gacacagggc agccgctctg gctctagctc cagctccggg 60
accctctggg aaccccccggg acccatgtga cccagcggcc cctcgcgctg taagtctccc 120
gggacggcag ggcagtgagg gaggcgaggg 150

<210> SEQ ID NO 907
<211> LENGTH: 198
<212> TYPE: DNA
<213> ORGANISM: Homo Sapiens

<400> SEQUENCE: 907
agcgaggaca tctggaagaa attcgagctg gtgccatcgc cccccacgtc gccgccctgg 60
ggcttgggtc ccggcgcagg ggacccggcc cccgggattg gtcccccgga gccgtggccc 120
ggagggtgca ccggagacga agcggaatcc cggggccact cgaaaggctg gggcaggaac 180
tacgcctcca tcatacgc 198

<210> SEQ ID NO 908
<211> LENGTH: 152
<212> TYPE: DNA
<213> ORGANISM: Homo Sapiens

<400> SEQUENCE: 908
caagaggcca atgagggggc agtgcccggc attatgcaac ccgcctcccc gcccgcccgg 60
tggagcttcc actcggctgc gggctggagc ggcggcgggc aggcgtgcgg aggacactcc 120
tgcgaccagg taggcatctc tgcggccatc ct 152

<210> SEQ ID NO 909
<211> LENGTH: 163
<212> TYPE: DNA
<213> ORGANISM: Homo Sapiens

<400> SEQUENCE: 909
ctacctgtaa ctgggcctgt tgctgtctcc tagcacaaac tctcagagcc catccccacc 60
cagcagttcc attgcctaca gcctcctgag tgccagctca gagcaggaca acccgtccac 120
cagtggctgc aggtacgtcg ggtgaggctg gaggagaggt ctg 163

<210> SEQ ID NO 910
<211> LENGTH: 296
<212> TYPE: DNA
<213> ORGANISM: Homo Sapiens

<400> SEQUENCE: 910
gatggcgcct cagaagcacg gcggtggggg agggggcggc tcggggccca gcgcggggtc 60
cgggggaggc ggcttcgggg gttcggcggc ggtggcggcg gcgacggctt cgggcggcaa 120
atccggcggc gggagctgtg gagggggtgg cagttactcg gcctcctcct cctcctccgc 180
ggcggcagcg gcgggggctg cggtgttacc ggtgaagaag ccgaaaatgg agcacgtcca 240
ggctgaccac gagcttttcc tccaggcctt tgagagtgag tgtgtgcgag gctttg 296

<210> SEQ ID NO 911
<211> LENGTH: 283
<212> TYPE: DNA
<213> ORGANISM: Homo Sapiens

<400> SEQUENCE: 911
gggctccgta gacgctttcc gcatcactct ccttcctcgg gctgccggga gtcccgggac 60
ctggcggggc cggcatgacg ggcttctcgg gggcccgccg cacgcccggc agcctccgga 120
gacgcgcgcc gagcccggct cccacggcct ctgaggctcg gcggggctgc ggctgcctgg 180
cgggcgggct ccggagcttt cctgagcggc attagcccac ggcttggccc ggacgcgacc 240
aaaggctctt ctggagaagc ccagagcact gggcaatcgt tac 283

<210> SEQ ID NO 912
<211> LENGTH: 162
<212> TYPE: DNA
<213> ORGANISM: Homo Sapiens

<400> SEQUENCE: 912
ctgccttctc ccctgaagag agacgcgggg ggagggggt gcggcgagcg gccccgctct 60
ctccccaccg ctccgctcgc accccagtgt aatgagggtc accccctccc cccagctggc 120
ccgggagggg gcgcggggca cggtaactag tgcgctgggg tg 162

<210> SEQ ID NO 913
<211> LENGTH: 51
<212> TYPE: DNA
<213> ORGANISM: Artificial Sequence
<220> FEATURE:
<223> OTHER INFORMATION: synthesized

```
<220> FEATURE:
<221> NAME/KEY: misc_feature
<222> LOCATION: (51)..(51)
<223> OTHER INFORMATION: labelled with inverted dT

<400> SEQUENCE: 913

aagagcgtcg tgtagggaaa gagtgtagat ctcggtggtc gccgtatcat t            51


<210> SEQ ID NO 914
<211> LENGTH: 65
<212> TYPE: DNA
<213> ORGANISM: Artificial Sequence
<220> FEATURE:
<223> OTHER INFORMATION: synthesized
<220> FEATURE:
<221> NAME/KEY: misc_feature
<222> LOCATION: (35)..(41)
<223> OTHER INFORMATION: n is a, c, g, or t
<220> FEATURE:
<221> NAME/KEY: misc_feature
<222> LOCATION: (65)..(65)
<223> OTHER INFORMATION: labelled with inverted dT

<400> SEQUENCE: 914

cctcagcaag agcacacgtc tgaactccag tcacnnnnnn natctcgtat gccgtcttct     60

gcttg                                                                 65
```

NUCLEIC ACID CAPTURE METHOD

CROSS-REFERENCE TO RELATED APPLICATIONS

The present application is a continuation-in-part application of U.S. application Ser. No. 15/911,161 filed Mar. 4, 2018, which claims benefit of U.S. Provisional Application No. 62/482,189 filed Apr. 6, 2017, is a continuation of PCT Application No. PCT/US2018/019788 filed Feb. 26, 2018, and is a continuation-in-part of U.S. Non-provisional application Ser. No. 15/908,190 filed Feb. 28, 2018, which is a continuation of PCT Application No. PCT/US2018/016778 filed on Feb. 4, 2018. The disclosures of all of the above applications are hereby incorporated by reference in their entirety.

REFERENCE TO SEQUENCE LISTING SUBMITTED ELECTRONICALLY

The content of the electronically submitted sequence listing, file name CAPTURE_ST25.txt, size 190,896 bytes, and date of creation Dec. 23, 2020, filed herewith, is incorporated herein by reference in its entirety.

TECHNICAL FIELD

This present disclosure relates generally to the area of diagnostics and prognostics, specifically to the field of biomarker technologies, more specifically to nucleic acid assays for genetic and genomic analysis, and in more particular to a method and a kit for targeted enrichment of nucleic acid sequences in nucleic acid assays.

BACKGROUND

Genome sequencing, especially the recent next generation sequencing (NGS) technology, has emerged as a tool for global analysis of all genetic information behind a disease or an individual. For example, NGS has been widely used clinically for disease diagnostics, companion diagnostics for personalized therapeutics and disease monitoring.

SUMMARY OF THE INVENTION

In a first aspect, the present disclosure provides a method for enriching at least one target nucleic acid sequence from a biological sample. The method comprises the following two steps (1) and (2):

(1) providing at least one pair of RNA probe sets and a solid support;

Herein, each of the at least one pair of RNA probe sets comprises a first RNA probe set and a second RNA probe set configured to concurrently and respectively target two antiparallel strands of a duplex segment in each of the at least one target nucleic acid sequence, wherein each RNA probe in any of the first RNA probe set and the second RNA probe set is labelled with an immobilization portion configured to allow immobilization onto the solid support. The solid support is labelled with at least one coupling partner, each capable of forming a secure coupling to the immobilization portion labelled onto each RNA probe in any of the first RNA probe set and the second RNA probe set.

(2) capturing each strand of the at least one target nucleic acid sequence from the biological sample through concurrent hybridization of the two antiparallel strands of the duplex segment in the each of the at least one target nucleic acid sequence with both the first RNA probe set and the second RNA probe set in the each of the at least one pair of RNA probe sets respectively, and immobilization onto the solid support.

Herein each of the at least one target nucleic acid sequence can be a double-stranded nucleic acid molecule, such as a double-stranded DNA molecule, a double-stranded RNA molecule, or a DNA-RNA hybrid molecule, or can be a single-stranded nucleic acid molecule (i.e. DNA or RNA) having a hairpin structure. As such, by means of the at least one pair of RNA probe sets where a first RNA probe set and a second RNA probe set in each pair respectively target two antiparallel strands of a duplex segment in each target nucleic acid sequence, each strand of the at least one target nucleic acid sequence can be captured or enriched from the biological sample.

For a typical example, each of the at least one target nucleic acid sequence in the biological sample can be a double-stranded DNA molecule, which has a plus strand and a minus strand that runs antiparallelly to form a duplex. By means of the at least one pair of RNA probe sets where a first RNA probe set and a second RNA probe set in each pair respectively target both of the two antiparallel strands (i.e. the plus strand and the minus strand) of each target nucleic acid sequence, each strand, including both the plus strand and the minus strand, of each target DNA molecule, can be captured or enriched from the biological sample.

According to certain embodiments of the method, the step (2) of capturing each strand of the at least one target nucleic acid sequence from the biological sample comprises the following sub-steps:

contacting both the first RNA probe set and the second RNA probe set in the each of the at least one pair of RNA probe sets with the at least one target nucleic acid sequence in the biological sample; and immobilizing the at least one target nucleic acid sequence on the solid support.

Herein, each RNA probe in any of the first RNA probe set and the second RNA probe set in the each of the at least one pair of RNA probe sets can have a length of about 100-150 nt. As such, the sub-step of contacting both the first RNA probe set and the second RNA probe set in the each of the at least one pair of RNA probe sets with the at least one target nucleic acid sequence in the biological sample can be performed at a temperature of about 62-70° C., and preferably at a temperature of about 67.5° C. The contacting sub-step can last for about 6-24 hours, and preferably for about 12 hours, yet such lasting time period can vary depending on actual conditions.

Herein, further according to certain embodiments, the first RNA probe set and the second RNA probe set in the each of the at least one pair of RNA probe sets respectively target a different portion of the duplex segment in the each of the at least one target nucleic acid sequence. Herein, because the first RNA probe set and the second RNA probe set in the each of the at least one pair of RNA probe sets respectively target a different portion of the duplex segment of any target nucleic acid sequence, they do not have complementary sequences with each other.

According to other embodiments, the first RNA probe set and the second RNA probe set in the each of the at least one pair of RNA probe sets respectively target a substantially same portion of the duplex segment in the each of the at least one target nucleic acid sequence. Herein, because the first RNA probe set and the second RNA probe set in the each of the at least one pair of RNA probe sets respectively target a substantially same portion of the duplex segment of any target nucleic acid sequence, they may contain complementary sequences with each other.

In these embodiments of the method as described above, in the sub-step of contacting both the first RNA probe set and the second RNA probe set in the each of the at least one pair of RNA probe sets with the at least one target nucleic acid sequence in the biological sample comprises: the first RNA probe set and the second RNA probe set in the each of the at least one pair of RNA probe sets can optionally be concurrently contacted with the two antiparallel sequences of the at least one target nucleic acid duplex sequence in a single hybridization reaction. In other words, in these embodiments of the method, the first RNA probe set and the second RNA probe set are configured to co-exist ("concurrently") with the at least one target nucleic acid sequence in a single hybridization reaction, i.e. both the first RNA probe set and the second RNA probe set are configured to simultaneously and respectively contact the two antiparallel sequences of the at least one target nucleic acid duplex sequence in the single hybridization reaction.

Herein, optionally, each probe in the first RNA probe set and each probe in the second RNA probe set can be configured to be physically separated from one another, such as being labelled on different region in the working surface of the solid support (e.g. a column or microfluidic channel) or on different magnetic beads.

Optionally, each probe in the first RNA probe set and each probe in the second RNA probe set can be configured not to be physically separated from one another, i.e. they co-exist in the single hybridization reaction, such as in Example 6 whose description will be provided in more detail below.

In addition to the concurrent manner set forth above, there are also other manners as well, such as the sequential manner or the separate manner.

As such, according to certain embodiments of the method, the sub-step of contacting both the first RNA probe set and the second RNA probe set in the each of the at least one pair of RNA probe sets with the at least one target nucleic acid sequence in the biological sample comprises sequentially:

contacting one of the first RNA probe set and the second RNA probe set in each of the at least one pair of RNA probe sets with the at least one target nucleic acid sequence in a first hybridization reaction; and contacting another of the first RNA probe set and the second RNA probe set in each of the at least one pair of RNA probe sets with the at least one target nucleic acid sequence in a second hybridization reaction.

According to some other embodiments of the method, the sub-step of contacting both the first RNA probe set and the second RNA probe set in the each of the at least one pair of RNA probe sets with the at least one target nucleic acid sequence in the biological sample comprises at least one round of:

separately contacting the first RNA probe set and the second RNA probe set in each of the at least one pair of RNA probe sets with the at least one target nucleic acid sequence in a third hybridization reaction and a fourth hybridization reaction, respectively; and combining the third hybridization reaction and the fourth hybridization reaction to thereby allow a fifth hybridization reaction to proceed.

In any of the embodiments of the method described above, one or more of the at least one target nucleic acid sequence in the biological sample may each be in a polynucleotide containing one or more other sequences. Accordingly in the method, the step (2) of capturing each strand of the at least one target nucleic acid sequence from the biological sample may, prior to or concurrent with the sub-step of contacting both the first RNA probe set and the second RNA probe set in the each of the at least one pair of RNA probe sets with the at least one target nucleic acid sequence in the biological sample, further comprise a sub-step of:

contacting at least one blocking oligo with the at least one target nucleic acid sequence such that the at least one blocking oligo respectively hybridizes with, and thereby blocks, one strand in at least one of the one or more other sequences in the polynucleotide.

Herein, there is no limitation to the position of the one or more other sequences in the polynucleotide relative to each target nucleic acid sequence. Optionally, they can be at a position flanking (i.e. 3'-end or 5'-end of) each target nucleic acid sequence. For example, each target nucleic acid sequence may be flanked by a first adaptor sequence and a second adaptor sequence (i.e. "one or more other sequences") in the polynucleotide, the at least one blocking oligo can be configured to respectively block one strand of the first adaptor sequence and one strand of the second adaptor sequence in the polynucleotide, and according to some embodiments, the at least one blocking oligo can be configured to respectively block both two antiparallel strands of the first adaptor sequence and both two antiparallel strands of the second adaptor sequence in the polynucleotide. Further according to some embodiments, the at least one blocking oligo comprises a first blocking oligo set and a second blocking oligo set, each comprising one or more blocking oligo, configured to respectively block two antiparallel strands of one of the first adaptor sequence and the second adaptor sequence in the polynucleotide, wherein the sub-step of contacting at least one blocking oligo with the at least one target nucleic acid sequence comprises: contacting one of the first blocking oligo set and the second blocking oligo set with the at least one target nucleic acid sequence; and contacting another of the first blocking oligo set and the second blocking oligo set with the at least one target nucleic acid sequence.

In addition to the above embodiments, the one or more other sequences may optionally be in the middle of each target nucleic acid sequence.

According to certain embodiments of the method, the step (1) of providing at least one pair of RNA probe sets and a solid support comprises: conjugating on the solid support via the immobilization portion labelled onto each RNA probe in any of the first RNA probe set and the second RNA probe set in the each of the at least one pair of RNA probe sets to thereby obtain at least one pair of solid support-conjugated RNA probe sets, each pair comprising a solid support-conjugated first RNA probe set and a solid support-conjugated second RNA probe set. Accordingly, the step (2) of capturing each strand of the at least one target nucleic acid sequence from the biological sample comprises: contacting both the solid support-conjugated first RNA probe set and the solid support-conjugated second RNA probe set in the each of the at least one pair of solid support-conjugated RNA probe sets with the at least one target nucleic acid sequence.

Herein, optionally, a working surface of at least one of a magnetic bead, a filter, a resin bead, a nanosphere, a plastic surface, a microtiter plate, a glass surface, a slide, a membrane, a microfluidic channel, a chip or a matrix may serve as the solid support.

In the above embodiments, there can be different options for the sub-step of contacting both the solid support-conjugated first RNA probe set and the solid support-conjugated second RNA probe set in the each of the at least one pair of solid support-conjugated RNA probe sets with the at least one target nucleic acid sequence.

Optionally, the contacting sub-step comprises: concurrently contacting both of the solid support-conjugated first RNA probe set and the solid support-conjugated second RNA probe set in the each of the at least one pair of solid support-conjugated RNA probe sets with the at least one target nucleic acid sequence.

Optionally, the contacting sub-step comprises: sequentially:

contacting one of the solid support-conjugated first RNA probe set and the solid support-conjugated second RNA probe set in the each of the at least one pair of solid support-conjugated RNA probe sets with the at least one target nucleic acid sequence in a sixth hybridization reaction; and contacting another of the solid support-conjugated first RNA probe set and the solid support-conjugated second RNA probe set in the each of the at least one pair of solid support-conjugated RNA probe sets with the at least one target nucleic acid sequence in a seventh hybridization reaction.

Optionally, the contacting sub-step comprises:

separately contacting the solid support-conjugated first RNA probe set and the solid support-conjugated second RNA probe set in the each of the at least one pair of solid support-conjugated RNA probe sets with the at least one target nucleic acid sequence in an eighth hybridization reaction and a ninth hybridization reaction, respectively; and combining the eighth hybridization reaction and the ninth hybridization reaction to thereby allow a tenth hybridization reaction to proceed.

In any of the embodiments of the method described above, there can be different manners for preparing the at least one pair of RNA probe sets.

According to certain embodiments, one or more of the at least one pair of RNA probe sets may be prepared through chemical synthesis. As such, the step (1) preparing at least one pair of RNA probe sets can comprise: performing chemical synthesis reactions to thereby obtain the one or more of the at least one pair of RNA probe sets. Each RNA probe in each of the one or more of the at least one pair of RNA probe sets can be labelled with the immobilization portion during the chemical synthesis reactions. Herein, the immobilization portion is covalently attached onto the solid support (i.e. each RNA probe is synthesized directly on the solid support conjugated with the immobilization portion thereof). Alternatively, each RNA probe in each of the one or more of the at least one pair of RNA probe sets can be labelled with the immobilization portion after the chemical synthesis reactions, and as such the step (1) preparing at least one pair of RNA probe sets further comprises: performing labelling reactions such that each RNA probe in each of the one or more of the at least one pair of RNA probe sets is labelled with the immobilization portion.

According to some other embodiments of the method, one or more of the at least one pair of RNA probe sets may be prepared through transcription. As such, the step (1) preparing at least one pair of RNA probe sets can comprise: performing transcription reactions to thereby obtain the one or more of the at least one pair of RNA probe sets.

Herein, the sub-step of performing transcription reactions to thereby obtain the one or more of the at least one pair of RNA probe sets can include: performing transcription reactions such that each RNA probe in any of the one or more of the at least one pair of RNA probe sets is labelled with the immobilization portion during each of the transcription reactions. According to some embodiments, each of the transcription reactions is performed in presence of NTPs labelled with the immobilization portion, where the NTPs comprises at least one of ATPs, UTPs, GTPs, and CTPs. Herein the NTPs labelled with the immobilization portion can preferably comprise biotin-labelled UTPs, and the biotin-labelled UTPs can have a relative molar percentage of 2%-100% in all UTPs present in each of the transcription reactions.

Alternatively, each RNA probe in any of the one or more of the at least one pair of RNA probe sets is labelled with the immobilization portion after each of the transcription reactions. As such, the sub-step of performing transcription reactions to thereby obtain the one or more of the at least one pair of RNA probe sets can include: performing the transcription reactions; and performing a labelling.

According to some embodiments, the above sub-step of performing the transcription reactions can comprise:

providing a plurality of DNA vectors, comprising at least one pair of DNA vectors, each pair comprising a first DNA vector and a second DNA vector configured to respectively allow transcription of a first RNA molecule and a second RNA molecule respectively targeting two antiparallel strands of a duplex segment in each of the one or more of the at least one target nucleic acid sequence; and performing the transcription reactions over the plurality of DNA vectors.

Herein, each of the plurality of DNA vectors can include a promoter, selected from one of a T3 promoter, a T7 promoter, or a SP6 promoter. At least one of the transcription reactions can be performed in vitro, or in vivo.

According to some embodiments of the method, the sub-step of performing transcription reactions over the plurality of DNA vectors comprises:

pooling the plurality of DNA vectors to obtain at least two DNA vector pools, such that the first DNA vector and the second DNA vector in the each pair of DNA vectors are not in a same DNA vector pool; and performing a transcription reaction over each of the at least two DNA vector pools respectively to obtain RNA molecules corresponding to the each of the at least two DNA vector pools.

After the sub-step of performing a transcription reaction over each of the at least two DNA vector pools respectively and prior to the sub-step of performing a labelling, the method can further comprise: performing a fragmentation reaction to the RNA molecules corresponding to the each of the at least two DNA vector pools.

According to some other embodiments of the method, rather than pooling the DNA vectors before transcription, the sub-step of performing transcription reactions over the plurality of DNA vectors comprises: performing a transcription reaction over each of the plurality of DNA vectors to thereby obtain an RNA molecule corresponding thereto.

As such, after the sub-step of performing a transcription reaction over each of the plurality of DNA vectors and prior to the sub-step of performing a labelling, the method can further include:

pooling the RNA molecule corresponding to each of the plurality of DNA vectors to obtain at least two RNA pools, such that a pair of RNA molecules respectively targeting two antiparallel strands of a duplex segment in any one of the one or more of the at least one target nucleic acid sequence are not in a same RNA pool; and performing a fragmentation reaction to each of the at least two RNA pools respectively.

Alternatively, after the sub-step of performing a transcription reaction over each of the plurality of DNA vectors and prior to the sub-step of performing a labelling, the method can further include:

performing a fragmentation reaction to the RNA molecule corresponding to each of the plurality of DNA vectors respectively to obtain fragmented RNA molecules corresponding to each of the plurality of DNA vectors; and pooling the fragmented RNA molecules corresponding to each of the plurality of DNA vectors such that a pair of fragmented RNA molecules respectively targeting two antiparallel strands of a duplex segment in any one of the one or more of the at least one target nucleic acid sequence are not in a same RNA probe set.

In any of the embodiments of the method as described above, the sub-step of performing a labelling can comprise: performing ligation reactions such that an immobilization portion-labelled nucleotide is ligated to one terminus, or to a middle, of each RNA probe in each of the at least one pair of RNA probe sets. In one example, in each of the ligation reactions, a 5' phosphate terminus of a biotin-labeled nucleotide can be ligated to a 3' hydroxyl terminus of each RNA probe in each of the at least one pair of RNA probe sets, and each of the ligation reactions can be performed by means of an RNA ligase, which can comprise at least one of T4 RNA ligase, or CircLigase RNA ligase.

According to some embodiments, the step of preparing at least one pair of RNA probe sets comprises: performing direct transcription on the solid support to thereby obtain the one or more of the at least one pair of RNA probe sets. This can be done, for example, by means of a RNA polymerase attached on the solid support.

According to some embodiments of the method, the immobilization portion can be configured to be able to form a stable non-covalent binding with a coupling partner conjugated onto surface of the solid support, and as such, the immobilization portion can comprise a biotin moiety, and correspondingly, the coupling partner conjugated onto surface of the solid support can comprise at least one of streptavidin, avidin, or an anti-biotin antibody. According to some other embodiments of the method, the immobilization portion can be configured to be able to form a covalent connection with a coupling partner conjugated onto surface of the solid support. The solid support can comprise at least one of a magnetic bead, a filter, a resin bead, a nanosphere, a plastic surface, a microtiter plate, a glass surface, a slide, a membrane, a microfluidic channel, a chip, or a matrix.

The method according to any one of the embodiments as described above can further include: eluting out the at least one target nucleic acid sequence from the solid support.

In a second aspect, the disclosure further provides a kit for enriching at least one target nucleic acid sequence from a biological sample.

According to some embodiments, the kit comprises at least one pair of RNA probe sets and a solid support labelled with a coupling partner on a surface thereof. Each pair of RNA probe sets comprises a first RNA probe set and a second RNA probe set configured to respectively target two antiparallel strands of a duplex segment in each of the at least one target nucleic acid sequence, wherein each RNA probe in any of the first RNA probe set and the second RNA probe set is labelled with an immobilization portion. The coupling partner is configured to be able to form a secure coupling to the immobilization portion to thereby allow immobilization of each RNA probe in any of the first RNA probe set and the second RNA probe set in the each of the at least one pair of RNA probe sets onto the solid support.

Herein, each RNA probe in any of the first RNA probe set and the second RNA probe set in the each of the at least one pair of RNA probe sets can have a length of about 100-150 nt.

In the kit, the first RNA probe set and the second RNA probe set in the each of the at least one pair of RNA probe sets can be configured to respectively target a substantially same portion, or different portions, of the duplex segment in the each of the at least one target nucleic acid sequence.

According to some embodiments of the kit, the immobilization portion can comprise a biotin moiety, the solid support comprises at least one of a magnetic bead, a filter, a resin bead, a nanosphere, a plastic surface, a microtiter plate, a glass surface, a slide, a membrane, a microfluidic channel, a chip, or a matrix, and the solid support can be labelled with at least one of streptavidin, avidin, or an anti-biotin antibody.

According to some embodiments, the kit further comprises an apparatus having a working surface as the solid support. The first RNA probe set and the second RNA probe set in each pair are respectively conjugated onto the working surface, arranged such that each RNA probe in the solid support-conjugated first RNA probe set does not substantially interact with each RNA probe in the solid support-conjugated second RNA probe set. Herein the apparatus can be one of a column, a microfluidic channel, or a chip.

Optionally, the solid support-conjugated first RNA probe set and the solid support-conjugated second RNA probe set in each pair can be respectively arranged at at least one, and preferably more than one, pair of two different regions of the working surface of the apparatus.

Optionally, the solid support-conjugated first RNA probe set and the solid support-conjugated second RNA probe set in each pair can be mixedly arranged on the working surface of the apparatus, configured such that each RNA probe from the first RNA probe set has a relatively large distance to each RNA probe from the second RNA probe set to thereby substantially prevent an interaction therebetween.

In any of the above embodiments, the apparatus can be configured to allow the biological sample to flow sequentially through the working surface for more than one round.

In the biological sample, one or more of the at least one target nucleic acid sequence are each in a polynucleotide comprising at least one un-targeted sequence. As such, the kit can further include at least one blocking oligo, configured to respectively hybridize with, and to thereby block, at least one strand of each of the at least one un-targeted sequence in the polynucleotide. If the at least one un-targeted sequence in the polynucleotide comprises a first adaptor sequence and a second adaptor sequence flanking each of the one or more of the at least one target nucleic acid sequence, the at least one blocking oligo can be configured to respectively block one strand of the first adaptor sequence and one strand of the second adaptor sequence in the polynucleotide, or to respectively block both two antiparallel strands of the first adaptor sequence and both two antiparallel strands of the second adaptor sequence in the polynucleotide. As such, in the kit, the at least one blocking oligo can comprise a first blocking oligo set and a second blocking oligo set, configured to respectively block two antiparallel strands of one of the first adaptor sequence and the second adaptor sequence in the polynucleotide. The first blocking oligo set and the second blocking oligo set can be configured to respectively target two different portions within the one of the first adaptor sequence and the second adaptor sequence in the polynucleotide.

According to some other embodiments, the kit can include a plurality of DNA vectors, NTPs comprising each of ATPs, UTPs, GTPs, and CTPs; immobilization portion-labelled NTPs, wherein NTPs comprises at least one of ATPs, UTPs, GTPs, and CTPs; and a solid support labelled with a coupling partner on a surface thereof. The plurality of DNA vectors comprises at least one pair of DNA vectors, each pair comprising a first DNA vector and a second DNA vector configured, via transcription thereover, to respectively obtain a first RNA probe set and a second RNA probe set targeting respectively two antiparallel strands of a duplex segment in each of the at least one target nucleic acid sequence. The coupling partner is configured to be able to form a secure coupling to the immobilization portion.

Herein, the immobilization portion can include a biotin moiety, and the NTPs labelled with the immobilization portion can comprise biotin-labelled UTPs, having a relative molar percentage of 2%-100% among all UTPs in the kit. The solid support can comprise comprises at least one of a magnetic bead, a filter, a resin bead, a nanosphere, a plastic surface, a microtiter plate, a glass surface, a slide, a membrane, a microfluidic channel, a chip, or a matrix, and the solid support can be labelled with at least one of streptavidin, avidin, or an anti-biotin antibody.

According to some embodiments, the kit can further include an RNA ligase, comprising at least one of T4 RNA ligase or CircLigase RNA ligase, which is configured to ligate a 3' hydroxyl terminus of each RNA probe in any of the first RNA probe set and the second RNA probe set generated from each of the at least one pair of DNA vectors with one of the immobilization portion-labeled NTPs.

Each of the plurality of DNA vectors may comprise a DNA template and a promoter. The DNA template may comprise a sequence corresponding to one of two antiparallel strands of a duplex segment in each of the at least one target nucleic acid sequence. The promoter can be configured to initiate a transcription reaction of the DNA template in a presence of an RNA polymerase compatible with the promoter. The promoter is selected from one of a T3 promoter, a T7 promoter, a SP6 promoter, and the kit can correspondingly further comprise a T3 RNA polymerase, a T7 RNA polymerase, or a SP6 RNA polymerase, corresponding to the promoter in each of the plurality of DNA vectors.

The kit can further comprise cells or viruses containing the RNA polymerase compatible with the promoter in each of the plurality of DNA vectors. The cells can include at least one of a bacterial cell line, a yeast cell line, or a mammalian cell line. Depending on the different host cells or host viruses, the promoter can be any of the T3 promoter, T7 promoter, and SP6 promoter, and can optionally be a tissue or cell line-specific promoter. There are no limitations herein.

In the kit, each of the plurality of DNA vectors can be a double-stranded DNA vector or a single-stranded DNA vector.

In the biological sample, one or more of the at least one target nucleic acid sequence are each in a polynucleotide comprising at least one un-targeted sequence. As such, the kit can further include at least one blocking oligo, configured to respectively hybridize with, and to thereby block, at least one strand of each of the at least one un-targeted sequence in the polynucleotide. If the at least one un-targeted sequence in the polynucleotide comprises a first adaptor sequence and a second adaptor sequence flanking each of the one or more of the at least one target nucleic acid sequence, the at least one blocking oligo can be configured to respectively block one strand of the first adaptor sequence and one strand of the second adaptor sequence in the polynucleotide, or to respectively block both two antiparallel strands of the first adaptor sequence and both two antiparallel strands of the second adaptor sequence in the polynucleotide. As such, in the kit, the at least one blocking oligo can comprise a first blocking oligo set and a second blocking oligo set, configured to respectively block two antiparallel strands of one of the first adaptor sequence and the second adaptor sequence in the polynucleotide. The first blocking oligo set and the second blocking oligo set can be configured to respectively target two different portions within the one of the first adaptor sequence and the second adaptor sequence in the polynucleotide.

In the above-mentioned method and kit, the nucleic acid sequences may comprise DNA and/or RNA sequences from a test sample. The nucleic acid sequences can be natural sequence obtained from an organism, or can be artificial sequences manufactured manually. There are no limitations herein.

The test sample can be a biological sample from an organism, or can be a sample obtained artificially or obtained after appropriate handling, as long as the test sample contain one or more nucleic acid sequences. The biological sample can be DNA, RNA or any samples composed of nucleic acid sequence(s), and the samples can be chemical synthesis products or extracted from an organism, such as multicellular animals, plants, fungi, protists, bacteria, archaea, or any types of the tissue culture of the above organisms. The organism can be from any domains from prokaryota and eukaryote. The test samples may be treated prior to enrichment. For example, the nucleic acid sequences in the biological sample can be amplified prior to enrichment and testing.

The nucleic acid sequences may contain genetic markers associated with human diseases including cancer, diabetes, heart diseases, and so on, but can also include markers associated with a phenotype such as height, weight, skin color, etc. The markers may include qualitative or quantitative genetic information.

Test samples can be from any appropriate sources in the patient's body that will have nucleic acids from a cancer or lesion that can be collected and tested. Test samples can be also from any appropriate sources derived from patient tissue, such as FFPE slides, FFPE tissue blocks, and test samples can be also from any appropriate sources derived from other biological specimens, such as fossils, body remains of ancient human species or animal species. Suitable test samples may be obtained from body tissue, stool, and body fluids, such as blood, tear, saliva, sputum, bronchoalveolar lavage, urine and different organ secreted juices. In some cases, the nucleic acids will be amplified prior to testing. The samples may be collected using any means conventional in the art, including from surgical samples, from biopsy samples, from endoscopic ultrasound (EUS), phlebotomy, etc. Obtaining the samples may be performed by the same person or a different person that conducts the subsequent analysis. Samples may be stored and/or transferred after collection and before analysis. Samples may be fractionated, treated, purified, enriched, prior to assay.

According to one aspect of the invention, a portion or all nucleic acids in a sample are enriched for nucleic acid analysis. A set of probes for one or more analytes of interest is synthesized. The probes are RNA probes. The probes are transcribed from DNA template sharing the same sequences as the target nucleic acids that are going to be enriched. The RNA probes are complementary to both plus and minus strands of a target nucleic acid analyte. The RNA probes complementary to plus and minus strands of a target nucleic acid analyte are synthesized in parallel reaction systems. The set of RNA probes can be massively generated by in vitro transcription using the target nucleic acid sequences as the templates. The RNA probes are bound to a solid support. The solid support is contacted with the sample comprising nucleic acids under hybridization conditions so that complementary nucleic acids in the sample are captured on the solid support, and the solid support is washed to remove non-complementary nucleic acids. Captured nucleic acids are eluted from the solid support for further analysis.

According to another aspect of the invention, a portion or all nucleic acids in a sample are enriched for nucleic acid analysis. A set of probes for one or more analytes of interested is synthesized. The probes are RNA probes. The probes are transcribed from DNA template sharing the same sequences as the target nucleic acids that are going to be enriched. The RNA probes are complementary to both plus and minus strands of a target nucleic acid analyte. The RNA probes complementary to plus and minus strands of a target nucleic acid analyte are synthesized in parallel reaction systems. The set of RNA probes can be massively generated by in vitro transcription using the target nucleic acid sequences as the templates. The transcribed or synthesized RNA probes are sheared into fragments by sonication. Modified nucleic acids (such as biotinylated Uracil) can be incorporated into the RNA probes or additional nucleic acid modifications can happen on the ends or within nucleic acid sequences of RNA probes, either of which allows the RNA probes to be immobilized or captured and extracted after the capture procedure. RNA probes are contacted with the sample compromising nucleic acids under hybridization conditions so that complementary nucleic acids in the sample are captured. The hybridization reaction mixture is contacted with a solid support which compromises chemical structures (such as avidin or streptavidin) that specifically react with the modification groups (such as biotin) on the RNA probes. RNA probes with their captured complementary nucleic acids are immobilized, or captured, on the solid support. The solid support is washed to remove non-complementary nucleic acids. Captured nucleic acids are eluted from the solid support for further analysis.

These and other embodiments which will be apparent to those of skill in the art upon reading the specification provide the art with methods for assessing, characterizing, and detecting genetic markers, such as cancer markers, and genetic analysis, such as SNV identification. In particular, it provides methods for enriching nucleic acids for desired analytes.

Throughout the disclosure, "upstream" and "downstream" are respectively defined as nucleic acid sequences at 5' end and 3' end of a strand of nucleic acid sequence (DNA strand or RNA strand), unless indicated otherwise.

Unless indicated otherwise, all DNA sequences disclosed herein have a direction from a 5' end to a 3' end thereof.

Unless indicated otherwise, an oligo can be a single-stranded DNA oligo, or a single-stranded RNA oligo, having a sequence of at least 2 nt.

The term "about" in the disclosure generally refers to plus or minus 10% of the indicated number. For example, "about 20" may indicate a range of 18 to 22, and "about 1" may mean from 0.9-1.1. Other meanings of "about" may be apparent from the context, such as rounding off, so, for example "about 1" may also mean from 0.5 to 1.4.

The term "probe" in this disclosure is referred to as a bait molecule that can be used for capturing or enriching a target molecule, unless indicated otherwise. Specifically, in this disclosure, an RNA probe is substantially a bait RNA molecule that are used to capture and enrich a target nucleic acid sequence, including a DNA sequence or an RNA sequence or any other nucleic acid sequences that could form hybridization molecules with the RNA probes.

As used herein, the term "hybridization" or "binding" or "annealing" refers to the pairing of complementary (including partially complementary) polynucleotide strands. Hybridization and the strength of hybridization (e.g., the strength of the association between polynucleotide strands) is impacted by many factors well known in the art including the degree of complementarity between the polynucleotides, stringency of the conditions involved affected by such conditions as the concentration of salts, the melting temperature (Tm) of the formed hybrid, the temperature of the hybridization reaction, the presence of other components, the molarity of the hybridizing strands and the G:C content of the polynucleotide strands. When one polynucleotide is said to "hybridize" to another polynucleotide, it means that there is some complementarity between the two polynucleotides or that the two polynucleotides form a hybrid under high stringency conditions. When one polynucleotide is said to not hybridize to another polynucleotide, it means that there is no sequence complementarity between the two polynucleotides or that no hybrid forms between the two polynucleotides at a high stringency condition. Related, the terms "target", "targeting", or alike in the disclosure, such as in a phrase "an RNA probe targeting one strand of a DNA molecule" refers to the situation that the RNA probe can specifically hybridize, or bind, or anneal with the one strand of the DNA molecule.

As used herein, the term "complementary" refers to the concept of sequence complementarity between regions of two polynucleotide strands (e.g. a double-stranded structure) or between two regions of the same polynucleotide strand (e.g. a "loop" or "hairpin" structure). It is known that an adenine base of a first polynucleotide region is capable of forming specific hydrogen bonds ("base pairing") with a base of a second polynucleotide region which is antiparallel to the first region if the base is thymine or uracil. Similarly, it is known that a cytosine base of a first polynucleotide strand is capable of base pairing with a base of a second polynucleotide strand which is antiparallel to the first strand if the base is guanine. A first region of a polynucleotide is complementary to a second region of the same or a different polynucleotide if, for example, when the two regions are arranged in an antiparallel fashion, at least one nucleotide of the first region is capable of base pairing with a base of the second region. Therefore, it is not required for two complementary polynucleotides to base pair at every nucleotide position. "Complementary" refers to a first polynucleotide that is 100% or "fully" complementary to a second polynucleotide and thus forms a base pair at every nucleotide position. "Complementary" also refers to a first polynucleotide that is not 100% complementary (e.g., 90%, or 80% or 70% complementary) contains mismatched nucleotides at one or more nucleotide positions. In one embodiment, two complementary polynucleotides are capable of hybridizing to each other under high stringency hybridization conditions.

As used herein, the term "target nucleic acid" or "target" refers to a nucleic acid containing a target nucleic acid sequence to be identified. A target nucleic acid may be single-stranded or double-stranded, and often is DNA, RNA, a derivative of DNA or RNA, or a combination thereof. A "target nucleic acid sequence," "target sequence" or "target region" means a specific sequence comprising all or part of the sequence of a single-stranded nucleic acid. A target sequence may be within a nucleic acid template, which may be any form of single-stranded or double-stranded nucleic acid. A template may be a purified or isolated nucleic acid, or may be non-purified or non-isolated.

A target or target nucleic acid usually exists within a portion or all of a polynucleotide, and is usually a polynucleotide analyte. The identity of the target nucleotide sequence generally is known to an extent sufficient to allow preparation of various probe/bait sequences hybridizable with the target material. The target material is generally a fraction of a larger pool of molecules or it may be substantially the entire molecule such as a polynucleotide as described above.

The term "antiparallel strands" of a duplex segment of a nucleic acid sequence refers to the situation where two strands of nucleic acid sequences align in opposite directions (i.e., one strand in a 5' end-3' end direction, and the other in a 3' end-5' end direction) and form a double-stranded (i.e. "duplex") structure due to the hybridization of the two strands. It is possible that such two antiparallel strands of the duplex segment are two complimentary DNA strands ("DNA-DNA") of a double-stranded DNA segment, two complimentary RNA strands ("RNA-RNA") of a double-stranded RNA segment, or two complimentary DNA and RNA strands ("DNA-RNA") of a double-stranded DNA-RNA segment. The nucleic acid sequence can be double-stranded, and the two antiparallel strands of the duplex segment thereof are respectively the two complimentary strands of the nucleic acid sequence. Alternatively, the nucleic acid sequence can be single-stranded, where the two antiparallel strands of the duplex segment substantially forms a "hairpin" or a "loop" segment of the single-stranded nucleic acid sequence.

The term "RNA polymerase compatible with a promoter" is defined as an RNA polymerase that can recognize the promoter to thereby initiate a transcription of RNA molecules using a DNA template at a downstream of the promoter.

The terms "first", "second", "third", "fourth", "fifth", etc., are intended to refer to a different object (i.e. component, composition, process, etc.) and indicates or suggests no actual order in the disclosure.

BRIEF DESCRIPTION OF THE DRAWINGS

(FIG. 8A) For each of the six NGS DNA libraries derived from different amounts (500 ng, 20 ng, 1 ng, 100 pg, 20 pg and 10 pg) of input genomic DNA, enrichment efficiency of 298 cancer related genes were calculated. Recovery ratios of double strand DNA capture and single strand DNA capture for all 298 genes in six libraries were quantified by real-time PCR assays detecting each gene's abundance in the libraries before and after captures with different approaches (targeting double DNA strands or targeting single DNA strand). (FIG. 8B) A plasmid was constructed with an insert sequence composed of amplicon regions of five genes whose GC contents cover a broad range (27.3% to 74.1%). (FIG. 8C) Real-time PCR analysis of sequential dilutions of the plasmid illustrated in 3E. 1, 10, 100, 1,000 and 10,000 femtomoles of the plasmids were added as template for the detection. $C_t$ value for each gene obtained from each plasmid amount was plotted, and trend lines were shown. (FIG. 8D) A original genomic DNA NGS library, and the library molecules captured by RNA probes targeting a single DNA strand or both DNA strands of a target sequence region were analyzed on an agarose gel;

(FIG. 10A) Bar plot of percentage of initial reads, mapped reads and reads remained after filtering. Results were obtained from three technical replicates. Numbers of reads were shown under each bar with the unit of 1 million reads. (FIG. 10B) Stacked bar plot of subgroups of filtered reads in triple replicates. (FIG. 10C) Coverage efficiency correlation with read numbers. The percentage of target bases covered at ≥10×, ≥20×, ≥50× and ≥100× depths with 5 million to 50 million reads were shown;

(FIG. 11B) an NGS whole genome sequencing study with DNA extracted from normal human tissue (without whole exome enrichment through any methods);

FIGS. 13A-13N show the 298-gene panel real-time PCR parameters;

FIG. 14 shows data yield from RNA probe-based DNA double strand capture WES sequencing; and FIGS. 15A-15E show results of mutation and ultra-rare mutation detection by RNA probe-based DNA double strand capture NGS.

DETAILED DESCRIPTION OF THE INVENTION

In a sequencing technology such as NGS, the enrichment of nucleic acids from diluted samples or the capture of specific nucleic acid sequences from a sample comprising a complex pool of nucleic acids is often a crucial step, but can be challenging tasks in many cases. Enrichment for desired sequences can make assays feasible that would otherwise fall below detection limits, and can improve the performance of a genetic or genomic assay.

The present disclosure provides a method for enriching nucleic acid sequences from a biological sample, which substantially utilizes RNA probes that target both of two antiparallel strands of a duplex segment of a target sequence to be enriched in a sample.

Figure 1A:
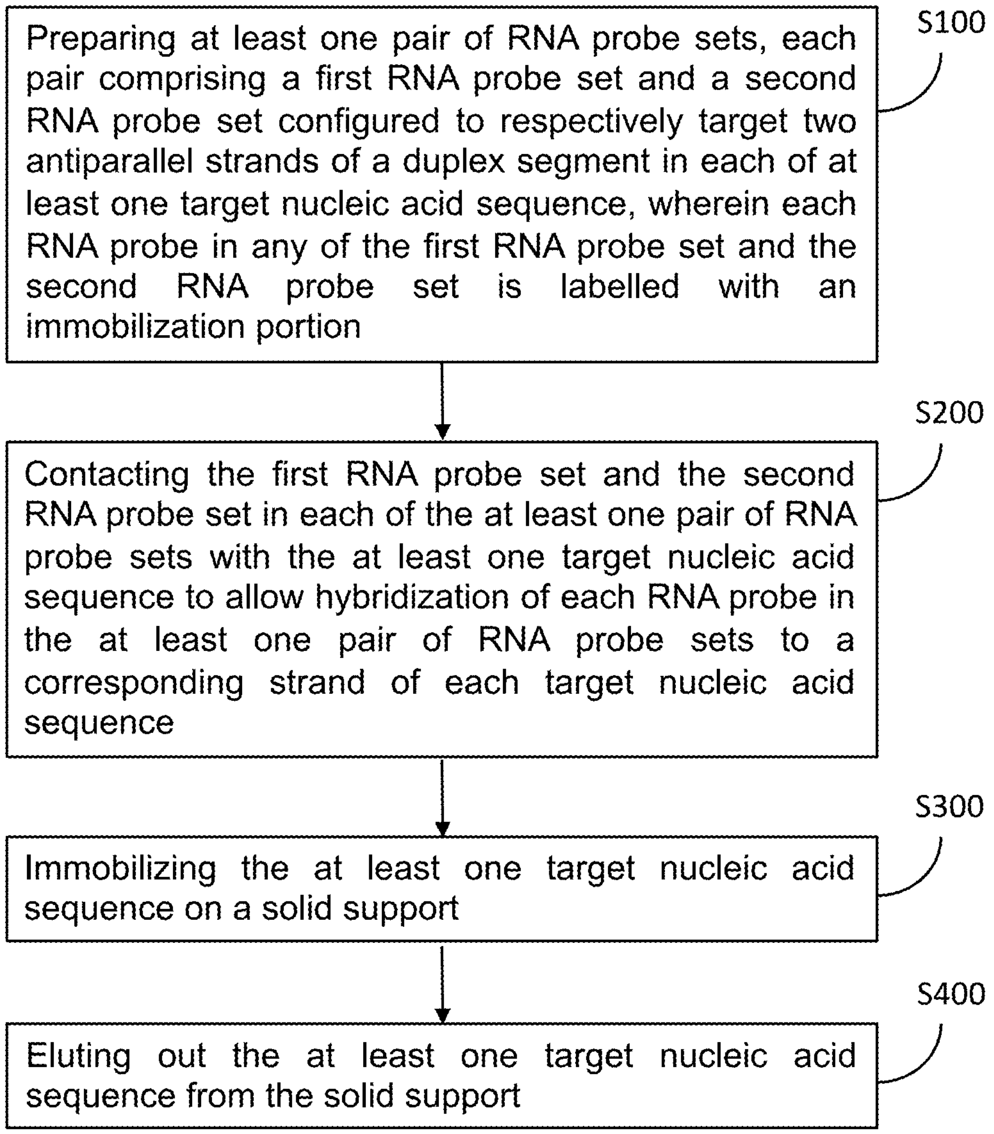
FIGS. 1A-1C respectively illustrate a flow chart of a method for enriching at least one target nucleic acid sequence from a biological sample according to two embodiments of the disclosure.

FIG. 1A illustrates a flow chart of the method for enriching at least one target nucleic acid sequence from a biological sample according to some embodiments of the disclosure. As shown in FIG. 1A, the method comprises steps as set forth in S100-S400:

S100: Preparing at least one pair of RNA probe sets, each pair comprising a first RNA probe set and a second RNA probe set configured to respectively target two antiparallel strands of a duplex segment in each of at least one target nucleic acid sequence, wherein each RNA probe in any of the first RNA probe set and the second RNA probe set is labelled with an immobilization portion.

Specifically, each pair of RNA probe sets comprises a first RNA probe set and a second RNA probe set, corresponding to one another, and each comprising one or more RNA probes. The one or more RNA probes in the first RNA probe set and the one or more RNA probes in the second RNA probe set are configured to respectively target two antiparallel strands of a duplex segment (i.e. double-stranded segment) of one of the at least one target nucleic acid sequence in the biological sample. Each RNA probe in any of the first RNA probe set and the second RNA probe set is labelled with, or comprises, an immobilization portion, configured to allow an immobilization by a solid support which will be described below in detail.

Herein, there is no limitation to the source of the biological sample, to the type of the at least one target nucleic acid sequence, or to the type of the duplex segment in each of the at least one target nucleic acid sequence.

The biological sample may be a tissue sample, from which at least one target nucleic acid sequence is obtained through a DNA or RNA purification protocol. The biological sample may be a cell-free DNA sample obtained from plasma, which contains the at least one target nucleic acid sequence in the sample. The biological sample may be derived from a treated sample, and contain, for example, a barcoded DNA library as disclosed in U.S. patent application Ser. No. 15/908,190, where each of the at least one target nucleic acid sequence contains a barcoded adaptor at one or both ends thereof. Other possibilities are possible as well.

The at least one target nucleic acid sequence in the biological sample can comprise one or more DNA molecules, one or more RNA molecules, one or more DNA-RNA hybrid molecules, or any of their combinations.

The duplex segment in each of the at least one target nucleic acid sequence may be formed by two separate DNA strands of a double-stranded DNA molecule, two separate RNA strands of a double-stranded RNA molecule, or one DNA strand and one RNA strand of a DNA-RNA hybrid molecule. The duplex segment may also be an intra-strand hairpin or alike formed within one single DNA strand or within one single RNA strand. In any of the aforementioned cases, a duplex segment substantially comprises two strand segments from one single strand (i.e. intra-strand duplex) or from two separate strands (i.e. inter-strand duplex), each having a sequence allowing a hybridization therebetween (e.g. having a sequence substantially complimentary to each other) and each running antiparallelly to each other to thereby form a double-stranded (i.e. duplex) structure.

Regardless of the type of a target nucleic acid sequence (DNA or RNA), or the type of the duplex segment therein (inter-strand or intra-strand), a first RNA probe set and a second RNA probe set can be configured to respectively target the two antiparallel strands of a duplex segment of each of the at least one target nucleic acid sequence in the biological sample, which together form a pair of RNA probe sets corresponding to the each of the at least one target nucleic acid sequence. Herein, throughout the disclosure, and also unless indicated otherwise, the two antiparallel strands of a duplex segment of each of the at least one target nucleic acid sequence in the biological sample are termed a plus strand and a minus strand of the each of the at least one target nucleic acid sequence.

In other words, the at least one RNA probe in the first RNA probe set and the at least one RNA probe in the second RNA probe set are respectively configured to target the plus strand and the minus strand, or alternatively the minus strand and the plus strand, of one of the at least one target nucleic acid sequence. By means of the at least one pair of RNA probe sets where a first RNA probe set and a second RNA probe set in each pair respectively target two antiparallel strands of a duplex segment in each target nucleic acid sequence, each strand of the at least one target nucleic acid sequence can be captured or enriched from the biological sample. For a typical example, each target nucleic acid sequence can be a double-stranded DNA molecule, which has a plus strand and a minus strand that runs antiparallelly to form a duplex. By means of the at least one pair of RNA probe sets where a first RNA probe set and a second RNA probe set in each pair respectively target both of the two antiparallel strands (i.e. the plus strand and the minus strand) of each target nucleic acid sequence, each strand, including both the plus strand and the minus strand, of each target DNA molecule, can be captured or enriched from the biological sample.

This notably contrasts with a conventional approach where only one strand of each target nucleic acid sequence is captured since only one RNA probe or one RNA probe set targeting only one strand of each target nucleic acid sequence is utilized. More specifically, in conventional approach a valid capture is typically a $1^{st}$ degree reaction between two complementary sequences that are respectively from a target nucleic acid sequence and a probe. However, in this present disclosure, a valid capture is a $2^{nd}$ degree reaction between a target nucleic acid molecule having a duplex segment (e.g. a duplex double-stranded DNA molecule) and each of a pair of RNA probes (i.e. a first RNA probe and a second RNA probe) that respectively target the two antiparallel strands of the duplex segment, where the hybridization of one strand in the duplex segment of the target nucleic acid molecule with one of the pair of RNA probes can help expose the other strand of the duplex segment to thereby facilitate the hybridization of the other of the pair of RNA probes therewith. Therefore a higher capture efficiency can be realized, and such an effect has been observed in the experiment as detailed below.

Herein, the solid support can comprise at least one of a magnetic bead, a microfluidic channel, a filter, a resin bead, a nanosphere, a plastic surface, a microtiter plate, a glass surface, a slide, a membrane, a microfluidic channel, a chip, or a matrix, which is labelled, conjugated, or attached, with the coupling partner corresponding to the immobilization portion. The solid support can be part of an apparatus, such as a chip, a column, a tube, or a channel (such as a microfluidic channel in a microfluidic chip).

The immobilization portion labelled on each RNA probe can include a biotin moiety, and correspondingly the solid support can comprise comprises at least one of a magnetic bead, a filter, a resin bead, a nanosphere, a plastic surface, a microtiter plate, a glass surface, a slide, a membrane, a microfluidic channel, a chip, or a matrix, and the solid support can be labelled with at least one of streptavidin, avidin, or an anti-biotin antibody. As such, the RNA probes labelled with, or carrying, the biotin moiety can form a secure non-covalent binding with the solid support conjugated with a biotin-coupling partner, such as streptavidin, avidin, or an anti-biotin antibody, which facilitates the capture of target nucleic acid sequences hybridized by the RNA probes. Other examples of the immobilization portion-coupling partner pair can include, but is not limited to, a carbohydrate-lectin pair, an antigen-antibody pair and a negative charged group-positive charged group static interacting pair.

In addition to the above embodiments where each RNA probe binds to the solid support through a non-covalent binding between the immobilization portion and the coupling partner pair, the secure coupling between each RNA probe and the solid support can be via a covalent connection (or cross-linking). As such, the immobilization portion and the coupling partner can respectively be one and another of a cross-linking pair. Examples of the cross-linking pair include an NHS ester-primary amine pair, a sulfhydryl-reactive chemical group pair (e.g. cysteines, or other sulfhydryls such as maleimides, haloacetyls, and pyridyl disulfides), an oxidized sugar-hydrazide pair, photoactivatable nitrophenyl azide's UV triggered addition reaction with double bonds leading to insertion into C—H and N—H sites or subsequent ring expansion to react with a nucleophile (e.g., primary amines), or carbodiimide activated carboxyl groups to amino groups (primary amines), etc. It is noted that the RNA probes can be conjugated on the solid support after synthesis, or can be synthesized directly on the solid support. Any method that could result in RNA probes to be linked on a solid support can be adopted. There is no limitation herein.

Herein it is noted that the first RNA probe set and the second RNA probe set in each of the at least one pair of RNA probe sets can be configured to target a same portion, or a distinct portion, of the duplex segment in one of at least one target nucleic acid sequence.

Figure 1B:
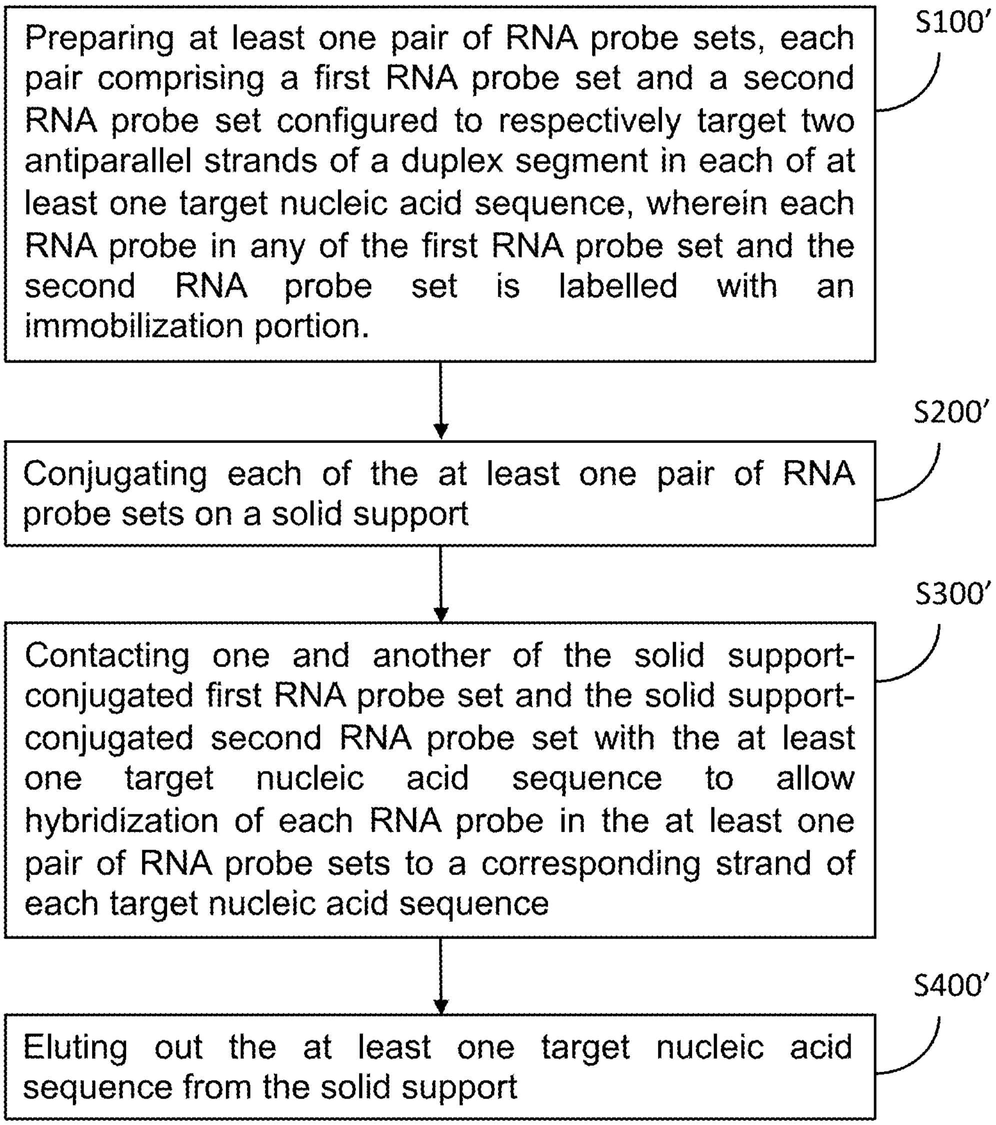
Figure 1C:
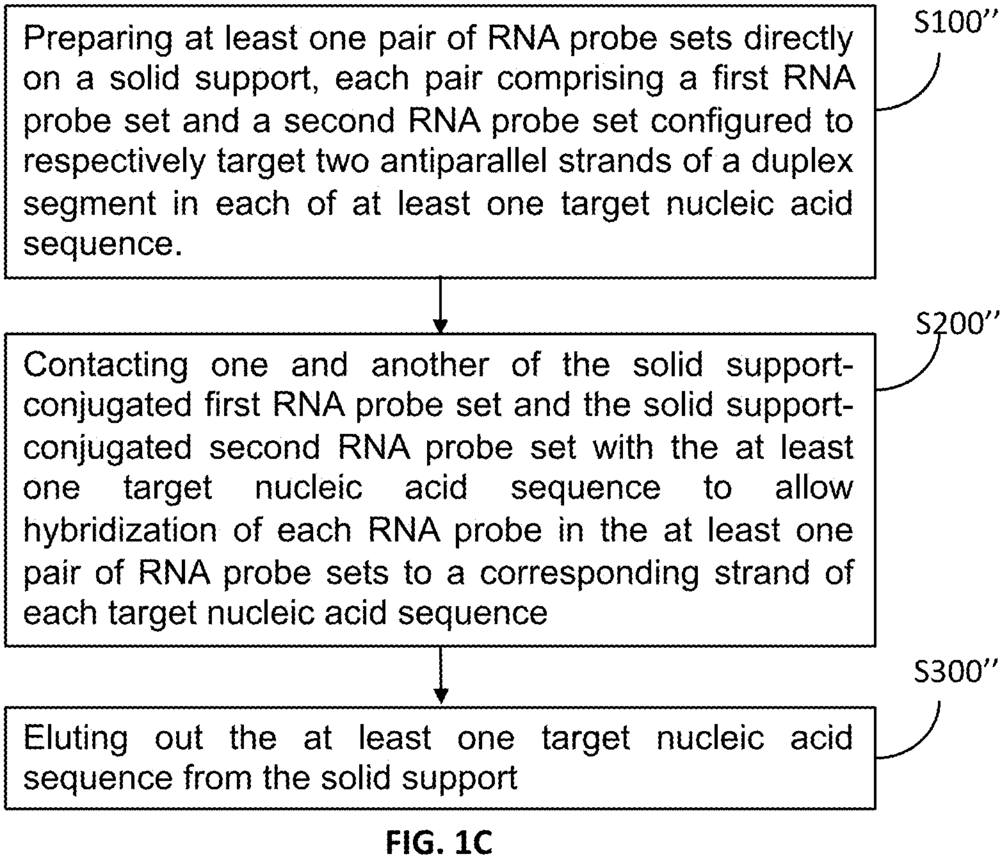
Figure 1D:
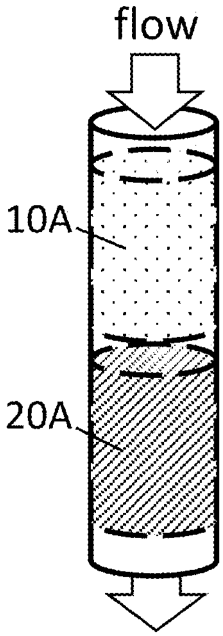
FIGS. 1D-1J respectively illustrate a schematic structure of an apparatus having each pair of RNA probe sets arranged on an inner surface thereof to allow the capture of target nucleic acid sequences from the biological sample according to several different embodiments of the disclosure.

According to some embodiments, a first RNA probe set and a second RNA probe set in a corresponding pair of RNA probe set are configured to target a same portion of the duplex segment of one target nucleic acid sequence, and as such, the RNA probe(s) in the first RNA probe set and the RNA probe(s) in the second RNA probe set have substantially complimentary sequences. As such, in certain embodiments where the RNA probes between the first RNA probe set and the second RNA probe set could potentially interact, or interfere, with one another in a single hybridization due to the unwanted hybridization therebetween, such as in cases where the RNA probes are labelled onto beads or matrix, contacting of the biological sample containing target nucleic acid sequences by the first RNA probe set and the second RNA probe set is preferably performed in a sequential manner. This can be realized by sequentially contacting the biological sample containing target nucleic acid sequences with magnetic beads respectively carrying one and another of the first RNA probe set and the second RNA probe set, which will be described in detail below. This can also be realized by allowing the biological sample to flow sequentially through two different layers (10A and 20A) of a column which comprise a matrix conjugated respectively with the first RNA probe set and the second RNA probe set, as illustrated in FIG. 1D.

Figure 1E:
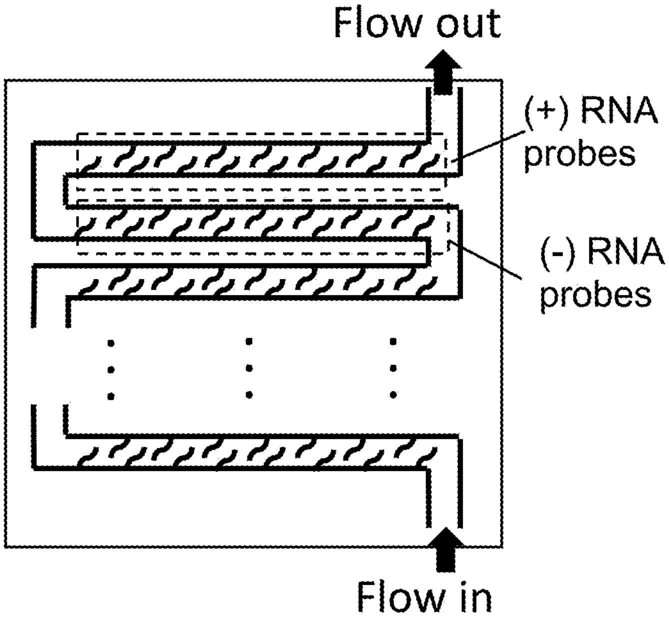
Figure 1F:
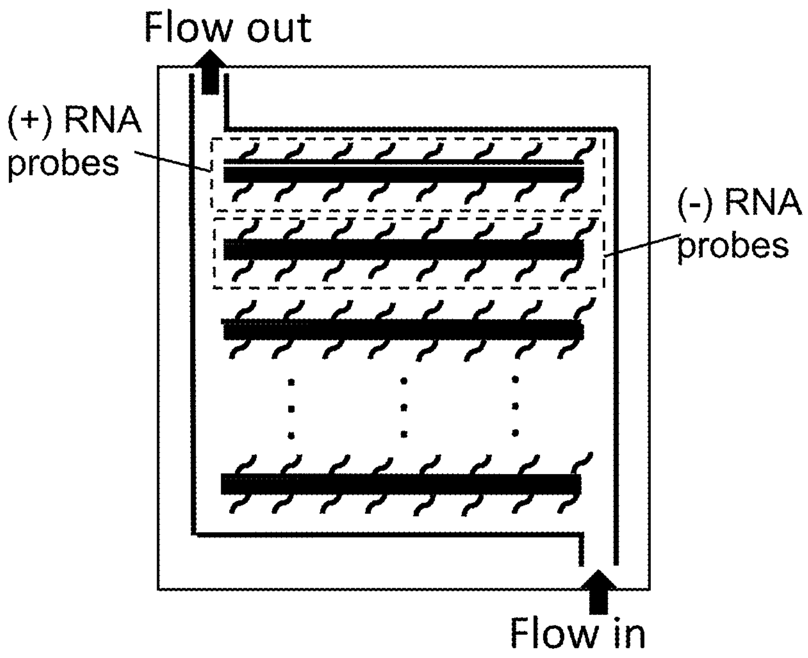

It is noted, however, in some other embodiments where the RNA probes are separately conjugated onto a solid support which has no or little interactions due to, for example, positional compartmentation on the surface of the solid support, such as in cases where RNA probes from the first RNA probe set and RNA probes from the second RNA probe set are separately conjugated onto different regions of a microfluidic channel (FIG. 1E) or different regions of a chip (FIG. 1F), or are mixedly arranged on a common region of a microfluidic channel (FIG. 1G) or a chip (FIG. 1H) with a relatively large distance between each RNA probe from the first RNA probe set and each RNA probe from the second RNA probe set (thereby substantially preventing an interaction therebetween), there is no need for a sequential contact between the biological sample with the first RNA probe set and the second RNA probe set, and the biological sample can be applied to contact both the first RNA probe set and the second RNA probe set simultaneously. Yet depending on certain practical needs, the biological sample can still be allowed to sequentially contact RNA probes in the first RNA probe set and the second RNA probe set by flowing sequentially through two different regions of a microfluidic channel or a chip corresponding respectively to the first RNA probe set and the second RNA probe set as illustrated in FIG. 1E and FIG. 1F.

Figure 1G:
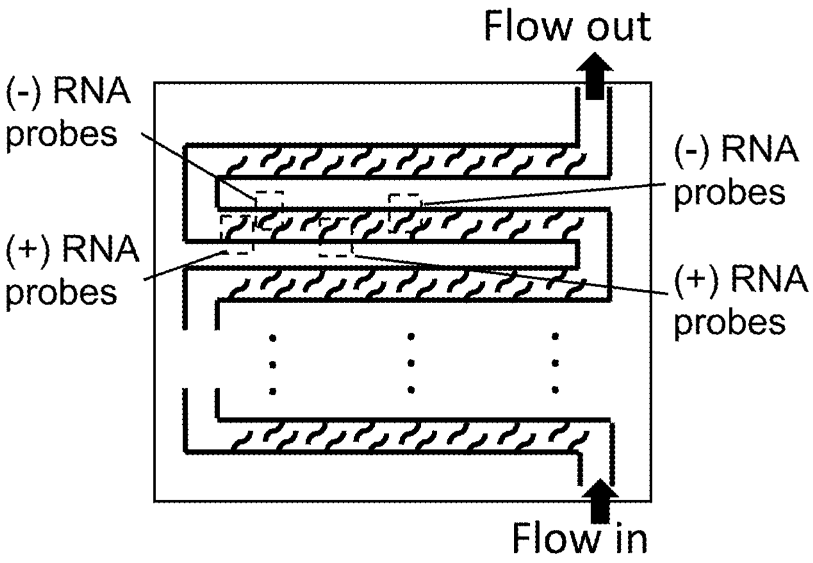
Figure 1H:
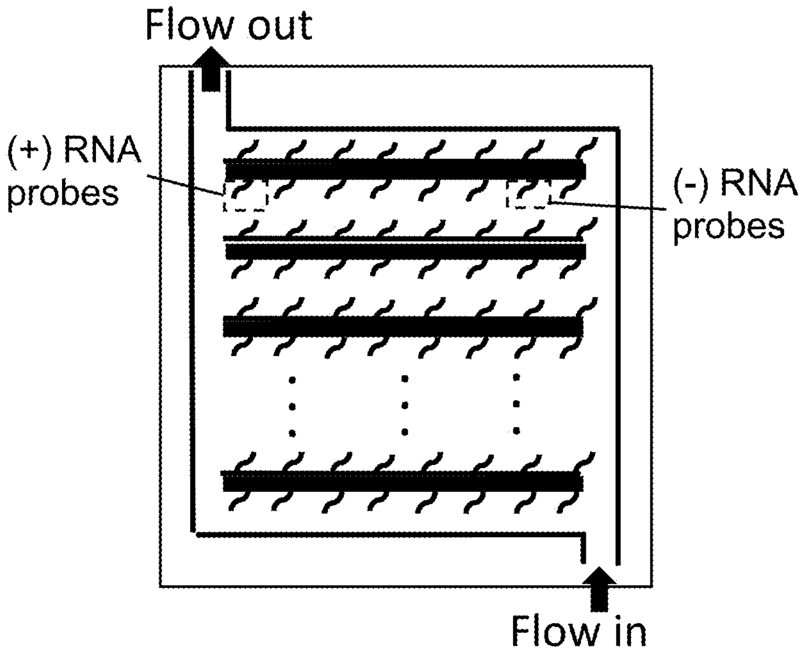
Figure 1I:
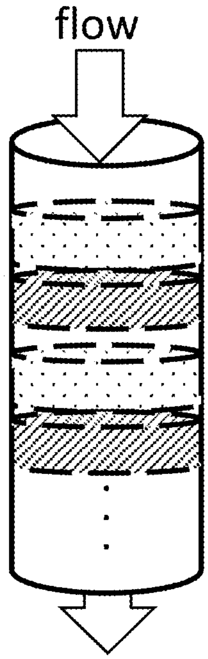
Figure 1J:
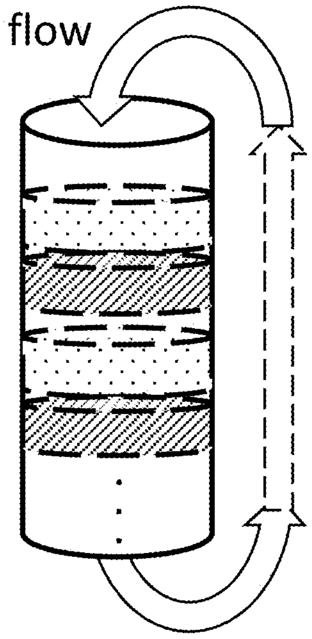

It is further noted that the employment of a column or a microfluidic channel further provides a convenience for repeated contacts of the biological sample with RNA probes, either by arranging the first RNA probe set and the second RNA probe set in series (as illustrated in FIG. 1I), by arranging the biological sample to recirculate (as illustrated in FIG. 1J), or by combination of these two approaches. The details for each of these above different embodiments of the method for capturing target nucleic acid sequences from the biological sample by means of the at least one pair of RNA probe sets will be provided below.

As such, the above FIGS. 1D-1J respectively illustrate several different embodiments where each pair of RNA probe sets arranged on an inner surface of an apparatus (microfluidic channel or a chip) to allow the capture of target nucleic acid sequences from the biological sample. It is noted that these embodiments are illustrating only, and there can be other apparatuses as well.

According to some other embodiments, a first RNA probe set and a second RNA probe set in a corresponding pair of RNA probe set are configured to target a different portion of the duplex segment of one target nucleic acid sequence. In other words, a first RNA probe set and a second RNA probe set in a corresponding pair of RNA probe set are respectively configured to target a first portion in a first strand and a second portion in a second strand of the one target nucleic acid sequence, wherein the first strand and the second strand are the two antiparallel strands of the duplex segment, and the first portion and the second portion are two different portions of the duplex segment of the one target nucleic acid sequence. As such, the RNA probe(s) in the first RNA probe set and the RNA probe(s) in the second RNA probe set have substantially no complimentary sequences. As such, the biological sample containing target nucleic acid sequences can be applied to contact both the first RNA probe set and the second RNA probe set simultaneously, regardless of what type of solid support is utilized for coupling with the RNA probes.

In order to prepare the at least one pair of RNA probe sets in step S100, any one of the first RNA probe set and the second RNA probe set in each pair can be prepared by a manner of direct chemical synthesis or by a manner of transcription, or by a various combination of these approaches, and can be labelled with the immobilization portion during or after the synthesis/transcription process. These different embodiments will be described below in detail.

According to some embodiments, each RNA probe in any of the first RNA probe set and the second RNA probe set corresponding to each of the at least one pair of RNA probes can be synthesized directly by chemical reactions (i.e. the manner of direct chemical synthesis). Depending on different situations, the immobilization portion can be labelled to each RNA probe during the synthesis process or after the synthesis process, or each RNA probe can be directly synthesized from a solid support that is covalently connected with one end of each RNA probe through the immobilization portion.

According to some other embodiments, each RNA probe in any of the first RNA probe set and the second RNA probe set for each pair of the RNA probe sets can be respectively and separately obtained through a transcription reaction (i.e. the manner of transcription) over a pair of DNA vectors corresponding thereto, and the immobilization portion can be labelled to each RNA probe during the transcription process or after the transcription process.

Regarding the transcription process, each of the pair of DNA vectors can comprise a DNA template and a promoter (i.e. transcription promoter). The DNA template can comprise a sequence whose transcription gives rise to an RNA molecule corresponding to either of the two antiparallel strands of the duplex segment of the one target nucleic acid sequence. The promoter is configured to be recognized by an RNA polymerase to thereby allow the transcription reaction to occur, and can be at an upstream of, a downstream of, or within a target DNA sequence in the DNA vector.

Compared with the manner of direct chemical synthesis, this transcription-based approach to obtain RNA probes is relatively more cost-effective, and allows for the production of a relatively larger amount of the RNA probes.

In the aforementioned embodiments where the at least one RNA probe in each of the at least one pair of RNA probe sets is prepared by transcription, step S100 can comprise:

S110: preparing a plurality of DNA vectors, comprising at least one pair of DNA vectors, each pair comprising a first DNA vector and a second DNA vector configured to respectively allow a separate transcription of a first RNA molecule and a second RNA molecule targeting respectively two antiparallel strands of a duplex segment of each of the at least one target nucleic acid sequence.

Figure 3A:
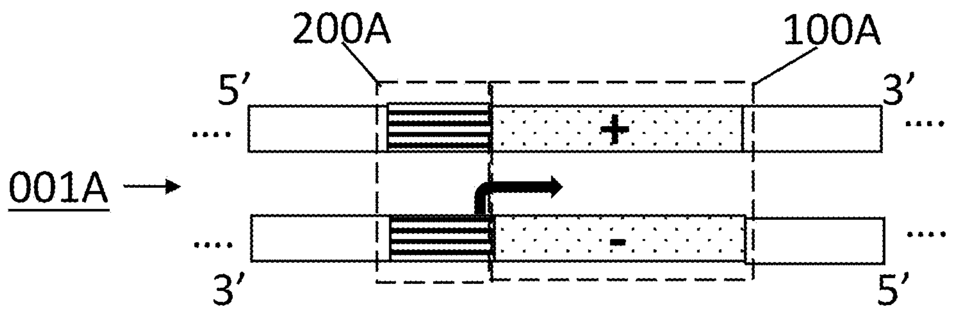
FIG. 3A and FIG. 3B respectively illustrate a structural diagram of the first DNA vector and the second DNA vector for transcriptionally obtaining the first RNA molecule targeting a plus strand and the second RNA molecule targeting a minus strand of a target nucleic acid sequence according to some embodiments of the disclosure.
Figure 3B:
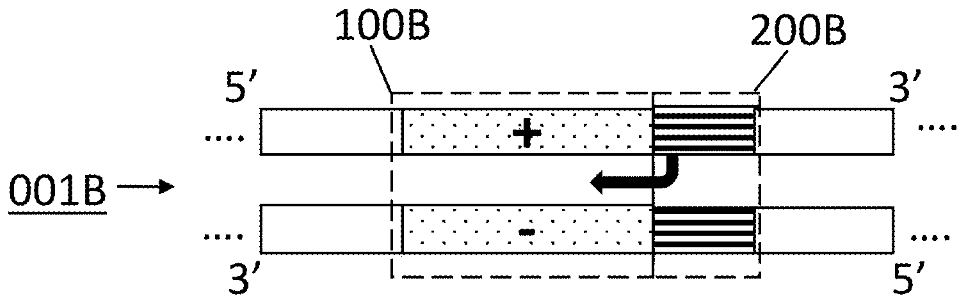

According to some embodiments as illustrated in FIG. 3A and FIG. 3B, the first DNA vector 001A and the second DNA vector 001B in each of the at least one pair of DNA vectors can respectively comprise a first DNA template 100A at a downstream of a first transcription promoter 200A and a second DNA template 100B at a downstream of a second transcription promoter 200B. Each of the first DNA template 100A and the second DNA template 100B is substantially a double-stranded DNA segment (indicated by the box with dotted lines in the two figures), configured to allow transcription of RNA molecules using one strand thereof as a template under action of the transcription promoter in a transcription reaction.

Specifically, the first DNA vector 001A comprises a first transcription promoter 200A at a 5' end (i.e. upstream) of a strand of the double-stranded first DNA template 100A that corresponds to a plus strand of the one target nucleic acid sequence (as indicated by the "+" sign), and thus is configured to allow the transcription of a first RNA molecule complementary to a minus strand of the one target nucleic acid sequence (as indicated by the "−" sign) as a transcription template. As such, the RNA molecules produced by the first DNA vector 001A can specifically target (i.e. hybridize or bind or anneal with) the minus strand of the one target nucleic acid sequence.

The second DNA vector 001B comprises a second transcription promoter 200B at a 5' end (i.e. upstream) of a strand of the double-stranded first DNA template 100B that corresponds to a minus strand of the one target nucleic acid sequence (as indicated by the "−" sign), and thus is configured to allow the transcription of a second RNA molecule complementary to a plus strand of the one target nucleic acid sequence (as indicated by the "+" sign) as a transcription template. As such, the RNA molecules produced by the second DNA vector 001B can specifically target (i.e. hybridize or bind or anneal with) the plus strand of the one target nucleic acid sequence.

As such, in each corresponding pair of DNA vectors, the first DNA vector 001A and the second DNA vector 001*b* respectively allow transcription of a first RNA molecule that specifically target the minus strand and a second RNA molecule that specifically target the plus strand of the one target nucleic acid sequence.

In each of the at least one pair of DNA vectors (i.e. the first DNA vector and the second DNA vector) as described above, the first promoter 200A and the second promoter 200B can be substantially same or different, and different pairs of DNA vectors can have same or different promoters. These promoters can include a T3 promoter, a T7 promoter, a SP6 promoter, or a species-specific or tissue-specific promoter. Herein, the double-stranded DNA segment in each of the first DNA vector and the second DNA vector that correspond to each target nucleic acid sequence in the sample can comprise a genomic DNA fragment, a gene coding sequence (CDS) or such sequences in an existing construct (such as commercially available gene expression constructs), or can be derived from reverse-transcription of an RNA sequence, such as an mRNA sequence, or can comprise segments that are artificially synthesized or assembled.

It is noted that the above embodiments as shown in FIG. 3A and FIG. 3B, where each of the first DNA vector 001A and the second DNA vector 001B in each pair of DNA vectors is substantially a double-stranded DNA vector, and each of the first DNA template 100A and the second DNA template 100B exists as a double-stranded DNA segment and is at a downstream of a transcription promoter, serves as an illustrating example only and does not impose a limitation to the scope of the present disclosure. Other embodiments are also possible.

Figure 3C:
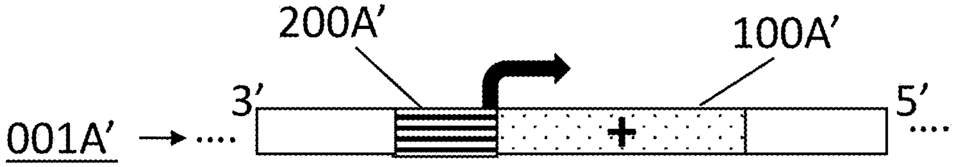
FIG. 3C and FIG. 3D respectively illustrate a structural diagram of the first DNA vector and the second DNA vector according to some other embodiments of the disclosure.
Figure 3D:
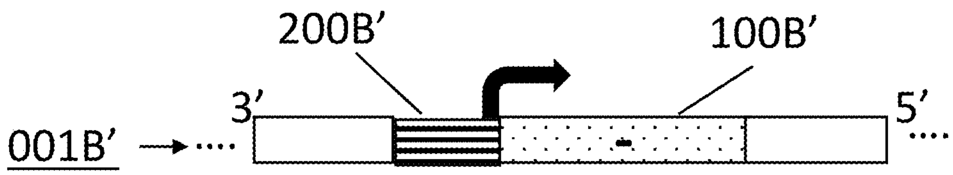

For example, according to some other embodiments as illustrated in FIG. 3C and FIG. 3D, each of the first DNA vector 001A' and the second DNA vector 001B' can be a single-stranded DNA vector (such as a phagemid or phasmid, or a vector containing a cDNA molecule produced from a reverse-transcription reaction from an RNA sequence). The first DNA vector 001A' comprises a first promoter 200A' at a 3' end of a first DNA template 100A' which corresponds to a plus strand of a duplex segment of one target nucleic acid sequence (as indicated by the "+" sign). The second DNA vector 001B' comprises a second promoter 200B' at a 3' end of a second DNA template 100A' which corresponds to a minus strand of the duplex segment of the one target nucleic acid sequence (as indicated by the "−" sign). Thus transcription of the first DNA vector 001A' and the second DNA vector 001B' can respectively produce RNA molecules that target the plus strand and the minus strand of the duplex segment of the one target nucleic acid sequence.

According to yet some other embodiments of the disclosure, the first DNA vector and the second DNA vector in each pair of DNA vectors can be of a different type. For example, the first DNA vector can be a double-stranded DNA vector whereas the second DNA vector can be a single-stranded DNA vector, and it is further configured such that transcription of the first DNA vector and the second DNA vector can respectively produce RNA molecules that target the two antiparallel strands (e.g. plus strand/minus strand or minus strand/plus strand) of the duplex segment of the one target nucleic acid sequence.

In any of the above embodiments of the DNA vectors, a transcription promoter is disposed at an upstream of a target DNA sequence. The relative position of the transcription promoter is not limited to the upstream of a target DNA sequence, and can be within, or at a downstream of a target DNA sequence as well, depending on specific cases.

As such, there is no limitation to the nature and type of the first DNA vector and the second DNA vector in each pair of DNA vectors, as long as the respective transcription reaction over the first DNA vector and the second DNA vector can give rise to the first RNA molecule and the second RNA molecule targeting respectively two antiparallel strands of a duplex segment of each target nucleic acid sequence.

After sub-step S110, there are several embodiments of step 100 of the method where the first RNA probe set and the second RNA probe set in each of at least one pair of RNA probe sets are obtained by transcription reactions over the first DNA vector and the second DNA vector in each of the plurality of DNA vectors, and each probe in any of the first RNA probe set and the second RNA probe set is labelled with, or carries, the immobilization portion.

Figure 2A:
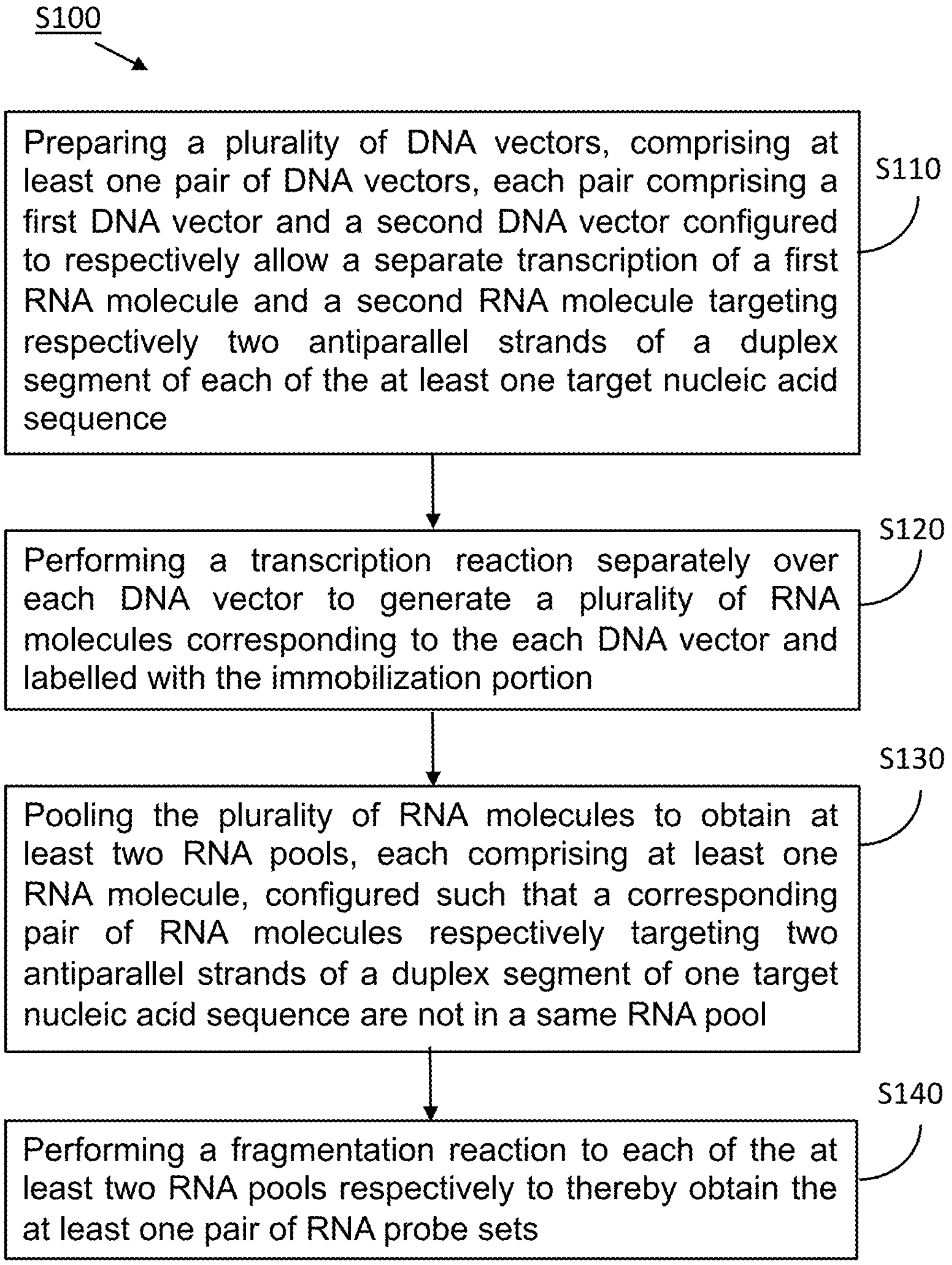
FIG. 2A and FIG. 2B respectively illustrate a flow chart of step S100 as shown in FIG. 1A according to two embodiments of the disclosure.

According to some preferred embodiments as illustrated in FIG. 2A, the immobilization portion is labelled during transcription process. As such, after sub-step S110, step S100 of the method further comprises:

S120: performing a transcription reaction separately over each DNA vector to generate a plurality of RNA molecules corresponding to the each DNA vector and labelled with the immobilization portion.

Herein the transcription reaction can be a regular in vitro transcription reaction, and involves an RNA polymerase and four nucleoside triphosphates (ATP, UTP, GTP, CTP, collectively as NTPs). The RNA polymerase can recognize a transcription promoter (i.e. the first DNA transcription promoter or the second DNA transcription promoter) of a DNA template (i.e. the first DNA template or the second DNA template corresponding respectively to the two antiparallel strands of each target nucleic acid sequence), to thereby allow the transcription of RNA molecules having sequences targeting/complementary to the plus strand/minus strand of each nucleic acid sequences (i.e. the first RNA molecule and the second RNA molecule). The RNA polymerase can be any enzyme that triggers DNA-dependent RNA polymerization, and can be, for example a T7 RNA polymerase.

The RNA molecules can be purified from the reaction using an RNA purification protocol, and the DNA molecules in the reaction can be eliminated by applying enzymes that can degrade DNA molecules, such as DNase. Such enzymes need to be completely removed from the RNA molecules if the targeted nucleic acid sequences being captured include DNA molecules, but this removal step can be skipped if the targeted nucleic acid sequences are nucleic acids that are not susceptible to DNase-induced damage, such as RNA molecules. Other approaches to remove DNA molecules or to separate RNA molecules from the DNA molecules are also possible. For example, the DNA vectors are pre-immobilized to solid support that could be readily removed from the reaction after the transcription reaction is finished without removing the transcribed RNA.

The RNA molecules can be directly extracted from the system through applying the interaction between the coupling pairs, such as using streptavidin beads to extract RNA molecules that are biotinylated. The transcription reaction can also be an in vivo transcription reaction, and can be synthesized in an organism, such as a bacterium (e.g. *E. coli*), a fungus (e.g. yeast), a mammalian cell line, etc. The RNA molecules can be extracted based on a regular RNA extraction protocol, and can be left in the system to perform real-time labeling or capturing of its target nucleic acid sequences.

Herein the sub-step S120 can directly generate a plurality of RNA molecules, each labelled with the immobilization portion. Specifically, the immobilization portion labelled on each of the RNA molecules, which is further labelled on the RNA probes derived from the RNA molecules, can facilitate the immobilization (or capturing) of the at least one target nucleic acid sequence on a solid support in step S300 (see below), due to a stable coupling between the immobilization portion and the solid support.

Figure 7A:
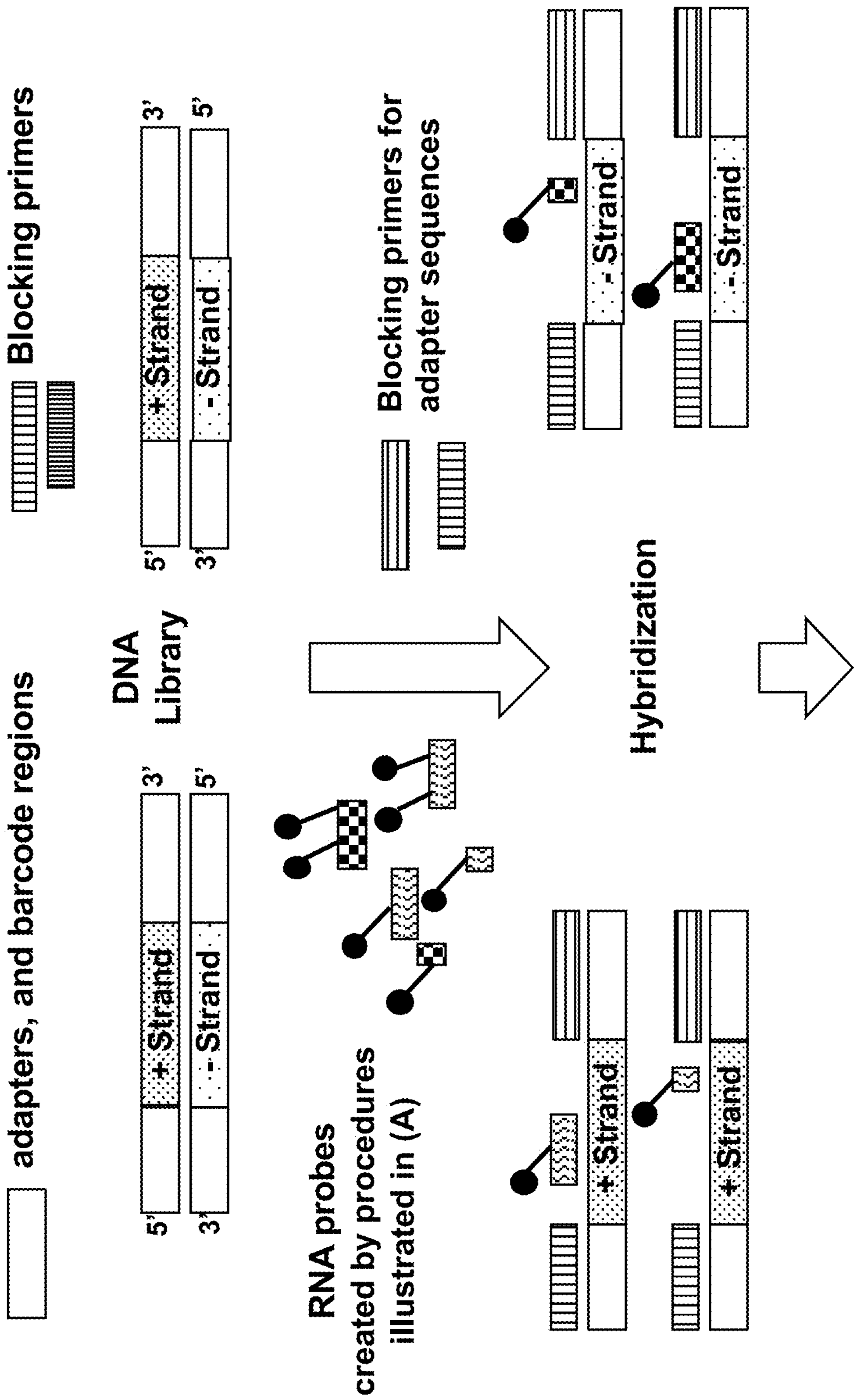
FIGS. 7A and 7B illustrate the process of enriching target sequences from a DNA library generated for a NGS-based sequencing assay.
Figure 7B:
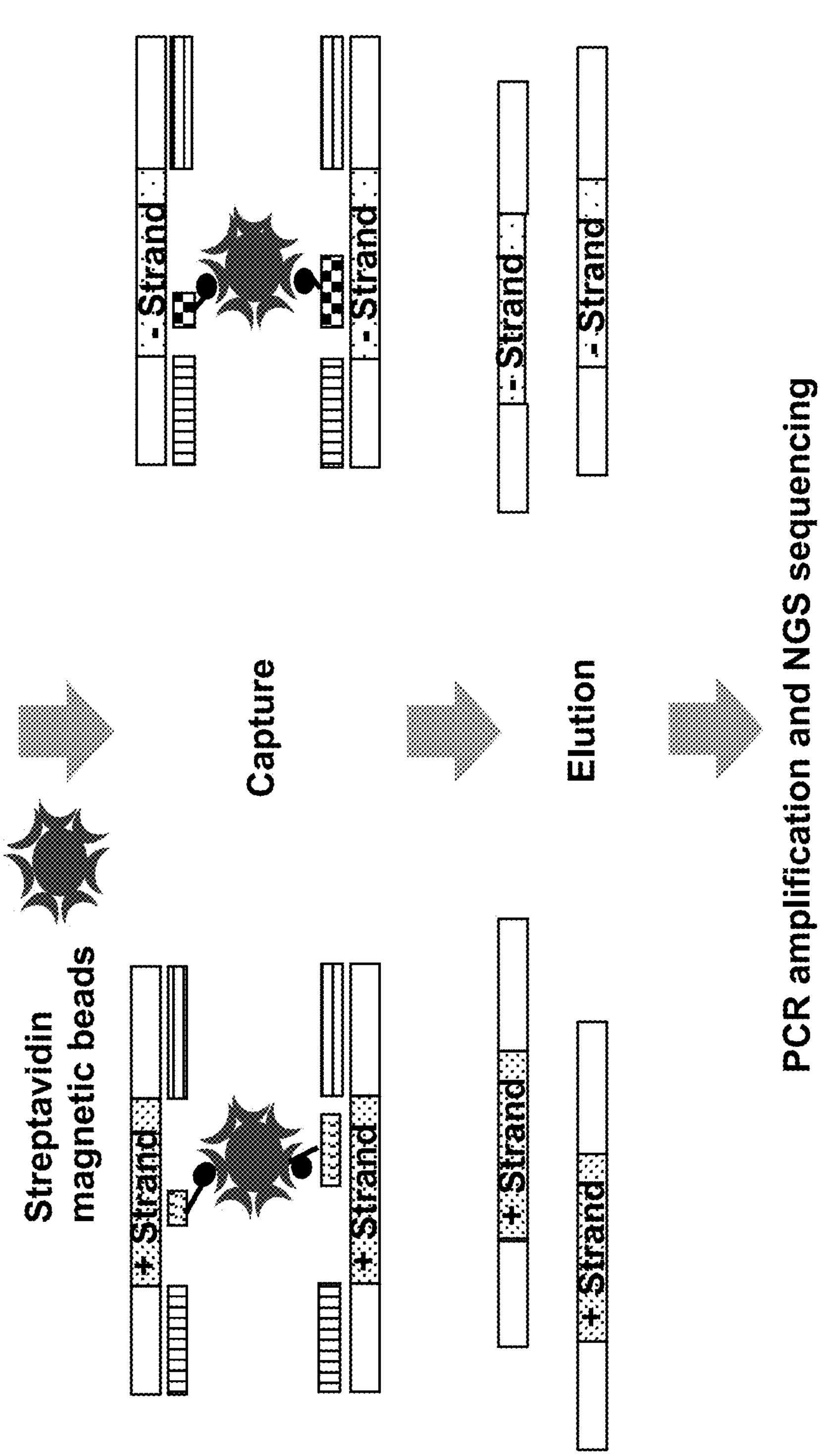

The stable coupling can be mediated by a secure and stable non-covalent binding, or by a covalent connection (i.e. cross-linking) between the immobilization portion and a corresponding coupling partner conjugated onto the solid support. Depending on different types of a solid support, and different types of coupling between each RNA probe labelled with the immobilization portion and the solid support conjugated with the coupling partner, there can be different embodiments. For example, in some preferred embodiments, the immobilization portion is a biotin moiety, and the coupling partner can be a streptavidin, avidin, or an anti-biotin antibody, which is attached onto, or conjugated with a solid support such as magnetic beads, as illustrated in FIG. 7A and FIG. 7B. In another example, each RNA probe is conjugated onto an inner surface of a microfluidic channel or a chip via a covalent connection, as illustrated in FIGS. 1E-1H.

As such, through the stable coupling between each immobilization portion on each RNA probe that derives from the RNA molecules obtained thereby and the coupling partner corresponding thereto that is conjugated onto the solid support, the at least one RNA probe can be immobilized by the solid support, in turn facilitating subsequent enrichment, isolation, and purification of target nucleic acid sequences.

It is noted that in order to introduce convenience for other applications (e.g. visualization), each RNA probe can be further labelled with other functional portion(s) in addition to the immobilization portion. Examples include a dye, a fluorophore group, or a chemical group, etc.

In some specific embodiments that are preferred, the transcription reaction in sub-step S120 can include addition of a mix of UTPs comprising biotin-labelled UTPs (i.e. herein the biotin moiety serves as an immobilization portion in the at least one functional portion) and non-biotin-labelled UTPs, wherein the biotin-labelled UTPs have a relative molar percentage of ~2%-100% of the total UTPs. In other words, among all the UTPs added in the reaction, the biotin-labelled UTPs can take a molar percentage between about 2% and about 100% (i.e. all the UTPs added are biotin-labelled UTPs). As such, after transcription, each of the plurality of RNA molecules with a length of about 200 nt can be labelled with biotin in some or all of its U residue.

S130: pooling the plurality of RNA molecules to obtain at least two RNA pools, each comprising at least one RNA molecule, configured such that a corresponding pair of RNA molecules respectively targeting two antiparallel strands of a duplex segment of one target nucleic acid sequence are not in a same RNA pool.

After transcription in sub-step S120, the plurality of labelled RNA molecules can be pooled into at least two RNA pools (or called RNA libraries), each comprising at least one RNA molecule. It is configured that a corresponding pair of RNA molecules (i.e. the first RNA molecule and the second RNA molecule that respectively targets two antiparallel strands of a duplex segment of one target nucleic acid sequence) are not in a same RNA pool to thereby avoid an interference in subsequent steps of hybridization and enrichment of target nucleic acid sequences.

In one specific embodiment, a plurality of RNA molecules are pooled into two RNA pools (a first RNA pool and a second RNA pool), and the first RNA pool and the second RNA pool respectively includes RNA molecules that each specifically target one, but not both, of the plus strand and the minus strand of each target nucleic acid sequence.

It is noted that the sub-step S130 can be modified depending on different needs. For example, when doing pooling, each of the plurality of RNA molecules can have a same ratio, or can have a different ratio in order to ensure a highly efficient capture/enrichment of the different sequence fragments of the at least one target nucleic acid sequences in the biological sample. For example, in cases where some specific target nucleic acid sequences are difficult to capture (which can be based on previous knowledge, or can be known by a preliminary experiment applying all of the steps S100-S400, and identifying some target nucleic acid sequences that are unsatisfactorily captured), the abundance for the pair of RNA probe sets, or the abundance for the RNA probes targeting one specific strand corresponding to these specific target nucleic acid sequences can be increased (e.g. by ~10 fold or higher, or by ~1.5 fold; there is no limitation herein) in the sub-step S130 to thereby increase the efficiency for capture.

It is further noted that in addition to the above optimization (i.e. adjustment of ratios) in sub-step S130, a different segment in one target sequence can be selected for generation RNA probes in order for an optimized capture if RNA probes generated from one particular target segment are not able to offer expected capturing efficiency.

S140: performing a fragmentation reaction to each of the at least two RNA pools respectively to thereby obtain the at least one pair of RNA probe sets.

In order to facilitate the efficiency in the subsequent steps S200 and S300, the relatively long RNA molecules in each RNA pool can be preferably fragmented into relatively shorter fragments of ~100-150 nt, which can be done, for example, by enzymatic reactions or sonication. Conditions for the enzymatic reactions or sonication reactions for nucleic acids are well-known in the field and can be used as is appropriate and convenient. After fragmentation, the at least one RNA probe in each of the at least two RNA probe pools can have a length of at least 2 nt, preferably 100-150 nt.

Herein it is noted that it is possible to reverse the order of sub-steps S130 and S140. For example, after sub-step S120 to obtain the plurality of RNA molecules labelled with at least one functional portion, the plurality of RNA molecules can be fragmented (i.e. S140) before pooling (i.e. S130) to thereby obtain the at least one pair of RNA probe sets.

Figure 2B:
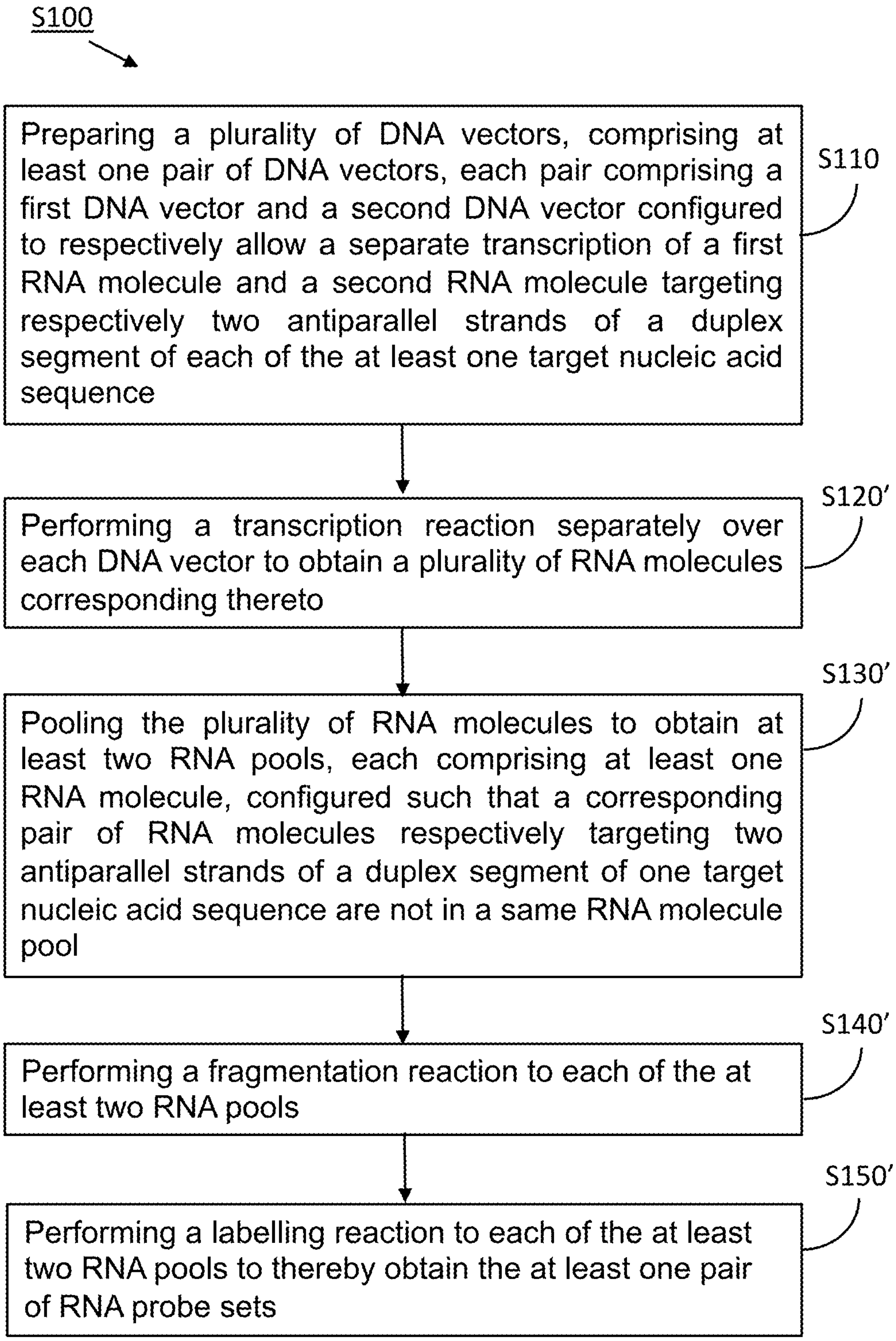

Besides the embodiments as mentioned above, according to some other embodiments of the disclosure, a plurality of RNA molecules can alternatively be transcribed without labeling, and the at least one functional portion can be labelled thereafter. FIG. 2B illustrates one embodiment of step S100. As shown in the figure, after sub-step S110, step 100 further comprises:

S120': performing a transcription reaction separately over each DNA vector to obtain a plurality of RNA molecules corresponding thereto.

Herein the sub-step S120' is substantially identical to the aforementioned sub-step S120, except that no functional portion-labelled NTPs (e.g. biotin-labelled UTP), is added to the transcription reaction.

S130': pooling the plurality of RNA molecules to obtain at least two RNA pools, each comprising at least one RNA molecule, configured such that a corresponding pair of RNA molecules respectively targeting two antiparallel strands of a duplex segment of one target nucleic acid sequence are not in a same RNA molecule pool.

Herein the sub-step S130' is substantially identical to the aforementioned sub-step S130, and the technical details are thus skipped herein.

S140': performing a fragmentation reaction to each of the at least two RNA pools.

Herein the sub-step S140' is substantially identical to the aforementioned sub-step S140, and the technical details are thus skipped herein.

S150': performing a labelling reaction to each of the at least two RNA pools to thereby obtain the at least one pair of RNA probe sets.

Herein through S150', the immobilization portion can be labelled onto each RNA probe in any of the at least two RNA pools. According to some preferred embodiment, the immobilization portion is a biotin moiety, and can be labelled at a 5' end, and/or a 3' end, and/or an intra-strand nucleic acid residue of each RNA probe in this sub-step. It is noted that other functional portion(s) may also be labelled onto each RNA probe in any of the at least two RNA pools. The technical details have been provided above and are skipped herein.

Herein it is noted that it is possible to alter the order of sub-steps S130'-S150'. For example, after sub-step S120' to obtain the plurality of RNA molecules, the plurality of RNA molecules can be fragmented (i.e. S140') and labelled (i.e. S150') before pooling (i.e. S130) to thereby obtain the at least one pair of RNA probe sets. Alternatively, after sub-step S120', the plurality of RNA molecules can be labelled (i.e. S150') before fragmentation (i.e. S140') and pooling (i.e. S130) to thereby obtain the at least one pair of RNA probe sets. There are no limitations herein.

In the following, two specific embodiments are provided to respectively illustrate two different processes of preparing one pair of RNA probe sets (i.e. a first RNA probe set and a second RNA probe set), which respectively target the two antiparallel strands (i.e. the plus strand and the minus strand) of a double-stranded segment of one target nucleic acid sequence.

Figure 4A:
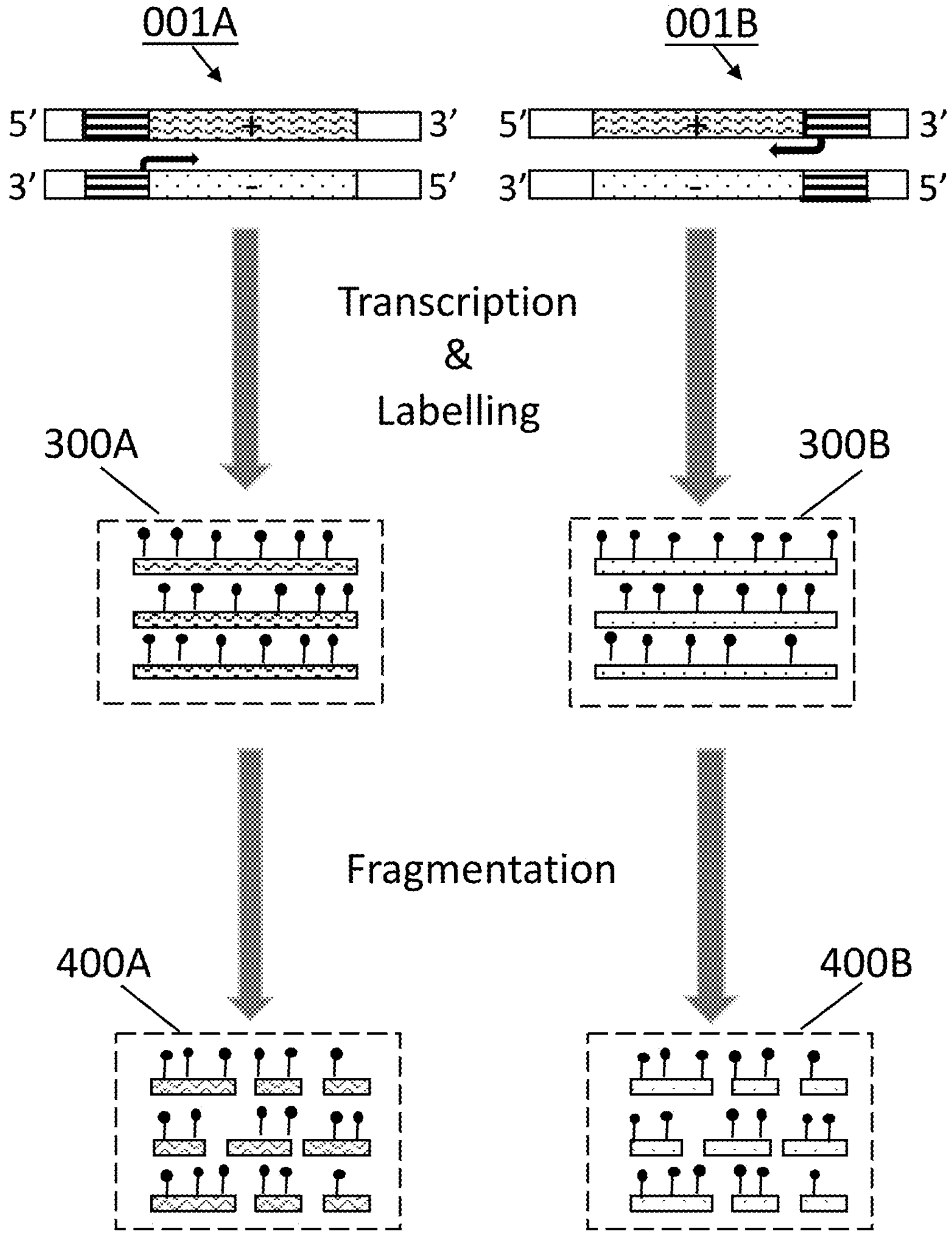
FIG. 4A and FIG. 4B respectively illustrate the process of preparing one pair of RNA probe sets respectively targeting a plus strand and a minus strand of one target nucleic acid sequence according to two embodiments of the disclosure.

In one embodiment as illustrated in FIG. 4A, the pair of RNA probe sets are prepared and biotin-labelled during a same transcription and labelling process. Specifically, the two transcription reactions are respectively performed over the first DNA vector 001A and the second DNA vector 001B as shown in FIGS. 3A and 3B to thereby separately generate a plurality of first RNA molecules 300A and a plurality of second RNA molecules 300B, configured to respectively target the minus strand and the plus strand of the one target nucleic acid sequence to be enriched or captured. At the same time, the plurality of first RNA molecules 300A and the plurality of second RNA molecules 300A' are each also labelled with one or more biotin moieties (shown as a filled dot linked with each RNA probe in FIG. 4A). This can be done by providing to the transcription reaction a mixture of UTPs comprising biotinylated UTPs (i.e. biotin-labelled UTPs) and regular UTPs (i.e. non-biotin-labelled UTPs), wherein the biotin-labelled UTPs can have a relative molar percentage of ~2%-100% of the total amount of UTPs.

In one specific example, a mixture of biotin-labelled UTPs and regular UTPs having a ratio of 1/3 (i.e. the biotin-labelled UTPs have a relative molar percentage of 25% of the total amount of UTPs) can be added to the transcription reaction. As such, about ¼ of U residues in the whole RNA sequence can be found to be labelled with a biotin moiety. Then after the process of transcription and labelling, the plurality of first RNA molecules 300A and the plurality of second RNA molecules 300A' are separately fragmented into the first RNA probe set 500A and the second RNA probe set 500B, which can preferably be ~100-150 nt in length.

Figure 4B:
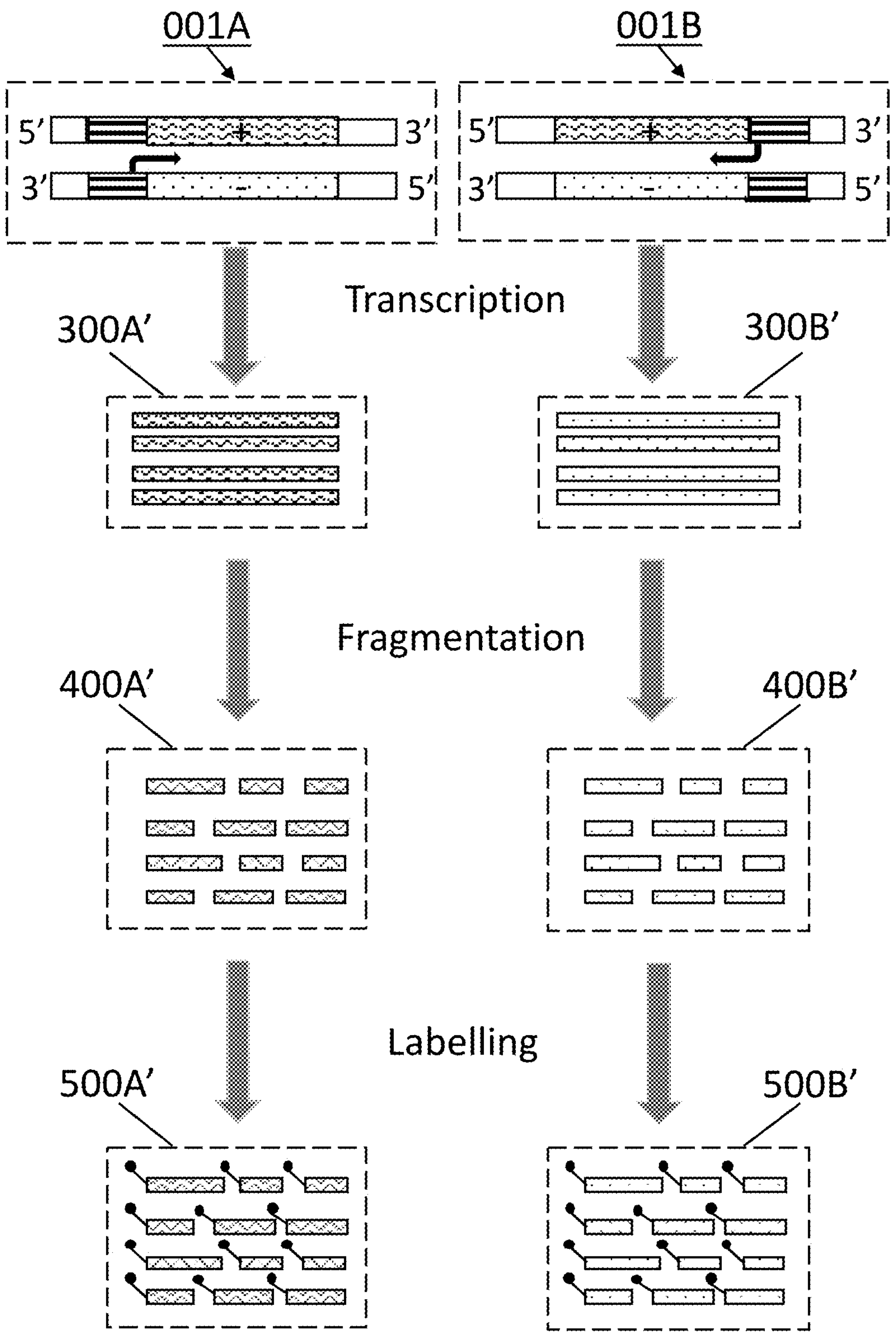

In another embodiment as illustrated in FIG. 4B, the pair of RNA probe sets are biotin-labelled after the transcription process. Specifically, the two transcription reactions can be respectively performed over the first DNA vector 001A the second DNA vector 001B as shown in FIGS. 3A and 3B to thereby separately generate a plurality of first RNA molecules 300A' and a plurality of second RNA molecules 300B', configured to respectively target the minus strand and the plus strand of the one target nucleic acid sequence to be enriched or to be captured. After transcription, the plurality of first RNA molecules 300A' and second RNA molecules 300B' are separately fragmented into the first RNA probe set 400A' and the second RNA probe set 400B', which are then respectively labelled with the biotin moiety (shown as a filled dot linked with one end of each RNA probe) to thereby obtain biotin-labelled first RNA probe set 500A' and second RNA probe set 500B'.

Herein labelling of the biotin moiety at a 5' end of each RNA probe is for illustrating purpose only, which can be at a 3'-end or an intra-strand segment thereof as well. According to some specific embodiment, in each of the ligation reactions, a 5' phosphate terminus of a biotin-labeled nucleotide can be ligated to a 3' hydroxyl terminus of each RNA probe in each of the at least one pair of RNA probe sets, which can be catalyzed by means of an RNA ligase. The RNA ligase can comprise at least one of T4 RNA ligase or CircLigase RNA ligase.

According to some other embodiment, the immobilization portion can be labelled in an intra-strand segment of an RNA probe, in a form of an RNA adduct (or a chemical addon) by means of a technology known to the field, whose description is skipped herein.

As such, after the above mentioned sub-steps S110-S140 (illustrated in FIG. 2A) or sub-steps S110-S150' (illustrated in FIG. 2B), at least two RNA probe pools are generated, each comprising at least one immobilization portion-labelled RNA probe. Together, the at least two RNA probe pools substantially includes at least one pair of RNA probe sets, each pair comprising a first labelled RNA probe set and a second labelled RNA probe set, respectively targeting two antiparallel strands of a duplex segment of one of the at least one target nucleic acid sequence.

After preparation of the at least one pair of RNA probe sets in step S100, the at least one pair of RNA probe sets can be used to contact with target nucleic acid sequences for hybridization before capture and enrichment of the at least one target nucleic acid sequence using the at least one pair of RNA probe sets as baits.

S200: Contacting the first RNA probe set and the second RNA probe set in each of the at least one pair of RNA probe sets with the at least one target nucleic acid sequence to allow hybridization of each RNA probe in the at least one pair of RNA probe sets to a corresponding strand of each target nucleic acid sequence.

Depending on whether the first RNA probe set and the second RNA probe set corresponding to a pair of RNA probe sets interfere with each other, such as having complimentary sequences to thereby be able to form an unwanted duplex structure when mixed together, S200 can be carried out in different manners.

According to some embodiments, the first RNA probe set and the second RNA probe set corresponding to a pair of RNA probe sets do not have substantially complimentary sequence (such as in one above-mentioned embodiment where the first RNA probe set and the second RNA probe set corresponding to a pair of RNA probe sets target two different portions of the duplex segment of the target nucleic acid sequence), or are conjugated to a solid support that do not readily interfere with each other (such as in one above-mentioned embodiment where the first RNA probe set and the second RNA probe set corresponding to a pair of RNA probe sets are conjugated to different regions of a microfluidic channel on a microfluidic chip), step S200 can comprise:

S200*a*: Contacting both the first RNA probe set and the second RNA probe set with the at least one target nucleic acid sequence in a single hybridization reaction.

According to some other embodiments, the first RNA probe set and the second RNA probe set in each pair have substantially complimentary sequences and thus can interfere with each other in a single hybridization reaction with the target nucleic acid sequences, as such, different embodiments of the method can be employed.

According to some embodiments, the first RNA probe set and the second RNA probe set in each pair can be configured to hybridize with the at least one target nucleic acid sequence in a sequential manner. Herein the "sequential manner" is referred to as a manner where the first RNA probe set and the second RNA probe set in each pair are allowed to contact with, and thereby to hybridize with, the at least one target nucleic acid sequence in the biological sample one after another. There is no limitation to the specific order: for example, the first RNA probe set is added to the hybridization reaction first, followed by the second RNA probe set, or alternatively, the second RNA probe set is added to the hybridization reaction first, followed by the first RNA probe set.

Figure 5A:
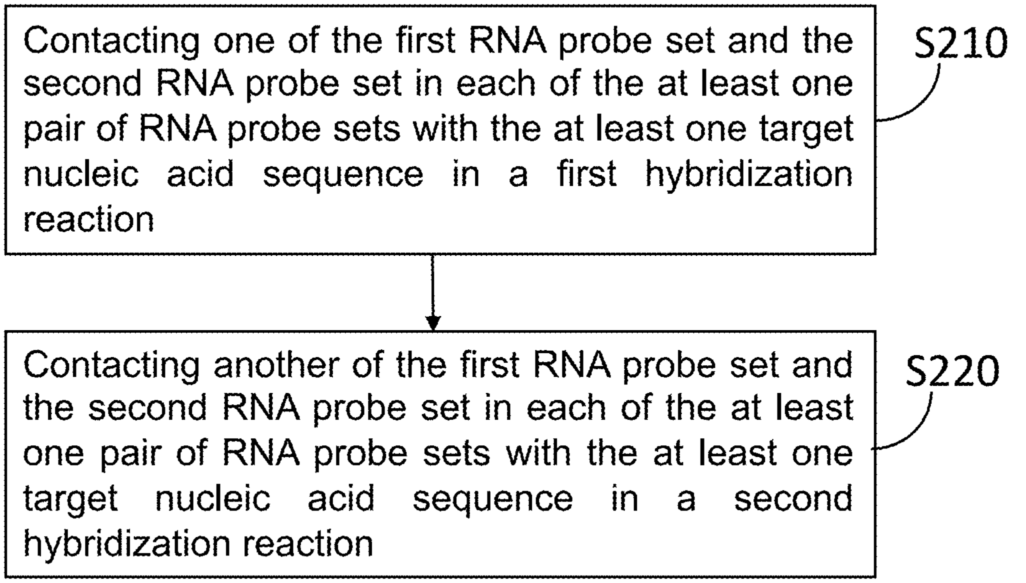
FIG. 5A and FIG. 5B respectively illustrate a flow chart of step S200 of the method according to two embodiments of the disclosure.

Specifically, according to some embodiments where the first RNA probe set and the second RNA probe set in each pair of RNA probe sets is labelled onto magnetic beads, the step S200 includes the following sub-steps, as illustrated in FIG. 5A:

S210: Contacting one of the first RNA probe set and the second RNA probe set in each of the at least one pair of RNA probe sets with the at least one target nucleic acid sequence in a first hybridization reaction; and

S220: Contacting another of the first RNA probe set and the second RNA probe set in each of the at least one pair of RNA probe sets with the at least one target nucleic acid sequence in a second hybridization reaction.

Figure 5B:
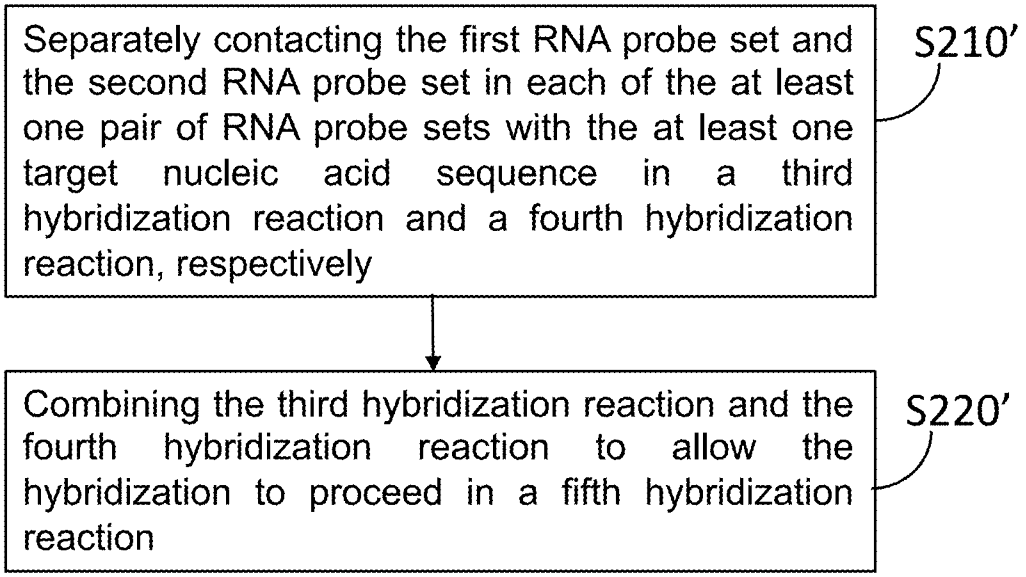

Alternatively, the first RNA probe set and the second RNA probe set in each pair can be configured to hybridize with the at least one target nucleic acid sequence in two separate hybridization reactions, which are then combined to react in another hybridization reaction. This is substantially a special situation for the sequential approach, and specifically, as shown in FIG. 5B, step S200 includes the following sub-steps:

S210': Separately contacting the first RNA probe set and the second RNA probe set in each of the at least one pair of RNA probe sets with the at least one target nucleic acid sequence in a third hybridization reaction and a fourth hybridization reaction, respectively; and

S220': Combining the third hybridization reaction and the fourth hybridization reaction to allow the hybridization to proceed in a fifth hybridization reaction.

Herein it is noted that "first", "second", "third", "fourth", and "fifth" are intended to refer to a different hybridization reaction and indicates or suggests no actual order in the reactions. It is further noted that any of the aforementioned hybridization reactions (i.e. the first, second, third, fourth, or fifth hybridization reaction) can occur at a temperature that substantially allows each RNA probe to hybridize efficiently with a corresponding strand of each target nucleic sequence.

For example, in some embodiments, each RNA probe has a length of ~100-~150 nt, and the temperature a hybridization reaction can be at a range of ~40-90° C., preferably at ~62-70° C., and more preferably at ~67.5° C. Such a hybridization temperature allows a high efficiency and a balanced specificity for the capture and enrichment of target nucleic acid sequences (see below). However, it is noted that these embodiments serve as illustrating examples only, and do not limit the scope of the disclosure. Other hybridization conditions, for example, RNA probes of a different length, at different abundances, a hybridization temperature, etc., can also be applied depending on specific needs.

Furthermore, the incubation time for each hybridization reaction can vary, depending on different configurations. According to some embodiments where the hybridization reaction occurs between RNA probes carrying the biotin moiety and the target nucleic acid sequences in the sample, the incubation time can be 6-24 hours, and preferably 12 hours, to ensure an efficient hybridization of each RNA probe to its corresponding strand of the target nucleic acid targets. According to some other embodiments where the hybridization reaction occurs between RNA probes conjugated onto an inside surface microfluidic channel and the target nucleic acid sequences in the sample, the incubation time can be several seconds to several hours, depending on the temperature and the pressure for the reaction. There are no limitations herein.

Figure 8A:
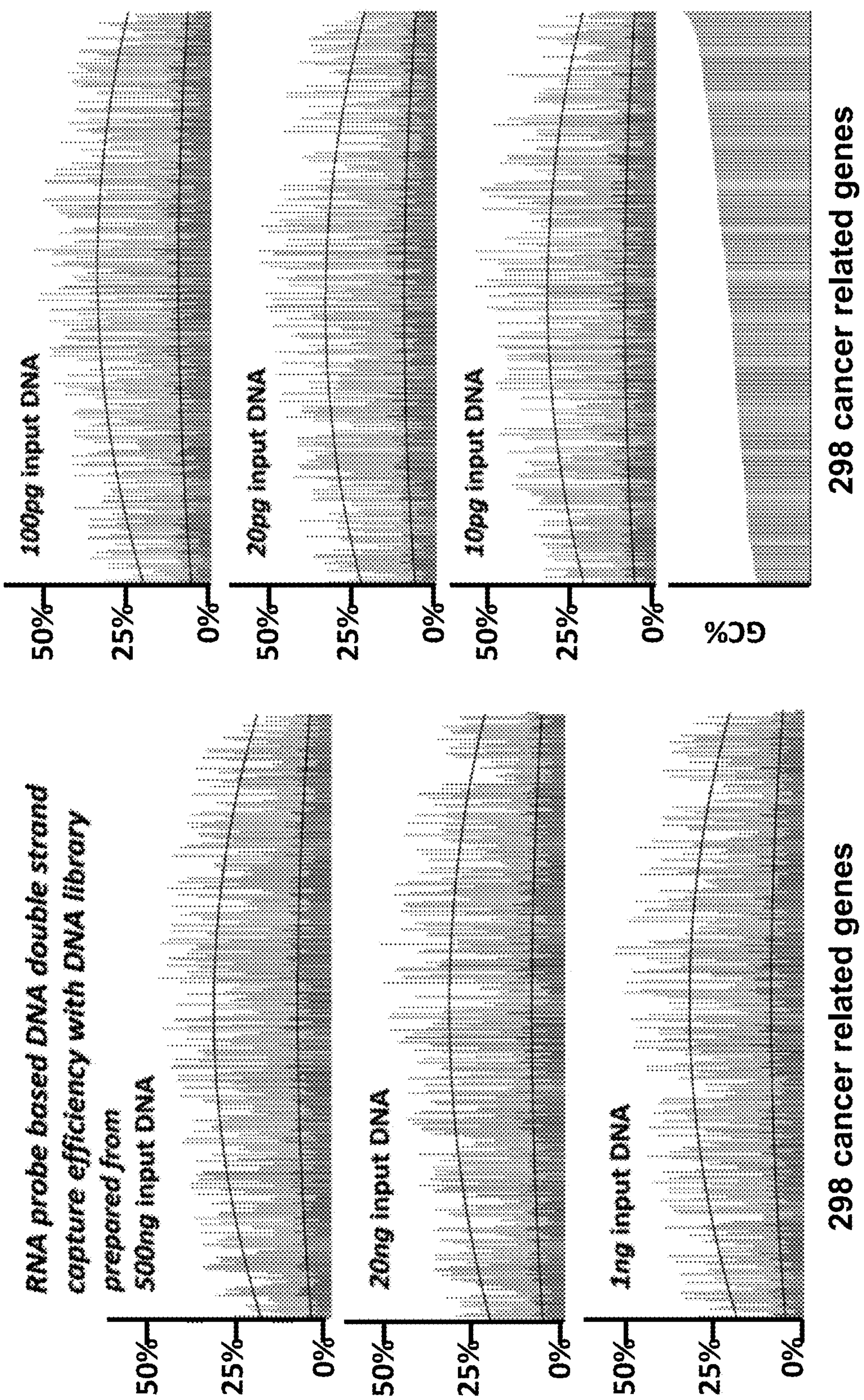
FIGS. 8A-8D show a performance evaluation of DNA double strand capture based on the method.

By sequentially adding the two RNA probe sets (i.e. the first RNA probe set and the second RNA probe set) in each pair in the hybridization reaction as described in the above embodiments, the unwanted formation of probe-probe hybridizations between themselves if simultaneously added can be effectively reduced. In addition, the sequential approach as described above has been proved to be more efficient in capturing target nucleic acid sequences. As has been demonstrated in an experiment that is described below, the capturing of a target DNA sequence utilizing a pair of complementary RNA probes that target both strands of the target DNA sequence can achieve an over 3-fold increase in the capture efficiency compared to the approach utilizing only one RNA probe that targets one single strand of the same target DNA sequence, as illustrated in FIG. 8A which will be described in detail below.

It is noted that in the above mentioned two approaches as illustrated in FIGS. 5A and 5B, the first RNA probe set and the second RNA probe set in each pair, once allowed to contact with the biological sample containing the at least one target nucleic acid sequence, are not removed from the reaction. Other embodiments are also possible.

For example, after each of the first RNA probe set and the second RNA probe set in each pair has contacted with the biological sample containing the at least one target nucleic acid sequence, each of the first RNA probe set and the second RNA probe set can be separated from the biological sample, allowing a capture of a portion of the at least one target nucleic acid sequence by the RNA probes in each of the first RNA probe set and the second RNA probe set, and the biological sample can be allowed to contact with each of the first RNA probe set and the second RNA probe set in each pair again.

It is noted that these embodiments actually allow the biological sample containing the at least one target nucleic acid sequence to repeatedly contact with the first RNA probe set and the second RNA probe set in each pair of RNA probe sets corresponding thereto. As such, the capture of the at least one target nucleic acid sequence from the biological sample can have a relatively higher efficiency after multiple rounds of sequential contact.

As such, the step S200 can include:

S211: Sequentially contacting the at least one target nucleic acid sequence with one and another of the first RNA probe set and the second RNA probe set in each of the at least one pair of RNA probe sets; and optionally S212: Repeating S211 for at least one more time.

In one specific embodiment, the first RNA probe set and the second RNA probe set in each corresponding pair are respectively labelled onto magnetic beads, and as such, step S200 specifically comprises:

S211*a*: Contacting one of the first RNA probe set and the second RNA probe set with the biological sample containing the at least one target nucleic acid sequence;

S211*b*: Removing the one of the first RNA probe set and the second RNA probe set from the biological sample;

S211*c*: Contacting another of the first RNA probe set and the second RNA probe set with the biological sample; and S211*d*: Removing the another of the first RNA probe set and the second RNA probe set from the biological sample.

These sub-steps S211*a*-S211*d* can be performed for only one time, or optionally can be repeated for at least one more time (i.e. S212).

In another specific embodiment, the first RNA probe set and the second RNA probe set in each corresponding pair are respectively conjugated onto the solid support (e.g. a matrix or a surface), which are respectively arranged at two different regions of an apparatus, such as a column or a microfluidic channel of a microfluidic chip. In one example as illustrated in FIG. 1D, a matrix conjugated with the first RNA probe set and a matrix conjugated with the second RNA probe set can be arranged at two different layers (10A and 10B) of a column. In another example as illustrated in FIG. 1E or FIG. 1F, the first RNA probe set and the second RNA probe set in each corresponding pair can be respectively immobilized onto two different regions of a microfluidic channel or chip along the direction of flow.

The apparatus (i.e. the column or the microfluidic channel) can be further configured to allow the biological sample to flow sequentially through the two different regions of the apparatus to thereby allow the biological sample containing the at least one target nucleic acid sequence to sequentially contact with the first RNA probe set and the second RNA probe set in each pair, which further supports repeated contact/separation to thereby increase the capture efficiency.

As such, step S200 can comprise:

S211*a*': Allowing the biological sample containing the at least one target nucleic acid sequence to sequentially flow through the two different regions of the apparatus to thereby allow a sequential contact thereof with, one and another of the first RNA probe set and the second RNA probe set; and Optionally S212': Repeating S211*a*' for at least one more time.

It is noted that in the embodiment having S211*a*' and S212' where a column or a microfluidic channel is employed, it is possible that the repeating step (i.e. S212') is realized by arranging more than one pair of the first RNA probe set and the second RNA probe set in series on the column or the microfluidic channel along a direction of flow (illustrated in FIG. 1F), by arranging the sample to recirculate (i.e. by arranging the sample to flow into the column and the microfluidic channel again after flow out for more than one rounds, as illustrated in FIG. 1G), or by a combination of these two above approaches as well.

Figure 6A:
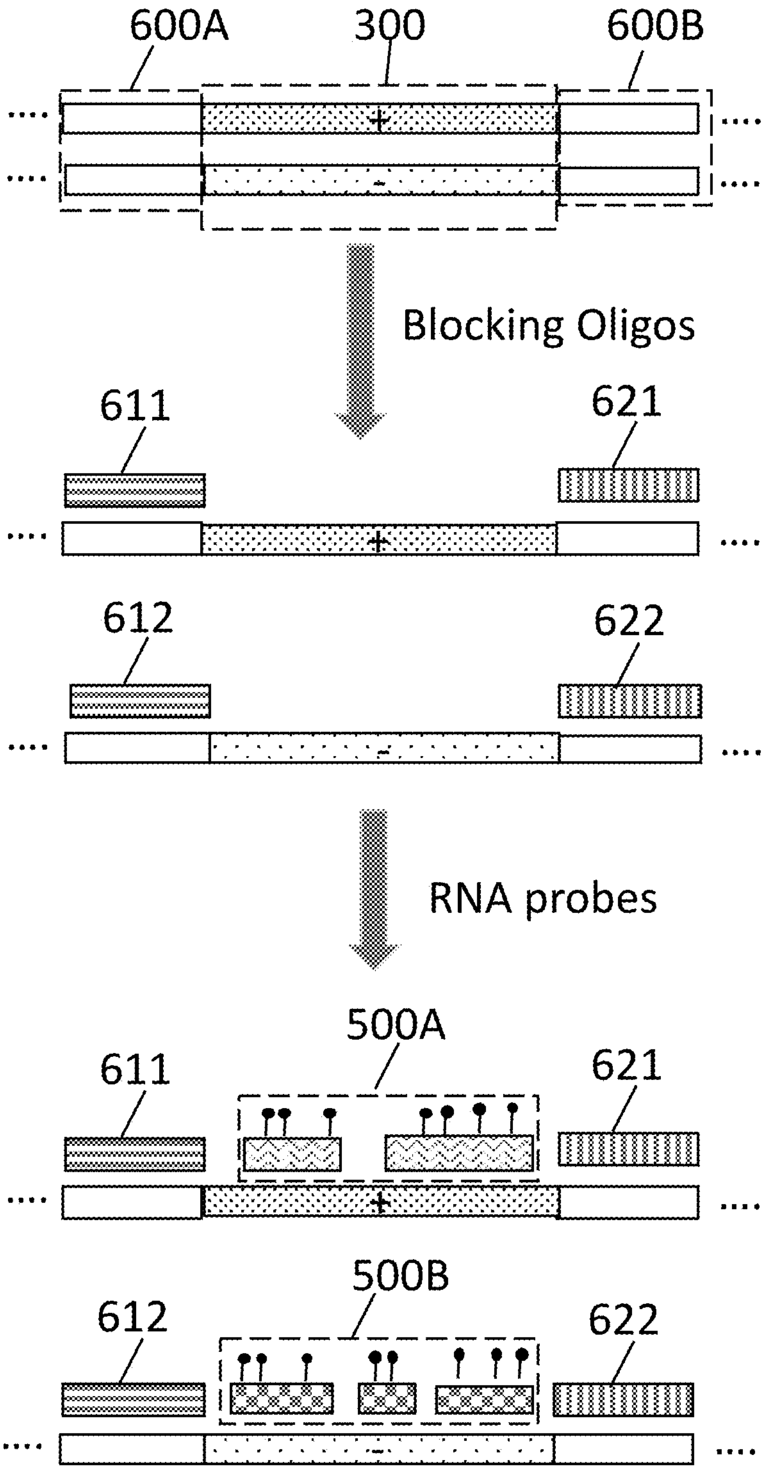
FIG. 6A is a schematic diagram of the hybridization process of RNA probes with target nucleic acid sequences according to some embodiments with blocking oligos applied.

According to some embodiments of the disclosure, one or more target nucleic acids sequence in the biological sample may each be present in a polynucleotide which also contains at least one not-desired-to-be-captured sequences (termed "un-targeted sequence" hereafter). For example, in one specific embodiment as illustrated in FIG. 6A, the at least one target nucleic acid sequence is in a DNA library, and each target nucleic acid sequence is flanked by a pair of adaptor sequences, such as PE sequencing adapters having a length of ~70 bp, which are substantially the un-targeted sequences. The presence of the at least one un-targeted sequence (e.g. one or two adaptor sequences) may potentially interfere with the enrichment or capture of the at least one target nucleic acid sequence by the RNA probes.

As such, in order to effectively eliminate the interference of the at least one un-targeted sequence, according to some embodiments of the disclosure, prior to or concurrent with step S200, the method further comprises:

S199: contacting at least one blocking oligo with the at least one target nucleic acid sequence, such that the at least one blocking oligo respectively hybridizes with, and thereby blocks, at least one strand of each of the at least one un-targeted sequence.

In one example, each target nucleic acid sequence is a double-stranded DNA sequence flanked by a pair of adaptor sequences (i.e. a first adaptor sequence 600A and a second adaptor sequence 600B as illustrated in FIG. 6A). As such, a set of blocking oligos comprising a first blocking oligo specifically targeting one strand of the first adaptor sequence 600A and a second blocking oligo specifically targeting one strand of the second adaptor sequence 600B, can be utilized in sub-step S201 to facilitate the hybridization of corresponding RNA probes with the each target nucleic acid sequence without the interference from the un-targeted sequences (i.e. the flanking adaptor sequences).

Herein, it is noted that there can be multiple arrangements for the set of blocking oligos. For example, the set of blocking oligos can consist of two blocking oligos, and can have a blocking oligo pair of (611 and 621), (611 and 622), (612 and 621), or (612 and 622), as long as the two blocking oligos target the two adaptor sequences 600A and 600B respectively, as shown in FIG. 6A. Alternatively, the set of blocking oligos can consist of three blocking oligos, having a combination of (611, 612 and 621), (611, 612 and 622), (611, 621 and 621), or (612, 621 and 622). Alternatively, the set of blocking oligos can consist of four blocking oligos (611, 612, 621 and 622), which substantially form two pairs of blocking oligos, 611/612 and 621/622, each pair corresponding to two strands of the first adaptor sequence 600A and two strands of the second adaptor sequence 600B, respectively, as illustrated in FIG. 6A.

It is noted that in order to avoid the unwanted annealing, hybridization, or binding, between two blocking oligos that target the two complimentary strands in any of the two adaptor sequences (600A or 600B), the two oligos can be added for hybridization and blocking in a sequential manner, or in a separate-and-combining manner, just as the addition of the first RNA probe set and the second RNA probe set in each of the at least one pair of RNA probe sets as illustrated in FIG. 5A or FIG. 5B.

Multiple embodiments for the at least one blocking olio are possible. For example, each of the at least one blocking oligo employed in S199 can be a single-stranded DNA oligo, or a single-stranded RNA oligo, which has a length of at least 2 nt and can be obtained based on a conventional technology known by people of ordinary skills in the field.

According to some embodiments, the at least one blocking oligo can comprise one or more blocking oligo sets, configured such that each blocking oligo set comprises one or more oligos which specifically target one of the two antiparallel strands of each of the at least one un-targeted sequence in a target nucleic acid sequence.

In one illustrating example of the at least one blocking oligo, it can be configured such that two blocking oligos (or two blocking oligo sets) respectively target two different portions of a duplex segment of each of the one or two adaptor sequences in a target nucleic acid sequence (i.e. a first portion in a first strand and a second portion in a second strand, where the first strand and the second strand are the two antiparallel strands in a duplex segment of each of the one or two adaptor sequences in the target nucleic acid sequence, and the first portion and the second portion are two different portions of the duplex segment of the target nucleic acid sequence.) This arrangement allows the simultaneous addition of the at least one blocking oligo in a blocking reaction without temporal separation, and brings about convenience.

In another example, two blocking oligos (or two blocking oligo sets) respectively target a same portion of a duplex segment of each of the one or two adaptor sequences in a target nucleic acid sequence, and as such, the two blocking oligos (or oligo sets) need to be allowed to contact the at least one target sequence in the biological sample in a sequential manner, or in a separate and then combined manner.

FIG. 6A shows one specific embodiment as an illustrating example.

In order for the set of blocking oligos to hybridize with, and thereby to block, the corresponding strand in each of the pair of two adaptor sequences respectively, the blocking hybridization reaction can occur at a substantially same temperature as the aforementioned hybridization reactions respectively required for hybridizing the first RNA probe set 500A and the second RNA probe set 500B to each corresponding strand of each target nucleic acid sequence. As such, according to some embodiments, the blocking hybridization reaction can be at a range of ~40-90° C., preferably at ~62-70° C., and more preferably at ~67.5° C.

As such, by applying a corresponding set of blocking oligos 611, 612, 621, and/or 622 to block each of the two strands of the first adaptor sequence 600A and each of the two strands of the second adaptor sequence 600B that flank each of the at least one target nucleic acid sequence in the DNA library in the sample (as illustrated in FIG. 6A), the potential interference by each strand of the first adaptor sequence 600A and the second adaptor sequence 600B can be minimized.

According to some other embodiments, only one adaptor sequence is next to each double-stranded target nucleic acid sequence, and as such, one blocking oligo (which targets one of the two strands of the adaptor sequence) or a set of two blocking oligos (which respectively target two strands of the adaptor sequence) can be used.

According to yet some other embodiments, each target nucleic acid sequence is single-stranded in the biological sample and is flanked by two adaptor sequences, and as such, a set of two blocking oligos respectively targeting the two adaptor sequences can be used. There are other possibilities as well, and the specific design is dependent on actual situation. There are no limitations herein.

It is noted that one or more adaptor sequences as described above serve only as illustrating examples for the at least one un-targeted sequence in a polynucleotide sequence containing a target nucleic acid sequence, and do not limit the scope of the disclosure.

S300: immobilizing the at least one target nucleic acid sequence on a solid support;

Herein step S300 can be performed by means of the immobilization portion in the at least one functional portion that has been labelled onto each of the at least one RNA probe, as mentioned above.

Specifically, S300 can be carried out by means of a stable binding (i.e. non-covalent binding) between the immobilization portion in each RNA probe and a coupling partner immobilized on a surface of a solid support. In some specific embodiments where the immobilization portion is a biotin moiety, the coupling partner can be a streptavidin, avidin, or an anti-biotin antibody, attached onto, or conjugated with a solid support such as magnetic beads. Other examples of the immobilization portion-coupling partner pair can include, but is not limited to, a carbohydrate-lectin pair, an antigen-antibody pair and a negative charged group-positive charged group static interacting pair.

Alternatively, S300 can be carried out by means of a cross-link (i.e. covalent connection) between the immobilization portion and a coupling partner attached onto a solid support. In some specific embodiments, the immobilization portion can be a first coupling partner, which can form a cross-link with a second coupling partner, allowing for the further immobilization of the captured sequences. As such, the first coupling partner and the second coupling partner are respectively one and another of a cross-linking pair, selected from one of an NHS ester-primary amine pair, a sulfhydryl-reactive chemical group pair (e.g. cysteines, or other sulfhydryls such as maleimides, haloacetyls, and pyridyl disulfides), an oxidized sugar-hydrazide pair, photoactivatable nitrophenyl azide's UV triggered addition reaction with double bonds leading to insertion into C—H and N—H sites or subsequent ring expansion to react with a nucleophile (e.g., primary amines), or carbodiimide activated carboxyl groups to amino groups (primary amines), etc. . . . There are no limitations herein.

By means of this step of the method, the target nucleic acid molecules are isolated, enriched, or captured from the biological sample via the labelled RNA probes. Solid supports that can be used may be any that are convenient for the particular purpose and situation.

S400: eluting out the at least one target nucleic acid sequence from the solid support.

After the immobilization of the at least one target nucleic acid sequence to the solid support through the at least one immobilization portion-labelled RNA probe in step S300, the plurality of immobilized target nucleic acid sequences are enriched or captured, which can then be eluted from the solid support in step S400 to facilitate the subsequent treatment and analysis, such as PCR amplification, a sequencing assay (such as next generation sequencing and other sequencing assays), PCR-based detection, microarray assays, construction of gene fragments into clones, transfection and transduction, and all other nucleic acid based applications. There are no limitations herein.

According to some embodiments of the method, the step S400 can include a washing process followed by an elution process. In the washing process, the hybridized molecules extracted by the solid supports can be washed to remove unspecific nucleic acid binders, including nucleic acids that are binding to probes or binding to solid supports or binding to any other moieties due to unspecific interactions. Specifically, the washing process can be carried out by saline-sodium citrate (SSC) buffer with 0.1% SDS.

In the elution process, nucleic acid sequences that are hybridized to the RNA probes can be eluted through heat-induced strand dissociation or through nucleic acid denaturing reagents, such as 0.1M sodium hydroxide. After separation of the probe from the target nucleic acid molecule through elution, a neutralizing buffer, such as Tris-HCl pH7.5, can be used to treat the target nucleic acid molecule portion of the elution reaction to further neutralize the effects initiated by the denaturing buffer if initially utilized.

According to some embodiments of the method, rather than immobilizing the at least one target nucleic acid sequence on the solid support (i.e. step S300) after hybridizing the RNA probes generated by step S100 with the at least one target nucleic acid sequences (i.e. step S200), the RNA probes generated by step S100 can be first immobilized on the solid support (and thus become solid support-immobilized RNA probes or solid support-conjugated RNA probes), and then can be allowed to contact with the target nucleic acid sequences for capturing. As such, the method can comprise the following steps, as illustrated in FIG. 1B:

S100': Preparing at least one pair of RNA probe sets, each pair comprising a first RNA probe set and a second RNA probe set configured to respectively target two antiparallel strands of a duplex segment in each of at least one target nucleic acid sequence, wherein each RNA probe in any of the first RNA probe set and the second RNA probe set is labelled with an immobilization portion;

S200': Conjugating each of the at least one pair of RNA probe sets on a solid support;

S300': Contacting one and another of the solid support-conjugated first RNA probe set and the solid support-conjugated second RNA probe set with the at least one target nucleic acid sequence to allow hybridization of each RNA probe in the at least one pair of RNA probe sets to a corresponding strand of each target nucleic acid sequence; and

S400': Eluting out the at least one target nucleic acid sequence from the solid support.

Herein, steps S100' and S400' in the embodiments of the method as described above are substantially same as steps S100 and S400 in the aforementioned embodiments of the method as illustrated in FIG. 1A. The solid support can be magnetic beads, non-magnetic beads, resin matrix, filter, membrane, or a different type that has been mentioned above.

Specifically, in a manner similar to the above embodiments where the RNA probes are immobilized to the solid support only after their hybridizations with target nucleic acid sequences, a pair of solid support-immobilized RNA probe sets (i.e. the solid support-conjugated first RNA probe set and the solid support-conjugated second RNA probe set in the pair) can be allowed to sequentially contact with the at least one target nucleic acid (i.e. one after another), or to separately contact with the at least one target nucleic acid in two hybridization reactions and then to combine the two hybridization reactions.

As such, according to a first embodiment which is substantially a sequential manner, S300' includes:

S310: Contacting one of the solid support-conjugated first RNA probe set and the solid support-conjugated second RNA probe set with the at least one target nucleic acid sequence in a sixth hybridization reaction; and

S320: Contacting another of the solid support-conjugated first RNA probe set and the solid support-conjugated second RNA probe set with the at least one target nucleic acid sequence in a seventh hybridization reaction.

According to a second embodiment, S300' includes:

S310': Separately contacting the solid support-conjugated first RNA probe set and the solid support-conjugated second RNA probe set in each pair of solid support-conjugated RNA probe sets with the at least one target nucleic acid sequence in an eighth hybridization reaction and a ninth hybridization reaction, respectively; and

S320': Combining the eighth hybridization reaction and the ninth hybridization reaction to thereby allow a tenth hybridization reaction to proceed.

It is noted that depending on the specific properties of the solid support, it is possible that a pair of RNA probe sets conjugated on the solid support have little or acceptable level of interactions among RNA probes having complimentary sequences. As such, according to a third embodiment, a solid support-conjugated first RNA probe set and a solid support-conjugated second RNA probe set in each corresponding pair can be allowed to contact with the at least one target nucleic acid in a single hybridization reaction without being separated temporally. For example, if beads are used, the beads-conjugated first and second RNA probe set in each corresponding pair can be combined in a single reaction for the simultaneous capture of different strands of a duplex segment of a target nucleic acid sequence. Alternatively, a glass surface can be used for conjugation of both the first and the second RNA probe set in each corresponding pair thereon and can allow a simultaneous capture of different strands of a duplex segment of a target nucleic acid sequence in a single reaction.

It is further noted that according to a fourth embodiment, a first RNA probe set and a second RNA probe set in each corresponding pair can be conjugated at a different region of the solid support, such as at a different segment of a microfluidic channel on a microfluidic chip, which allows a sample containing the at least one target nucleic acid sequence to sequentially flow through the different segments of the microfluidic channel corresponding to the pair of solid support-conjugated RNA probe sets to thereby allow a sequential capture of the two different strands of a duplex segment of a target nucleic acid sequence. Such a configuration allows a repeated use of RNA probes conjugated on the solid support.

According to some embodiments of the method, rather than conjugating each of the at least one pair of RNA probe sets on a solid support after preparing the at least one pair of RNA probe sets (i.e. steps S100' and S200' in the above mentioned method shown in FIG. 1B), the RNA probes in each of the at least one pair of RNA probe sets can be directly prepared on the solid support. As such, the method can comprise the following steps, as illustrated in FIG. 1C:

S100": Preparing at least one pair of RNA probe sets directly on a solid support, each pair comprising a first RNA probe set and a second RNA probe set configured to respectively target two antiparallel strands of a duplex segment in each of at least one target nucleic acid sequence;

S200": Contacting one and another of the solid support-conjugated first RNA probe set and the solid support-conjugated second RNA probe set with the at least one target nucleic acid sequence to allow hybridization of each RNA probe in the at least one pair of RNA probe sets to a corresponding strand of each target nucleic acid sequence; and

S300": Eluting out the at least one target nucleic acid sequence from the solid support.

Herein, steps S200" and S300" in the embodiments of the method as described above are substantially same as steps S300' and S400' in the aforementioned embodiments of the method as illustrated in FIG. 1B. The solid support can be magnetic beads, non-magnetic beads, resin matrix, filter, membrane, or a different type that has been mentioned above.

Herein, step S100" can be realized by direct chemical synthesis or by direct transcription on the solid support. In cases where the direct transcription on the solid support, a RNA polymerase can be attached onto the solid support.

The method, as illustrated by the various embodiments as described above, has the following advantageous features:

First, a pair of RNA probes which respectively target two antiparallel strands (i.e. a plus strand and a minus strand) of a duplex segment of each target nucleic acid sequence are both employed for the enrichment or capture of both strands of each of the target nucleic acid sequences, resulting in a higher enrichment efficiency compared with a conventional method where there is only one set of RNA probes targeting only one of the two strands of each target nucleic acid sequence.

Second, the nucleic acid sequence capture approach as described above can substantially capture both of the two antiparallel strands that typically belong to a same molecule of each target nucleic acid sequence and have complementary sequences, and can thus bring additional advantages in certain applications having a high requirement for sequence accuracy, such as single-nucleotide variation (SNV) calling. In an exemplary application in detecting SNVs in a sample, only an SNV observed on both of the two complementary strands in a target DNA sequence that have been respectively captured by a corresponding pair of RNA probe sets respectively targeting both of the two complementary strands is a bona fide SNV, whereas an SNV observed only on one, but not on both, of the two complementary strands in a target DNA sequence is likely to represent a false positive signal introduced by PCR. As such, the nucleic acid sequence capture approach disclosed herein allows for an error-proof application.

Third, each RNA probe can be prepared by transcription, which allows a large amount of RNA probes to be cost-effectively and conveniently obtained. This allows the target nucleic acid sequences to be enriched/captured at a significantly higher efficiency due to the much higher probe/target ratio. Additionally, this further allows a quantification of each RNA probe, in turn causing each RNA probe to be conveniently tweaked to increase the efficiency of capturing some specific target nucleic acid sequences that are difficult to capture by, for example, using a 10-fold higher amount of RNA probes for capturing.

Fourth, the above advantageous features together can have an additional advantage such that the hybridization of a first RNA probe with its corresponding strand of each target nucleic acid sequence could help expose the other complementary strand of each target nucleic acid sequence, thereby could kinetically favor the subsequent hybridization of another RNA probe with the complimentary strand of the each target nucleic acid sequence, leading to a favorable capturing of each of the two strands of each target nucleic acid sequence in the biological sample.

Due to these above advantages, the method disclosed herein is expected to have a variety of applications, as follows:

First, it allows for the capture and analysis of sequence variants and/or copy number variants, including without limitation, a point mutation, a deletion, an amplification, a loss of heterozygosity, a rearrangement, and/or a duplication. These genetic variants may be associated with human diseases, specific phenotypes, etc. The analyses include sequencing, hybridization assay, ligation assay, etc. Due to its ultra-sensitivity, the method disclosed herein allows for the capture and analysis of rare variants, especially ultra-rare variants/mutations, and copy number variants, and can be employed in capture and enrichment of nucleic acids from mitochondria, chloroplast, plastid, bacterial or viral pathogens, environmental DNA (eDNA), etc., and can also be employed in capture and enrichment of nucleic acids for population genetics studies, SNP typing and deep phylogenies, RAD (Restriction-site-Associated DNA sequencing) or GBS (Genotyping By Sequencing) locus enrichment. There is no limitation herein.

Second, it allows for enrichment and molecular cloning of specific target nucleic acid sequences blended in a DNA sample, such as ancient DNA and nucleic acid materials from museum specimens, which typically have a poor DNA quality and have a typically serious contamination of other organisms (esp. microorganisms) over many years' storage in nature environment, or contamination of modern human DNA due to inappropriate sample handlings.

Figure 6B:
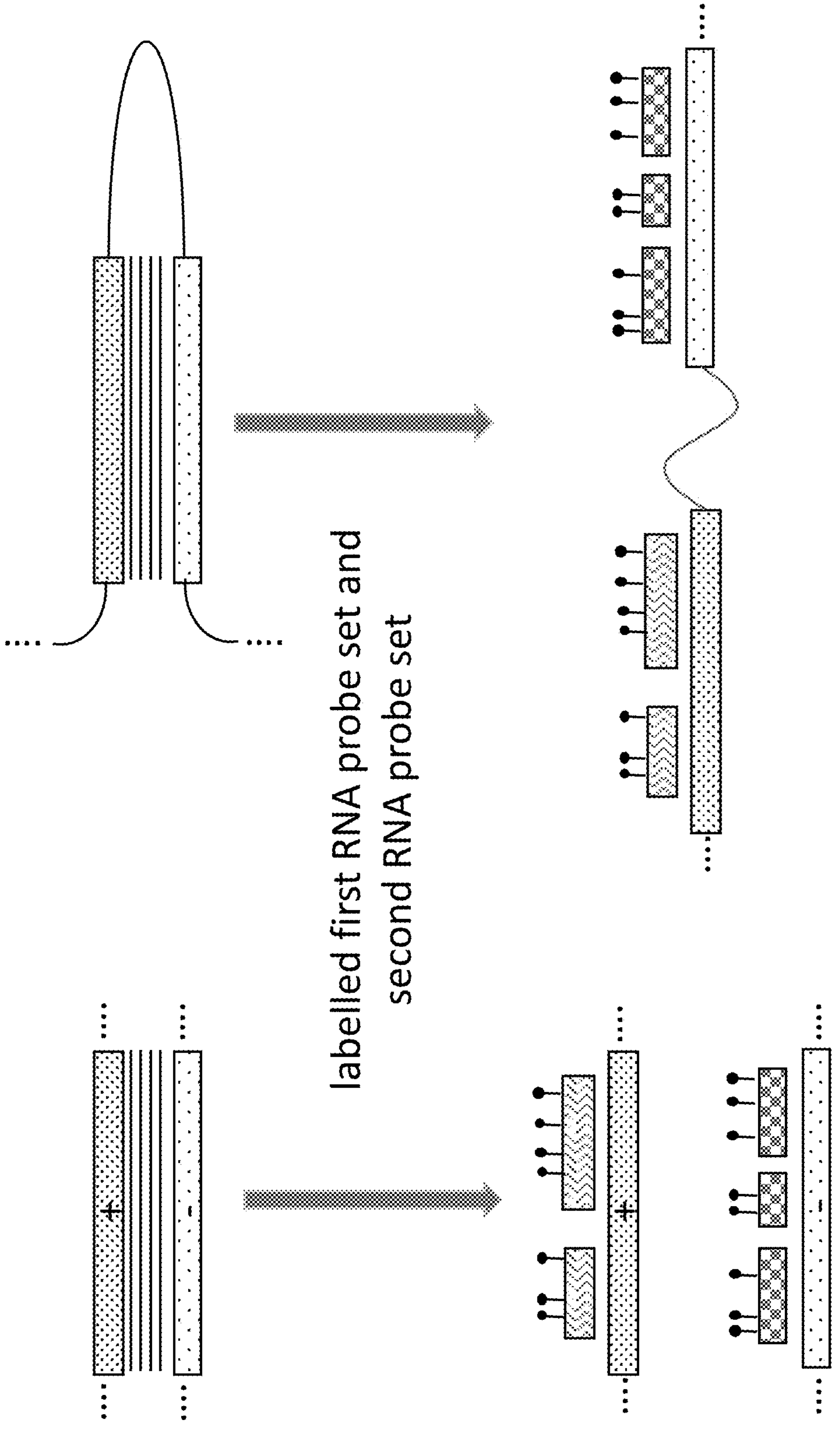
FIG. 6B illustrates a double-stranded target nucleic acid sequence consisting of a plus strand and a minus strand, and a single-stranded target nucleic acid sequence whose duplex segment having a hairpin structure, can be targeted for capturing and enrichment using the method disclosed herein.

Third, the method can be applied broadly to capture a variety of nucleic acid sequences in a test sample, which can include a double-stranded nucleic acid sequence, which consists of a plus strand and a minus strand, as illustrated in FIG. 6B, left panel), and can also include a single-stranded nucleic acid sequence having a duplex segment, which substantially forms a loop or a hairpin (as illustrated in FIG. 6B, right panel), and the nucleic acid sequences can include DNAs, RNAs, or DNA-RNA hybrid molecules.

It is noted that even in situations where any of the target nucleic acid sequences does not form a duplex structure (i.e. the target nucleic acid sequence has only a single-stranded segment), such as a case where cDNA is synthesized via reverse transcription yet the mRNA template is degraded due to an RNase-induced digestion, the method as described above can still be applied to capture a target nucleic acid sequence as long as any of the first RNA probe set or the second RNA probe set can target the single-stranded segment of the target nucleic acid sequence.

Fourth, the method as disclosed herein, if combined with the use of a method and a kit for constructing a barcoded nucleic acid library as disclosed in the U.S. patent application Ser. No. 15/908,190 (i.e. if used to enrich and capture target nucleic acid sequences in the barcoded DNA library by the kit and method disclosed therein), can allow an ultra-sensitive error-proof assays for the detection and characterization of target nucleic acid sequences in a biological sample.

In the following, several illustrating examples are provided to illustrate the several applications of the method disclosed herein.

FIG. 7A and FIG. 7B show a diagram of the nucleic acid sequence enrichment method according to some embodiments of the present disclosure.

As illustrated in FIG. 7A and FIG. 7B, double-stranded DNA molecules in a NGS DNA library are dissociated and the shared adapter, index and universal primer sequences among all molecules were hybridized by blocking oligos, and the target DNA sequences are further captured by RNA probes that are complementary to the DNA molecules that are composed of antiparallel double strands. Both the + strand and the − strand from the same DNA molecule are captured respectively by at least one complementary RNA probe. After immobilization of the captured DNA sequences on the solid support (i.e. streptavidin magnetic beads), the target sequences are extracted from the original library and the target DNA molecules being captured can be eluted from the probe after a series of wash and elution steps. After amplification, the library is ready for direct NGS sequencing or other assays.

Any means of testing for a sequence variant or sequence copy number variant, including without limitation, a point mutation, a deletion, an amplification, a loss of heterozygosity, a rearrangement, a duplication, may be used. Sequence variants may be detected by sequencing, by hybridization assay, by ligation assay, etc. The defined locations of some mutations permit focused assays limited to an exon, domain, or codon. But un-targeted assays may also be used, where the location of a mutation is unknown. If locations of the relevant sequence variants are defined, specific assays which focus on the identified locations may be used. Any assay that is performed on a test sample involves a transformation, for example, a chemical or physical change or act. Assays and determinations are not performed merely by a perceptual or cognitive process in the body of a person.

Probes and/or primers and/or template for RNA probe synthesis may contain the wild-type or a sequence variant, including without limitation, a point mutation, a deletion flanking sequence, a rearrangement location, may be used. These can be used in a variety of different assays, as will be convenient for the particular situation. Selection of assays may be based on cost, facilities, equipment, electricity availability, speed, reproducibility, compatibility with other assays, invasiveness of sample collection, sample preparation, etc.

Any of the assay results may be recorded or communicated, as a positive act or step. Communication of an assay result, diagnosis, identification, or prognosis, may be, for example, orally between two people, in writing, whether on paper or digital media, by audio recording, into a medical chart or record, to a second health professional, or to a patient. The results and/or conclusions and/or recommendations based on the results may be in a natural language or in a machine or other code. Typically, such records are kept in a confidential manner to protect the private information of the patient or the project.

Collections of RNA probes, primers, control samples, and reagents can be assembled into a kit for use in the methods. The reagents can be packaged with instructions, or directions to an address or phone number from which to obtain instructions. An electronic storage medium may be included in the kit, whether for instructional purposes or for recordation of results, or as means for controlling assays and data collection.

Control samples can be obtained from the same patient from a tissue that is not apparently diseased. Alternatively, control samples can be obtained from a healthy individual or a population of apparently healthy individuals. Control samples may be from the same type of tissue or a different type of tissue than the test sample. Control samples may be provided together with the RNA probes, primers, and reagents in a kit for use in the method, where the control samples may be a standard reference sample for the purpose of validating the performance of the kit and the operation performed by the user.

The data described below document the results for the identification of ultra-rare mutations from a whole exome sequencing study using RNA probes targeting both strands of the target DNA molecules. There is no doubt that SNVs can be detected with confidence only when the sequencing system's error rate is significantly lower than the frequency of identified SNVs. Therefore, baseline error rate of an NGS pipeline is critical for its performance of detecting ultra-rare SNVs. Combing the RNA probe-based capture of both DNA strands with the single-stranded library construction, an improved NGS methods with the base line error rate as $2.25\times10^{-10}$ was created. Such high-accuracy pipeline is dependent on the massive amount of DNA library target molecules captured by the RNA probes targeting both DNA strands.

FIGS. 8A-8D show that reduced amounts of variants were re-detected from sequentially diluted samples. No variant was re-detected from 1:10,000 diluted group. Coverage of re-sequencing is ~5,000×. The efficiency of capture through a paired sets of RNA probes is significantly stronger than the efficiency of capture through a single set of RNA probe for any target sequence.

FIGS. 15A, 15B, 15C, 15D and 15E show sequence variants detected by RNA probe-based DNA double strand capture NGS, validation results by Sanger sequencing and ultra-rare mutation redetection results are shown and ranked by Mutant Allele Fraction.

Figure 12:
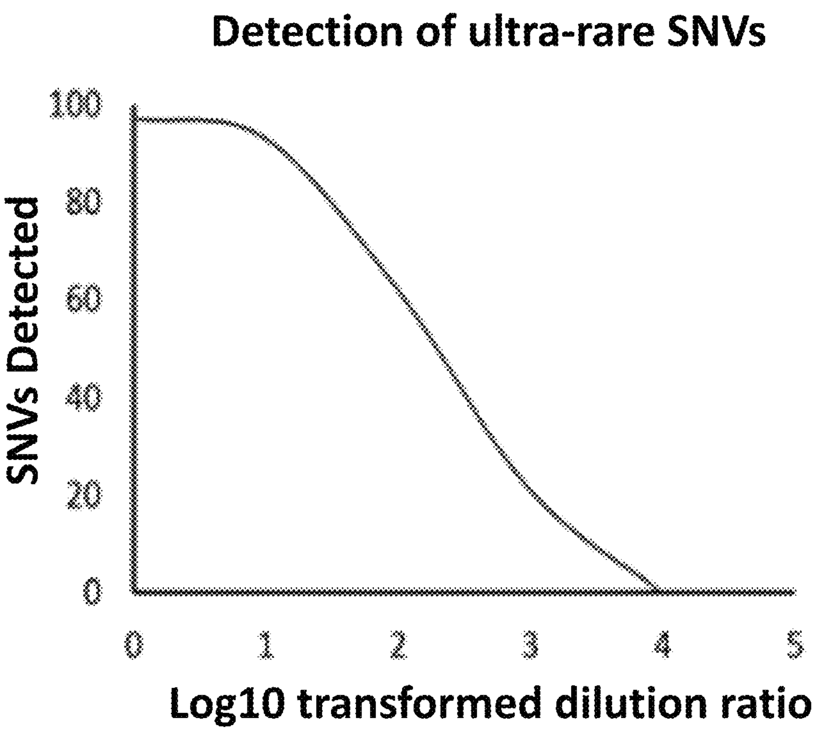
FIG. 12 shows detection of ultra-rare SNVs in libraries created from normal DNA spiked with sequentially diluted tumor DNA samples.

The ultra-rare mutation detection performance of this method with the target molecules captured by RNA probes targeting both strands of the DNA molecules was then evaluated by the success rate of re-detecting the 38 Sanger sequencing validated sequence variants in the libraries created from normal DNA samples which were spiked with sequential dilutions of tumor DNA. The library is constructed by a barcoded single-strand molecule-based approach and the target enrichment of the whole exome region of the human genome is performed by RNA probe-based DNA double strand capture. As the dilution folds increased, as expected, fewer and fewer variants were detected (FIG. 12), and when the tumor DNA sample was diluted 1,000 folds (the diluted sample containing 0.1 ng tumor DNA and 100 ng normal DNA), only 21 out of the 38 validated variants can be detected (FIGS. 15 A-E). The allelic fractions of these 21 SNVs in the 1:1000 diluted sample range from 0.03% to 0.005% with an average of 0.013% (FIGS. 15 A-E). No sequence variant was detected in 1:10,000 diluted sample which may presumably be due to the limitation of sequencing depth that has been achieved. For each sample, the targeted sequencing was performed with an average depth of 5,000×, which theoretically only allows us to see SNVs down to the frequency of 1/5000 (0.02%). To observe ultra-rare SNVs with even lower frequency, a greater than 5000× coverage is needed. It is also helpful to design capturing probes targeting only a small number of genes. With a smaller number of different nucleic acid sequences captured by the RNA probes targeting both strands of a smaller cohort of target genes, instead of the entire human genome exome, more copies of the target nucleic acids can be enriched, and this method can achieve a much greater sequencing depth with a significantly improved accuracy of ultra-rare SNV calling. The extremely low baseline error rate of this method allows ultra-rare SNV calling at the whole exome level with high accuracy, and the depth of NGS sequencing becomes the only limiting factor for such applications.

An RNA probe-based DNA double strand capture approach was reported as an improved method to enrich DNA molecules for NGS purpose, particularly targeted NGS. Such improved performance has been demonstrated in a human genome WES study. Aside from WES, another very important application of RNA probe-based DNA double strand capturing would be the targeted resequencing of a gene panel. Targeted re-sequencing is one of the most popular NGS applications, and it allows people to sequence a small cohort of gene targets to extreme depths, usually thousands of folds of coverage. And such sequencing depth can facilitate the detection of ultra-rare mutations with great sensitivity. In an RNA probe-based DNA double strand capture pipeline, attempts were made to capture the entire exome of all human genes, where an over 98% coverage with the depth of over 200× was achieved on a standard NGS platform. More importantly, the detection limit of this method for rare-mutation detection on whole exome scale is as low as 0.03%, which is made possible by the massively improved capture efficiency of the target molecules by the RNA probes targeting both DNA strands. For an even smaller cohort of target genes, the depth and coverage of RNA probe-based DNA double strand capturing NGS can be further increased, and the performance of ultra-rare mutation detection can be subsequently improved over several additional orders of magnitude.

Other than identifying ultra-rare SNVs with high sensitivity and accuracy, RNA based double strand capture method can also be adopted for gene copy number variant (CNV) assays. Barcoded single-stranded library construction links a unique barcode to every single-stranded DNA molecules. Such barcode information can not only be used to label the molecules and create super reads to reduce PCR errors, but also be used as a location marker for DNA fragments. After RNA probe-based DNA double strand capturing, NGS sequencing, and mapping the super reads back to the human genome, the barcode on each super read can be assigned to the position where the super read sequence is mapped. Therefore, a human genome can be reconstructed by unique barcodes. Copy number information can be represented by the diversity of barcodes at subgenomic loci. A highly efficient capture reaction with equal efficiency for all genomic regions offered by RNA probe-based DNA double strand capture is the key to a successful CNV calling.

Aside from CNV analysis, large structural variants frequently observed in cancer genomes can also be analyzed through RNA probe-based DNA double strand enrichment. RNA probes can be designed to enrich subgenomic regions flanking popular genome breakpoints specifically. A highly sensitive pipeline for translocation and large indel identification could be built based on the high efficiency of RNA probe-based DNA double strand capture.

In addition to applications in basic research, RNA probe-based DNA double strand capturing has a great potential in clinical NGS fields. It has been demonstrated that this method can highly efficiently construct NGS DNA libraries with very low amount of DNA materials 20 pg). Meanwhile it can detect ultra-rare mutations with high confidence. Such features are critical for NGS based clinical diagnostics where the samples are often limited and highly heterogeneous. A typical example would be the NGS sequencing of FFPE samples. FFPE has been a standard sample preparation method for many decades. Historically archived FFPE sample is a very valuable resource for retrospective studies in biomedical research. However, due to chemical modifications during specimen preparation and chronic damages to the tissue blocks or slides over long-term storage, it has been a challenging task to conduct NGS studies with FFPE samples. Poor DNA quality and artificial sequence changes are two major issues coming along with FFPE based NGS studies. RNA probe-based DNA double strand capturing is offering great benefit for FFPE based WES studies. WES data have been reported to be discordant between FFPE and fresh frozen samples at lower coverage levels (~20×), however, this discrepancy can be reduced when higher coverages are achieved. And recently, Allen et al. reported a reciprocal overlap of 90% somatic mutations between FFPE and fresh frozen tissue samples for the positions with sufficient sequencing (Van Allen, Wagle et al. 2014). In Allen's study, an RNA probe-based DNA single strand capture approach was applied, where its capture efficiency is far lower than RNA probe-based DNA double strand capture approach as was shown in data. With the enhanced capture efficiency by this method, WES studies with FFPE samples will offer comparable data quality to WES studies with fresh frozen tissues.

This method has a great potential to discover novel low-frequency disease-causing variants in biomedical and clinical applications, and can identify more actionable therapeutic targets for patients. This method can fulfill an unprecedented level of personalized precision medicine by revealing the most complete patient genomic profile to date including high-frequency, low-frequency and particularly ultra-low-frequency mutations. This method can also be applied in other clinical applications, like circulating DNA sequencing from body fluid samples, where only limited amount of DNA materials is available. In clinical NGS applications, it is critical to highly efficiently capture target DNA molecules from NGS libraries constructed with very limited amount of highly heterogeneous samples thus being less- or non-invasive; to highly efficiently enrich target sequences thereby reaching a great sequencing depth with limited cost and improved diagnostic sensitivity; and to remove artificial sequencing errors as completely as possible for the best diagnostic specificity. This method, utilizing two sets of RNA probes to capture the two strands of DNA antiparallel molecules simultaneously, has been demonstrated to meet these needs with great potentials in numerous NGS applications.

Example 1

Materials and Methods

Tumor and Normal Tissue Sample

The paired tumor and normal tissue samples from a pancreatic cancer patient of Asian race were obtained in accordance with guidelines and regulations from Tianjin Medical University Cancer Institute & Hospital, P.R. China after Institutional Review Board (IRB) approval at Tianjin Medical University, and under full compliance with HIPAA guidelines. An informed consent for conducting this study was obtained from the patient. The tumor tissue sample has an estimated neoplastic content of 43.4%.

Library Preparation

Genomic DNA from patient normal and tumor fresh frozen tissues was extracted using DNeasy Blood & Tissue Kit (Qiagen) and sheared into 150 bp fragments with Diagenode's Bioruptor at a program of 7 cycles of 30 seconds ON/90 seconds OFF using 0.65 ml Bioruptor® Microtubes. Barcoded single-stranded library preparation starts from a complete dissociation of DNA duplex to form single-stranded DNA and tagging the 3' end of each DNA single strand individually with a unique digital barcode. Barcoded single-stranded adapters have been disclosed in U.S. patent application Ser. No. 15/908,190, the disclosure is incorporated herein in its entirety. Pre-dephosphorylated fragmented DNA samples were mixed with barcoded single-stranded adapter (final concentration 0.15 uM), 20% PEG-8000, 100 U CircLigase II, and incubated at 60° C. for 1 hour. After immobilizing the ligation product on Streptavidin-coupled Dynabeads (ThermoFisher Scientific), each barcoded single-stranded DNA molecule is subject to an individual single-cycled PCR reaction to form its complementary strand. A DNA primer complimentary to the single-stranded adapter was annealed and extended using Bst 3.0 polymerase at 50° C. for 30 minutes. Blunt-end repair using T4 DNA polymerase was performed at 25° C. for 15 minutes. A double-stranded adapter was then ligated to the 5' end of the DNA duplex using T4 DNA ligase with an incubation at 16° C. for 1 hour. The library is eluted from the beads by an incubation at 95° C. for 1 minute. High fidelity PCR amplification is performed to amplify the DNA sequence as well as the unique barcode. Adapter sequences are designed to be compatible with Illumina sequencing platforms.

RNA Probe Synthesis

To obtain RNA probes complementary to both strands of target subgenomic regions, particularly the exome regions, the entire exome sequences for every human gene were cloned by sequence synthesis and molecular cloning based on Hg19 reference human genome sequences. In brief, exome sequences in 32,524 CCDS IDs containing −50 bp and +50 bp intronic sequences were cloned into pcDNA 6.2 vector. For extremely large human genes, e.g. DMD, PTPRD, CNTNAP2, etc., their related target sequences were separated and subcloned into multiple vectors. The total DNA sequences used to generate RNA probes cover a 72.6 Mb genome region, where all the exomes with their −50 bp and +50 bp flanking intronic sequences, as well as 5' and 3' UTRs for each gene were included. Two clones for each target sequence were constructed, where a T7 promoter was inserted at the 5' end of the plus strand in the "+" clone and at the 5' end of the minus strand in the "−" clone (FIG. 4B and FIGS. 7A and 7B). Two pools of clones were established for any give number of genes following the rule that the two clones for the same DNA sequence are separated into two systems, where one system (FIG. 4B and FIGS. 7A and 7B, left panel, "+" Clone) produced the RNA probes targeting the plus strand of the DNA target, and the other system (FIG. 4B and FIGS. 7A and 7B, right panel, "−" Clone) produced the RNA probes targeting the minus strand of the DNA target through in vitro transcription. ATP, CTP, GTP, UTP, and Biotin-16/11-UTP were added in each transcription system at the concentration of 1 mM, 1 mM, 1 mM, 0.7 mM and 0.3 mM. RNA products were further sheared into 100-150 nt fragments with a Covaris S220 focused-ultra-sonicator (Covaris). The fragmented RNA probes are ready for RNA probe-based DNA double strand capture applications. The two RNA probe libraries for each target DNA sequence were created separately and were never mixed until the actual capture procedure was carried out. In this study, RNA probes targeting both plus and minus strands of the whole exome sequences were created (including −50 bp and +50 bp flanking intronic sequences and 5'/3' UTRs) for all human genes and a cancer-related 298-gene panel.

RNA Probe-Based DNA Double Strand Capture

RNA probe-based DNA double strand capture was performed to capture the whole exome of human genome following a library construction or a standard NGS library construction. In RNA probe-based DNA double strand capture, both DNA strands of the target regions are captured by a pair of complementary RNA probes where each DNA strand is targeted by its complementary RNA probe, individually. A hybridization mixture was prepared containing 500 ng DNA library, 2 ug of RNA probes (1 ug from "+" clone transcripts and 1 ug from "−" clone transcripts, targeting Hg19 human exomes including −50 bp and +50 bp flanking intronic sequences, as well as 5' and 3' UTRs as described before), 7 ul Human Cot-1 DNA (ThermoFisher Scientific), 3 ul Herring Sperm DNA Solution (ThermoFisher Scientific), 10 μl blocking Oligos (1 nmol/ul each) with following sequences:

Blocking Oligo 1: 5'-AAGAGCGTCGTGTAGGGAAAGAGTGTAGATCTCGGTG GTCGCCGTATCATT-3' Inverted dT (SEQ ID NO. 913, where the last T is labelled with an inverted dT)

Blocking Oligo 2: 5'-CCTCAGCAAGAGCACACGTCTGAACTCCAGTCAC-NN-NNNNN-ATCTCGTATGCCGTCTTCTGCTTG-3' Inverted dT (SEQ ID NO. 914, where N can be any of A, T, C, and G, and the last G is labelled with an inverted dT)

The hybridization mixture is heated for 5 minutes at 95° C., then held at 67.5° C. 25 ul pre-warmed (67.5° C.) 2.8× hybridization buffer (14×SSPE, 14×Denhardt's, 14 mM EDTA, 0.28% SDS) was added. The mixture was slowly pipetted up and down 8 to 10 times. The hybridization mixture was incubated for 24 hours at 67.5° C. with a heated lid.

After hybridization, 50 μl Dynal MyOne Streptavidin Cl magnetic beads (ThermoFisher Scientific) were washed three times by adding 200 μl of binding buffer (1M NaCl, 10 mM Tris-HCl, pH 7.5, and 1 mM EDTA), and re-suspended in 200 μl Binding buffer. The hybridization mixture was added to the bead solution gently and was subsequently incubated on a thermomixer at 850 rpm for 30 minutes at room temperature. To wash the beads, the supernatant was removed from beads on a Dynal magnetic separator and the beads were re-suspended in 500 W Wash Buffer A (1×SSC/0.1% SDS), and incubated for 15 minutes at room temperature. Beads were then washed three times, each with 500 μl pre-warmed Wash Buffer B (0.1×SSC and 0.1% SDS) after incubation at 65° C. for 10 minutes. To elute captured DNA, beads were re-suspended in 50 μl 0.1M NaOH at RT for 10 minutes. The supernatant was transferred into a new 1.5 ml microcentrifuge tube after magnetic separation, and mixed with 50 μl Neutralizing Buffer (1M Tris-HCl, pH 7.5). DNA was purified with a Qiagen MinElute column and eluted in 17 μl of 70° C. EB buffer to obtain 15 μl of captured DNA library. The captured DNA library was amplified by Phusion Hot Start polymerase (New England Biolabs) using Illumina PE primer 1 and 2. The PCR program used was: 98° C. for 30 seconds; 6~10 (depending on capture yield) cycles of 98° C. for 10 seconds, 65° C. for 30 seconds, 72° C. for 30 seconds; and a final incubation at 72° C. for 5 minutes. The PCR product was purified using GeneJET PCR Purification kit (ThermoFisher Scientific).

Real-Time PCR Assay

FIGS. 13A-13N illustrate 298 cancer-related gene targets, primer pairs, amplicon sequences, amplicon GC % and amplification efficiency constant for each real-time PCR detection are listed.

Real-time PCR assays with SYBR green detection was carried out using an ABI PRISM 7500 Sequence Detection System (Applied Biosystems). Briefly, the reaction conditions consisted of 500 ng of genomic DNA or DNA library products, 0.2 μM primers, and SYBR Green Real-Time PCR Master Mix (ThermoFisher Scientific) in a final volume of 20 μl. Each cycle consisted of denaturation at 95° C. for 15 seconds, annealing at 58.5° C. for 5 seconds and extension at 72° C. for 20 seconds, respectively. Gene specific primers were designed using Primer 3 (Untergasser, Cutcutache et al. 2012) and their sequences are provided in FIG. 8. Reactions were run in triplicate in three independent experiments. The primer pair's standard amplification curve for each gene was established through using sequential dilutions of the "+" clone constructs containing the amplicon sequence. Amplification efficiencies for 298 target amplicons were established and listed in FIG. 8. Gene abundance ratios between different samples were calculated by the raising the gene specific amplification efficiency (AE) to the power of $\Delta C_t$ value between different samples. For example, the ratio (r)

of gene abundance in sample A vs sample B can be calculated through real-time PCR assay by: $r_{(A/B)}=AE^{\Delta Ct}$, where $\Delta C_t=C_{t(sample\ B)}-C_{t(sample\ A)}$ Whole Exome Sequencing FIG. 14 show that initial mapped reads represent raw reads that contain the 12 nt barcode and mapped to the reference genome. Unique read family represents the number of URF. Each URF has a unique barcode and its sequence is obtained by consolidating read sequences arise from the same DNA molecule by PCR amplification. PCR errors are removed by requesting a sequence uniformity for over 95% of the reads within a URF. Super read duplexes represent the number of DNA duplex whose two strands are coming from two super reads.

Whole exome sequencing was performed on an Illumina HiSeq 2500 platform according to manufacturer's manual. Total numbers of on-target reads from randomly chosen 5 million to 50 million reads were calculated. After trimming and barcoded super read grouping, SNVs were called with GATK (version 3.6) in a default mode as recommended by the GATK documentation with reference genome of Hg19 (McKenna, Hanna et al. 2010). In brief, for every sample (tumor or normal DNA), sequencing result was preprocessed by mapping to reference genome with BWA (version 0.7.10), and duplicates were marked with Picard (version 2.0.1). Base Recalibration was performed to generate the reads ready for SNV analysis. For individually processed T/N pair reads, Indel Realignment was performed to generate pairwise-processed T/N pair reads. HaplotypeCaller was used for raw SNV calling. Output from variant calling was directly used for SNV detection by MuTect (version 1). Mutations were filtered through a 4-step approach introduced in the section "Mutation and ultra-rare mutation detection". Low-quality variant with a Phred score<30.0 was abandoned. Paired SNVs from complementary reads bearing different barcodes were identified as true mutations and subject to further validation through Sanger sequencing. The data yields after each step of data analysis for an RNA probe-based DNA double strand capturing NGS study were shown in FIG. 14. SNVs identified and Sanger sequencing validation results were provided in FIGS. 15 A-E.

Mutation and Ultra-Rare Mutation Detection

The significantly increased number of unique reads obtained through RNA probe-based DNA double strand capturing enabled us to apply stringent filters with the following 4-step procedure.

- Step 1) group reads with the same barcode that are representing PCR duplicates of an original barcoded single-stranded DNA molecule, and call it a unique read family (URF);
- Step 2) combine reads within each URF obtained from Step 1) by requesting >95% sequence identity among the reads;
- Step 3) extract the unique DNA sequence and the barcode sequence for each URF, and call it a "super read"
- Step 4) for all the super reads identified in Step 3), find their paired complementary super reads, and only score sequence variants with matched complementary sequences from paired super reads. To accommodate damaged DNA molecules in the sample, complementary super reads may not be at the same length.

To evaluate the performance of RNA probe-based DNA double strand capture in detecting low frequency (ultra-rare) mutations, 100 ng tumor DNA sample was sequentially diluted by 10, 100, 1,000 and 10,000 folds, and spiked each of them into the same amount (100 ng) of genomic DNA extracted from the paired normal tissue of the aforementioned cancer patient. This design can simulate early stages of cancer occurrence, and represent the major obstacles in early cancer diagnostics using NGS, which is the very low allelic fractions of tumor specific mutations in the sample.

Build a Highly Accurate Reference Exome for Ultra-Rare Mutation Identification

To highly accurately assess the baseline mutation frequency of barcoded single-stranded library and RNA probe-based DNA double strand capturing pipeline, six replicates of standard NGS DNA libraries were constructed in parallel, each using 100 ng normal DNA input. These six replicates of exome datasets were used to re-build reference exome database for this particular patient by requesting that if the same SNV was observed in ≥5 out of 6 independent datasets, the SNVs can be considered as germline variants and the reference exome sequence database will be updated. For a standard NGS pipeline, the error rate is 1%, and the chance to see the same random error at a fixed position for 5 times is $(\frac{1}{3}\times1\%)^5=4.12\times10^{-13}$. This number means that if this approach is used to sequence the whole human genome once, there is presumably going to be only one artificial error, because $3\times10^{12}$ human genome bases X $(4.12\times10^{-13})=1.24$. However, only the human exome sequences are enriched and sequences, which is occupying only 1.5% of human genome, therefore the chance to see a single artificial error within the entire human exome is only 1.86% (=1.5%×1.24). An updated highly accurate normal exome reference database of the patient was built accordingly.

Example 2

RNA Probe-Based DNA Double Strand Capture Achieved a High Enrichment Efficiency

A method is developed to enrich targeted subgenomic sequences by RNA probe-based capture of both strands from the same DNA molecule, simultaneously. To assess the capture efficacy, RNA probes were created for the exome regions of the 298-gene panel adopted in this study. Real-time PCR assays were performed to detect and quantify the subgenomic regions of this gene panel in NGS library before and after RNA probe-based enrichment. No re-amplification of the library was performed after the capture to ensure that the amounts of DNA molecules obtained from RNA probe-based enrichment represent the captured yields for each gene.

Figure 8B:
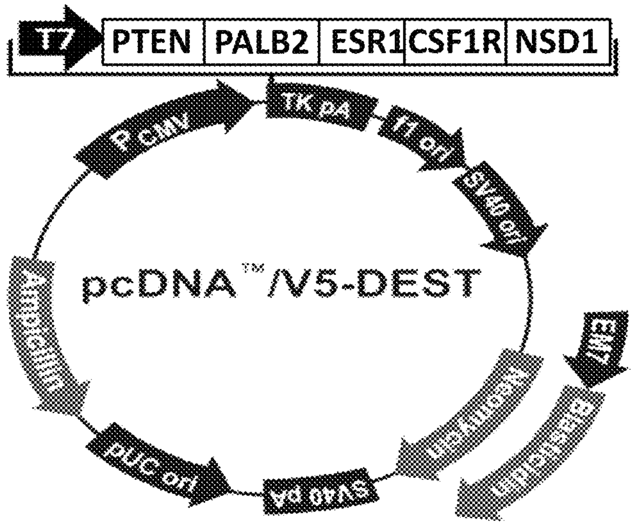
Figure 8C:
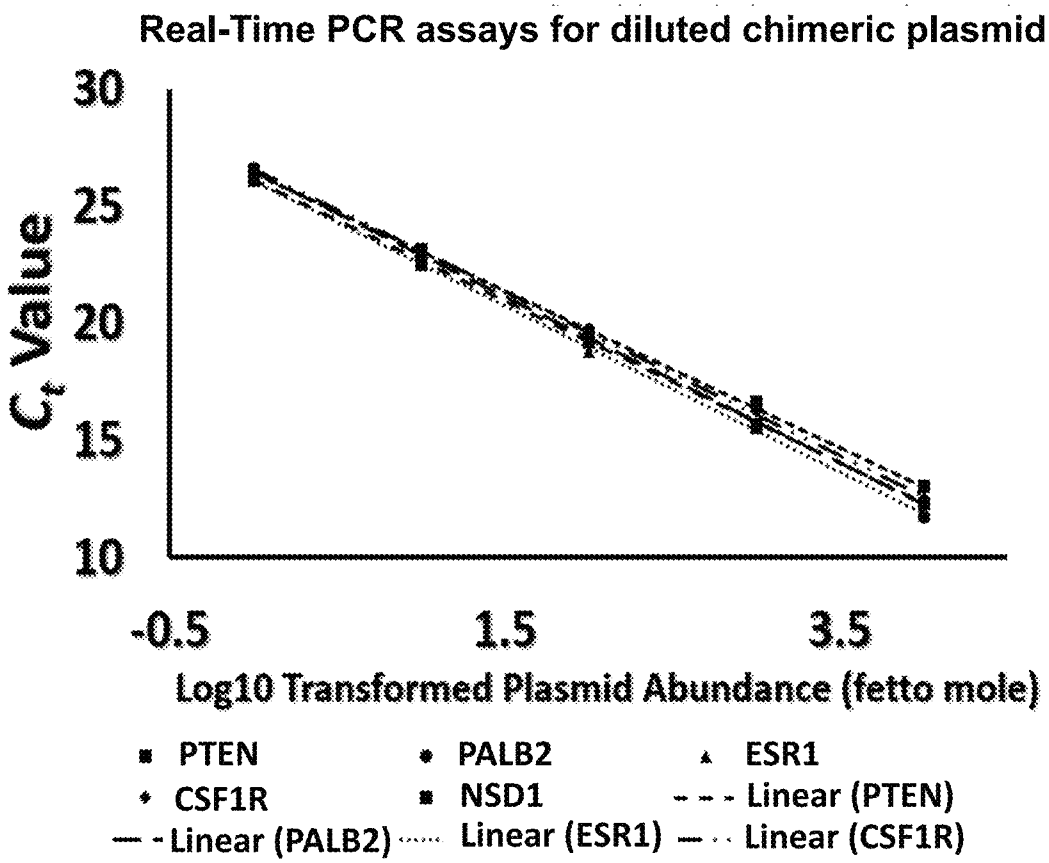
Figure 8D:
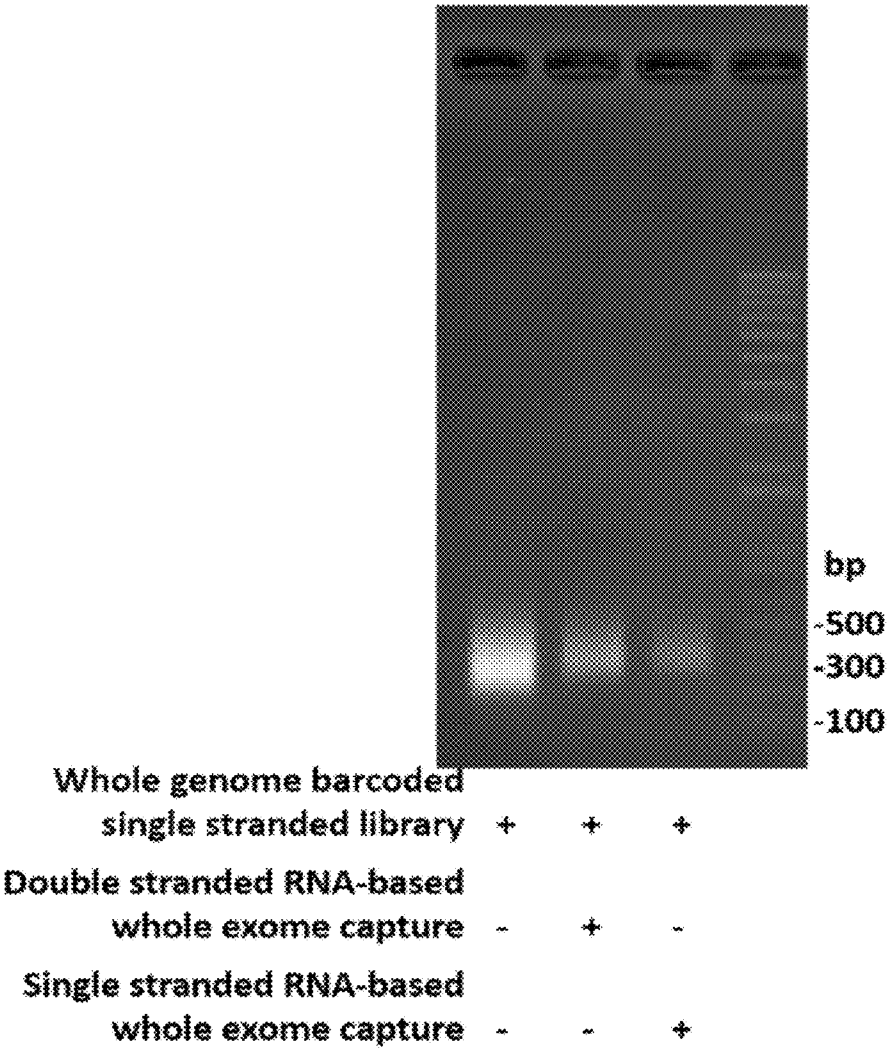

FIG. 8A shows that for each of the six DNA libraries derived from different amounts (500 ng, 20 ng, 1 ng, 100 pg, 20 pg and 10 pg) of input genomic DNA, enrichment efficiency of 298 cancer-related genes were calculated. Recovery ratios of DNA single and double strand captures by RNA probes for all 298 genes in six libraries were quantified by real-time PCR assays detecting each gene's abundance in the libraries before and after single strand capture or double strand capture; FIG. 8B shows that an insert sequence composed of amplicon regions of five genes whose GC contents cover a broad range (27.3% to 74.1%) was cloned into a pcDNA vector; FIG. 8C shows that Real-time PCR analysis of sequential dilutions of the plasmid. 1, 10, 100, 1,000 and 10,000 femtomoles of the plasmids were added as templates for the assays. Ct value for each gene observed from different plasmid template amount was plotted, and trend lines were shown. No significant GC-dependent amplification bias was observed for real-time PCR assays; FIG. 8D shows that a whole genome library, and whole exome libraries captured by RNA based DNA single and double strand captures were analyzed on an agarose gel.

The same set of six libraries created from a sequentially diluted DNA input was adopted again. Such results indicate that each gene's capture ratio is in consistency for all six libraries (FIG. 8A). Such findings demonstrate that RNA probe-based DNA double strand capture efficiency for each gene is not dependent on the initial However, the capture ratios of different genes did vary to a significant extent (10.4% to 49.8%). Further investigation showed that RNA probe-based capture ratios for different genes were loosely correlated with the GC content of their amplicons (FIG. 8A). A very weak correlation (average $R^2$=0.12) between amplicon GC contents and their RNA probe-based capture efficiencies were shown (FIG. 8A).

Library construction, RNA probe-based capture or the Real-time PCR assays are all potentially responsible for this GC content associated enrichment bias. Previous results have demonstrated that library construction is not significantly biased by GC content. Next, real-time PCR was investigated to check its potential GC content bias. 5 genes were chosen, PTEN, PALB2, ESR1, CSF1R, and NSD1, with distinct GC % in their amplicon sequences at 27.3%, 39.3%, 50.5%, 62%, and 74.1%, respectively (FIGS. 13A-13N). A plasmid (pcDNA 6.2 vector) containing a DNA insert composed of all five genes' amplicon regions separated by a 100 bp flanking sequence is cloned (FIG. 8B) and sequentially diluted to simulate variable amounts of the gene fragments after capture. All 5 gene fragments were cloned into the same plasmid to ensure the equal abundance between different genes in every diluted sample. Real-time PCR was performed to detect the copy number of plasmids by detecting each of the five genes in a series of diluted plasmid samples. As shown in FIG. 8C, there is no obvious GC-content-associated bias observed from the real-time PCR amplifications of all five genes using these primers. The 298 pairs of primers adopted in real-time PCR assays were designed with their $T_m$ values all falling into a narrow range of 57° C. to 61° C. This restriction of $T_m$ and short amplicon sequences with similar lengths (around 150 bp) helped ensure the uniformity of real-time PCR assays for all genes (FIGS. 13A-13N). Therefore, the only possible step, where the GC content related capture ratio bias is created, should be the RNA probe-based capture itself. Enrichment bias for hybridization-based subgenomic capture has been reported to be owing to GC content. Whole exome capture NGS studies were conducted to assess further the impact of GC content to the RNA probe-based capture efficiency of target subgenomic regions.

It is important to note that in this RNA probe-based capture, complementary RNA probes were used to capture both DNA strands of the target regions, and attempts were made to assess if there is any capture efficiency difference between using only one set of RNA probes to capture only one strand of target DNA and using two sets of RNA probes to capture both strands of target DNA simultaneously. These two capture methods were performed in parallel with two equal aliquots (500 ng) of DNA libraries, where each library was created from the same 20 ng genomic DNA. A whole genome library, captured yields by RNA probes targeting both strands of DNA molecules or RNA probes targeting only a single strand of the DNA target molecule were analyzed on an agarose gel (FIG. 8D). Real-time PCRs for the 298-gene panel were performed to evaluate the capture ratios of RNA probe single strand capture and double strand capture for all the genes (FIG. 8A). The average capture ratios for the target nucleic acid sequence capture method as disclosed herein (i.e. the double strand-targeting RNA probe-based capture method) is 29.2% across all genes in different libraries, much higher than the ratios observed from the conventional single strand-targeting RNA probe-based capture approach (~8.5% on average). These results have demonstrated that to capture target DNA sequences by complementary RNA probes through hybridizing to both strands of the DNA duplex molecule simultaneously achieved an over 3-fold increase in capture efficiency compared to capturing a DNA single strand alone through RNA probes.

Example 3

Whole Exome Sequencing

Figure 10A:
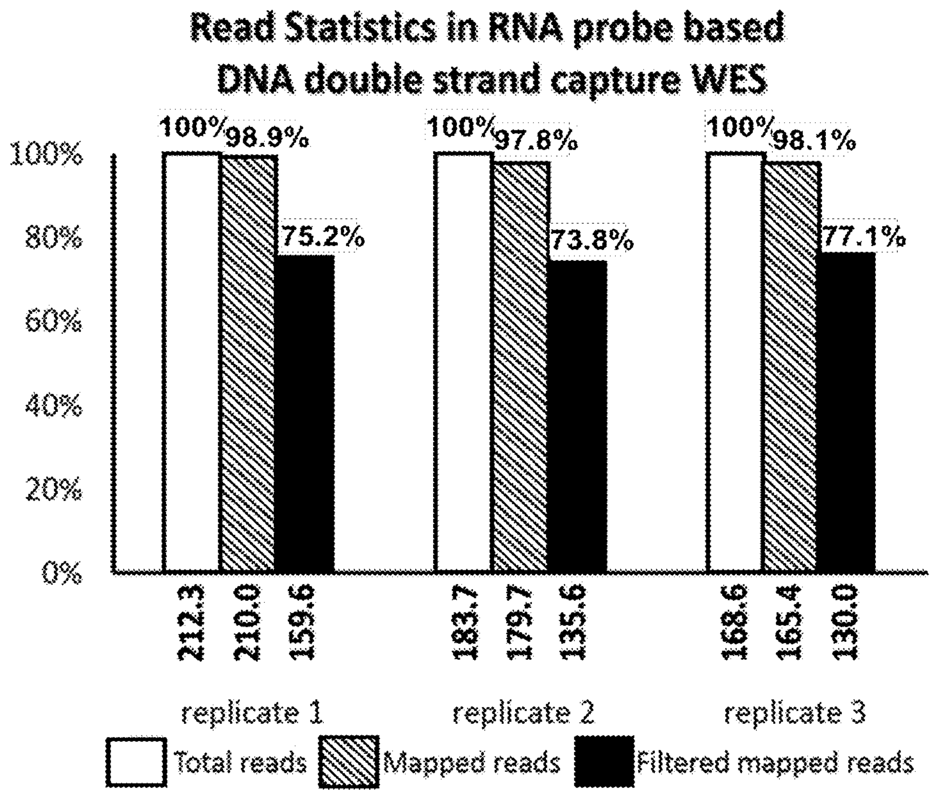
FIGS. 10A-10C show read statistics.
Figure 10B:
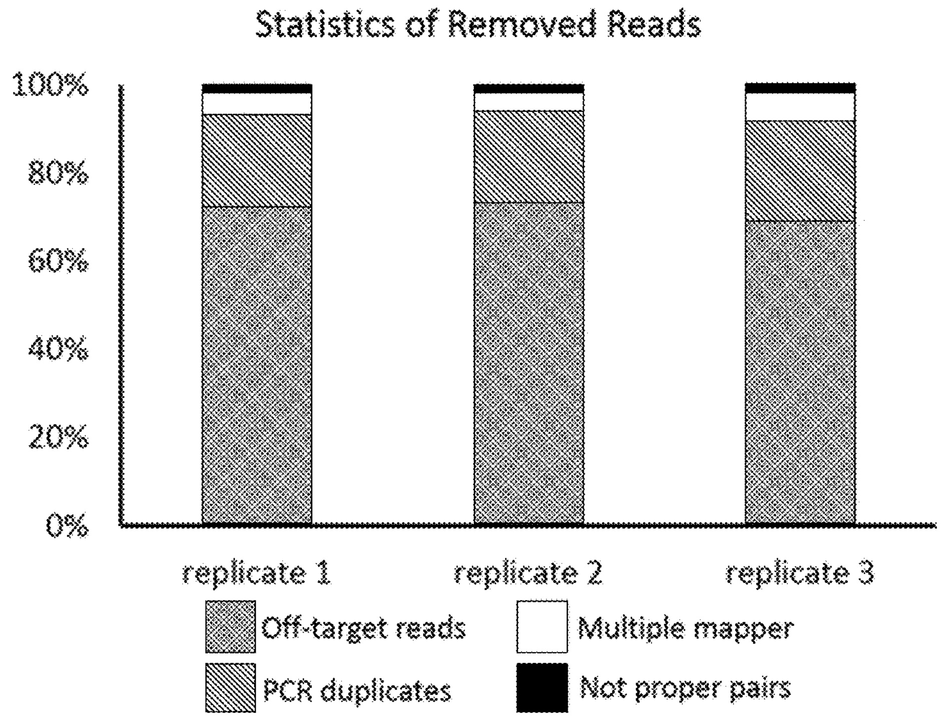
Figure 10C:
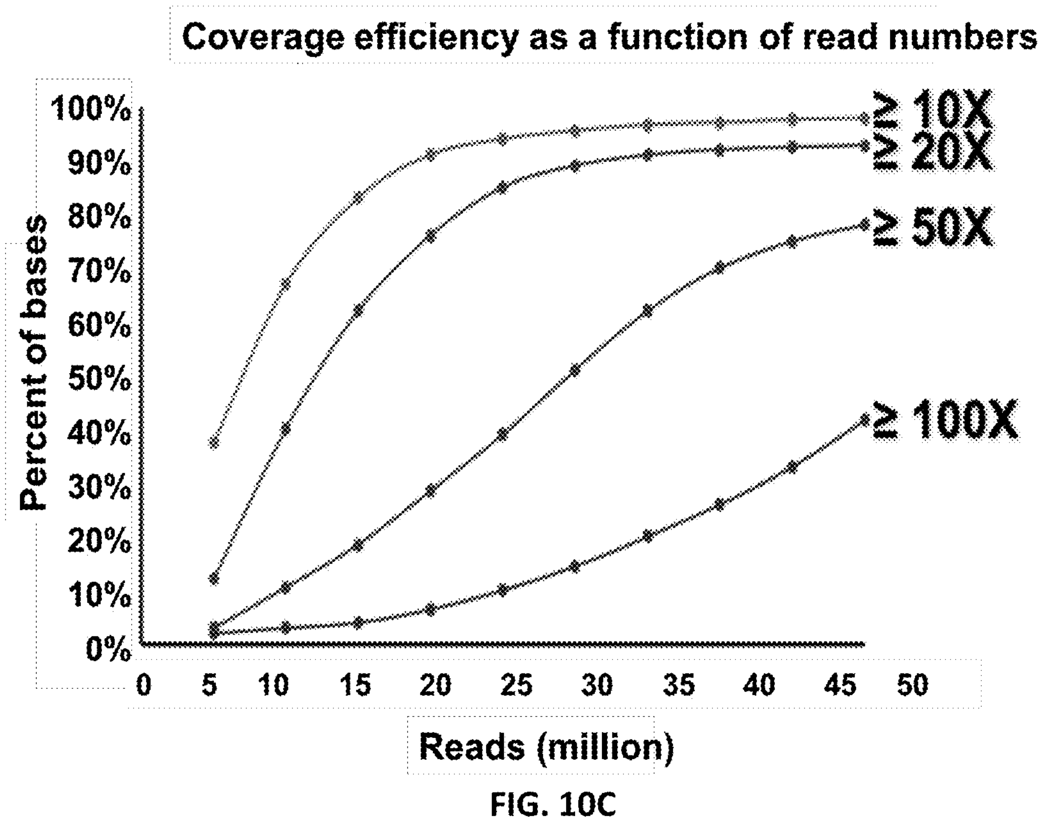

FIG. 10A shows a bar plot of percentage of initial reads, mapped reads and reads remained after filtering. Results were obtained from three technical replicates. Numbers of reads were shown under each bar with the unit of 1 million reads. FIG. 10B shows a stacked bar plot of subgroups of filtered reads in triple replicates. FIG. 10C shows a coverage efficiency correlation with read numbers. The percentage of target bases covered at ≥10×, ≥20×, ≥50× and 100× depths with 5 million to 50 million reads were shown.

To evaluate the performance of RNA probe-based DNA double strand capture in NGS, WES assays were performed using this method and compared the data to what obtained through standard NGS library preparation with a standard exome enrichment procedure. All libraries were constructed with 100 ng genomic DNA derived from the normal tissue of the cancer patient, and three technical replicates were performed for each sample. All NGS runs were carried out on the same Illumina HiSeq 2500 platform with the same technical specifications of the runs. As shown in FIG. 10A, an average of 188 million reads were obtained from RNA probe-based DNA double strand capturing WES, where 98.3% were aligned to the human genome, and the total read counts were significantly more (1.6 folds) than that from the standard sequencing pipeline. The higher numbers of reads for the libraries presumably came from the ultra-sensitive single-stranded DNA library construction, and the much more efficient RNA probe-based enrichment designed to capture both DNA strands (including DNA molecules that have damages ranging from minor single strand breaks to major damages on both strands).

All NGS data were analyzed on the same software pipeline with the same settings. Raw reads were filtered to remove duplicates, multiple mappers, improper pairs, and off-target reads. On average 75.4% reads were retained after filtering (FIG. 10A). For the reads that were removed, 71.8% were off-target reads, which were mapped to the human genome but outside of the target regions, 21.6% were PCR duplicates, and the remaining reads were mapped to multiple sites of the genome or not mapped at all (FIG. 10B). No statistically significant difference was observed in all the specifications measures for the three technical replicates in this experiment, which indicates that library construction and RNA probe-based DNA double strand capturing pipeline is technically highly reproducible (FIGS. 10A, and 10B).

Figure 11A:
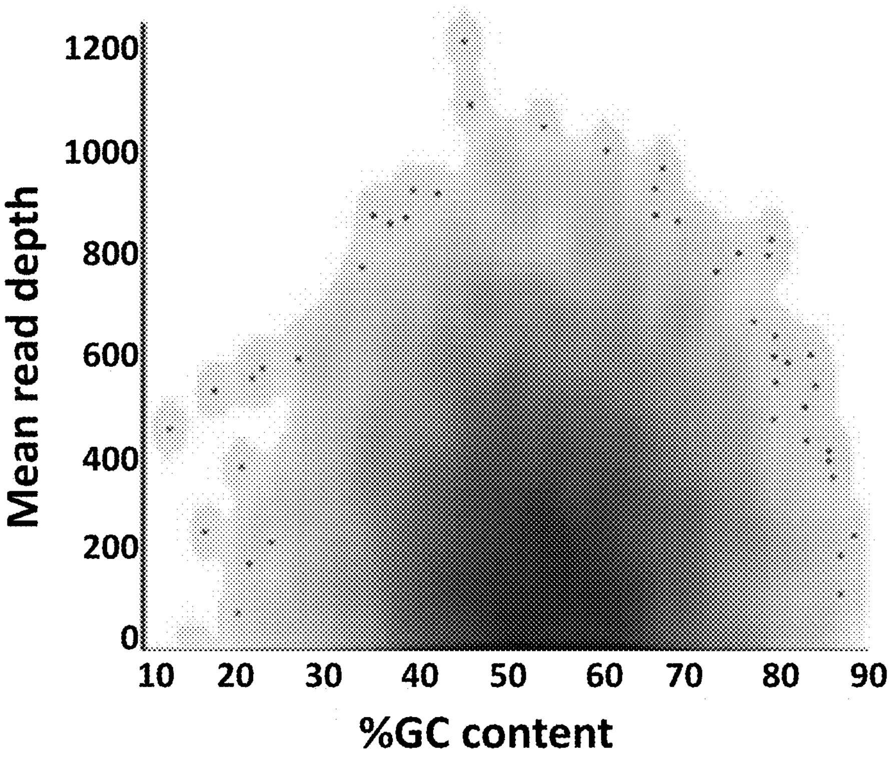
FIGS. 11A and 11B show density plots of read depths to demonstrate the relationship between GC content and normalized mean read depth for (FIG. 11A) an NGS WES study using RNA probe-based DNA double strand capture approach with DNA extracted from normal human tissue.

Next, the correlation between coverage efficiency and sequencing depth in NGS library with RNA probe-based DNA double strand capturing was evaluated. Filtered reads were randomly selected in 5 million read increments from 5 million to 50 million. The fractions of the retained on-target reads covering the depths of at least 10×, 20×, 50×, and 100× were plotted using randomly selected 5 to 50 million reads (FIG. 10C). 20 million reads could cover close to 90% of the target bases with no less than 10× depth. With 50 million reads, over 90% target bases were covered by at least 20×. The efficiency of coverage is not only dependent on the efficiency of library construction but also dependent on the length of the sheared molecules that were initially incorporated into the pipeline. For the current study, the average length of sheared DNA molecule is 150 bp. These real-time PCR results for the 298-gene panel indicated that enrichment efficiency of the library construction approach is not significantly biased by GC content (FIG. 8). Density plots were created to show GC content against normalized mean read depth for RNA probe-based DNA double strand capture WES study with normal tissue DNA (FIG. 11A), and DNA library WGS study with normal tissue DNA (without enrichment for whole exome, FIG. 11B).

Figure 11B:
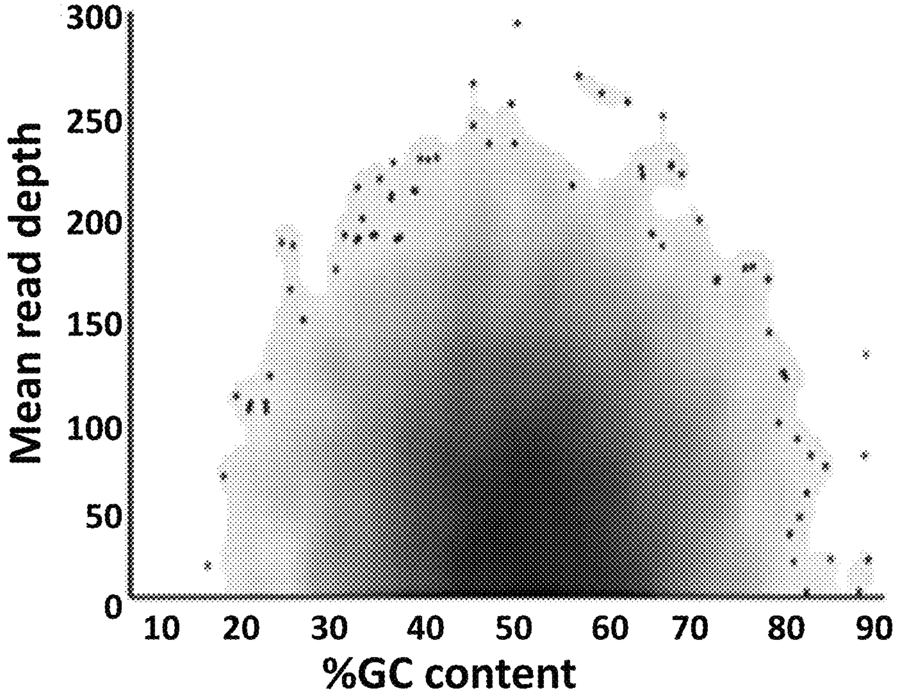

To assess the impact of GC content on WES result, normalized mean read depth against GC content was plotted. There is a correlation between GC content and read depth in the WES experiment (FIG. 11A), and this bias is reduced in a WGS study (FIG. 11B). In this method, the mean read depth ratios of GC50%/GC20%=1.55, which is significantly lower than the ratio of 2.0 reported by numerous studies (Benjamini and Speed 2012, Meienberg, Zerjavic et al. 2015), which demonstrates a lower GC bias in this method.

Example 4

Detection of SNVs

Figure 9A:
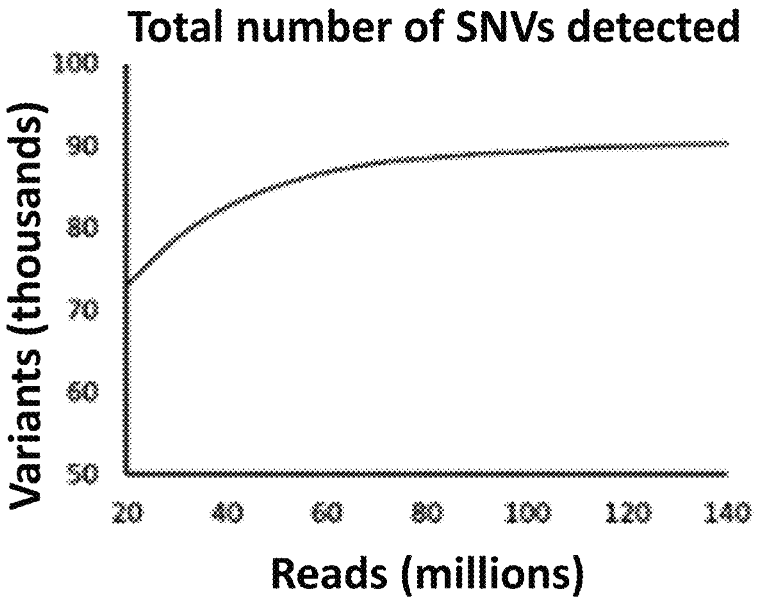
FIGS. 9A and 9B show SNV-calling trends and statistics of RNA probe-based DNA double strand capture WES (Whole Exome Sequencing) study.
Figure 9B:
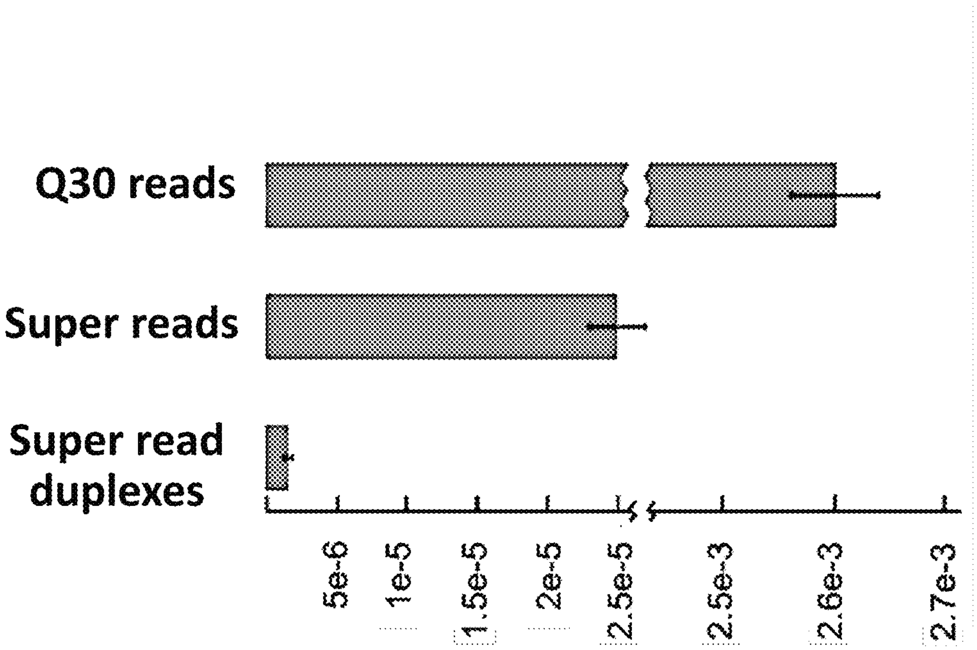

FIG. 9A shows that total number of SNVs detected at increasing read count thresholds. Sensitivity increases at higher read counts but quickly reaches a plateau with more than 80 million reads. FIG. 9B shows average SNV frequencies of normal tissue DNA measured by three approaches: a standard NGS approach where barcodes were directly trimmed off, a super read based approach by barcoded single-stranded library based NGS without matching variants from both DNA strands (without the last step of the 4-step procedure), and a super read approach by barcoded single-stranded library based NGS matching the SNV on both strands (all steps in the 4-step procedure were performed). All three approaches were performed with RNA probe-based DNA double strand capture WES.

One of the most important goals of exome sequencing is to identify sequence variants that are disease-causing or of clinical significance. To evaluate the sensitivity and specificity of sequence variant identification performance of library construction and RNA probe-based DNA double strand capturing, a WES study was conducted with 100 ng genomic DNA from a pair of normal and tumor tissue samples obtained from the same cancer patient. The same SNV calling pipeline was used for all data analysis in this study. Briefly, the normal DNA libraries created by library construction and RNA probe-based DNA double strand capturing method was sequenced and the data were analyzed using a standard data analysis pipeline, where the single-stranded barcodes were directly trimmed off, and 78,721 SNVs were detected from the exonic sequences of normal DNA sample at a read count of 30 million (error frequency $2.6\times10^{-3}$, FIG. 9A). The total number of SNVs detected from 30 million reads of the normal tissue DNA is significantly higher than what was reported on other platforms (Clark, Chen et al. 2011). Next, further investigation was made to check if there is any bias in SNVs identified using the standard NGS data analysis workflow. Transition-transversion (ts/tv) ratio is routinely used to evaluate the specificity of new SNP calls. The ts/tv ratio on the target regions of WES was calculated to be 2.766, higher than the reported ts/tv ratios of 2.0-2.1 for WGS data. The ts/tv ratio in CCDS exonic regions as was then determined as 3.225, which falls into the range of 3.0~3.3 for reported exonic variations. The reason for RNA probe-based DNA double strand capture for whole exome sequencing to have a higher ts/tv ratio than reported WGS studies is because target regions of sequencing are enriched for exons, and only contain UTRs and short flanking sequences within introns.

The accuracy of mutations enriched by DNA based mutation calling was then examined. Following the 4-step data analysis procedure introduced in Materials and Methods, super reads were generated after Step 3). Steps 1-3 helped to reduce the mutation frequency by over two orders of magnitude from $2.6\times10^{-3}$ down to $2.5\times10^{-5}$ by removing most PCR related errors (FIG. 9B). This result indicates that PCR related artificial mutations dramatically reduce NGS sequencing accuracy. To detect rare mutations, or even ultra-rare mutations using NGS, a correction for PCR errors is mandatory. As outlined in Step 4), attempts were then made to further reduce artificial errors of mutation calling by using the redundant sequence information offered by complementary DNA strands that were originally from the same DNA duplex molecule. These results indicated that such procedure resulted in a single base mutation frequency of $1.6\times10^{-6}$ (FIG. 9B). For any single base in the DNA sequences, the possibility of having the same artificial error on a paired position is $\frac{1}{3}\times(2.5\times10^{-5})^2=2.08\times10^{-19}$, which is equivalent to one artificial error per $4.8\times10^{9}$ nucleotides. This is the theoretical error rate for the pipeline. The total amount of DNA sequence data and the remaining amount of data after each step can be found in FIG. 14, where a stepwise drop of data amount is correlated to the increase of mutation calling stringency.

To determine the accuracy of variant detection by library construction and RNA probe-based DNA double strand capturing for clinically relevant mutations, the WES data generated from the normal and tumor tissue pair were analyzed side-by-side. For all assessed heterozygous exonic positions, the result was filtered through such 4-step procedure. The filtered result showed that for RNA probe-based DNA double strand capturing, WES study identified 97 sequence variants that were exclusively detected in tumor tissue DNA sample with 100× coverage at different fractions. 40 moderate- to high-abundance (>5%) variants were subject to Sanger sequencing validation, and 38 were confirmed (FIGS. 15A-15E). Two variants failed to be validated where both allelic fractions were low and beyond the detection limit of Sanger sequencing. 57 sequence variants (with mutant allele fractions<5%) were not subject to Sanger sequencing validation at all, due to the limited sensitivity of Sanger sequencing (Tsiatis, Norris-Kirby et al. 2010).

Example 5

A Protocol for RNA Probe-Based DNA Double Strand Capture

Production of the RNA Probes

The entire exome sequences for every human gene by sequence synthesis and molecular cloning based on Hg19 reference human genome sequences. In brief, exome sequences in 32,524 CCDS IDs containing −50 bp and +50 bp intronic sequences were cloned into pcDNA 6.2 vector. The total DNA sequences used to generate RNA probes cover a 72.6 Mb genome region, where all the exomes with their −50 bp and +50 bp flanking intronic sequences, as well as 5' and 3' UTRs for each gene were included.

Two clones for each target sequence were constructed, where a T7 promoter was inserted at the 5' end of the plus strand in the "+" clone and the 5' end of the minus strand in the "−" clone (FIG. 4B and FIGS. 7A and 7B).

Two pools of clones were established for any give number of genes following the rule that the two clones for the same DNA sequence are separated into two systems, where one system (FIG. 4B and FIGS. 7A and 7B, left panel, "+" Clone) produced the RNA probes targeting the plus strand of the DNA target, and the other system (FIG. 4B and FIGS. 7A and 7B, right panel "−" Clone) produced the RNA probes targeting the minus strand of the DNA target through in vitro transcription.

AmpliScribe™ T7 Flash™ Biotin-RNA Transcription kit is used for RNA probe production and amplification Prepare the mix as following:

| component | volume per reaction (μl) |
|---|---|
| Plasmid library with T7 promoter(100 ng) | 5.5 |
| T7 flash buffer 10X | 2 |
| NTP/biotin-UTP premix | 8 |
| 100 mM DTT | 2 |
| RNase Inhibitor | 0.5 |
| AmpliScribeT7 Flash enzyme | 2 |
| Total | 20 |

Mix well and incubate at 30° C. for 4 hours.

Add 1 μl DNaseI. Incubate at 37° C. for 15 minutes.

Purify the RNA probes using 2×RNA AMPure beads. Elute into 80 μl. You should have 150 μg probe now.

sonication of the RNA products to generate 100-150 nt RNA fragments as probes

Turn on BioRuptor and water bath (set to 3° C.) at least 45 minutes before starting.

Place up to 1 μg of RNA adjusted to 57 μl with 1×TE buffer in a BioRuptor microtube.

Shear with below setting for a target size range of 100-150 nt:

| Setting | value |
|---|---|
| Intensity | H |
| On:Off | 30:30 |
| Cycles | 35 |

Hybridize the probes with the DNA library

Mix the following components as DNA library+block mix at room temperature:

4.3 μl of DNA library (150 ng/ul)

3 μl of Human Cot-1 DNA (Life Technologies 15279-101)

3 μl of Salmon sperm (Life Technologies 15632-011)

0.7 μl Customized blocking oligos mix (1000 μM), sequence shown below:

Blocking Oligo 1 (as set forth in SEQ ID NO. 913)

Blocking Oligo 2 (as set forth in SEQ ID NO. 914)

Mix well by pipetting.

Transfer the DNA-library+block mix to 384-well PCR plate. Seal the plate will microAmp clear adhesive film (cat #4306311 from ABI) for tight sealing.

Centrifuge the plate briefly to collect the liquid at the bottom of the well.

Run the following thermocycler program (with 105° C. heated lid):

95° C. for 5 minutes;

67.5° C. forever

Prepare the Hybridization Buffer immediately after putting DNA-library+block mix in the thermocycler. Mix the following components at room temperature to prepare the Hybridization Buffer:

| component | volume in 1 reaction (μl) |
|---|---|
| 20 × SSPE | 12.5 |
| 0.5M EDTA | 0.5 |
| 50 × Denhardt's | 5 |
| 10% SDS | 6.5 |
| Total | 24.5 |

With the 384-well plate in the thermocycler at 67.5° C., transfer 24.5 μl of Hybridization Buffer into a new well of the plate, seal the plate with adhesive film.

Incubate the Hybridization Buffer at 67.5° C. for at least 5 minutes (could be longer) while the RNA-Probe Library get prepared.

Prepare the RNA probes immediately after putting the Hybridization Buffer in the thermocycler. Mix the following components on ice to prepare the RNA probes:

| component | volume in 1 reaction (μl) |
|---|---|
| RNA probes from "+" clone transcripts (800 ng/μl) | 2.5 |
| RNA probes from"−"clone transcripts (800 ng/μl) | 2.5 |
| RNase Inhibitor (20 U/μl) | 0.5 |
| Nuclease-free water | 1.5 |
| Total | 7 |

With the 384-well plate in the thermocycler at 67.5° C., transfer 7 μl of RNA probes into a new well of the plate, seal the plate with adhesive film.

Incubate the RNA probes at 75.5° C. for 2 minutes with the heated lid.

Open the lid and maintain the plate at 75.5° C. Take 13 μl of pre-heated Hybridization Buffer and add it to the RNA probes.

Transfer 10 μl of DNA-library+block mix to the RNA probes.

Mix well by slowly pipetting up and down several times. The hybridization mixture should be ~30 μl.

Seal the well with double adhesive film.

Incubate the hybridization mixture for 12~48 hours at 67.5° C. with heated lid at 105° C.

Extracting the Hybridized RNA-DNA Molecules

Wash 50 μl Dynal MyOne Streptavidin Cl magnetic beads (ThermoFisher Scientific) with 200 μl Binding buffer (1M NaCl, 10 mM Tris-HCl, pH 7.5, and 1 mM EDTA) three times in 1.5 ml microfuge tube and resuspend in 200 μl binding buffer.

Add the entire hybridization mixture directly from the thermocycler to the bead solution, and invert the tube to mix several times.

Rotate the hybridization mixture/bead solution 360 deg. for 15 minutes at room temperature.

After binding, the beads are separated from the solution on a Dynal magnetic separator and the supernatant is removed.

Washing Procedure

Wash the beads for 15 minutes at room temperate in 500 μl wash buffer I (1×SSC/0.1% SDS).

Wash the beads for 15 minutes at 67.5° C. on a heating block with shaking, three times in 500 μl 67.5° C. pre-heated wash buffer II (0.1×SSC/0.1% SDS).

Mix the beads in 50 μl 0.1M NaOH at room temperature for 10 minutes.

Transfer the supernatant to a new tube.

Add 50 μl of Neutralizing buffer (1M Tris-HCl, pH 7.5).

Neutralized DNA is desalted and concentrated by AMPure beads with ratio 1:1 (beads:sample), elute in 20 μl 1×TE buffer.

Post-Capture Amplification

PCR Mix Contains: (Per Reaction)

| | |
|---|---|
| Captured DNA | 20 ul |
| Water | 65 ul |
| DMSO | 2.5 ul |
| 5X Phusion Buffer | 10 ul |
| 10 mM dNTPs | 1 ul |
| Index PE primer II | 0.25 ul |
| PE primer I | 0.25 ul |
| HotStart Phusion | 1 ul |

mix well

Amplification Conditions:

| | | |
|---|---|---|
| Step1: 1 cycle | 98° C. | 1 minute |
| Step 2: 14 cycles of | 98° C. | 10 seconds |
| | 65° C. | 30 seconds |
| | 72° C. | 30 seconds |
| Step 3: 1 cycle | 72° C. | 5 minutes |
| Step 4: 1 cycle | 4° C. | hold |

The PCR is done in two wells for each sample, 50 ul each. Then the amplified PCR product was purified using AMPure beads with ratio 1:1 (beads:sample), elute in 30 ul 1×TE buffer.

Use Qubit to quantify yield. You will have ~20 ng/ul in general.

Example 6

Real-time PCR assay: Real-time PCR assays with SYBR green detection was carried out using an ABI PRISM 7500 Sequence Detection System (Applied Biosystems). Briefly, the reaction conditions consisted of 500 ng of genomic DNA or DNA library products, 0.2 μM primers, and SYBR Green Real-Time PCR Master Mix (ThermoFisher Scientific) in a final volume of 20 μl. Each cycle consisted of denaturation at 95° C. for 15 seconds, annealing at 58.5° C. for 5 seconds and extension at 72° C. for 20 seconds, respectively. Gene specific primers were designed using Primer 3 and their sequences are provided in the table shown in FIGS. 13A-13N. Reactions were run in triplicate in three independent experiments. The primer pair's standard amplification curve for each gene was established through using sequential dilutions of the "+" clone constructs containing the amplicon sequence, which was originally created to generate the DEEPER-Capture RNA probes. Amplification efficiencies for 298 target amplicons were established and listed in the table shown in FIGS. 13A-13N. Gene abundance ratios between different samples were calculated by the raising the gene specific amplification efficiency (AE) to the power of $\Delta C_t$ value between different samples. For example, the ratio (r) of gene abundance in sample A vs sample B can be calculated through real-time PCR assay by:

$$r_{(A/B)}=AE^{\Delta C_t}, \text{ where } \Delta C_t=C_{t(sample\ B)}-C_{t(sample\ A)} \quad \text{(Equation 1)}$$

Build a highly accurate reference exome for ultra-rare mutation identification: To highly accurately assess the baseline mutation frequency of DEEPER-Seq pipeline, we constructed six replicates of standard NGS DNA libraries in parallel, each using 100 ng normal DNA input. We used these six replicates of exome datasets to re-build our own reference exome database for this particular patient by requesting that if the same SNV was observed in ≥5 out of 6 independent datasets, we considered the SNVs as germline variants and updated our reference exome sequence database. For a standard NGS pipeline, the error rate is 1%, and the chance to see exactly the same random error at a fixed position for 5 times is $(1/3*1\%)^5=4.12\times10^{-13}$. This number means that if we use this approach to sequence the whole human genome once, we are presumably going to have only one artificial error, because $3\times10^{12}$ human genome bases X $(4.12\times10^{-13})=1.24$. However, we are enriching and sequencing the human exome, which is occupying only 1.5% of human genome, therefore the chance to see a single artificial error within the entire human exome is only 1.86% (=1.5%×1.24). An updated highly accurate normal exome reference database of the patient was built accordingly.

Discussion

DEEPER-Library Offers the Ultimate Ability to Detect Ultra-Rare Mutation in Limited Amount of Samples or Damaged Samples The DEEPER-Library creates a large number of barcoded DNA read families (URFs), where each family arises from a single-stranded DNA molecule. After sequencing the library, DNA molecules within the URF can be identified and grouped based on the fact that they all share an identical barcode sequence. Only the URF with at least 3 reads and with 95% molecule members sharing the same sequence at any giving position is adopted as a read family to generate the consensus sequence (a super read). This step efficiently removes artificial PCR errors that occur during repeated rounds of library amplification.

If an artificial error occurs at the very first step of PCR amplification, it will propagate to at most 50% of the PCR products of that sequence. Artificial variants that arise due to PCR errors or sequencing errors can be removed based on the fact that errors occur along with multiple rounds of PCR amplifications, thus being observed from only a subgroup of the reads sharing the same unique barcode. A filter can be adopted to abandon the URF whose sequence uniformity is lower than a threshold, and for this study such threshold was set as 95%. A higher threshold can further improve the sequencing accuracy, but will lead to a lower number of super reads. With a large number of high fidelity super reads collected, each super read, bearing a unique barcode, is aligned to its complementary super read by virtual of sharing a complementary consensus sequence but being differently barcoded. By mapping the super reads arising from both DNA strands individually, artificial errors in super reads can be removed in such a way that a sequence variant at a position is considered real only if a matched sequence variant can be observed at the same position from the other complementary DNA strand super read with a different barcode. The possibility for any artificial sequence variants to have a matched artificial variant at the same position from a complementary DNA strand is $<6.45\times10^{-14}$ per base.

DEEPER-Capture Based DNA Capture Enables Ultimately the Best Capture Efficiency

In 1960, DNA-RNA hybridization was reported for the first time before the term was invented. Since then, numerous studies have reported that an RNA probe can bind to its complementary DNA target sequence with a much stronger affinity than a DNA probe. In DEEPER-Capture, capture efficiency is greatly improved by using a large amount of RNA probes to capture both DNA strands of the same DNA duplex molecule, simultaneously. DEEPER-Capture achieves an unprecedented 29.2% capture ratio on average, and this phenomenal high efficiency is achieved presumably due to two reasons:

1) The large number of single-stranded RNA probes used in DEEPER-Capture may improve the hybridization reaction. The excessive amount of RNA probes will push the balance of the binding reaction towards forming RNA-DNA duplex, and RNA duplex that can then be easily removed by RNase treatment if needed. The logistics of standard single-stranded RNA probe based capture (Half-DEEPER-Capture) and DEEPER-Capture can be illustrated by the following equations with the assumption that RNA-Probe$_{(-)}$ and RNA-Probe$_{(+)}$ have the complementary sequences and can capture DNA$_{(+)}$ and DNA$_{(-)}$ strands, individually:

Standard Single-Stranded RNA Probe Based Capture (Half-DEEPER-Capture):

$$DNA_{(+)}:DNA_{(-)}+RNA\text{-}Probe_{(-)} \rightleftharpoons DNA_{(+)}+DNA_{(-)}+RNA\text{-}Probe_{(-)} \rightleftharpoons DNA_{(+)}:RNA\text{-}Probe_{(-)}+DNA_{(-)}(*)$$

$$Rate_{capturing\ DNA\ single\ strand}=k_1\cdot[DNA_{(+)}:DNA_{(-)}]\cdot[RNA\text{-}Probe_{(-)}] \quad \text{(Equation 2)}$$

*the reaction equation shows the balance of single-stranded RNA$_{(-)}$ probe capturing the single-stranded DNA$_{(+)}$ target, and the same balance holds for single-stranded RNA$_{(+)}$ probe capturing the single-stranded DNA$_{(-)}$ target (not shown here). For any given DNA sequence, only one strand, either DNA$_{(+)}$ or DNA$_{(-)}$, can be captured, not both.

Double-Stranded Probe Capturing (DEEPER-Capture):

$$DNA_{(+)}:DNA_{(-)}+RNA\text{-}Probe_{(+)}+RNA\text{-}Probe_{(-)} \rightleftharpoons DNA_{(+)}+DNA_{(-)}+RNA\text{-}Probe_{(+)}+RNA\text{-}Probe_{(-)} \rightleftharpoons DNA_{(+)}:RNA\text{-}Probe_{(-)}+DNA_{(-)}:RNA\text{-}Probe_{(+)}+RNA\text{-}Probe_{(+)}:RNA\text{-}Probe_{(-)}$$

$$Rate_{capturing\ DNA\ double\ strands}=k_2\cdot[DNA_{(+)}:DNA_{(-)}]\cdot[RNA\text{-}Probe_{(+)}]\cdot[RNA\text{-}Probe_{(-)}] \quad \text{(Equation 3)}$$

As shown in the equations (2) and (3), in DEEPER-Capture, the concentrations of RNA-Probe(+) and RNA-Probe$_{(-)}$ are adjusted to be significantly excessive as opposed to the concentration of the target DNA duplex molecules [DNA$_{(+)}$:DNA$_{(-)}$]. As shown in Equation 2, the rate of the hybridization reaction between single-stranded RNA probes and single-stranded DNA molecules can be improved by increasing the [RNA-Probe$_{(-)}$] concentration. Furthermore, as shown in Equation 3, when RNA-Probe$_{(+)}$ is added, the hybridization is even more efficient by the fact that the rate is multiplied by the factor of another large concentration value [RNA-Probe$_{(+)}$].

2) DEEPER-Capture may improve the hybridization reaction by depleting one DNA strand, thus helping to expose the other DNA strand to a large amount of complementary RNA probes, both of which may synergistically increase the reaction constant $k_2$ to be significantly larger than $k_1$. When a DNA duplex is placed in a heated environment around its $T_m$, the two complementary DNA strands are either separated (for strands or regions with low GC content) or loosely associated (high GC regions). When one of the two complementary DNA strands is captured by an RNA probe, the other DNA strand can be more accessible to its complementary RNA probes. Therefore, DEEPER-Capture may improve target capture efficiency by achieving a much larger $k_2$ over $k_1$.

It has been reported that in NGS capture methods, overlapping baits improves sensitivity and are superior to an immediately adjacent or spaced design, and relatively long baits and RNA-based baits can increase capturing efficiency. The DEEPER-Capture method we reported here utilizes randomly sheared massive amounts of RNA probes with their length ranging from 100 to 150 nt, which are heavily overlapped and covering the target DNA regions thousands of times. We demonstrated the superior capturing efficiency of the RNA probes designed and synthesized by our pipeline. Our findings once again supported the previous observations of RNA probes in capture operation. More importantly, we reported for the first time that when the overlapping RNA probes are in excessive amount (compared to DNA molecules) and are targeting both DNA strands simultaneously, a significantly improved capture efficiency can be achieved.

Off-target enrichment was one of the biggest concerns in DEEPER-Capture. The highly efficient DEEPER-Capture approach relies on a large amount of RNA probes that are overlapping with each other and are complementary to both DNA strands of the same targeted genomic region. A major side reaction would be the formation of RNA duplex molecules, RNA$_{(+)}$:RNA$_{(-)}$, from two complementary RNA single strands. However, this side interaction may have only limited negative impact on the formation of DNA$_{(+/-)}$:RNA-Probe$_{(-/+)}$ hybrids. Furthermore, RNA duplex molecules as well as the excessive amount of RNA probes can be removed by RNase treatment if necessary, and the captured target DNA sequences won't be affected. A major concern for off-target enrichment in NGS is the proportion of unwanted genomic DNA fragments that are being enriched through unspecific hybridization. To address this issue, we optimized capturing conditions with different buffer systems, capture reaction temperatures, incubation times and blocking primer sequences and concentrations, etc. Under the optimized condition, DEEPER-Capture showed that only an average of 16.4% of the total reads are off-target reads in a WES study (FIG. 11B). This is an acceptable ratio for most NGS applications and is lower than other target enrichment methods. Further improvements can be achieved with additional optimized conditions or procedures.

There are several widely used commercial kits designed to capture DNA subgenomic regions. Agilent, NimbleGen and Illumina are three major vendors in this field. Based on chemical natures of their probes, these commercially available approaches can be classified into two categories: 1) RNA probes: Agilent's SureSelect; 2) DNA probes: Roche's NimbleGen SeqCap, Illumina's TruSeq and Nextera. Several studies have been conducted to compare these capture methods in terms of their performance in WES. All the platforms mentioned above can capture over 90% of the unique sequences in a WES study with a minimal sample input ranging from 50 ng (Illumina Nextera) to 1.1 ug (NimbleGene). Agilent SureSelect offers the only RNA probe-based (single-stranded RNA probes) capture method on the market, and has been reported to perform successful capture with down to 6.25 ng input DNA to achieve ~300× mean depth of coverage with an SNV detection sensitivity >96% for high prevalence SNVs (allelic fractions>15%). As we introduced above, RNA baits have unprecedented advantages over DNA baits, such that it bind to target DNA much stronger than DNA probes, and that RNA baits do not interfere with downstream PCR reactions and can be easily removed. Like us, Agilent adopted RNA probes, but their RNA baits are targeting only one strand of the DNA targets with very limited probe amount. However, in DEEPER- Capture we are capturing both DNA strands simultaneously with an excessive amount of probes, thus achieving an over 3 folds improved efficiency comparing to a single-stranded capture approach.

REFERENCE

Benjamini, Y. and T. P. Speed (2012). "Summarizing and correcting the GC content bias in high-throughput sequencing." Nucleic Acids Res 40(10): e72.

Clark, M. J., et al. (2011). "Performance comparison of exome DNA sequencing technologies." Nat Biotechnol 29(10): 908-914.

McKenna, A., et al. (2010). "The Genome Analysis Toolkit: a MapReduce framework for analyzing next-generation DNA sequencing data." Genome Res 20(9): 1297-1303.

Meienberg, J., et al. (2015). "New insights into the performance of human whole-exome capture platforms." Nucleic Acids Res 43(11): e76.

Tsiatis, A. C., et al. (2010). "Comparison of Sanger sequencing, pyrosequencing, and melting curve analysis for the detection of KRAS mutations: diagnostic and clinical implications." J Mol Diagn 12(4): 425-432.

Untergasser, A., et al. (2012). "Primer3—new capabilities and interfaces." Nucleic Acids Res 40(15): e115.

Van Allen, E. M., et al. (2014). "Whole-exome sequencing and clinical interpretation of formalin-fixed, paraffin-embedded tumor samples to guide precision cancer medicine." Nat Med 20(6): 682-688.

The invention claimed is:

1. A method for enriching at least one target nucleic acid sequence each in a polynucleotide from a biological sample, wherein the polynucleotide comprises one or more other sequences, the method comprising:

a) a providing step: providing at least one pair of RNA probe sets and a solid support having a working surface, wherein:

i) the solid support comprises a working surface functionalized with coupling partners to bind immobilization portions of the RNA probes;

ii) each of the at least one pair of RNA probe sets comprises a first RNA probe set and a second RNA probe set configured to concurrently and respectively target two antiparallel strands of a duplex segment in each of the at least one target nucleic acid sequence;

iii) each RNA probe in any of the first RNA probe set and the second RNA probe set comprises an immobilization portion for attachment to the solid support; and b) a capturing step: capturing the two antiparallel strands of the duplex segment from the biological sample, wherein:

i) the two antiparallel strands of the duplex segment in the at least one target nucleic acid sequence are hybridized concurrently and respectively to the first RNA probe set and the second RNA probe set in the at least one pair of RNA probe sets; and ii) the immobilization portion of each RNA probe binds to the coupling partners on the solid support during or after hybridization, thereby capturing the target nucleic acid sequence on the solid support;

c) a blocking step: blocking non-target sequences, wherein prior to or concurrent with the hybridization:

i) at least one blocking oligonucleotide is hybridized with the polynucleotide in the biological sample, such that the at least one blocking oligonucleotide hybridizes with and blocks one strand in at least one of the one or more other sequences in the polynucleotide; and ii) the hybridization of said at least one blocking oligonucleotide sterically or competitively inhibits hybridization of RNA probes to non-target sequences and thereby reduces non-specific binding of the RNA probes.

2. The method of claim 1, wherein each RNA probe in any of the first RNA probe set and the second RNA probe set in the each of the at least one pair of RNA probe sets has a length of about 100-150 nucleotides (nt), wherein:

the contacting both the first RNA probe set and the second RNA probe set in the each of the at least one pair of RNA probe sets with the at least one target nucleic acid sequence in the biological sample is performed at a temperature of about 62-70° C.

3. The method of claim 1, wherein the first RNA probe set and the second RNA probe set in the each of the at least one pair of RNA probe sets respectively target a different portion of the duplex segment in the each of the at least one target nucleic acid sequence.

4. The method of claim 1, wherein the first RNA probe set and the second RNA probe set in each pair respectively hybridize to complementary regions on the two antiparallel strands of the same region of the at least one target nucleic acid sequence.

5. The method of claim 4, wherein the hybridization occurs in a single hybridization reaction, wherein contacting both the first RNA probe set and the second RNA probe set are concurrently hybridized to the two antiparallel strands of the duplex segment in each of the at least one target nucleic acid sequence.

6. The method of claim 5, wherein, for the at least one pair of RNA probe sets, each probe in the first RNA probe set and each probe in the second RNA probe set are immobilized at physically separated positions on the working surface of the solid support.

7. The method of claim 5, wherein in the each of the at least one pair of RNA probe sets, each probe in the first RNA probe set and each probe the second RNA probe set are not physically separated from one another.

8. The method of claim 4, wherein the contacting both the first RNA probe set and the second RNA probe set in the each of the at least one pair of RNA probe sets with the at least one target nucleic acid sequence in the biological sample comprises sequentially:

contacting one of the first RNA probe set and the second RNA probe set in each of the at least one pair of RNA probe sets with the at least one target nucleic acid sequence in a first hybridization reaction; and contacting another of the first RNA probe set and the second RNA probe set in each of the at least one pair of RNA probe sets with the at least one target nucleic acid sequence in a second hybridization reaction.

9. The method of claim 4, wherein the contacting both the first RNA probe set and the second RNA probe set in the each of the at least one pair of RNA probe sets with the at least one target nucleic acid sequence in the biological sample comprises at least one round of:

separately contacting the first RNA probe set and the second RNA probe set in each of the at least one pair of RNA probe sets with the at least one target nucleic acid sequence in a third hybridization reaction and a fourth hybridization reaction, respectively; and combining the third hybridization reaction and the fourth hybridization reaction to thereby allow a fifth hybridization reaction to proceed.

10. The method of claim 1, wherein the RNA probes in each of the at least one pair of RNA probe sets are attached to immobilized on the working surface of the solid support prior to the capturing step to form at least one pair of immobilized RNA probe sets, each pair comprising an immobilized first RNA probe set and an immobilized second RNA probe set; and wherein in the capturing step, the immobilized first RNA probe set and the immobilized second RNA probe set hybridize to the two antiparallel strands of the duplex segment in each of the at least one target nucleic acid sequence.

11. The method of claim 10, wherein the working surface is selected from the group consisting of a magnetic bead, a filter, a resin bead, a nanosphere, a plastic surface, a microtiter plate, a glass surface, a slide, a membrane, a microfluidic channel, a chip, and a matrix, wherein the solid support can be labelled, conjugated, or attached with a coupling partner corresponding to the immobilization portion.

12. The method of claim 10, wherein the immobilized first RNA probe set and the immobilized second RNA probe set:

Concurrently hybridize to the two antiparallel strands of each of the at least one target nucleic acid sequence.

13. The method of claim 10, wherein the contacting both the immobilized first RNA probe set and the immobilized second RNA probe set in the each of the at least one pair of immobilized RNA probe sets with the at least one target nucleic acid sequence comprises sequentially:

contacting one of the immobilized first RNA probe set and the immobilized second RNA probe set in the each of the at least one pair of immobilized RNA probe sets with the at least one target nucleic acid sequence in a sixth hybridization reaction; and contacting another of the immobilized first RNA probe set and the immobilized second RNA probe set in the each of the at least one pair of immobilized RNA probe sets with the at least one target nucleic acid sequence in a seventh hybridization reaction.

14. The method of claim 10, wherein the contacting both the immobilized first RNA probe set and the immobilized second RNA probe set in the each of the at least one pair of immobilized RNA probe sets with the at least one target nucleic acid sequence comprises:

separately contacting the immobilized first RNA probe set and the immobilized second RNA probe set in the each of the at least one pair of immobilized RNA probe sets with the at least one target nucleic acid sequence in an eighth hybridization reaction and a ninth hybridization reaction, respectively; and combining the eighth hybridization reaction and the ninth hybridization reaction to thereby allow a tenth hybridization reaction to proceed.

* * * * *